(12) United States Patent
Cohen et al.

(10) Patent No.: US 7,105,353 B2
(45) Date of Patent: Sep. 12, 2006

(54) METHODS OF IDENTIFYING INDIVIDUALS FOR INCLUSION IN DRUG STUDIES

(75) Inventors: Daniel Cohen, Paris (FR); Marta Blumenfeld, Paris (FR); Ilya Chumakov, Vaux-le Penil (FR)

(73) Assignee: Serono Genetics Institute S.A., Evry (FR)

( * ) Notice: Subject to any disclaimer, the term of this patent is extended or adjusted under 35 U.S.C. 154(b) by 496 days.

(21) Appl. No.: 10/367,438

(22) Filed: Feb. 14, 2003

(65) Prior Publication Data

US 2003/0180773 A1    Sep. 25, 2003

Related U.S. Application Data

(62) Division of application No. 09/463,075, filed as application No. PCT/IB98/01193 on Jul. 17, 1998, now abandoned.

(60) Provisional application No. 60/082,614, filed on Apr. 21, 1998.

(30) Foreign Application Priority Data

Jul. 18, 1997  (EP)  .................................. 97401740

(51) Int. Cl.
  *G01N 33/00*  (2006.01)
  *C12Q 1/68*  (2006.01)
  *C07H 21/04*  (2006.01)

(52) U.S. Cl. .......................... 436/94; 435/6; 536/23.1; 536/24.31

(58) Field of Classification Search .................... 435/6, 435/183, 91, 1, 91.2, 287.2; 536/23.1, 24.3
See application file for complete search history.

(56) References Cited

U.S. PATENT DOCUMENTS 5,804,388 A    9/1998  Aguirre et al.
5,880,105 A *  3/1999  Bergsma et al. .............. 514/44
6,087,107 A    7/2000  Sheffield et al.

FOREIGN PATENT DOCUMENTS

| EP | 0 785 280 A2 | 7/1997 |
|---|---|---|
| WO | WO 91 13075 A | 9/1991 |
| WO | WO 95/12607 | 5/1995 |
| WO | WO 98/20165 | 5/1998 |
| WO | WO 99/04038 | 1/1999 |
| WO | WO 99/32644 | 7/1999 |

OTHER PUBLICATIONS

Benjamin Lewin, Genes V, Oxford University Press, 1994, glossary.*

Benham, F., et al., "A Method for Generating Hybrids Containing Nonselected Fragments of Human Chromosomes", GENOMICS, vol. 4, pp. 509-517, 1989.

Chea, M., et al., "Accessing Genetic Information with High-Density DNA Arrays", SCIENCE, vol. 274, pp. 610-614, Oct. 25, 1996.

Cherif, D., et al., "Simultaneous Localization of Cosmids and Chromosome R-banding by Fluorescence Microscopy: Application to Regional Mapping of Human Chromosome 11", Proc. Natl. Acad. Sci., vol. 87, pp. 6639-6643, Sep. 1990.

Chumakov, I. M., et al., "A YAC Contig Map of the Human Genome", NATURE, vol. 377, pp. 175-287, Sep. 28, 1995.

(Continued)

*Primary Examiner*—Bradley L. Sisson
(74) *Attorney, Agent, or Firm*—Saliwanchik, Lloyd & Saliwanchik

(57)    ABSTRACT

The present invention relates to genomic maps comprising biallelic markers, new biallelic markers, and methods of using biallelic markers.

22 Claims, 16 Drawing Sheets

21

OTHER PUBLICATIONS

Cox, D., et al., "Radiation Hybrid Mapping: A somatic Cell Genetic Method for Constructing High-Resolution Maps of Mammalian Chromosomes", SCIENCE, vol. 250, pp. 245-250, Oct. 12, 1990.

Cox, et al., "Assessing Mapping Progress in the Human Genome Project", SCIENCE, vol. 265, pp. 2031-2032, 1994.

Excoffier, L., et al., "Maximum-Likelihood Estimation of Molecular Haplotype Frequencies in a Diploid Population", Mol. Biol. Evol., 12(5):921-927, 1995.

Fan, J., et al., "Genetic Mapping: Finding and Analyzing Single-Nucleotide Polymorphisms with High-Density DNA Arrays", Am. J. Human Genetics, vol. 71, No. 4, 1997.

Foster, J., et al., "A High-Resolution Whole Genome Radiation Hybrid Map of Human Chromosome 17q22-q25.3 Across the Genes for G*H* and T*K*", GENOMICS, vol. 33, pp. 185-192, 1996.

Frazier, K., et al., "A Radiation Hybrid Map of the Region on Human Chromosome 22 Containing the Neurofibromatosis Type 2 Locus", GENOMICS, vol. 14, pp. 574-584, 1992.

Hudson, T., et al., "An STS-Based Map of the Human Genome", SCIENCE, vol. 270, pp. 1945-1954, Dec. 22, 1995.

Kim, et al., "Construction and Characterization of a Human Bacterial Artificial Chromosome Library", GENOMICS, vol. 34, pp. 213-218, 1996.

Kruglyak, L., "The Use of a Genetic Map of Biallelic Markers In Linkage Studies", Nature Genetics, vol. 17, Sep. 17, 1997.

Ledbetter, S., et al., Rapid Isolation of DNA Probes within Specific Chromosome Regions by Interspersed Repetitive Sequence Polymerase Chain Reaction, GENOMICS, vol. 6, pp. 475-481, 1990.

Noether, Gottfried E., "Introduction to Statistics—The Nonparametric Way", Springer-Verlag.

Obermayr, F., "A High-Resolution Radiation Hybrid Map of the Region Surrounding the Gorlin Syndrome Gene", Eur. J. Hum. Genet. vol. 4, pp. 242-245, 1996.

Raeymaekers, P., et al., "A Radiation Hybrid Map with 60 Loci Covering the Entire Short Arm of Chromosome 12", GENOMICS, vol. 29, pp. 170-178, 1995.

Sapolsky, R., et al., "High-Throughput Polymorphism Screening and Genotyping with High-Density Oligonucleotide Arrays", Genetic Analysis, vol. 14, pp. 187-192, 1999.

Schork, N., et al., "Linkage Disequilibrium Mapping for Quantitative Traits within Case/Control Settings", Am. J. Human Genetics, vol. 61, No. 4 Suppl. p. A293, 1997.

Schuler, G.D., et a., A Gene Map of the Human Genome, SCIENCE, vol. 274, pp. 540-546, Oct. 25, 1996.

Syvanen, A., et al., "Identification of Individuals by Analysis of Biallelic DNA Markers, Using PCR and Solid-Phase Minisequencing", Am. J. Hum. Genet. 52:46-59, 1993.

Wang, D., et al., "Toward a Third Generation Genetic Map of the Human Genome Based on Bi-Allelic Polymorphisms", Am. J. Human Genet., vol. 59, p. A3, 1996.

Wang, D., et al., "Large-Scale Identification, Mapping and Genotyping of Single-Nucleotide Polymorphisms in the Human Genome", SCIENCE, vol. 280, pp. 1077-1082, May 15, 1998.

Warrington, J.A., et al., "Radiation Hybrid Map of 13 Loci on the Long Arm of Chromosome 5", GENOMICS, vol. 11, pp. 701-708, 1991.

Xiong, Li Jin, Biallelic Markers in Genetics Studies of Human Diseases: Their Power, Accuracy, and Density in Population-based Linkage Analyses.

Chumakov, I., et al., "Continuum of Overlapping Clones Spanning the Entire Human Chromosome 21q", NATURE, vol. 359, pp. 380-387.

Cohen, D., et al., "A First-Generation Physical Map of the Human Genome", NATURE, vol. 366, pp. 698-701, Mar. 14, 1996.

Dib, C., et al., "A Comprehensive Genetic Map of the Huma Genome Based on 5,264 Microsatellites", NATURE, vol. 380, pp. 152-154, Mar. 14, 1996.

Doggett, N.A., et al., "An Integrated Physical Map of Human Chromosome 16", NATURE, vol. 377, pp. 335-365, Sep. 28, 1995.

EMBL Database Accession No. HS448E20, Nov. 23, 1999.

Gemmill, R.M., "A Second-Generation YAC Contig Map of Human Chromosome 3", NATURE, vol. 377, pp. 299-319, Sep. 28, 1995.

Hacia, J.G., et al., "Detection of Heterozygous Mutations in BRCA1 Using High Density Oligonucleotide Arrays and Two-Colour Fluroescence Analysis", NATURE, vol. 14, pp. 441-447, Dec. 14, 1996.

Hawley, M.E., et al., HAPLO: A Program Using the EM Algorithm to Estimate the Frequencies of Multi-Site Haplotypes, J. Or Heredity, 86(5): 409-411 (1995).

Kozal, M.J., et al., "Extensive Polymorphisms Observed in HIV-1 Clade B Protease Gene Using High-Density Oligonucleotide Arrays", NATURE, vol. 2, pp. 753-759, Jul. 1996.

Larin, Z., et al., "Fluorescence *In Situ* Hybridisation of Multiple Probes on a Single Microscope Slide", Nucleic Acids Research, vol. 22, No. 18, pp. 3689-3692, 1994.

Risch, N., et al., "The Future of Genetic Studies of Complex Human Diseases", SCIENCE, vol. 273, pp. 1516-1517, Sep. 13, 1996.

Shoemaker, D.D., et al., "Quantitative Phenotypic Analysis of Yeast Deletion Mutants Using a Highly Parallel Molecular Bar-Coding Strategy", NATURE, vol. 14, pp. 450-456, Dec. 14, 1996.

Wang D., et al., "Abstracts of papers presented at the 1997 meeting on Genome Mapping & Sequencing", Cold Spring Harbor Laboratory, p. 17, May 14-18, 1997.

Woo, Sung-Sick, et al., "Construction and Characterization of a Bacterial Artificial Chromosome Library of Sorghum Bicolor", Nucleic Acids Research, vol. 22, No. 22, pp. 4922-4931, 1994.

Wang et al., "Toward a third generation genetic map of the human genome based on bi-allelic polymorphisms," Am. J. Hum. Con., (1996) 59(4)Suppl.; p. A3.

Gyapay, G., et al., "The 1993-94 Généthon Human Genetic Linkage Map", *Nature Genetics* (1994), 7:246-249.

Lewin, B., *Genes V*, Oxford University Press, New York, 1994, glossary.

\* cited by examiner p-VALUE DISTRIBUTION

| # aff | 150 | | | | | |
|---|---|---|---|---|---|---|
| # non aff | 150 | | | | | |
| pAi non aff Δ pAi | 0 | 0,1 | 0,2 | 0,3 | 0,4 | 0,5 |
| 0,05 | 8,7699E-05 | 0,06407752 | 0,14252002 | 0,19106311 | 0,21543442 | 0,22009395 |
| 0,1 | 1,9149E-08 | 0,00060364 | 0,00467774 | 0,01023571 | 0,01382303 | 0,01382303 |
| 0,15 | 3,0618E-12 | 1,3319E-06 | 3,8827E-05 | 0,0001478 | 0,0002343 | 0,00020218 |
| 0,2 | 3,2153E-16 | 9,1413E-10 | 9,0305E-08 | 5,733E-07 | 9,6336E-07 | 5,733E-07 |
| 0,25 | 2,0791E-20 | 2,2614E-13 | 6,2679E-11 | 5,873E-10 | 8,7113E-10 | 2,5396E-10 |
| 0,3 | 7,8245E-25 | 2,152E-17 | 1,3261E-14 | 1,5189E-13 | 1,5189E-13 | 1,3261E-14 |
| 0,35 | 1,6192E-29 | 7,9823E-22 | 8,4152E-19 | 9,1669E-18 | 4,2713E-18 | 5,5844E-20 |
| 0,4 | 1,7336E-34 | 1,1282E-26 | 1,524E-23 | 1,1488E-22 | 1,524E-23 | 1,1282E-26 |

| # aff | 200 | | | | | |
|---|---|---|---|---|---|---|
| # non aff | 200 | | | | | |
| pAi non aff Δ pAi | 0 | 0,1 | 0,2 | 0,3 | 0,4 | 0,5 |
| 0,05 | 5,9233E-06 | 0,03250945 | 0,09039173 | 0,13111935 | 0,15260313 | 0,15678006 |
| 0,1 | 8,649E-11 | 7,4765E-05 | 0,00109084 | 0,00302686 | 0,00447365 | 0,00447365 |
| 0,15 | 8,0215E-16 | 2,3653E-08 | 2,0257E-06 | 1,1771E-05 | 2,1573E-05 | 1,7772E-05 |
| 0,2 | 4,1762E-21 | 1,5375E-12 | 6,7374E-10 | 7,764E-09 | 1,5417E-08 | 7,764E-09 |
| 0,25 | 1,1282E-26 | 2,525E-17 | 4,4025E-14 | 8,5532E-13 | 1,4423E-12 | 2,8149E-13 |
| 0,3 | 1,4722E-32 | 1,1488E-22 | 5,8424E-19 | 1,4886E-17 | 1,4886E-17 | 5,8424E-19 |
| 0,35 | 8,6169E-39 | 1,4784E-28 | 1,5457E-24 | 3,6958E-23 | 1,3394E-23 | 4,197E-26 |
| 0,4 | 2,0885E-45 | 5,2308E-35 | 7,6438E-31 | 1,1224E-29 | 7,6438E-31 | 5,2308E-35 | aff   affected individuals
non aff   non affected individuals
pAi non aff   allele frequency in non affected individuals
Δ pAi   % Difference in allele frequency between affected and non-affected individuals

Figure 3 (I)

p-VALUE DISTRIBUTION

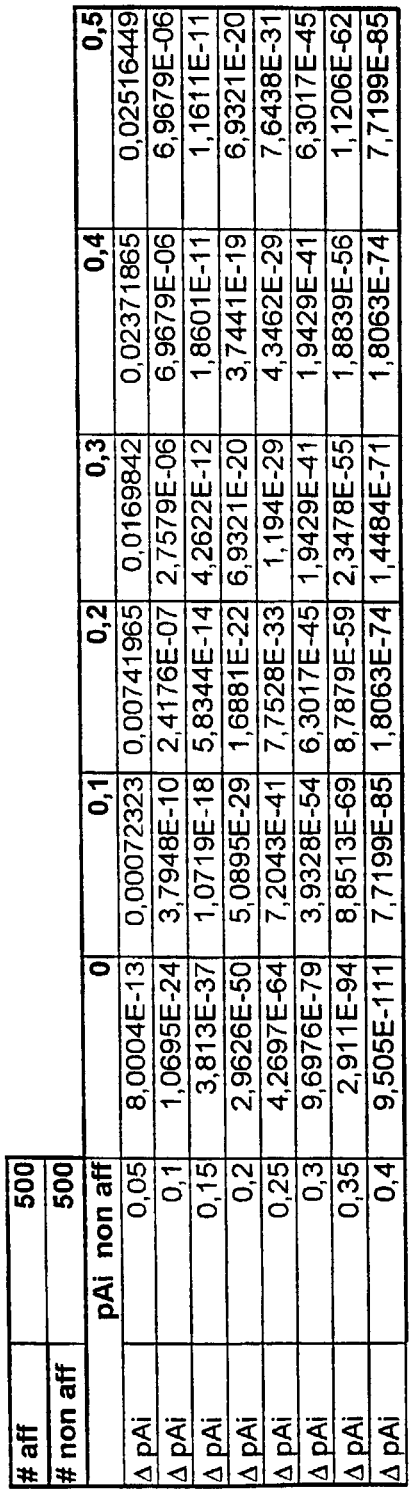
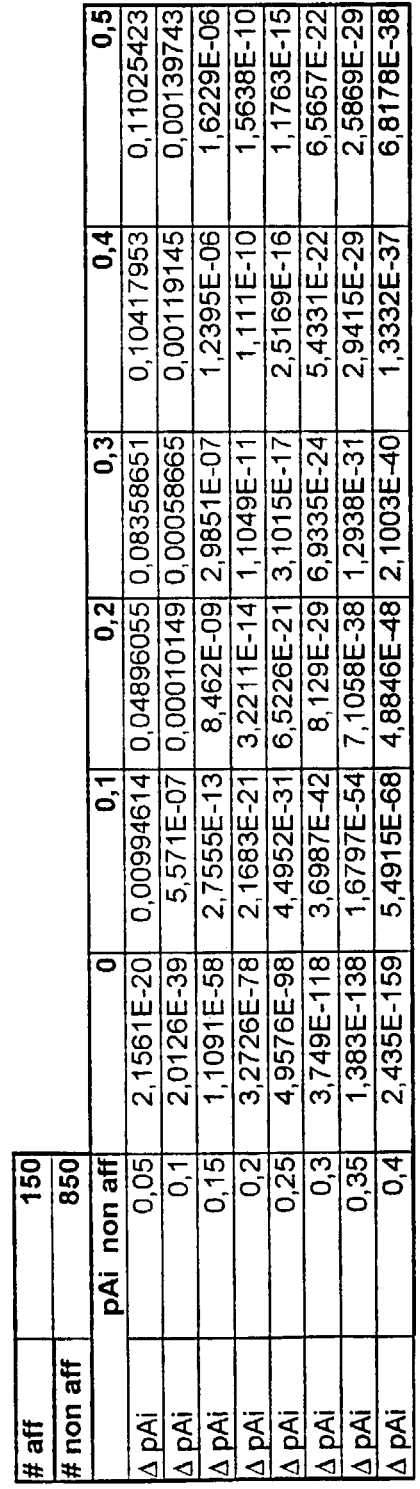

| # aff | 500 | | | | | | |
|---|---|---|---|---|---|---|---|
| # non aff | 500 | | | | | | |
| pAi non aff | 0 | 0,1 | 0,2 | 0,3 | 0,4 | 0,5 | |
| Δ pAi 0,05 | 8,0004E-13 | 0,00072323 | 0,00741965 | 0,0169842 | 0,02371865 | 0,02516449 | |
| Δ pAi 0,1 | 1,0695E-24 | 3,7948E-10 | 2,4176E-07 | 2,7579E-06 | 6,9679E-06 | 6,9679E-06 | |
| Δ pAi 0,15 | 3,813E-37 | 1,0719E-18 | 5,8344E-14 | 4,2622E-12 | 1,8601E-11 | 1,1611E-11 | |
| Δ pAi 0,2 | 2,9626E-50 | 5,0895E-29 | 1,6881E-22 | 6,9321E-20 | 3,7441E-19 | 6,9321E-20 | |
| Δ pAi 0,25 | 4,2697E-64 | 7,2043E-41 | 7,7528E-33 | 1,194E-29 | 4,3462E-29 | 7,6438E-31 | |
| Δ pAi 0,3 | 9,6976E-79 | 3,9328E-54 | 6,3017E-45 | 1,9429E-41 | 1,9429E-41 | 6,3017E-45 | |
| Δ pAi 0,35 | 2,911E-94 | 8,8513E-69 | 8,7879E-59 | 2,3478E-55 | 1,8839E-56 | 1,1206E-62 | |
| Δ pAi 0,4 | 9,505E-111 | 7,7199E-85 | 1,8063E-74 | 1,4484E-71 | 1,8063E-74 | 7,7199E-85 | |

| # aff | 150 | | | | | | |
|---|---|---|---|---|---|---|---|
| # non aff | 850 | | | | | | |
| pAi non aff | 0 | 0,1 | 0,2 | 0,3 | 0,4 | 0,5 | |
| Δ pAi 0,05 | 2,1561E-20 | 0,00994614 | 0,04896055 | 0,08358651 | 0,10417953 | 0,11025423 | |
| Δ pAi 0,1 | 2,0126E-39 | 5,571E-07 | 0,00010149 | 0,00058665 | 0,00119145 | 0,00139743 | |
| Δ pAi 0,15 | 1,1091E-58 | 2,7555E-13 | 8,462E-09 | 2,9851E-07 | 1,2395E-06 | 1,6229E-06 | |
| Δ pAi 0,2 | 3,2726E-78 | 2,1683E-21 | 3,2211E-14 | 1,1049E-11 | 1,111E-10 | 1,5638E-10 | |
| Δ pAi 0,25 | 4,9576E-98 | 4,4952E-31 | 6,5226E-21 | 3,1015E-17 | 2,5169E-16 | 1,1763E-15 | |
| Δ pAi 0,3 | 3,749E-118 | 3,6987E-42 | 8,129E-29 | 6,9335E-24 | 5,4331E-22 | 6,5657E-22 | |
| Δ pAi 0,35 | 1,383E-138 | 1,6797E-54 | 7,1058E-38 | 1,2938E-31 | 2,9415E-29 | 2,5869E-29 | |
| Δ pAi 0,4 | 2,435E-159 | 5,4915E-68 | 4,8846E-48 | 2,1003E-40 | 1,3332E-37 | 6,8178E-38 | | aff    affected individuals
non aff    non affected individuals
pAi non aff    allele frequency in non affected individuals
Δ pAi    % Difference in allele frequency between affected and non-affected individuals

Figure 3 (II)

p-VALUE DISTRIBUTION

| # aff | 200 |
|---|---|
| # non aff | 500 |

| | 0 | 0,1 | 0,2 | 0,3 | 0,4 | 0,5 |
|---|---|---|---|---|---|---|
| pAi non aff | | | | | | |
| Δ pAi 0,05 | 1,0628E-12 | 0,00789803 | 0,03942584 | 0,06867566 | 0,08621572 | 0,09083704 |
| Δ pAi 0,1 | 3,4525E-24 | 4,4217E-07 | 5,6883E-05 | 0,00031976 | 0,0006363 | 0,00070881 |
| Δ pAi 0,15 | 5,9036E-36 | 4,3025E-13 | 3,3635E-09 | 9,2134E-08 | 3,319E-07 | 3,5871E-07 |
| Δ pAi 0,2 | 4,7325E-48 | 1,5566E-20 | 1,0346E-14 | 1,7218E-12 | 1,1512E-11 | 1,00471E-11 |
| Δ pAi 0,25 | 1,6694E-60 | 3,5436E-29 | 2,0473E-21 | 2,2178E-18 | 1,1498E-17 | 1,3524E-17 |
| Δ pAi 0,3 | 2,4613E-73 | 7,2498E-39 | 3,0748E-29 | 2,0601E-25 | 3,4525E-24 | 7,4807E-25 |
| Δ pAi 0,35 | 1,4447E-86 | 1,6945E-49 | 3,9559E-38 | 1,4118E-33 | 2,662E-32 | 1,4118E-33 |
| Δ pAi 0,4 | 3,214E-100 | 5,3051E-61 | 4,7325E-48 | 7,1282E-43 | 1,0691E-41 | 7,2652E-44 |

| # aff | 500 |
|---|---|
| # non aff | 1000 |

| | 0 | 0,1 | 0,2 | 0,3 | 0,4 | 0,5 |
|---|---|---|---|---|---|---|
| pAi non aff | | | | | | |
| Δ pAi 0,05 | 6,4766E-24 | 5,7827E-05 | 0,00172627 | 0,00551541 | 0,00882876 | 0,00978249 |
| Δ pAi 0,1 | 6,5309E-47 | 3,065E-14 | 1,0301E-09 | 4,3205E-08 | 1,8833E-07 | 2,2731E-07 |
| Δ pAi 0,15 | 1,1969E-70 | 2,0716E-27 | 3,7441E-19 | 4,6626E-16 | 6,9719E-15 | 6,9719E-15 |
| Δ pAi 0,2 | 3,3252E-95 | 1,1636E-43 | 1,6614E-31 | 8,5632E-27 | 4,1421E-25 | 1,9885E-25 |
| Δ pAi 0,25 | 1,227E-120 | 1,7683E-62 | 1,5329E-46 | 3,1722E-40 | 8,6765E-39 | 3,6071E-39 |
| Δ pAi 0,3 | 5,303E-147 | 1,526E-83 | 4,2697E-64 | 2,5968E-56 | 3,9328E-54 | 2,5968E-56 |
| Δ pAi 0,35 | 2,36E-174 | 1,184E-106 | 4,5658E-84 | 4,7426E-75 | 4,26245E-73 | 4,0958E-77 |
| Δ pAi 0,4 | 9,446E-203 | 1,082E-131 | 2,137E-106 | 1,8014E-96 | 3,3252E-95 | 6,725E-102 | aff    affected individuals
non aff   non affected individuals
pAi non aff  allele frequency in non affected individuals
Δ pAi    % Difference in allele frequency between affected and non-affected individuals

Figure 3 (III)

APO E REGION HAPLOTYPE FREQUENCY ANALYSIS

| POPULATIONS | | | | | | AD CASES (225) | | | AD CONTROLS (248) | | |
|---|---|---|---|---|---|---|---|---|---|---|---|
| markers | 99-366 | 99-344 | 99-359 | 99-355 | | haplotype frequencies | | odds-ratio | P value | | |
| p value | 3,01E-01 | 1,11E-01 | 6,63E-01 | 1,38E-01 | | cases | controls | | | | |
| haplotype 1 | C | G | | | | 0,404 | 0,308 | 1,52 | 3,05E-03 | *** | |
| haplotype 2 | | G | A | | | 0,203 | 0,165 | 1,29 | 1,24E-01 | * | |
| haplotype 3 | | | G | G | | 0,375 | 0,306 | 1,36 | 2,83E-02 | ** | |
| haplotype 4 | C | | A | | | 0,264 | 0,209 | 1,36 | 5,95E-02 | ** | |
| haplotype 5 | | G | | A | | 0,115 | 0,071 | 1,70 | 1,64E-02 | ** | |
| haplotype 6 | C | | | A | | 0,15 | 0,129 | 1,19 | 3,59E-01 | * | |
| haplotype 7 | T | | G | G | | 0,225 | 0,122 | 2,09 | 4,76E-05 | ***** | |
| haplotype 8 | T | A | G | G | | 0,228 | 0,108 | 2,44 | 2,05E-06 | ****** | |

Figure 7

PROSTATE CANCER HAPLOTYPE FREQUENCY ANALYSIS

| | PROSTATE CANCER | NON-AFFECTED |
|---|---|---|
| characteristics of populations | CASES (281) 143 sporadic cases + 138 familial cases | CONTROLS (130) > 65 years PSA<4 |

| markers | 99-123 | 4-26 | 4-14 | 4-77 | 99-217 | 4-67 | 99-213 | 99-221 | 99-135 | haplotype frequencies | | relative risk | pvalue | |
|---|---|---|---|---|---|---|---|---|---|---|---|---|---|---|
| BACs | C | E | E | F | F | F | F | F | G | | | | | |
| genes | | | | <------PG1------> | | | | | | | | | | |
| p value | 2,00E-01 | 1,00E-01 | 1,00E-01 | 2,00E-02 | 2,00E-02 | 8,00E-04 | 9,00E-02 | 7,00E-01 | 2,00E-01 | cases | controls | | | |
| haplotype 8 >304kb< | C | A | C | G | T | T | C | A | A | 0,075 | 0,018 | 4,42 | 9,00E-04 | *** |
| haplotype 7 >286kb< | | A | C | G | T | T | C | A | A | 0,095 | 0,016 | 6,46 | 6,00E-05 | **** |
| haplotype 6 <186kb> | | A | C | G | T | T | C | A | | 0,116 | 0,019 | 6,78 | 1,00E-05 | ***** |
| haplotype 5 <171kb> | | | C | G | T | T | C | A | | 0,117 | 0,013 | 10,06 | 9,00E-07 | ******* |
| haplotype 4 <83kb> | | | | G | T | T | C | A | | 0,117 | 0,025 | 5,17 | 2,00E-05 | ***** |
| haplotype 3.1 <54kb> | | | | | T | T | C | A | | 0,117 | 0,027 | 4,78 | 2,00E-05 | ***** |
| haplotype 3.2 <54kb> | | | | G | | T | C | | | 0,222 | 0,109 | 2,33 | 4,00E-05 | ***** |
| haplotype 2.2 <39kb> | | | | G | | T | C | | | 0,251 | 0,134 | 2,17 | 2,00E-04 | **** |
| haplotype 2 <32kb> | | | | | T | T | | | | 0,226 | 0,112 | 2,32 | 1,00E-04 | *** |
| haplotype 1.1 <17 kb> | | | | | | T | | | | 0,256 | 0,146 | 2,01 | 3,00E-04 | **** |
| haplotype 1.2 <15 kb> | | | | | T | | C | | | 0,233 | 0,129 | 2,05 | 6,00E-04 | *** |

Figure 12

PROSTATE CANCER HAPLOTYPE SIMULATIONS (100 ITERATIONS)
| markers | 4-14 | 4-77 | 99-217 | 4-67 | 99-213 | 99-221 | haplotype frequencies | | relative risk | pvalue |
|---|---|---|---|---|---|---|---|---|---|---|
| | | | | | | | cases | controls | | |
| haplotype | C | G | T | T | G | A | 0,117 | 0,013 | 10,06 | 9,00E-07 |
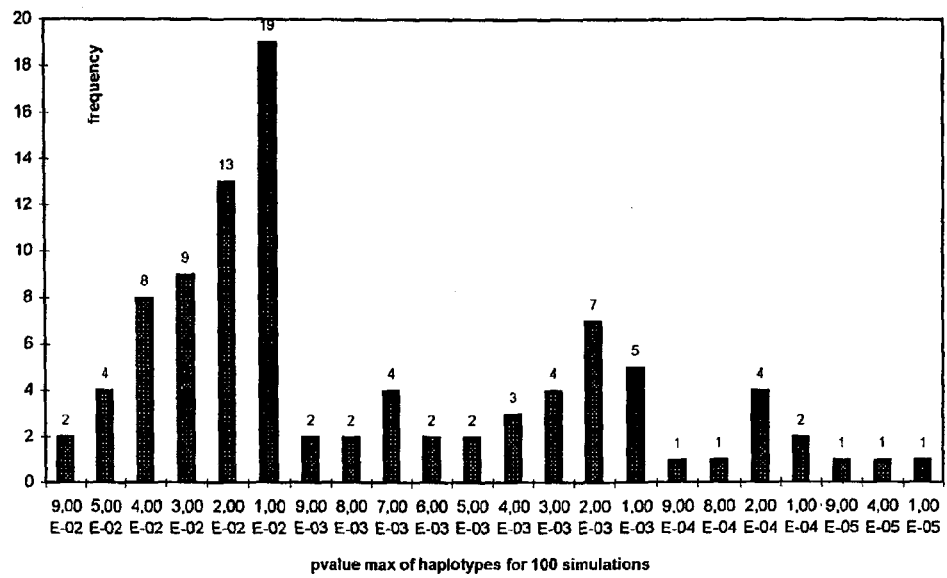
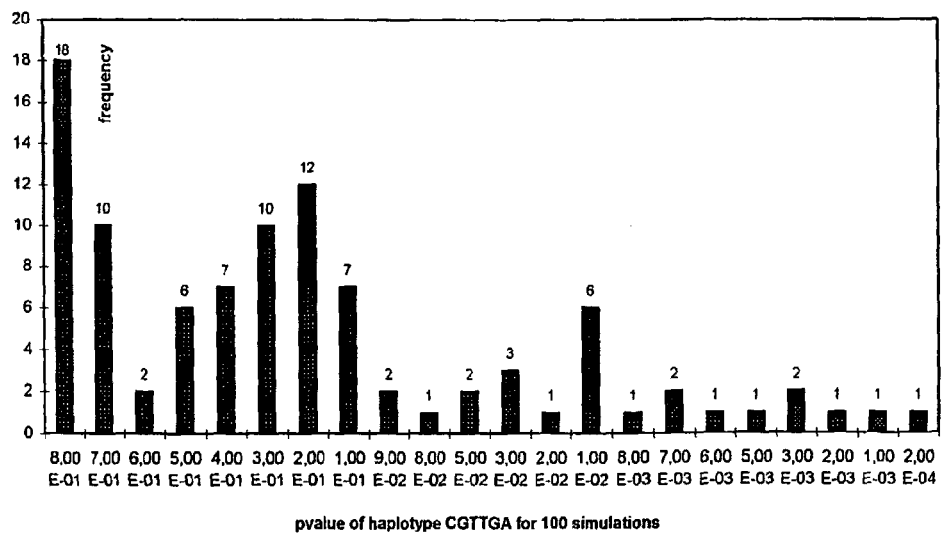
Figure 13

SEQUENCE LISTING (1) GENERAL INFORMATION:

(iii) NUMBER OF SEQUENCES: 336

(2) INFORMATION FOR SEQ ID NO: 1:

(i) SEQUENCE CHARACTERISTICS:
      (A) LENGTH: 47 base pairs
      (B) TYPE: NUCLEIC ACID
      (C) STRANDEDNESS: SINGLE
      (D) TOPOLOGY: LINEAR (ii) MOLECULE TYPE: DNA (vi) ORIGINAL SOURCE:
      (A) ORGANISM: Homo sapiens (ix) FEATURE:
      (A) NAME/KEY: polymorphic fragment 99-2103-270
      (B) LOCATION: 1..47

(ix) FEATURE:
      (A) NAME/KEY: polymorphic base
      (B) LOCATION: 24
      (D) OTHER INFORMATION: base g (ix) FEATURE:
      (A) NAME/KEY: Potential microsequencing oligo 99-2103-270
      (B) LOCATION: 1..23

```
        (ix) FEATURE:
             (A) NAME/KEY: Potential microsequencing oligo 99-2103-270
             (B) LOCATION: complement 25..47

(xi) SEQUENCE DESCRIPTION: SEQ ID NO: 1:

CTTGGATTCA TATGAGACAG CTAGCAGACC TTCAATTTTT CTACACT                    47

(2) INFORMATION FOR SEQ ID NO: 2:

(i) SEQUENCE CHARACTERISTICS:
             (A) LENGTH: 47 base pairs
             (B) TYPE: NUCLEIC ACID
             (C) STRANDEDNESS: SINGLE
             (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: polymorphic fragment 99-2228-301
             (B) LOCATION: 1..47

(ix) FEATURE:
             (A) NAME/KEY: polymorphic base
             (B) LOCATION: 24
             (D) OTHER INFORMATION: base a (ix) FEATURE:
             (A) NAME/KEY: Potential microsequencing oligo 99-2228-301
             (B) LOCATION: 1..23

(ix) FEATURE:
             (A) NAME/KEY: Potential microsequencing oligo 99-2228-301
             (B) LOCATION: complement 25..47

(xi) SEQUENCE DESCRIPTION: SEQ ID NO: 2:

CCCTGCTTAT CCCTGTAAGG TGGAGACCCA TATGGGCAAG GCCAGAC                    47

(2) INFORMATION FOR SEQ ID NO: 3:

(i) SEQUENCE CHARACTERISTICS:
             (A) LENGTH: 47 base pairs
             (B) TYPE: NUCLEIC ACID
             (C) STRANDEDNESS: SINGLE
             (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: polymorphic fragment 99-2229-240
             (B) LOCATION: 1..47

(ix) FEATURE:
             (A) NAME/KEY: polymorphic base
             (B) LOCATION: 24
             (D) OTHER INFORMATION: base g (ix) FEATURE:
             (A) NAME/KEY: Potential microsequencing oligo 99-2229-240
             (B) LOCATION: 1..23

(ix) FEATURE:
             (A) NAME/KEY: Potential microsequencing oligo 99-2229-240
             (B) LOCATION: complement 25..47

(xi) SEQUENCE DESCRIPTION: SEQ ID NO: 3:

TCGTCATCGT GGCCTGGGCT ACAGACTACC TGTTCCAGTC CTTCCAG                    47
```

(2) INFORMATION FOR SEQ ID NO: 4:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2240-281
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2240-281
        (B) LOCATION: 1..23

(ix) FEATURE:
        (A) NAME/KEY: Potential microsequencing oligo 99-2240-281
        (B) LOCATION: complement 25..47

(xi) SEQUENCE DESCRIPTION: SEQ ID NO: 4:

GCAATCTTAA TAACTTTTTA TTTCAGTAAT TCGAATCTTT TTTTTCT                47

(2) INFORMATION FOR SEQ ID NO: 5:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2242-206
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2242-206
        (B) LOCATION: 1..23

(ix) FEATURE:
        (A) NAME/KEY: Potential microsequencing oligo 99-2242-206
        (B) LOCATION: complement 25..47

(xi) SEQUENCE DESCRIPTION: SEQ ID NO: 5:

GTGTTTTCTT TTAGTCAAAT TATCTTATAT TTTACTTTTT TCTTAAG                47

(2) INFORMATION FOR SEQ ID NO: 6:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2244-83
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2244-83
        (B) LOCATION: 1..23

(ix) FEATURE:
        (A) NAME/KEY: Potential microsequencing oligo 99-2244-83
        (B) LOCATION: complement 25..47

(xi) SEQUENCE DESCRIPTION: SEQ ID NO: 6:

TAATTGTAGA TACTAAGACC ATTATGCTTA AACCATGTAG GTACTGA                47

(2) INFORMATION FOR SEQ ID NO: 7:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2246-340
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2246-340
        (B) LOCATION: 1..23

(ix) FEATURE:
        (A) NAME/KEY: Potential microsequencing oligo 99-2246-340
        (B) LOCATION: complement 25..47

(xi) SEQUENCE DESCRIPTION: SEQ ID NO: 7:

ATTTATATGT TAAATGCAGA GAAAAAGAAA AATAAGTTTT GCAGTAA                47

(2) INFORMATION FOR SEQ ID NO: 8:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2248-76
        (B) LOCATION: 1..47

(ix) FEATURE:

```
        (A) NAME/KEY: polymorphic base
        (B) LOCATION: 24
        (D) OTHER INFORMATION: base c (ix) FEATURE:
        (A) NAME/KEY: Potential microsequencing oligo 99-2248-76
        (B) LOCATION: 1..23

(ix) FEATURE:
        (A) NAME/KEY: Potential microsequencing oligo 99-2248-76
        (B) LOCATION: complement 25..47

(xi) SEQUENCE DESCRIPTION: SEQ ID NO: 8:

GACAGAGAGG GAAGGTAATC TTCCCCTGAA GTCTGCCCAT CCCCTGG                47

(2) INFORMATION FOR SEQ ID NO: 9:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2250-236
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2250-236
        (B) LOCATION: 1..23

(ix) FEATURE:
        (A) NAME/KEY: Potential microsequencing oligo 99-2250-236
        (B) LOCATION: complement 25..47

(xi) SEQUENCE DESCRIPTION: SEQ ID NO: 9:

ATGTATCCAA AACAGAATTA ACACACTTTG GGTTTTTTAT TTTTATT               47

(2) INFORMATION FOR SEQ ID NO: 10:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2251-151
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2251-151
        (B) LOCATION: 1..23

(ix) FEATURE:
```

```
        (A) NAME/KEY: Potential microsequencing oligo 99-2251-151
        (B) LOCATION: complement 25..47

(xi) SEQUENCE DESCRIPTION: SEQ ID NO: 10:

TGAAAAGAAG TTCAGACGAT TGCAGATAGA CTAGTTTGGC TGTTGTG                47

(2) INFORMATION FOR SEQ ID NO: 11:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2269-179
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2269-179
        (B) LOCATION: 1..23

(ix) FEATURE:
        (A) NAME/KEY: Potential microsequencing oligo 99-2269-179
        (B) LOCATION: complement 25..47

(xi) SEQUENCE DESCRIPTION: SEQ ID NO: 11:

AAAATAAAGA AATTCCTAGA GACATACAGC CTATCAAGAT CAAACCA                47

(2) INFORMATION FOR SEQ ID NO: 12:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2271-403
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2271-403
        (B) LOCATION: 1..23

(ix) FEATURE:
        (A) NAME/KEY: Potential microsequencing oligo 99-2271-403
        (B) LOCATION: complement 25..47

(xi) SEQUENCE DESCRIPTION: SEQ ID NO: 12:

AGGCATTTAT TCATATTTA TTAACCTTGA TTTTCTTATC TTCAAGT                 47

(2) INFORMATION FOR SEQ ID NO: 13:
```

```
    (i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2272-409
        (B) LOCATION: 1..47

(ix) FEATURE:
        (A) NAME/KEY: polymorphic base
        (B) LOCATION: 24
        (D) OTHER INFORMATION: base g (ix) FEATURE:
        (A) NAME/KEY: Potential microsequencing oligo 99-2272-409
        (B) LOCATION: 1..23

(ix) FEATURE:
        (A) NAME/KEY: Potential microsequencing oligo 99-2272-409
        (B) LOCATION: complement 25..47

(xi) SEQUENCE DESCRIPTION: SEQ ID NO: 13:

AAAAGCACTG CAATTATTTT GGAGACTGTG AAATATTGCA AGTTTTA                47

(2) INFORMATION FOR SEQ ID NO: 14:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2273-528
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2273-528
        (B) LOCATION: 1..23

(ix) FEATURE:
        (A) NAME/KEY: Potential microsequencing oligo 99-2273-528
        (B) LOCATION: complement 25..47

(xi) SEQUENCE DESCRIPTION: SEQ ID NO: 14:

ACTTGAAGAT AAGAAAATCA AGGCTAATAA ATATGAAATA AATGCCT                47

(2) INFORMATION FOR SEQ ID NO: 15:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA
```

```
    (vi) ORIGINAL SOURCE:
         (A) ORGANISM: Homo sapiens (ix) FEATURE:
         (A) NAME/KEY: polymorphic fragment 99-2275-466
         (B) LOCATION: 1..47

(ix) FEATURE:
         (A) NAME/KEY: polymorphic base
         (B) LOCATION: 24
         (D) OTHER INFORMATION: base c (ix) FEATURE:
         (A) NAME/KEY: Potential microsequencing oligo 99-2275-466
         (B) LOCATION: 1..23

(ix) FEATURE:
         (A) NAME/KEY: Potential microsequencing oligo 99-2275-466
         (B) LOCATION: complement 25..47

(xi) SEQUENCE DESCRIPTION: SEQ ID NO: 15:

TTGATGATAG CATTAAATAC TCCCAAAAAC TGTGAATAGG GATACTA                    47

(2) INFORMATION FOR SEQ ID NO: 16:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2278-276
         (B) LOCATION: 1..47

(ix) FEATURE:
         (A) NAME/KEY: polymorphic base
         (B) LOCATION: 24
         (D) OTHER INFORMATION: base a (ix) FEATURE:
         (A) NAME/KEY: Potential microsequencing oligo 99-2278-276
         (B) LOCATION: 1..23

(ix) FEATURE:
         (A) NAME/KEY: Potential microsequencing oligo 99-2278-276
         (B) LOCATION: complement 25..47

(xi) SEQUENCE DESCRIPTION: SEQ ID NO: 16:

GAAAAAAATG GGAACATCTT CACAGCCTGT GCATCTCCAA CAAGATT                    47

(2) INFORMATION FOR SEQ ID NO: 17:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2312-358
         (B) LOCATION: 1..47

(ix) FEATURE:
         (A) NAME/KEY: polymorphic base
```

```
        (B) LOCATION: 24
        (D) OTHER INFORMATION: base c (ix) FEATURE:
        (A) NAME/KEY: Potential microsequencing oligo 99-2312-358
        (B) LOCATION: 1..23

(ix) FEATURE:
        (A) NAME/KEY: Potential microsequencing oligo 99-2312-358
        (B) LOCATION: complement 25..47

(xi) SEQUENCE DESCRIPTION: SEQ ID NO: 17:

TTGAAGAGAG AGATGGAAAA AAACGTAGGC CTTCTGGGTA AATGGCC                47

(2) INFORMATION FOR SEQ ID NO: 18:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2315-213
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2315-213
        (B) LOCATION: 1..23

(ix) FEATURE:
        (A) NAME/KEY: Potential microsequencing oligo 99-2315-213
        (B) LOCATION: complement 25..47

(xi) SEQUENCE DESCRIPTION: SEQ ID NO: 18:

AGATGGATTC TACCCACAGG CAAAAGAAAA CCTTATTTTA AAAATAA                47

(2) INFORMATION FOR SEQ ID NO: 19:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2320-292
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2320-292
        (B) LOCATION: 1..23

(ix) FEATURE:
        (A) NAME/KEY: Potential microsequencing oligo 99-2320-292
```

(B) LOCATION: complement 25..47

(xi) SEQUENCE DESCRIPTION: SEQ ID NO: 19:

ACTCTCATTC ACTAAACTTC AACCGTTTTT ATAAATTTAA TGAATTT                47

(2) INFORMATION FOR SEQ ID NO: 20:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2321-82
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2321-82
        (B) LOCATION: 1..23

(ix) FEATURE:
        (A) NAME/KEY: Potential microsequencing oligo 99-2321-82
        (B) LOCATION: complement 25..47

(xi) SEQUENCE DESCRIPTION: SEQ ID NO: 20:

TAAAGCTTAC TGAGTGTCCA CTCCGGATAC CTACTCAAAT ATTTCCT                47

(2) INFORMATION FOR SEQ ID NO: 21:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2324-338
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2324-338
        (B) LOCATION: 1..23

(ix) FEATURE:
        (A) NAME/KEY: Potential microsequencing oligo 99-2324-338
        (B) LOCATION: complement 25..47

(xi) SEQUENCE DESCRIPTION: SEQ ID NO: 21:

AGATAGAAGA CAAAATCGCA GGAAAAGAAA TCCCTCAACA GTAAAAA               47

(2) INFORMATION FOR SEQ ID NO: 22:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2333-423
            (B) LOCATION: 1..47

(ix) FEATURE:
            (A) NAME/KEY: polymorphic base
            (B) LOCATION: 24
            (D) OTHER INFORMATION: base g (ix) FEATURE:
            (A) NAME/KEY: Potential microsequencing oligo 99-2333-423
            (B) LOCATION: 1..23

(ix) FEATURE:
            (A) NAME/KEY: Potential microsequencing oligo 99-2333-423
            (B) LOCATION: complement 25..47

(xi) SEQUENCE DESCRIPTION: SEQ ID NO: 22:

GAGACGCTAT CTATGCAAGG AGGGTGTTCA ACATTTGGAC AGCCACG                47

(2) INFORMATION FOR SEQ ID NO: 23:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2341-485
            (B) LOCATION: 1..47

(ix) FEATURE:
            (A) NAME/KEY: polymorphic base
            (B) LOCATION: 24
            (D) OTHER INFORMATION: base c (ix) FEATURE:
            (A) NAME/KEY: Potential microsequencing oligo 99-2341-485
            (B) LOCATION: 1..23

(ix) FEATURE:
            (A) NAME/KEY: Potential microsequencing oligo 99-2341-485
            (B) LOCATION: complement 25..47

(xi) SEQUENCE DESCRIPTION: SEQ ID NO: 23:

ACACATCTGT CTGTTACCTA CACCTTACAA AGAATCGCAC AGGCTCT                47

(2) INFORMATION FOR SEQ ID NO: 24:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:

(A) ORGANISM: Homo sapiens (ix) FEATURE:
            (A) NAME/KEY: polymorphic fragment 99-2342-217
            (B) LOCATION: 1..47

(ix) FEATURE:
            (A) NAME/KEY: polymorphic base
            (B) LOCATION: 24
            (D) OTHER INFORMATION: base c (ix) FEATURE:
            (A) NAME/KEY: Potential microsequencing oligo 99-2342-217
            (B) LOCATION: 1..23

(ix) FEATURE:
            (A) NAME/KEY: Potential microsequencing oligo 99-2342-217
            (B) LOCATION: complement 25..47

(xi) SEQUENCE DESCRIPTION: SEQ ID NO: 24:

TAGAGCCTTG GACTTTCATG ACACTTCTAG AAACAGCCCA GATTGTG          47

(2) INFORMATION FOR SEQ ID NO: 25:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2362-270
            (B) LOCATION: 1..47

(ix) FEATURE:
            (A) NAME/KEY: polymorphic base
            (B) LOCATION: 24
            (D) OTHER INFORMATION: base a (ix) FEATURE:
            (A) NAME/KEY: Potential microsequencing oligo 99-2362-270
            (B) LOCATION: 1..23

(ix) FEATURE:
            (A) NAME/KEY: Potential microsequencing oligo 99-2362-270
            (B) LOCATION: complement 25..47

(xi) SEQUENCE DESCRIPTION: SEQ ID NO: 25:

TCTCTCTTGG GTGGTTCCTC AACATGTGTG ACCTTGACCA AGTATTG          47

(2) INFORMATION FOR SEQ ID NO: 26:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2364-329
            (B) LOCATION: 1..47

(ix) FEATURE:
            (A) NAME/KEY: polymorphic base
            (B) LOCATION: 24

(D) OTHER INFORMATION: base g (ix) FEATURE:
        (A) NAME/KEY: Potential microsequencing oligo 99-2364-329
        (B) LOCATION: 1..23

(ix) FEATURE:
        (A) NAME/KEY: Potential microsequencing oligo 99-2364-329
        (B) LOCATION: complement 25..47

(xi) SEQUENCE DESCRIPTION: SEQ ID NO: 26:

ATATAAAATG ATGAACCATA TACGTGAGGC AAGGTAACAT ATAATTG                47

(2) INFORMATION FOR SEQ ID NO: 27:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2367-61
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2367-61
        (B) LOCATION: 1..23

(ix) FEATURE:
        (A) NAME/KEY: Potential microsequencing oligo 99-2367-61
        (B) LOCATION: complement 25..47

(xi) SEQUENCE DESCRIPTION: SEQ ID NO: 27:

TAAACATTTC ATTATTTCAG AAAATAAATAT GCATTTTCAC CAACACA              47

(2) INFORMATION FOR SEQ ID NO: 28:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2371-93
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2371-93
        (B) LOCATION: 1..23

(ix) FEATURE:
        (A) NAME/KEY: Potential microsequencing oligo 99-2371-93
        (B) LOCATION: complement 25..47

(xi) SEQUENCE DESCRIPTION: SEQ ID NO: 28:

CTCTAAACTT TCCTAATACT TACATCACTG CCTACTTTTT ACATAAT            47

(2) INFORMATION FOR SEQ ID NO: 29:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2378-200
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2378-200
        (B) LOCATION: 1..23

(ix) FEATURE:
        (A) NAME/KEY: Potential microsequencing oligo 99-2378-200
        (B) LOCATION: complement 25..47

(xi) SEQUENCE DESCRIPTION: SEQ ID NO: 29:

GAGAACTTCC TGTTGAACCT GTTATAGAAC TGTCCTGTCG TCCAAGA            47

(2) INFORMATION FOR SEQ ID NO: 30:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2381-394
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2381-394
        (B) LOCATION: 1..23

(ix) FEATURE:
        (A) NAME/KEY: Potential microsequencing oligo 99-2381-394
        (B) LOCATION: complement 25..47

(xi) SEQUENCE DESCRIPTION: SEQ ID NO: 30:

AGTGGTCTTC AGGTTATTGG TAGAGAAAAG TAGGGGAGCT AAAGGTG            47

(2) INFORMATION FOR SEQ ID NO: 31:

(i) SEQUENCE CHARACTERISTICS:

```
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2413-368
            (B) LOCATION: 1..47

(ix) FEATURE:
            (A) NAME/KEY: polymorphic base
            (B) LOCATION: 24
            (D) OTHER INFORMATION: base a (ix) FEATURE:
            (A) NAME/KEY: Potential microsequencing oligo 99-2413-368
            (B) LOCATION: 1..23

(ix) FEATURE:
            (A) NAME/KEY: Potential microsequencing oligo 99-2413-368
            (B) LOCATION: complement 25..47

(xi) SEQUENCE DESCRIPTION: SEQ ID NO: 31:

ATTTTAAGAG GAAAACTTAA TGGAAGAATT GTACATAATA TTTCATT                          47

(2) INFORMATION FOR SEQ ID NO: 32:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2419-285
            (B) LOCATION: 1..47

(ix) FEATURE:
            (A) NAME/KEY: polymorphic base
            (B) LOCATION: 24
            (D) OTHER INFORMATION: base c (ix) FEATURE:
            (A) NAME/KEY: Potential microsequencing oligo 99-2419-285
            (B) LOCATION: 1..23

(ix) FEATURE:
            (A) NAME/KEY: Potential microsequencing oligo 99-2419-285
            (B) LOCATION: complement 25..47

(xi) SEQUENCE DESCRIPTION: SEQ ID NO: 32:

AAGGGATCAA GCAGTGCCCA CTCCCCACCC TCCAGGGAGC TGTGACT                          47

(2) INFORMATION FOR SEQ ID NO: 33:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens
```

(ix) FEATURE:
        (A) NAME/KEY: polymorphic fragment 99-2559-253
        (B) LOCATION: 1..47

(ix) FEATURE:
        (A) NAME/KEY: polymorphic base
        (B) LOCATION: 24
        (D) OTHER INFORMATION: base g (ix) FEATURE:
        (A) NAME/KEY: Potential microsequencing oligo 99-2559-253
        (B) LOCATION: 1..23

(ix) FEATURE:
        (A) NAME/KEY: Potential microsequencing oligo 99-2559-253
        (B) LOCATION: complement 25..47

(xi) SEQUENCE DESCRIPTION: SEQ ID NO: 33:

CAGGTGTTTT CATGCCCTCT TAGGGTGTGT CACATCATCC ATCTCAA                47

(2) INFORMATION FOR SEQ ID NO: 34:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2566-112
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2566-112
        (B) LOCATION: 1..23

(ix) FEATURE:
        (A) NAME/KEY: Potential microsequencing oligo 99-2566-112
        (B) LOCATION: complement 25..47

(xi) SEQUENCE DESCRIPTION: SEQ ID NO: 34:

GCCTTCACAA CCGCAGAGGC AAGAGAAGGA GCTTGGCCAC CCTGACT                47

(2) INFORMATION FOR SEQ ID NO: 35:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2567-329
        (B) LOCATION: 1..47

(ix) FEATURE:
        (A) NAME/KEY: polymorphic base
        (B) LOCATION: 24
        (D) OTHER INFORMATION: base g (ix) FEATURE:
        (A) NAME/KEY: Potential microsequencing oligo 99-2567-329
        (B) LOCATION: 1..23

(ix) FEATURE:
        (A) NAME/KEY: Potential microsequencing oligo 99-2567-329
        (B) LOCATION: complement 25..47

(xi) SEQUENCE DESCRIPTION: SEQ ID NO: 35:

CACTGTCAGA TATGAAATGA TGCGTGGCTT TCTTTGGGCT ATATTTG                    47

(2) INFORMATION FOR SEQ ID NO: 36:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2570-218
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2570-218
        (B) LOCATION: 1..23

(ix) FEATURE:
        (A) NAME/KEY: Potential microsequencing oligo 99-2570-218
        (B) LOCATION: complement 25..47

(xi) SEQUENCE DESCRIPTION: SEQ ID NO: 36:

GGAAAGTTCC AAATTATGAG AAGCGAGGCC TCTGAAGTGG CTAAGTT                    47

(2) INFORMATION FOR SEQ ID NO: 37:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2571-242
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2571-242
        (B) LOCATION: 1..23

(ix) FEATURE:
        (A) NAME/KEY: Potential microsequencing oligo 99-2571-242
        (B) LOCATION: complement 25..47

-continued (xi) SEQUENCE DESCRIPTION: SEQ ID NO: 37:

ATAATGAATG AGTATTTGAT ATTATATAAT TAAATGTGTC AGCATTT                47

(2) INFORMATION FOR SEQ ID NO: 38:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2610-121
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2610-121
        (B) LOCATION: 1..23

(ix) FEATURE:
        (A) NAME/KEY: Potential microsequencing oligo 99-2610-121
        (B) LOCATION: complement 25..47

(xi) SEQUENCE DESCRIPTION: SEQ ID NO: 38:

ATACCCCTTC CCTAGGTATG GCTATATGCT GCACTTAGAA AATTCTC                47

(2) INFORMATION FOR SEQ ID NO: 39:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2615-83
        (B) LOCATION: 1..47

(ix) FEATURE:
        (A) NAME/KEY: polymorphic base
        (B) LOCATION: 24
        (D) OTHER INFORMATION: base c (ix) FEATURE:
        (A) NAME/KEY: Potential microsequencing oligo 99-2615-83
        (B) LOCATION: 1..23

(ix) FEATURE:
        (A) NAME/KEY: Potential microsequencing oligo 99-2615-83
        (B) LOCATION: complement 25..47

(xi) SEQUENCE DESCRIPTION: SEQ ID NO: 39:

AACAAATCAC AAGTTGGCAA AAGCAGCAAA TTCTCATCTT CTGGGAA                47

(2) INFORMATION FOR SEQ ID NO: 40:

(i) SEQUENCE CHARACTERISTICS:
        (A) LENGTH: 47 base pairs

```
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2620-227
            (B) LOCATION: 1..47

(ix) FEATURE:
            (A) NAME/KEY: polymorphic base
            (B) LOCATION: 24
            (D) OTHER INFORMATION: base a (ix) FEATURE:
            (A) NAME/KEY: Potential microsequencing oligo 99-2620-227
            (B) LOCATION: 1..23

(ix) FEATURE:
            (A) NAME/KEY: Potential microsequencing oligo 99-2620-227
            (B) LOCATION: complement 25..47

(xi) SEQUENCE DESCRIPTION: SEQ ID NO: 40:

TTGACTGGGC TCCTGATGTG TCCAGGGTAT CTTGCTGGCT GTTTTGC                47

(2) INFORMATION FOR SEQ ID NO: 41:

(i) SEQUENCE CHARACTERISTICS:
            (A) LENGTH: 44 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2624-407
            (B) LOCATION: 1..44

(ix) FEATURE:
            (A) NAME/KEY: polymorphic base
            (B) LOCATION: 24
            (D) OTHER INFORMATION: base g (ix) FEATURE:
            (A) NAME/KEY: Potential microsequencing oligo 99-2624-407
            (B) LOCATION: 1..23

(ix) FEATURE:
            (A) NAME/KEY: Potential microsequencing oligo 99-2624-407
            (B) LOCATION: complement 25..44

(xi) SEQUENCE DESCRIPTION: SEQ ID NO: 41:

ATCTGGCCAT AGGCAGAACA TTGGGGAGA GATGGGAAA GAGA                     44

(2) INFORMATION FOR SEQ ID NO: 42:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens
```

(ix) FEATURE:
        (A) NAME/KEY: polymorphic fragment 99-2625-70
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2625-70
        (B) LOCATION: 1..23

(ix) FEATURE:
        (A) NAME/KEY: Potential microsequencing oligo 99-2625-70
        (B) LOCATION: complement 25..47

(xi) SEQUENCE DESCRIPTION: SEQ ID NO: 42:

AGTGACTCAA CCAGAAAGAG AGCAGGAGAG AGGACGAAGA GAGGAGA                47

(2) INFORMATION FOR SEQ ID NO: 43:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2630-67
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-2630-67
        (B) LOCATION: 1..23

(ix) FEATURE:
        (A) NAME/KEY: Potential microsequencing oligo 99-2630-67
        (B) LOCATION: complement 25..47

(xi) SEQUENCE DESCRIPTION: SEQ ID NO: 43:

TAAATTCTGC CTAGAAGATT AAGATTGGTC CAGAACAGGG AGTGTTT                47

(2) INFORMATION FOR SEQ ID NO: 44:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2633-129
        (B) LOCATION: 1..47

(ix) FEATURE:
        (A) NAME/KEY: polymorphic base
        (B) LOCATION: 24
        (D) OTHER INFORMATION: base a (ix) FEATURE:
            (A) NAME/KEY: Potential microsequencing oligo 99-2633-129
            (B) LOCATION: 1..23

(ix) FEATURE:
            (A) NAME/KEY: Potential microsequencing oligo 99-2633-129
            (B) LOCATION: complement 25..47

(xi) SEQUENCE DESCRIPTION: SEQ ID NO: 44:

TAGCTATTTC TTCCCCTAGG CAAAGTAGAC AATGAGAGAA CCCTTGA                47

(2) INFORMATION FOR SEQ ID NO: 45:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2634-341
            (B) LOCATION: 1..47

(ix) FEATURE:
            (A) NAME/KEY: polymorphic base
            (B) LOCATION: 24
            (D) OTHER INFORMATION: base a (ix) FEATURE:
            (A) NAME/KEY: Potential microsequencing oligo 99-2634-341
            (B) LOCATION: 1..23

(ix) FEATURE:
            (A) NAME/KEY: Potential microsequencing oligo 99-2634-341
            (B) LOCATION: complement 25..47

(xi) SEQUENCE DESCRIPTION: SEQ ID NO: 45:

GGAATCAATA TTTATTTATT ATCAACAGGT GAGACATTAT TTATTTA                47

(2) INFORMATION FOR SEQ ID NO: 46:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2637-28
            (B) LOCATION: 1..47

(ix) FEATURE:
            (A) NAME/KEY: polymorphic base
            (B) LOCATION: 24
            (D) OTHER INFORMATION: base a (ix) FEATURE:
            (A) NAME/KEY: Potential microsequencing oligo 99-2637-28
            (B) LOCATION: 1..23

(ix) FEATURE:
            (A) NAME/KEY: Potential microsequencing oligo 99-2637-28
            (B) LOCATION: complement 25..47

(xi) SEQUENCE DESCRIPTION: SEQ ID NO: 46:

CCATCACTTC CTCCTAGTGA AAAATCAAAG GAGGGTGGGT TTTATAG                47

(2) INFORMATION FOR SEQ ID NO: 47:

(i) SEQUENCE CHARACTERISTICS:
       (A) LENGTH: 47 base pairs
       (B) TYPE: NUCLEIC ACID
       (C) STRANDEDNESS: SINGLE
       (D) TOPOLOGY: LINEAR (ii) MOLECULE TYPE: DNA (vi) ORIGINAL SOURCE:
       (A) ORGANISM: Homo sapiens (ix) FEATURE:
       (A) NAME/KEY: polymorphic fragment 99-2642-255
       (B) LOCATION: 1..47

(ix) FEATURE:
       (A) NAME/KEY: polymorphic base
       (B) LOCATION: 24
       (D) OTHER INFORMATION: base a (ix) FEATURE:
       (A) NAME/KEY: Potential microsequencing oligo 99-2642-255
       (B) LOCATION: 1..23

(ix) FEATURE:
       (A) NAME/KEY: Potential microsequencing oligo 99-2642-255
       (B) LOCATION: complement 25..47

(xi) SEQUENCE DESCRIPTION: SEQ ID NO: 47:

TGAGGGTGTT TCCAGAAGAG ACTAGCATTT GAATCTGAAG TGAGTAA              47

(2) INFORMATION FOR SEQ ID NO: 48:

(i) SEQUENCE CHARACTERISTICS:
       (A) LENGTH: 47 base pairs
       (B) TYPE: NUCLEIC ACID
       (C) STRANDEDNESS: SINGLE
       (D) TOPOLOGY: LINEAR (ii) MOLECULE TYPE: DNA (vi) ORIGINAL SOURCE:
       (A) ORGANISM: Homo sapiens (ix) FEATURE:
       (A) NAME/KEY: polymorphic fragment 99-2645-118
       (B) LOCATION: 1..47

(ix) FEATURE:
       (A) NAME/KEY: polymorphic base
       (B) LOCATION: 24
       (D) OTHER INFORMATION: base g (ix) FEATURE:
       (A) NAME/KEY: Potential microsequencing oligo 99-2645-118
       (B) LOCATION: 1..23

(ix) FEATURE:
       (A) NAME/KEY: Potential microsequencing oligo 99-2645-118
       (B) LOCATION: complement 25..47

(xi) SEQUENCE DESCRIPTION: SEQ ID NO: 48:

CACAAATTAA TTGCATTGTT ATAGGCTAGC AATGAAGAAT CTGAAAA              47

(2) INFORMATION FOR SEQ ID NO: 49:

(i) SEQUENCE CHARACTERISTICS:
       (A) LENGTH: 47 base pairs
       (B) TYPE: NUCLEIC ACID (C) STRANDEDNESS: SINGLE
                (D) TOPOLOGY: LINEAR (ii) MOLECULE TYPE: DNA (vi) ORIGINAL SOURCE:
                (A) ORGANISM: Homo sapiens (ix) FEATURE:
                (A) NAME/KEY: polymorphic fragment 99-2647-368
                (B) LOCATION: 1..47

(ix) FEATURE:
                (A) NAME/KEY: polymorphic base
                (B) LOCATION: 24
                (D) OTHER INFORMATION: base a (ix) FEATURE:
                (A) NAME/KEY: Potential microsequencing oligo 99-2647-368
                (B) LOCATION: 1..23

(ix) FEATURE:
                (A) NAME/KEY: Potential microsequencing oligo 99-2647-368
                (B) LOCATION: complement 25..47

(xi) SEQUENCE DESCRIPTION: SEQ ID NO: 49:

TTAAGGCCTT CAACTGATTA GACAAGGCCC ACTCACATTA TCTGACA                    47

(2) INFORMATION FOR SEQ ID NO: 50:

(i) SEQUENCE CHARACTERISTICS:
                (A) LENGTH: 47 base pairs
                (B) TYPE: NUCLEIC ACID
                (C) STRANDEDNESS: SINGLE
                (D) TOPOLOGY: LINEAR (ii) MOLECULE TYPE: DNA (vi) ORIGINAL SOURCE:
                (A) ORGANISM: Homo sapiens (ix) FEATURE:
                (A) NAME/KEY: polymorphic fragment 99-2649-107
                (B) LOCATION: 1..47

(ix) FEATURE:
                (A) NAME/KEY: polymorphic base
                (B) LOCATION: 24
                (D) OTHER INFORMATION: base a (ix) FEATURE:
                (A) NAME/KEY: Potential microsequencing oligo 99-2649-107
                (B) LOCATION: 1..23

(ix) FEATURE:
                (A) NAME/KEY: Potential microsequencing oligo 99-2649-107
                (B) LOCATION: complement 25..47

(xi) SEQUENCE DESCRIPTION: SEQ ID NO: 50:

CACAACTCTG GAGCCTTTTA TGAACAGGAC AGCAATGCAC TGAAACT                    47

(2) INFORMATION FOR SEQ ID NO: 51:

(i) SEQUENCE CHARACTERISTICS:
                (A) LENGTH: 47 base pairs
                (B) TYPE: NUCLEIC ACID
                (C) STRANDEDNESS: SINGLE
                (D) TOPOLOGY: LINEAR (ii) MOLECULE TYPE: DNA (vi) ORIGINAL SOURCE:
                (A) ORGANISM: Homo sapiens (ix) FEATURE:

```
        (A) NAME/KEY: polymorphic fragment 99-2103-270
        (B) LOCATION: 1..47
        (D) OTHER INFORMATION: variant version of SEQ ID1

(ix) FEATURE:
        (A) NAME/KEY: polymorphic base
        (B) LOCATION: 24
        (D) OTHER INFORMATION: base c; g in SEQ ID1

(ix) FEATURE:
        (A) NAME/KEY: Potential microsequencing oligo 99-2103-270
        (B) LOCATION: 1..23

(ix) FEATURE:
        (A) NAME/KEY: Potential microsequencing oligo 99-2103-270
        (B) LOCATION: complement 25..47

(xi) SEQUENCE DESCRIPTION: SEQ ID NO: 51:

CTTGGATTCA TATGAGACAG CTACCAGACC TTCAATTTTT CTACACT                      47

(2) INFORMATION FOR SEQ ID NO: 52:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2228-301
        (B) LOCATION: 1..47
        (D) OTHER INFORMATION: variant version of SEQ ID2

(ix) FEATURE:
        (A) NAME/KEY: polymorphic base
        (B) LOCATION: 24
        (D) OTHER INFORMATION: base g; a in SEQ ID2

(ix) FEATURE:
        (A) NAME/KEY: Potential microsequencing oligo 99-2228-301
        (B) LOCATION: 1..23

(ix) FEATURE:
        (A) NAME/KEY: Potential microsequencing oligo 99-2228-301
        (B) LOCATION: complement 25..47

(xi) SEQUENCE DESCRIPTION: SEQ ID NO: 52:

CCCTGCTTAT CCCTGTAAGG TGGGGACCCA TATGGGCAAG GCCAGAC                      47

(2) INFORMATION FOR SEQ ID NO: 53:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2229-240
        (B) LOCATION: 1..47
        (D) OTHER INFORMATION: variant version of SEQ ID3

(ix) FEATURE:
        (A) NAME/KEY: polymorphic base
        (B) LOCATION: 24
```

(D) OTHER INFORMATION: base t; g in SEQ ID3

(ix) FEATURE:
        (A) NAME/KEY: Potential microsequencing oligo 99-2229-240
        (B) LOCATION: 1..23

(ix) FEATURE:
        (A) NAME/KEY: Potential microsequencing oligo 99-2229-240
        (B) LOCATION: complement 25..47

(xi) SEQUENCE DESCRIPTION: SEQ ID NO: 53:

TCGTCATCGT GGCCTGGGCT ACATACTACC TGTTCCAGTC CTTCCAG                    47

(2) INFORMATION FOR SEQ ID NO: 54:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2240-281
        (B) LOCATION: 1..47
        (D) OTHER INFORMATION: variant version of SEQ ID4

(ix) FEATURE:
        (A) NAME/KEY: polymorphic base
        (B) LOCATION: 24
        (D) OTHER INFORMATION: base t; c in SEQ ID4

(ix) FEATURE:
        (A) NAME/KEY: Potential microsequencing oligo 99-2240-281
        (B) LOCATION: 1..23

(ix) FEATURE:
        (A) NAME/KEY: Potential microsequencing oligo 99-2240-281
        (B) LOCATION: complement 25..47

(xi) SEQUENCE DESCRIPTION: SEQ ID NO: 54:

GCAATCTTAA TAACTTTTTA TTTTAGTAAT TCGAATCTTT TTTTTCT                    47

(2) INFORMATION FOR SEQ ID NO: 55:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2242-206
        (B) LOCATION: 1..47
        (D) OTHER INFORMATION: variant version of SEQ ID5

(ix) FEATURE:
        (A) NAME/KEY: polymorphic base
        (B) LOCATION: 24
        (D) OTHER INFORMATION: base t; c in SEQ ID5

(ix) FEATURE:
        (A) NAME/KEY: Potential microsequencing oligo 99-2242-206
        (B) LOCATION: 1..23

(ix) FEATURE:

(A) NAME/KEY: Potential microsequencing oligo 99-2242-206
            (B) LOCATION: complement 25..47

(xi) SEQUENCE DESCRIPTION: SEQ ID NO: 55:

GTGTTTTCTT TTAGTCAAAT TATTTTATAT TTTACTTTTT TCTTAAG                47

(2) INFORMATION FOR SEQ ID NO: 56:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2244-83
        (B) LOCATION: 1..47
        (D) OTHER INFORMATION: variant version of SEQ ID6

(ix) FEATURE:
        (A) NAME/KEY: polymorphic base
        (B) LOCATION: 24
        (D) OTHER INFORMATION: base g; a in SEQ ID6

(ix) FEATURE:
        (A) NAME/KEY: Potential microsequencing oligo 99-2244-83
        (B) LOCATION: 1..23

(ix) FEATURE:
        (A) NAME/KEY: Potential microsequencing oligo 99-2244-83
        (B) LOCATION: complement 25..47

(xi) SEQUENCE DESCRIPTION: SEQ ID NO: 56:

TAATTGTAGA TACTAAGACC ATTGTGCTTA AACCATGTAG GTACTGA              47

(2) INFORMATION FOR SEQ ID NO: 57:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2246-340
        (B) LOCATION: 1..47
        (D) OTHER INFORMATION: variant version of SEQ ID7

(ix) FEATURE:
        (A) NAME/KEY: polymorphic base
        (B) LOCATION: 24
        (D) OTHER INFORMATION: base g; a in SEQ ID7

(ix) FEATURE:
        (A) NAME/KEY: Potential microsequencing oligo 99-2246-340
        (B) LOCATION: 1..23

(ix) FEATURE:
        (A) NAME/KEY: Potential microsequencing oligo 99-2246-340
        (B) LOCATION: complement 25..47

(xi) SEQUENCE DESCRIPTION: SEQ ID NO: 57:

ATTTATATGT TAAATGCAGA GAAGAAGAAA AATAAGTTTT GCAGTAA              47

(2) INFORMATION FOR SEQ ID NO: 58:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2248-76
        (B) LOCATION: 1..47
        (D) OTHER INFORMATION: variant version of SEQ ID8

(ix) FEATURE:
        (A) NAME/KEY: polymorphic base
        (B) LOCATION: 24
        (D) OTHER INFORMATION: base t; c in SEQ ID8

(ix) FEATURE:
        (A) NAME/KEY: Potential microsequencing oligo 99-2248-76
        (B) LOCATION: 1..23

(ix) FEATURE:
        (A) NAME/KEY: Potential microsequencing oligo 99-2248-76
        (B) LOCATION: complement 25..47

(xi) SEQUENCE DESCRIPTION: SEQ ID NO: 58:

```
GACAGAGAGG GAAGGTAATC TTCTCCTGAA GTCTGCCCAT CCCCTGG            47
```

(2) INFORMATION FOR SEQ ID NO: 59:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2250-236
        (B) LOCATION: 1..47
        (D) OTHER INFORMATION: variant version of SEQ ID9

(ix) FEATURE:
        (A) NAME/KEY: polymorphic base
        (B) LOCATION: 24
        (D) OTHER INFORMATION: base t; c in SEQ ID9

(ix) FEATURE:
        (A) NAME/KEY: Potential microsequencing oligo 99-2250-236
        (B) LOCATION: 1..23

(ix) FEATURE:
        (A) NAME/KEY: Potential microsequencing oligo 99-2250-236
        (B) LOCATION: complement 25..47

(xi) SEQUENCE DESCRIPTION: SEQ ID NO: 59:

```
ATGTATCCAA AACAGAATTA ACATACTTTG GGTTTTTTAT TTTTATT            47
```

(2) INFORMATION FOR SEQ ID NO: 60:

(i) SEQUENCE CHARACTERISTICS:
        (A) LENGTH: 47 base pairs
        (B) TYPE: NUCLEIC ACID
        (C) STRANDEDNESS: SINGLE

```
          (D) TOPOLOGY: LINEAR (ii) MOLECULE TYPE: DNA (vi) ORIGINAL SOURCE:
          (A) ORGANISM: Homo sapiens (ix) FEATURE:
          (A) NAME/KEY: polymorphic fragment 99-2251-151
          (B) LOCATION: 1..47
          (D) OTHER INFORMATION: variant version of SEQ ID10

(ix) FEATURE:
          (A) NAME/KEY: polymorphic base
          (B) LOCATION: 24
          (D) OTHER INFORMATION: base g; a in SEQ ID10

(ix) FEATURE:
          (A) NAME/KEY: Potential microsequencing oligo 99-2251-151
          (B) LOCATION: 1..23

(ix) FEATURE:
          (A) NAME/KEY: Potential microsequencing oligo 99-2251-151
          (B) LOCATION: complement 25..47

(xi) SEQUENCE DESCRIPTION: SEQ ID NO: 60:

TGAAAAGAAG TTCAGACGAT TGCGGATAGA CTAGTTTGGC TGTTGTG                47

(2) INFORMATION FOR SEQ ID NO: 61:

(i) SEQUENCE CHARACTERISTICS:
          (A) LENGTH: 47 base pairs
          (B) TYPE: NUCLEIC ACID
          (C) STRANDEDNESS: SINGLE
          (D) TOPOLOGY: LINEAR (ii) MOLECULE TYPE: DNA (vi) ORIGINAL SOURCE:
          (A) ORGANISM: Homo sapiens (ix) FEATURE:
          (A) NAME/KEY: polymorphic fragment 99-2269-179
          (B) LOCATION: 1..47
          (D) OTHER INFORMATION: variant version of SEQ ID11

(ix) FEATURE:
          (A) NAME/KEY: polymorphic base
          (B) LOCATION: 24
          (D) OTHER INFORMATION: base g; a in SEQ ID11

(ix) FEATURE:
          (A) NAME/KEY: Potential microsequencing oligo 99-2269-179
          (B) LOCATION: 1..23

(ix) FEATURE:
          (A) NAME/KEY: Potential microsequencing oligo 99-2269-179
          (B) LOCATION: complement 25..47

(xi) SEQUENCE DESCRIPTION: SEQ ID NO: 61:

AAAATAAAGA AATTCCTAGA GACGTACAGC CTATCAAGAT CAAACCA                47

(2) INFORMATION FOR SEQ ID NO: 62:

(i) SEQUENCE CHARACTERISTICS:
          (A) LENGTH: 47 base pairs
          (B) TYPE: NUCLEIC ACID
          (C) STRANDEDNESS: SINGLE
          (D) TOPOLOGY: LINEAR (ii) MOLECULE TYPE: DNA (vi) ORIGINAL SOURCE:
          (A) ORGANISM: Homo sapiens
```

(ix) FEATURE:
        (A) NAME/KEY: polymorphic fragment 99-2271-403
        (B) LOCATION: 1..47
        (D) OTHER INFORMATION: variant version of SEQ ID12

(ix) FEATURE:
        (A) NAME/KEY: polymorphic base
        (B) LOCATION: 24
        (D) OTHER INFORMATION: base g; a in SEQ ID12

(ix) FEATURE:
        (A) NAME/KEY: Potential microsequencing oligo 99-2271-403
        (B) LOCATION: 1..23

(ix) FEATURE:
        (A) NAME/KEY: Potential microsequencing oligo 99-2271-403
        (B) LOCATION: complement 25..47

(xi) SEQUENCE DESCRIPTION: SEQ ID NO: 62:

AGGCATTTAT TTCATATTTA TTAGCCTTGA TTTTCTTATC TTCAAGT                     47

(2) INFORMATION FOR SEQ ID NO: 63:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2272-409
        (B) LOCATION: 1..47
        (D) OTHER INFORMATION: variant version of SEQ ID13

(ix) FEATURE:
        (A) NAME/KEY: polymorphic base
        (B) LOCATION: 24
        (D) OTHER INFORMATION: base t; g in SEQ ID13

(ix) FEATURE:
        (A) NAME/KEY: Potential microsequencing oligo 99-2272-409
        (B) LOCATION: 1..23

(ix) FEATURE:
        (A) NAME/KEY: Potential microsequencing oligo 99-2272-409
        (B) LOCATION: complement 25..47

(xi) SEQUENCE DESCRIPTION: SEQ ID NO: 63:

AAAAGCACTG CAATTATTTT GGATACTGTG AAATATTGCA AGTTTTA                     47

(2) INFORMATION FOR SEQ ID NO: 64:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2273-528
        (B) LOCATION: 1..47
        (D) OTHER INFORMATION: variant version of SEQ ID14

(ix) FEATURE:
        (A) NAME/KEY: polymorphic base (B) LOCATION: 24
            (D) OTHER INFORMATION: base t; c in SEQ ID14

(ix) FEATURE:
            (A) NAME/KEY: Potential microsequencing oligo 99-2273-528
            (B) LOCATION: 1..23

(ix) FEATURE:
            (A) NAME/KEY: Potential microsequencing oligo 99-2273-528
            (B) LOCATION: complement 25..47

(xi) SEQUENCE DESCRIPTION: SEQ ID NO: 64:

ACTTGAAGAT AAGAAAATCA AGGTTAATAA ATATGAAATA AATGCCT                47

(2) INFORMATION FOR SEQ ID NO: 65:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2275-466
            (B) LOCATION: 1..47
            (D) OTHER INFORMATION: variant version of SEQ ID15

(ix) FEATURE:
            (A) NAME/KEY: polymorphic base
            (B) LOCATION: 24
            (D) OTHER INFORMATION: base t; c in SEQ ID15

(ix) FEATURE:
            (A) NAME/KEY: Potential microsequencing oligo 99-2275-466
            (B) LOCATION: 1..23

(ix) FEATURE:
            (A) NAME/KEY: Potential microsequencing oligo 99-2275-466
            (B) LOCATION: complement 25..47

(xi) SEQUENCE DESCRIPTION: SEQ ID NO: 65:

TTGATGATAG CATTAAATAC TCCTAAAAAC TGTGAATAGG GATACTA                47

(2) INFORMATION FOR SEQ ID NO: 66:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2278-276
            (B) LOCATION: 1..47
            (D) OTHER INFORMATION: variant version of SEQ ID16

(ix) FEATURE:
            (A) NAME/KEY: polymorphic base
            (B) LOCATION: 24
            (D) OTHER INFORMATION: base g; a in SEQ ID16

(ix) FEATURE:
            (A) NAME/KEY: Potential microsequencing oligo 99-2278-276
            (B) LOCATION: 1..23

```
    (ix) FEATURE:
         (A) NAME/KEY: Potential microsequencing oligo 99-2278-276
         (B) LOCATION: complement 25..47

(xi) SEQUENCE DESCRIPTION: SEQ ID NO: 66:

GAAAAAAATG GGAACATCTT CACGGCCTGT GCATCTCCAA CAAGATT                           47

(2) INFORMATION FOR SEQ ID NO: 67:

(i) SEQUENCE CHARACTERISTICS:
         (A) LENGTH: 47 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2312-358
         (B) LOCATION: 1..47
         (D) OTHER INFORMATION: variant version of SEQ ID17

(ix) FEATURE:
         (A) NAME/KEY: polymorphic base
         (B) LOCATION: 24
         (D) OTHER INFORMATION: base t; c in SEQ ID17

(ix) FEATURE:
         (A) NAME/KEY: Potential microsequencing oligo 99-2312-358
         (B) LOCATION: 1..23

(ix) FEATURE:
         (A) NAME/KEY: Potential microsequencing oligo 99-2312-358
         (B) LOCATION: complement 25..47

(xi) SEQUENCE DESCRIPTION: SEQ ID NO: 67:

TTGAAGAGAG AGATGGAAAA AAATGTAGGC CTTCTGGGTA AATGGCC                            47

(2) INFORMATION FOR SEQ ID NO: 68:

(i) SEQUENCE CHARACTERISTICS:
         (A) LENGTH: 47 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2315-213
         (B) LOCATION: 1..47
         (D) OTHER INFORMATION: variant version of SEQ ID18

(ix) FEATURE:
         (A) NAME/KEY: polymorphic base
         (B) LOCATION: 24
         (D) OTHER INFORMATION: base g; a in SEQ ID18

(ix) FEATURE:
         (A) NAME/KEY: Potential microsequencing oligo 99-2315-213
         (B) LOCATION: 1..23

(ix) FEATURE:
         (A) NAME/KEY: Potential microsequencing oligo 99-2315-213
         (B) LOCATION: complement 25..47

(xi) SEQUENCE DESCRIPTION: SEQ ID NO: 68:

AGATGGATTC TACCCACAGG CAAGAGAAAA CCTTATTTTA AAAATAA                            47
```

(2) INFORMATION FOR SEQ ID NO: 69:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2320-292
        (B) LOCATION: 1..47
        (D) OTHER INFORMATION: variant version of SEQ ID19

(ix) FEATURE:
        (A) NAME/KEY: polymorphic base
        (B) LOCATION: 24
        (D) OTHER INFORMATION: base t; c in SEQ ID19

(ix) FEATURE:
        (A) NAME/KEY: Potential microsequencing oligo 99-2320-292
        (B) LOCATION: 1..23

(ix) FEATURE:
        (A) NAME/KEY: Potential microsequencing oligo 99-2320-292
        (B) LOCATION: complement 25..47

(xi) SEQUENCE DESCRIPTION: SEQ ID NO: 69:

ACTCTCATTC ACTAAACTTC AACTGTTTTT ATAAATTTAA TGAATTT          47

(2) INFORMATION FOR SEQ ID NO: 70:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2321-82
        (B) LOCATION: 1..47
        (D) OTHER INFORMATION: variant version of SEQ ID20

(ix) FEATURE:
        (A) NAME/KEY: polymorphic base
        (B) LOCATION: 24
        (D) OTHER INFORMATION: base t; c in SEQ ID20

(ix) FEATURE:
        (A) NAME/KEY: Potential microsequencing oligo 99-2321-82
        (B) LOCATION: 1..23

(ix) FEATURE:
        (A) NAME/KEY: Potential microsequencing oligo 99-2321-82
        (B) LOCATION: complement 25..47

(xi) SEQUENCE DESCRIPTION: SEQ ID NO: 70:

TAAAGCTTAC TGAGTGTCCA CTCTGGATAC CTACTCAAAT ATTTCCT          47

(2) INFORMATION FOR SEQ ID NO: 71:

(i) SEQUENCE CHARACTERISTICS:
        (A) LENGTH: 47 base pairs
        (B) TYPE: NUCLEIC ACID

```
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2324-338
            (B) LOCATION: 1..47
            (D) OTHER INFORMATION: variant version of SEQ ID21

(ix) FEATURE:
            (A) NAME/KEY: polymorphic base
            (B) LOCATION: 24
            (D) OTHER INFORMATION: base c; a in SEQ ID21

(ix) FEATURE:
            (A) NAME/KEY: Potential microsequencing oligo 99-2324-338
            (B) LOCATION: 1..23

(ix) FEATURE:
            (A) NAME/KEY: Potential microsequencing oligo 99-2324-338
            (B) LOCATION: complement 25..47

(xi) SEQUENCE DESCRIPTION: SEQ ID NO: 71:

AGATAGAAGA CAAAATCGCA GGACAAGAAA TCCCTCAACA GTAAAAA                      47

(2) INFORMATION FOR SEQ ID NO: 72:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2333-423
            (B) LOCATION: 1..47
            (D) OTHER INFORMATION: variant version of SEQ ID22

(ix) FEATURE:
            (A) NAME/KEY: polymorphic base
            (B) LOCATION: 24
            (D) OTHER INFORMATION: base t; g in SEQ ID22

(ix) FEATURE:
            (A) NAME/KEY: Potential microsequencing oligo 99-2333-423
            (B) LOCATION: 1..23

(ix) FEATURE:
            (A) NAME/KEY: Potential microsequencing oligo 99-2333-423
            (B) LOCATION: complement 25..47

(xi) SEQUENCE DESCRIPTION: SEQ ID NO: 72:

GAGACGCTAT CTATGCAAGG AGGTTGTTCA ACATTTGGAC AGCCACG                      47

(2) INFORMATION FOR SEQ ID NO: 73:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens
```

```
    (ix) FEATURE:
         (A) NAME/KEY: polymorphic fragment 99-2341-485
         (B) LOCATION: 1..47
         (D) OTHER INFORMATION: variant version of SEQ ID23

(ix) FEATURE:
         (A) NAME/KEY: polymorphic base
         (B) LOCATION: 24
         (D) OTHER INFORMATION: base t; c in SEQ ID23

(ix) FEATURE:
         (A) NAME/KEY: Potential microsequencing oligo 99-2341-485
         (B) LOCATION: 1..23

(ix) FEATURE:
         (A) NAME/KEY: Potential microsequencing oligo 99-2341-485
         (B) LOCATION: complement 25..47

(xi) SEQUENCE DESCRIPTION: SEQ ID NO: 73:

ACACATCTGT CTGTTACCTA CACTTTACAA AGAATCGCAC AGGCTCT                47

(2) INFORMATION FOR SEQ ID NO: 74:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2342-217
         (B) LOCATION: 1..47
         (D) OTHER INFORMATION: variant version of SEQ ID24

(ix) FEATURE:
         (A) NAME/KEY: polymorphic base
         (B) LOCATION: 24
         (D) OTHER INFORMATION: base t; c in SEQ ID24

(ix) FEATURE:
         (A) NAME/KEY: Potential microsequencing oligo 99-2342-217
         (B) LOCATION: 1..23

(ix) FEATURE:
         (A) NAME/KEY: Potential microsequencing oligo 99-2342-217
         (B) LOCATION: complement 25..47

(xi) SEQUENCE DESCRIPTION: SEQ ID NO: 74:

TAGAGCCTTG GACTTTCATG ACATTTCTAG AAACAGCCCA GATTGTG                47

(2) INFORMATION FOR SEQ ID NO: 75:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: polymorphic fragment 99-2362-270
         (B) LOCATION: 1..47
         (D) OTHER INFORMATION: variant version of SEQ ID25

(ix) FEATURE:
```

(A) NAME/KEY: polymorphic base
        (B) LOCATION: 24
        (D) OTHER INFORMATION: base g; a in SEQ ID25

(ix) FEATURE:
        (A) NAME/KEY: Potential microsequencing oligo 99-2362-270
        (B) LOCATION: 1..23

(ix) FEATURE:
        (A) NAME/KEY: Potential microsequencing oligo 99-2362-270
        (B) LOCATION: complement 25..47

(xi) SEQUENCE DESCRIPTION: SEQ ID NO: 75:

TCTCTCTTGG GTGGTTCCTC AACGTGTGTG ACCTTGACCA AGTATTG                47

(2) INFORMATION FOR SEQ ID NO: 76:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2364-329
        (B) LOCATION: 1..47
        (D) OTHER INFORMATION: variant version of SEQ ID26

(ix) FEATURE:
        (A) NAME/KEY: polymorphic base
        (B) LOCATION: 24
        (D) OTHER INFORMATION: base c; g in SEQ ID26

(ix) FEATURE:
        (A) NAME/KEY: Potential microsequencing oligo 99-2364-329
        (B) LOCATION: 1..23

(ix) FEATURE:
        (A) NAME/KEY: Potential microsequencing oligo 99-2364-329
        (B) LOCATION: complement 25..47

(xi) SEQUENCE DESCRIPTION: SEQ ID NO: 76:

ATATAAAATG ATGAACCATA TACCTGAGGC AAGGTAACAT ATAATTG                47

(2) INFORMATION FOR SEQ ID NO: 77:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2367-61
        (B) LOCATION: 1..47
        (D) OTHER INFORMATION: variant version of SEQ ID27

(ix) FEATURE:
        (A) NAME/KEY: polymorphic base
        (B) LOCATION: 24
        (D) OTHER INFORMATION: base g; a in SEQ ID27

(ix) FEATURE:
        (A) NAME/KEY: Potential microsequencing oligo 99-2367-61
        (B) LOCATION: 1..23

(ix) FEATURE:
              (A) NAME/KEY: Potential microsequencing oligo 99-2367-61
              (B) LOCATION: complement 25..47

(xi) SEQUENCE DESCRIPTION: SEQ ID NO: 77:

TAAACATTTC ATTATTTCAG AAAGTAATAT GCATTTTCAC CAACACA                                47

(2) INFORMATION FOR SEQ ID NO: 78:

(i) SEQUENCE CHARACTERISTICS:
              (A) LENGTH: 47 base pairs
              (B) TYPE: NUCLEIC ACID
              (C) STRANDEDNESS: SINGLE
              (D) TOPOLOGY: LINEAR (ii) MOLECULE TYPE: DNA (vi) ORIGINAL SOURCE:
              (A) ORGANISM: Homo sapiens (ix) FEATURE:
              (A) NAME/KEY: polymorphic fragment 99-2371-93
              (B) LOCATION: 1..47
              (D) OTHER INFORMATION: variant version of SEQ ID28

(ix) FEATURE:
              (A) NAME/KEY: polymorphic base
              (B) LOCATION: 24
              (D) OTHER INFORMATION: base c; a in SEQ ID28

(ix) FEATURE:
              (A) NAME/KEY: Potential microsequencing oligo 99-2371-93
              (B) LOCATION: 1..23

(ix) FEATURE:
              (A) NAME/KEY: Potential microsequencing oligo 99-2371-93
              (B) LOCATION: complement 25..47

(xi) SEQUENCE DESCRIPTION: SEQ ID NO: 78:

CTCTAAACTT TCCTAATACT TACCTCACTG CCTACTTTTT ACATAAT                                47

(2) INFORMATION FOR SEQ ID NO: 79:

(i) SEQUENCE CHARACTERISTICS:
              (A) LENGTH: 47 base pairs
              (B) TYPE: NUCLEIC ACID
              (C) STRANDEDNESS: SINGLE
              (D) TOPOLOGY: LINEAR (ii) MOLECULE TYPE: DNA (vi) ORIGINAL SOURCE:
              (A) ORGANISM: Homo sapiens (ix) FEATURE:
              (A) NAME/KEY: polymorphic fragment 99-2378-200
              (B) LOCATION: 1..47
              (D) OTHER INFORMATION: variant version of SEQ ID29

(ix) FEATURE:
              (A) NAME/KEY: polymorphic base
              (B) LOCATION: 24
              (D) OTHER INFORMATION: base g; a in SEQ ID29

(ix) FEATURE:
              (A) NAME/KEY: Potential microsequencing oligo 99-2378-200
              (B) LOCATION: 1..23

(ix) FEATURE:
              (A) NAME/KEY: Potential microsequencing oligo 99-2378-200
              (B) LOCATION: complement 25..47

(xi) SEQUENCE DESCRIPTION: SEQ ID NO: 79:

```
GAGAACTTCC TGTTGAACCT GTTGTAGAAC TGTCCTGTCG TCCAAGA                           47
```

(2) INFORMATION FOR SEQ ID NO: 80:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2381-394
        (B) LOCATION: 1..47
        (D) OTHER INFORMATION: variant version of SEQ ID30

(ix) FEATURE:
        (A) NAME/KEY: polymorphic base
        (B) LOCATION: 24
        (D) OTHER INFORMATION: base g; a in SEQ ID30

(ix) FEATURE:
        (A) NAME/KEY: Potential microsequencing oligo 99-2381-394
        (B) LOCATION: 1..23

(ix) FEATURE:
        (A) NAME/KEY: Potential microsequencing oligo 99-2381-394
        (B) LOCATION: complement 25..47

(xi) SEQUENCE DESCRIPTION: SEQ ID NO: 80:

```
AGTGGTCTTC AGGTTATTGG TAGGGAAAAG TAGGGGAGCT AAAGGTG                           47
```

(2) INFORMATION FOR SEQ ID NO: 81:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2413-368
        (B) LOCATION: 1..47
        (D) OTHER INFORMATION: variant version of SEQ ID31

(ix) FEATURE:
        (A) NAME/KEY: polymorphic base
        (B) LOCATION: 24
        (D) OTHER INFORMATION: base g; a in SEQ ID31

(ix) FEATURE:
        (A) NAME/KEY: Potential microsequencing oligo 99-2413-368
        (B) LOCATION: 1..23

(ix) FEATURE:
        (A) NAME/KEY: Potential microsequencing oligo 99-2413-368
        (B) LOCATION: complement 25..47

(xi) SEQUENCE DESCRIPTION: SEQ ID NO: 81:

```
ATTTTAAGAG GAAAACTTAA TGGGAGAATT GTACATAATA TTTCATT                           47
```

(2) INFORMATION FOR SEQ ID NO: 82:

(i) SEQUENCE CHARACTERISTICS:
        (A) LENGTH: 47 base pairs (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2419-285
            (B) LOCATION: 1..47
            (D) OTHER INFORMATION: variant version of SEQ ID32

(ix) FEATURE:
            (A) NAME/KEY: polymorphic base
            (B) LOCATION: 24
            (D) OTHER INFORMATION: base t; c in SEQ ID32

(ix) FEATURE:
            (A) NAME/KEY: Potential microsequencing oligo 99-2419-285
            (B) LOCATION: 1..23

(ix) FEATURE:
            (A) NAME/KEY: Potential microsequencing oligo 99-2419-285
            (B) LOCATION: complement 25..47

(xi) SEQUENCE DESCRIPTION: SEQ ID NO: 82:

AAGGGATCAA GCAGTGCCCA CTCTCCACCC TCCAGGGAGC TGTGACT                    47

(2) INFORMATION FOR SEQ ID NO: 83:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2559-253
            (B) LOCATION: 1..47
            (D) OTHER INFORMATION: variant version of SEQ ID33

(ix) FEATURE:
            (A) NAME/KEY: polymorphic base
            (B) LOCATION: 24
            (D) OTHER INFORMATION: base t; g in SEQ ID33

(ix) FEATURE:
            (A) NAME/KEY: Potential microsequencing oligo 99-2559-253
            (B) LOCATION: 1..23

(ix) FEATURE:
            (A) NAME/KEY: Potential microsequencing oligo 99-2559-253
            (B) LOCATION: complement 25..47

(xi) SEQUENCE DESCRIPTION: SEQ ID NO: 83:

CAGGTGTTTT CATGCCCTCT TAGTGTGTGT CACATCATCC ATCTCAA                    47

(2) INFORMATION FOR SEQ ID NO: 84:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:

(A) ORGANISM: Homo sapiens (ix) FEATURE:
    (A) NAME/KEY: polymorphic fragment 99-2566-112
    (B) LOCATION: 1..47
    (D) OTHER INFORMATION: variant version of SEQ ID34

(ix) FEATURE:
    (A) NAME/KEY: polymorphic base
    (B) LOCATION: 24
    (D) OTHER INFORMATION: base g; a in SEQ ID34

(ix) FEATURE:
    (A) NAME/KEY: Potential microsequencing oligo 99-2566-112
    (B) LOCATION: 1..23

(ix) FEATURE:
    (A) NAME/KEY: Potential microsequencing oligo 99-2566-112
    (B) LOCATION: complement 25..47

(xi) SEQUENCE DESCRIPTION: SEQ ID NO: 84:

GCCTTCACAA CCGCAGAGGC AAGGGAAGGA GCTTGGCCAC CCTGACT         47

(2) INFORMATION FOR SEQ ID NO: 85:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2567-329
        (B) LOCATION: 1..47
        (D) OTHER INFORMATION: variant version of SEQ ID35

(ix) FEATURE:
        (A) NAME/KEY: polymorphic base
        (B) LOCATION: 24
        (D) OTHER INFORMATION: base t; g in SEQ ID35

(ix) FEATURE:
        (A) NAME/KEY: Potential microsequencing oligo 99-2567-329
        (B) LOCATION: 1..23

(ix) FEATURE:
        (A) NAME/KEY: Potential microsequencing oligo 99-2567-329
        (B) LOCATION: complement 25..47

(xi) SEQUENCE DESCRIPTION: SEQ ID NO: 85:

CACTGTCAGA TATGAAATGA TGCTTGGCTT TCTTTGGGCT ATATTTG         47

(2) INFORMATION FOR SEQ ID NO: 86:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2570-218
        (B) LOCATION: 1..47
        (D) OTHER INFORMATION: variant version of SEQ ID36

```
        (ix) FEATURE:
              (A) NAME/KEY: polymorphic base
              (B) LOCATION: 24
              (D) OTHER INFORMATION: base t; c in SEQ ID36

(ix) FEATURE:
              (A) NAME/KEY: Potential microsequencing oligo 99-2570-218
              (B) LOCATION: 1..23

(ix) FEATURE:
              (A) NAME/KEY: Potential microsequencing oligo 99-2570-218
              (B) LOCATION: complement 25..47

(xi) SEQUENCE DESCRIPTION: SEQ ID NO: 86:

GGAAAGTTCC AAATTATGAG AAGTGAGGCC TCTGAAGTGG CTAAGTT                47

(2) INFORMATION FOR SEQ ID NO: 87:

(i) SEQUENCE CHARACTERISTICS:
              (A) LENGTH: 47 base pairs
              (B) TYPE: NUCLEIC ACID
              (C) STRANDEDNESS: SINGLE
              (D) TOPOLOGY: LINEAR (ii) MOLECULE TYPE: DNA (vi) ORIGINAL SOURCE:
              (A) ORGANISM: Homo sapiens (ix) FEATURE:
              (A) NAME/KEY: polymorphic fragment 99-2571-242
              (B) LOCATION: 1..47
              (D) OTHER INFORMATION: variant version of SEQ ID37

(ix) FEATURE:
              (A) NAME/KEY: polymorphic base
              (B) LOCATION: 24
              (D) OTHER INFORMATION: base g; a in SEQ ID37

(ix) FEATURE:
              (A) NAME/KEY: Potential microsequencing oligo 99-2571-242
              (B) LOCATION: 1..23

(ix) FEATURE:
              (A) NAME/KEY: Potential microsequencing oligo 99-2571-242
              (B) LOCATION: complement 25..47

(xi) SEQUENCE DESCRIPTION: SEQ ID NO: 87:

ATAATGAATG AGTATTTGAT ATTGTATAAT TAAATGTGTC AGCATTT                47

(2) INFORMATION FOR SEQ ID NO: 88:

(i) SEQUENCE CHARACTERISTICS:
              (A) LENGTH: 47 base pairs
              (B) TYPE: NUCLEIC ACID
              (C) STRANDEDNESS: SINGLE
              (D) TOPOLOGY: LINEAR (ii) MOLECULE TYPE: DNA (vi) ORIGINAL SOURCE:
              (A) ORGANISM: Homo sapiens (ix) FEATURE:
              (A) NAME/KEY: polymorphic fragment 99-2610-121
              (B) LOCATION: 1..47
              (D) OTHER INFORMATION: variant version of SEQ ID38

(ix) FEATURE:
              (A) NAME/KEY: polymorphic base
              (B) LOCATION: 24
              (D) OTHER INFORMATION: base c; a in SEQ ID38

(ix) FEATURE:
              (A) NAME/KEY: Potential microsequencing oligo 99-2610-121
```

(B) LOCATION: 1..23

(ix) FEATURE:
        (A) NAME/KEY: Potential microsequencing oligo 99-2610-121
        (B) LOCATION: complement 25..47

(xi) SEQUENCE DESCRIPTION: SEQ ID NO: 88:

ATACCCCTTC CCTAGGTATG GCTCTATGCT GCACTTAGAA AATTCTC                47

(2) INFORMATION FOR SEQ ID NO: 89:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2615-83
        (B) LOCATION: 1..47
        (D) OTHER INFORMATION: variant version of SEQ ID39

(ix) FEATURE:
        (A) NAME/KEY: polymorphic base
        (B) LOCATION: 24
        (D) OTHER INFORMATION: base t; c in SEQ ID39

(ix) FEATURE:
        (A) NAME/KEY: Potential microsequencing oligo 99-2615-83
        (B) LOCATION: 1..23

(ix) FEATURE:
        (A) NAME/KEY: Potential microsequencing oligo 99-2615-83
        (B) LOCATION: complement 25..47

(xi) SEQUENCE DESCRIPTION: SEQ ID NO: 89:

AACAAATCAC AAGTTGGCAA AAGTAGCAAA TTCTCATCTT CTGGGAA                47

(2) INFORMATION FOR SEQ ID NO: 90:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2620-227
        (B) LOCATION: 1..47
        (D) OTHER INFORMATION: variant version of SEQ ID40

(ix) FEATURE:
        (A) NAME/KEY: polymorphic base
        (B) LOCATION: 24
        (D) OTHER INFORMATION: base g; a in SEQ ID40

(ix) FEATURE:
        (A) NAME/KEY: Potential microsequencing oligo 99-2620-227
        (B) LOCATION: 1..23

(ix) FEATURE:
        (A) NAME/KEY: Potential microsequencing oligo 99-2620-227
        (B) LOCATION: complement 25..47

(xi) SEQUENCE DESCRIPTION: SEQ ID NO: 90:

```
TTGACTGGGC TCCTGATGTG TCCGGGGTAT CTTGCTGGCT GTTTTGC                47
```

(2) INFORMATION FOR SEQ ID NO: 91:

(i) SEQUENCE CHARACTERISTICS:
        (A) LENGTH: 44 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2624-407
        (B) LOCATION: 1..44
        (D) OTHER INFORMATION: variant version of SEQ ID41

(ix) FEATURE:
        (A) NAME/KEY: polymorphic base
        (B) LOCATION: 24
        (D) OTHER INFORMATION: base t; g in SEQ ID41

(ix) FEATURE:
        (A) NAME/KEY: Potential microsequencing oligo 99-2624-407
        (B) LOCATION: 1..23

(ix) FEATURE:
        (A) NAME/KEY: Potential microsequencing oligo 99-2624-407
        (B) LOCATION: complement 25..44

(xi) SEQUENCE DESCRIPTION: SEQ ID NO: 91:

```
ATCTGGCCAT AGGCAGAACA TTGTGGGAGA GATGGGAAA GAGA                   44
```

(2) INFORMATION FOR SEQ ID NO: 92:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2625-70
        (B) LOCATION: 1..47
        (D) OTHER INFORMATION: variant version of SEQ ID42

(ix) FEATURE:
        (A) NAME/KEY: polymorphic base
        (B) LOCATION: 24
        (D) OTHER INFORMATION: base g; a in SEQ ID42

(ix) FEATURE:
        (A) NAME/KEY: Potential microsequencing oligo 99-2625-70
        (B) LOCATION: 1..23

(ix) FEATURE:
        (A) NAME/KEY: Potential microsequencing oligo 99-2625-70
        (B) LOCATION: complement 25..47

(xi) SEQUENCE DESCRIPTION: SEQ ID NO: 92:

```
AGTGACTCAA CCAGAAAGAG AGCGGGAGAG AGGACGAAGA GAGGAGA              47
```

(2) INFORMATION FOR SEQ ID NO: 93:

(i) SEQUENCE CHARACTERISTICS:

(A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2630-67
            (B) LOCATION: 1..47
            (D) OTHER INFORMATION: variant version of SEQ ID43

(ix) FEATURE:
            (A) NAME/KEY: polymorphic base
            (B) LOCATION: 24
            (D) OTHER INFORMATION: base g; a in SEQ ID43

(ix) FEATURE:
            (A) NAME/KEY: Potential microsequencing oligo 99-2630-67
            (B) LOCATION: 1..23

(ix) FEATURE:
            (A) NAME/KEY: Potential microsequencing oligo 99-2630-67
            (B) LOCATION: complement 25..47

(xi) SEQUENCE DESCRIPTION: SEQ ID NO: 93:

TAAATTCTGC CTAGAAGATT AAGGTTGGTC CAGAACAGGG AGTGTTT                47

(2) INFORMATION FOR SEQ ID NO: 94:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2633-129
            (B) LOCATION: 1..47
            (D) OTHER INFORMATION: variant version of SEQ ID44

(ix) FEATURE:
            (A) NAME/KEY: polymorphic base
            (B) LOCATION: 24
            (D) OTHER INFORMATION: base c; a in SEQ ID44

(ix) FEATURE:
            (A) NAME/KEY: Potential microsequencing oligo 99-2633-129
            (B) LOCATION: 1..23

(ix) FEATURE:
            (A) NAME/KEY: Potential microsequencing oligo 99-2633-129
            (B) LOCATION: complement 25..47

(xi) SEQUENCE DESCRIPTION: SEQ ID NO: 94:

TAGCTATTTC TTCCCCTAGG CAACGTAGAC AATGAGAGAA CCCTTGA                47

(2) INFORMATION FOR SEQ ID NO: 95:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2634-341
            (B) LOCATION: 1..47
            (D) OTHER INFORMATION: variant version of SEQ ID45

(ix) FEATURE:
            (A) NAME/KEY: polymorphic base
            (B) LOCATION: 24
            (D) OTHER INFORMATION: base g; a in SEQ ID45

(ix) FEATURE:
            (A) NAME/KEY: Potential microsequencing oligo 99-2634-341
            (B) LOCATION: 1..23

(ix) FEATURE:
            (A) NAME/KEY: Potential microsequencing oligo 99-2634-341
            (B) LOCATION: complement 25..47

(xi) SEQUENCE DESCRIPTION: SEQ ID NO: 95:

GGAATCAATA TTTATTTATT ATCGACAGGT GAGACATTAT TTATTTA                47

(2) INFORMATION FOR SEQ ID NO: 96:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2637-28
            (B) LOCATION: 1..47
            (D) OTHER INFORMATION: variant version of SEQ ID46

(ix) FEATURE:
            (A) NAME/KEY: polymorphic base
            (B) LOCATION: 24
            (D) OTHER INFORMATION: base g; a in SEQ ID46

(ix) FEATURE:
            (A) NAME/KEY: Potential microsequencing oligo 99-2637-28
            (B) LOCATION: 1..23

(ix) FEATURE:
            (A) NAME/KEY: Potential microsequencing oligo 99-2637-28
            (B) LOCATION: complement 25..47

(xi) SEQUENCE DESCRIPTION: SEQ ID NO: 96:

CCATCACTTC CTCCTAGTGA AAAGTCAAAG GAGGGTGGGT TTTATAG                47

(2) INFORMATION FOR SEQ ID NO: 97:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2642-255
            (B) LOCATION: 1..47
            (D) OTHER INFORMATION: variant version of SEQ ID47

(ix) FEATURE:
            (A) NAME/KEY: polymorphic base
            (B) LOCATION: 24
            (D) OTHER INFORMATION: base g; a in SEQ ID47

(ix) FEATURE:
            (A) NAME/KEY: Potential microsequencing oligo 99-2642-255
            (B) LOCATION: 1..23

(ix) FEATURE:
            (A) NAME/KEY: Potential microsequencing oligo 99-2642-255
            (B) LOCATION: complement 25..47

(xi) SEQUENCE DESCRIPTION: SEQ ID NO: 97:

TGAGGGTGTT TCCAGAAGAG ACTGGCATTT GAATCTGAAG TGAGTAA                47

(2) INFORMATION FOR SEQ ID NO: 98:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2645-118
            (B) LOCATION: 1..47
            (D) OTHER INFORMATION: variant version of SEQ ID48

(ix) FEATURE:
            (A) NAME/KEY: polymorphic base
            (B) LOCATION: 24
            (D) OTHER INFORMATION: base t; g in SEQ ID48

(ix) FEATURE:
            (A) NAME/KEY: Potential microsequencing oligo 99-2645-118
            (B) LOCATION: 1..23

(ix) FEATURE:
            (A) NAME/KEY: Potential microsequencing oligo 99-2645-118
            (B) LOCATION: complement 25..47

(xi) SEQUENCE DESCRIPTION: SEQ ID NO: 98:

CACAAATTAA TTGCATTGTT ATATGCTAGC AATGAAGAAT CTGAAAA                47

(2) INFORMATION FOR SEQ ID NO: 99:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2647-368
            (B) LOCATION: 1..47
            (D) OTHER INFORMATION: variant version of SEQ ID49

(ix) FEATURE:
            (A) NAME/KEY: polymorphic base
            (B) LOCATION: 24
            (D) OTHER INFORMATION: base g; a in SEQ ID49

(ix) FEATURE:

```
            (A) NAME/KEY: Potential microsequencing oligo 99-2647-368
            (B) LOCATION: 1..23

(ix) FEATURE:
            (A) NAME/KEY: Potential microsequencing oligo 99-2647-368
            (B) LOCATION: complement 25..47

(xi) SEQUENCE DESCRIPTION: SEQ ID NO: 99:

TTAAGGCCTT CAACTGATTA GACGAGGCCC ACTCACATTA TCTGACA                47

(2) INFORMATION FOR SEQ ID NO: 100:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2649-107
            (B) LOCATION: 1..47
            (D) OTHER INFORMATION: variant version of SEQ ID50

(ix) FEATURE:
            (A) NAME/KEY: polymorphic base
            (B) LOCATION: 24
            (D) OTHER INFORMATION: base t; a in SEQ ID50

(ix) FEATURE:
            (A) NAME/KEY: Potential microsequencing oligo 99-2649-107
            (B) LOCATION: 1..23

(ix) FEATURE:
            (A) NAME/KEY: Potential microsequencing oligo 99-2649-107
            (B) LOCATION: complement 25..47

(xi) SEQUENCE DESCRIPTION: SEQ ID NO: 100:

CACAACTCTG GAGCCTTTTA TGATCAGGAC AGCAATGCAC TGAAACT                47

(2) INFORMATION FOR SEQ ID NO: 101:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID1, SEQ
                ID51
            (B) LOCATION: 1..18

(xi) SEQUENCE DESCRIPTION: SEQ ID NO: 101:

CCTGGATTCT GACCCATC                                                18

(2) INFORMATION FOR SEQ ID NO: 102:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR
```

```
        (ii) MOLECULE TYPE: DNA (vi) ORIGINAL SOURCE:
             (A) ORGANISM: Homo sapiens (ix) FEATURE:
             (A) NAME/KEY: upstream amplification primer for SEQ ID2, SEQ
                 ID52
             (B) LOCATION: 1..18

(xi) SEQUENCE DESCRIPTION: SEQ ID NO: 102:

TCTACCTCTA CCTCTTTC                                                    18

(2) INFORMATION FOR SEQ ID NO: 103:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: upstream amplification primer for SEQ ID3, SEQ
                 ID53
             (B) LOCATION: 1..19

(xi) SEQUENCE DESCRIPTION: SEQ ID NO: 103:

CTTCCCATAC CTCTGATAC                                                   19

(2) INFORMATION FOR SEQ ID NO: 104:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: upstream amplification primer for SEQ ID4, SEQ
                 ID54
             (B) LOCATION: 1..18

(xi) SEQUENCE DESCRIPTION: SEQ ID NO: 104:

TTCAACAGTG AAGCCATC                                                    18

(2) INFORMATION FOR SEQ ID NO: 105:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY: upstream amplification primer for SEQ ID5, SEQ
                 ID55
             (B) LOCATION: 1..18
```

-continued (xi) SEQUENCE DESCRIPTION: SEQ ID NO: 105:

TGATGTGTGT GACTCAGG                                                  18

(2) INFORMATION FOR SEQ ID NO: 106:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID6, SEQ
            ID56
        (B) LOCATION: 1..18

(xi) SEQUENCE DESCRIPTION: SEQ ID NO: 106:

ATAGAGGAAC CAAACCTG                                                  18

(2) INFORMATION FOR SEQ ID NO: 107:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID7, SEQ
            ID57
        (B) LOCATION: 1..18

(xi) SEQUENCE DESCRIPTION: SEQ ID NO: 107:

AGCAGCATGG AAGCAAAC                                                  18

(2) INFORMATION FOR SEQ ID NO: 108:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID8, SEQ
            ID58
        (B) LOCATION: 1..18

(xi) SEQUENCE DESCRIPTION: SEQ ID NO: 108:

CTGATGAAAG TGGCTCTC                                                  18

(2) INFORMATION FOR SEQ ID NO: 109:

(i) SEQUENCE CHARACTERISTICS:
        (A) LENGTH: 19 base pairs
        (B) TYPE: NUCLEIC ACID

```
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID9, SEQ
            ID59
        (B) LOCATION: 1..19

(xi) SEQUENCE DESCRIPTION: SEQ ID NO: 109:

TGTATCTGAG GTCTAAAAC                                                  19

(2) INFORMATION FOR SEQ ID NO: 110:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID10, SEQ
            ID60
        (B) LOCATION: 1..18

(xi) SEQUENCE DESCRIPTION: SEQ ID NO: 110:

TATATGTAGA GGGTGAGG                                                   18

(2) INFORMATION FOR SEQ ID NO: 111:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID11, SEQ
            ID61
        (B) LOCATION: 1..19

(xi) SEQUENCE DESCRIPTION: SEQ ID NO: 111:

AGGCTAAGAA AAAAAGAGG                                                  19

(2) INFORMATION FOR SEQ ID NO: 112:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID12, SEQ
```

-continued

```
            ID62
        (B) LOCATION: 1..19

(xi) SEQUENCE DESCRIPTION: SEQ ID NO: 112:

TGAAAAGACT AAGTTCTGG                                              19

(2) INFORMATION FOR SEQ ID NO: 113:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID13, SEQ
            ID63
        (B) LOCATION: 1..18

(xi) SEQUENCE DESCRIPTION: SEQ ID NO: 113:

ATGCTAGAGG AAAGGAAC                                               18

(2) INFORMATION FOR SEQ ID NO: 114:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID14, SEQ
            ID64
        (B) LOCATION: 1..18

(xi) SEQUENCE DESCRIPTION: SEQ ID NO: 114:

ATACCAGGGA CTTTAGTG                                               18

(2) INFORMATION FOR SEQ ID NO: 115:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID15, SEQ
            ID65
        (B) LOCATION: 1..19

(xi) SEQUENCE DESCRIPTION: SEQ ID NO: 115:

AGATTCAGAC CAATTTCAC                                              19

(2) INFORMATION FOR SEQ ID NO: 116:
```

```
        (i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID16, SEQ
                ID66
            (B) LOCATION: 1..18

(xi) SEQUENCE DESCRIPTION: SEQ ID NO: 116:

TGCTTTGATT TGACCCTG                                                        18

(2) INFORMATION FOR SEQ ID NO: 117:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID17, SEQ
                ID67
            (B) LOCATION: 1..19

(xi) SEQUENCE DESCRIPTION: SEQ ID NO: 117:

GCCTATCTTG TTTTGACTG                                                       19

(2) INFORMATION FOR SEQ ID NO: 118:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID18, SEQ
                ID68
            (B) LOCATION: 1..19

(xi) SEQUENCE DESCRIPTION: SEQ ID NO: 118:

TTCAGAGCAA CAATTTTGG                                                       19

(2) INFORMATION FOR SEQ ID NO: 119:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens
```

```
    (ix) FEATURE:
         (A) NAME/KEY: upstream amplification primer for SEQ ID19, SEQ
             ID69
         (B) LOCATION: 1..20

(xi) SEQUENCE DESCRIPTION: SEQ ID NO: 119:

CCAAGTTTAT GAGATTAGAG                                                    20

(2) INFORMATION FOR SEQ ID NO: 120:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID20, SEQ
             ID70
         (B) LOCATION: 1..19

(xi) SEQUENCE DESCRIPTION: SEQ ID NO: 120:

CTAACCTAGA TGATCTTCC                                                     19

(2) INFORMATION FOR SEQ ID NO: 121:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID21, SEQ
             ID71
         (B) LOCATION: 1..18

(xi) SEQUENCE DESCRIPTION: SEQ ID NO: 121:

TGTCCCAAGT TTAGTTCC                                                      18

(2) INFORMATION FOR SEQ ID NO: 122:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID22, SEQ
             ID72
         (B) LOCATION: 1..21

(xi) SEQUENCE DESCRIPTION: SEQ ID NO: 122:

CCAGGAATAA TACTTTGCAT C                                                  21
```

(2) INFORMATION FOR SEQ ID NO: 123:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID23, SEQ ID73
        (B) LOCATION: 1..19

(xi) SEQUENCE DESCRIPTION: SEQ ID NO: 123:

CTCAGTTTTT CTTTCCACC                                                            19

(2) INFORMATION FOR SEQ ID NO: 124:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID24, SEQ ID74
        (B) LOCATION: 1..20

(xi) SEQUENCE DESCRIPTION: SEQ ID NO: 124:

GACTCAGGCA CAACTTTTAG                                                          20

(2) INFORMATION FOR SEQ ID NO: 125:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID25, SEQ ID75
        (B) LOCATION: 1..19

(xi) SEQUENCE DESCRIPTION: SEQ ID NO: 125:

TACAGCAATG GTATAAAGC                                                            19

(2) INFORMATION FOR SEQ ID NO: 126:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA

```
    (vi) ORIGINAL SOURCE:
         (A) ORGANISM: Homo sapiens (ix) FEATURE:
         (A) NAME/KEY: upstream amplification primer for SEQ ID26, SEQ
             ID76
         (B) LOCATION: 1..20

(xi) SEQUENCE DESCRIPTION: SEQ ID NO: 126:

TTATCCATCA TTTAGAAGGC                                                   20

(2) INFORMATION FOR SEQ ID NO: 127:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID27, SEQ
             ID77
         (B) LOCATION: 1..18

(xi) SEQUENCE DESCRIPTION: SEQ ID NO: 127:

CACTGGAGAT AGCTGAAC                                                     18

(2) INFORMATION FOR SEQ ID NO: 128:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID28, SEQ
             ID78
         (B) LOCATION: 1..19

(xi) SEQUENCE DESCRIPTION: SEQ ID NO: 128:

GTACTGTCAA ATCATCACC                                                    19

(2) INFORMATION FOR SEQ ID NO: 129:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID29, SEQ
             ID79
         (B) LOCATION: 1..18

(xi) SEQUENCE DESCRIPTION: SEQ ID NO: 129:
```

CGGGCATAAA AATGCAGG							18

(2) INFORMATION FOR SEQ ID NO: 130:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID30, SEQ
            ID80
        (B) LOCATION: 1..20

(xi) SEQUENCE DESCRIPTION: SEQ ID NO: 130:

GTATATGTGA AGGTTGTGGG							20

(2) INFORMATION FOR SEQ ID NO: 131:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID31, SEQ
            ID81
        (B) LOCATION: 1..19

(xi) SEQUENCE DESCRIPTION: SEQ ID NO: 131:

GTAAGATGTG ACTTGCTCC							19

(2) INFORMATION FOR SEQ ID NO: 132:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID32, SEQ
            ID82
        (B) LOCATION: 1..20

(xi) SEQUENCE DESCRIPTION: SEQ ID NO: 132:

CCAGCTTGAA TTTTGGTGAG							20

(2) INFORMATION FOR SEQ ID NO: 133:

(i) SEQUENCE CHARACTERISTICS:
        (A) LENGTH: 18 base pairs
        (B) TYPE: NUCLEIC ACID
        (C) STRANDEDNESS: SINGLE (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID33, SEQ
                ID83
            (B) LOCATION: 1..18

(xi) SEQUENCE DESCRIPTION: SEQ ID NO: 133:

GCATATCTTG GTGGTCTG                                                         18

(2) INFORMATION FOR SEQ ID NO: 134:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID34, SEQ
                ID84
            (B) LOCATION: 1..19

(xi) SEQUENCE DESCRIPTION: SEQ ID NO: 134:

AGGGTTCAAA GGAAGGAGG                                                        19

(2) INFORMATION FOR SEQ ID NO: 135:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID35, SEQ
                ID85
            (B) LOCATION: 1..20

(xi) SEQUENCE DESCRIPTION: SEQ ID NO: 135:

GAAAAAGAAG GGAAAGAAAG                                                       20

(2) INFORMATION FOR SEQ ID NO: 136:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID36, SEQ
                ID86

(B) LOCATION: 1..19

(xi) SEQUENCE DESCRIPTION: SEQ ID NO: 136:

GTTTGTCTTG GCTATTAAG                                                19

(2) INFORMATION FOR SEQ ID NO: 137:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID37, SEQ
            ID87
        (B) LOCATION: 1..18

(xi) SEQUENCE DESCRIPTION: SEQ ID NO: 137:

TGAAAAAGTG GGTAGCAG                                                 18

(2) INFORMATION FOR SEQ ID NO: 138:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID38, SEQ
            ID88
        (B) LOCATION: 1..19

(xi) SEQUENCE DESCRIPTION: SEQ ID NO: 138:

ATATCAGGGC AGGCACAAG                                                19

(2) INFORMATION FOR SEQ ID NO: 139:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID39, SEQ
            ID89
        (B) LOCATION: 1..18

(xi) SEQUENCE DESCRIPTION: SEQ ID NO: 139:

GGAAGAGGGC AACTTTAC                                                 18

(2) INFORMATION FOR SEQ ID NO: 140:

(i) SEQUENCE CHARACTERISTICS:

(A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID40, SEQ
            ID90
        (B) LOCATION: 1..18

(xi) SEQUENCE DESCRIPTION: SEQ ID NO: 140:

TGAAATGGGC TGTAGATG                                                       18

(2) INFORMATION FOR SEQ ID NO: 141:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID41, SEQ
            ID91
        (B) LOCATION: 1..18

(xi) SEQUENCE DESCRIPTION: SEQ ID NO: 141:

TTAAACCTTG GCTTCCTG                                                       18

(2) INFORMATION FOR SEQ ID NO: 142:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID42, SEQ
            ID92
        (B) LOCATION: 1..18

(xi) SEQUENCE DESCRIPTION: SEQ ID NO: 142:

TTCAACCTTT TGTCGCTG                                                       18

(2) INFORMATION FOR SEQ ID NO: 143:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens

```
    (ix) FEATURE:
         (A) NAME/KEY: upstream amplification primer for SEQ ID43, SEQ
             ID93
         (B) LOCATION: 1..19

(xi) SEQUENCE DESCRIPTION: SEQ ID NO: 143:

ATGTAACAGA TGTCCAAAG                                                    19

(2) INFORMATION FOR SEQ ID NO: 144:

(i) SEQUENCE CHARACTERISTICS:
         (A) LENGTH: 18 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID44, SEQ
             ID94
         (B) LOCATION: 1..18

(xi) SEQUENCE DESCRIPTION: SEQ ID NO: 144:

CTAAGGGTCT TCTTTCTG                                                     18

(2) INFORMATION FOR SEQ ID NO: 145:

(i) SEQUENCE CHARACTERISTICS:
         (A) LENGTH: 19 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID45, SEQ
             ID95
         (B) LOCATION: 1..19

(xi) SEQUENCE DESCRIPTION: SEQ ID NO: 145:

GGTGTATTTA GGTTTGTGG                                                    19

(2) INFORMATION FOR SEQ ID NO: 146:

(i) SEQUENCE CHARACTERISTICS:
         (A) LENGTH: 18 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: upstream amplification primer for SEQ ID46, SEQ
             ID96
         (B) LOCATION: 1..18

(xi) SEQUENCE DESCRIPTION: SEQ ID NO: 146:

CTACCATCAC TTTCCTCC                                                     18
```

-continued (2) INFORMATION FOR SEQ ID NO: 147:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID47, SEQ
            ID97
        (B) LOCATION: 1..18

(xi) SEQUENCE DESCRIPTION: SEQ ID NO: 147:

ATAACTAGGC ATCCAGAC                                                              18

(2) INFORMATION FOR SEQ ID NO: 148:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID48, SEQ
            ID98
        (B) LOCATION: 1..20

(xi) SEQUENCE DESCRIPTION: SEQ ID NO: 148:

CGACATAATT TGGTATGTAG                                                      20

(2) INFORMATION FOR SEQ ID NO: 149:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID49, SEQ
            ID99
        (B) LOCATION: 1..18

(xi) SEQUENCE DESCRIPTION: SEQ ID NO: 149:

TCACCAAGTG TCATCGTC                                                             18

(2) INFORMATION FOR SEQ ID NO: 150:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: upstream amplification primer for SEQ ID50, SEQ
                ID100
            (B) LOCATION: 1..19

(xi) SEQUENCE DESCRIPTION: SEQ ID NO: 150:

GAGACTTTGT AACTTTGTG                                                        19

(2) INFORMATION FOR SEQ ID NO: 151:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID1,
                SEQ ID51
            (B) LOCATION: 1..20

(xi) SEQUENCE DESCRIPTION: SEQ ID NO: 151:

GTCTTCATAA GTCTTCAGTG                                                       20

(2) INFORMATION FOR SEQ ID NO: 152:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID2,
                SEQ ID52
            (B) LOCATION: 1..18

(xi) SEQUENCE DESCRIPTION: SEQ ID NO: 152:

CAAAACACTC CCTCACAC                                                         18

(2) INFORMATION FOR SEQ ID NO: 153:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID3,
                SEQ ID53
            (B) LOCATION: 1..18

(xi) SEQUENCE DESCRIPTION: SEQ ID NO: 153:

```
CAGGTGATGT CTGGATAC                                              18

(2) INFORMATION FOR SEQ ID NO: 154:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID4,
            SEQ ID54
        (B) LOCATION: 1..21

(xi) SEQUENCE DESCRIPTION: SEQ ID NO: 154:

AAGACAACAA GAACTAAATC C                                          21

(2) INFORMATION FOR SEQ ID NO: 155:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID5,
            SEQ ID55
        (B) LOCATION: 1..20

(xi) SEQUENCE DESCRIPTION: SEQ ID NO: 155:

TCCCCAATAG ATTAAAGTTC                                            20

(2) INFORMATION FOR SEQ ID NO: 156:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID6,
            SEQ ID56
        (B) LOCATION: 1..18

(xi) SEQUENCE DESCRIPTION: SEQ ID NO: 156:

CTGAGCATCA AATAGGAG                                              18

(2) INFORMATION FOR SEQ ID NO: 157:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR
```

(ii) MOLECULE TYPE: DNA (vi) ORIGINAL SOURCE:
    (A) ORGANISM: Homo sapiens (ix) FEATURE:
    (A) NAME/KEY: downstream amplification primer for SEQ ID7,
        SEQ ID57
    (B) LOCATION: 1..21

(xi) SEQUENCE DESCRIPTION: SEQ ID NO: 157:

TCATTACAGA AAAAGCCAAA G                                      21

(2) INFORMATION FOR SEQ ID NO: 158:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID8,
            SEQ ID58
        (B) LOCATION: 1..20

(xi) SEQUENCE DESCRIPTION: SEQ ID NO: 158:

TCCTTCTCCA CCTAAAATTC                                        20

(2) INFORMATION FOR SEQ ID NO: 159:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID9,
            SEQ ID59
        (B) LOCATION: 1..18

(xi) SEQUENCE DESCRIPTION: SEQ ID NO: 159:

ACTGCTTCTG CTCTCTTG                                          18

(2) INFORMATION FOR SEQ ID NO: 160:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID10,
            SEQ ID60

(B) LOCATION: 1..20

(xi) SEQUENCE DESCRIPTION: SEQ ID NO: 160:

TGAACATACA AAAACACTGG                                                    20

(2) INFORMATION FOR SEQ ID NO: 161:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID11,
            SEQ ID61
        (B) LOCATION: 1..18

(xi) SEQUENCE DESCRIPTION: SEQ ID NO: 161:

AGAGTTGTTG GCATGTAG                                                      18

(2) INFORMATION FOR SEQ ID NO: 162:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID12,
            SEQ ID62
        (B) LOCATION: 1..18

(xi) SEQUENCE DESCRIPTION: SEQ ID NO: 162:

AACTGCTCAG CAACTGTG                                                      18

(2) INFORMATION FOR SEQ ID NO: 163:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID13,
            SEQ ID63
        (B) LOCATION: 1..21

(xi) SEQUENCE DESCRIPTION: SEQ ID NO: 163:

TTAGAACACT TTTATGGGAA C                                                  21

(2) INFORMATION FOR SEQ ID NO: 164:

(i) SEQUENCE CHARACTERISTICS:

```
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID14,
            SEQ ID64
        (B) LOCATION: 1..19

(xi) SEQUENCE DESCRIPTION: SEQ ID NO: 164:

GTCCTAGAAT GAGCAAATG                                                    19

(2) INFORMATION FOR SEQ ID NO: 165:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID15,
            SEQ ID65
        (B) LOCATION: 1..18

(xi) SEQUENCE DESCRIPTION: SEQ ID NO: 165:

AGAGAAAGAA CCAGAGCC                                                     18

(2) INFORMATION FOR SEQ ID NO: 166:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID16,
            SEQ ID66
        (B) LOCATION: 1..18

(xi) SEQUENCE DESCRIPTION: SEQ ID NO: 166:

TGGAGTCTAA ACTAGGTG                                                     18

(2) INFORMATION FOR SEQ ID NO: 167:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens
```

(ix) FEATURE:
            (A) NAME/KEY: downstream amplification primer for SEQ ID17,
                SEQ ID67
            (B) LOCATION: 1..18

(xi) SEQUENCE DESCRIPTION: SEQ ID NO: 167:

GGACCTTTTA AGAGTGTG                                                        18

(2) INFORMATION FOR SEQ ID NO: 168:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID18,
            SEQ ID68
        (B) LOCATION: 1..19

(xi) SEQUENCE DESCRIPTION: SEQ ID NO: 168:

TGGTTTCTTC AAACAAGAG                                                       19

(2) INFORMATION FOR SEQ ID NO: 169:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID19,
            SEQ ID69
        (B) LOCATION: 1..21

(xi) SEQUENCE DESCRIPTION: SEQ ID NO: 169:

AAGTTGGATA ACCTTCTTTT G                                                    21

(2) INFORMATION FOR SEQ ID NO: 170:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID20,
            SEQ ID70
        (B) LOCATION: 1..19

(xi) SEQUENCE DESCRIPTION: SEQ ID NO: 170:

TAGTTTCGTG AACTTATCC                                                       19

```
(2) INFORMATION FOR SEQ ID NO: 171:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID21,
            SEQ ID71
        (B) LOCATION: 1..21

(xi) SEQUENCE DESCRIPTION: SEQ ID NO: 171:

GTTTACATTA TGCCCCTTTT C                                           21

(2) INFORMATION FOR SEQ ID NO: 172:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID22,
            SEQ ID72
        (B) LOCATION: 1..18

(xi) SEQUENCE DESCRIPTION: SEQ ID NO: 172:

CTCCACTGCC ACAACTTC                                               18

(2) INFORMATION FOR SEQ ID NO: 173:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID23,
            SEQ ID73
        (B) LOCATION: 1..21

(xi) SEQUENCE DESCRIPTION: SEQ ID NO: 173:

TGCTCTGCTT GTAATGTTAT G                                           21

(2) INFORMATION FOR SEQ ID NO: 174:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA
```

(vi) ORIGINAL SOURCE:
            (A) ORGANISM: Homo sapiens (ix) FEATURE:
            (A) NAME/KEY: downstream amplification primer for SEQ ID24,
                SEQ ID74
            (B) LOCATION: 1..19

(xi) SEQUENCE DESCRIPTION: SEQ ID NO: 174:

CAAGGTTGCC AGTCACATC                                                19

(2) INFORMATION FOR SEQ ID NO: 175:

(i) SEQUENCE CHARACTERISTICS:
            (A) LENGTH: 18 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID25,
                SEQ ID75
            (B) LOCATION: 1..18

(xi) SEQUENCE DESCRIPTION: SEQ ID NO: 175:

ATGAAGATAC GCAGCCAG                                                 18

(2) INFORMATION FOR SEQ ID NO: 176:

(i) SEQUENCE CHARACTERISTICS:
            (A) LENGTH: 21 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID26,
                SEQ ID76
            (B) LOCATION: 1..21

(xi) SEQUENCE DESCRIPTION: SEQ ID NO: 176:

CTCATTTAAC TCCCATTCCT C                                             21

(2) INFORMATION FOR SEQ ID NO: 177:

(i) SEQUENCE CHARACTERISTICS:
            (A) LENGTH: 21 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: downstream amplification primer for SEQ ID27,
                SEQ ID77
            (B) LOCATION: 1..21

(xi) SEQUENCE DESCRIPTION: SEQ ID NO: 177:

```
TGCTTTTCTT GTCCCTGATT G                                               21
```

(2) INFORMATION FOR SEQ ID NO: 178:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID28,
            SEQ ID78
        (B) LOCATION: 1..20

(xi) SEQUENCE DESCRIPTION: SEQ ID NO: 178:

```
GCATTGAATC CGTAAATTTC                                                 20
```

(2) INFORMATION FOR SEQ ID NO: 179:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID29,
            SEQ ID79
        (B) LOCATION: 1..21

(xi) SEQUENCE DESCRIPTION: SEQ ID NO: 179:

```
CAGTTTTGGT CATTGTGGGA G                                               21
```

(2) INFORMATION FOR SEQ ID NO: 180:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID30,
            SEQ ID80
        (B) LOCATION: 1..21

(xi) SEQUENCE DESCRIPTION: SEQ ID NO: 180:

```
AAATCCAACT ATGTCACTTC C                                               21
```

(2) INFORMATION FOR SEQ ID NO: 181:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR

```
    (ii) MOLECULE TYPE: DNA (vi) ORIGINAL SOURCE:
         (A) ORGANISM: Homo sapiens (ix) FEATURE:
         (A) NAME/KEY: downstream amplification primer for SEQ ID31,
             SEQ ID81
         (B) LOCATION: 1..19

(xi) SEQUENCE DESCRIPTION: SEQ ID NO: 181:

AATGTCCCCT CCTCCTCTG                                                       19

(2) INFORMATION FOR SEQ ID NO: 182:

(i) SEQUENCE CHARACTERISTICS:
         (A) LENGTH: 20 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: downstream amplification primer for SEQ ID32,
             SEQ ID82
         (B) LOCATION: 1..20

(xi) SEQUENCE DESCRIPTION: SEQ ID NO: 182:

GCCACAAGTA TTTGGGTGCC                                                      20

(2) INFORMATION FOR SEQ ID NO: 183:

(i) SEQUENCE CHARACTERISTICS:
         (A) LENGTH: 19 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: downstream amplification primer for SEQ ID33,
             SEQ ID83
         (B) LOCATION: 1..19

(xi) SEQUENCE DESCRIPTION: SEQ ID NO: 183:

CCTACGGTTT GTCATAAAG                                                       19

(2) INFORMATION FOR SEQ ID NO: 184:

(i) SEQUENCE CHARACTERISTICS:
         (A) LENGTH: 21 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: downstream amplification primer for SEQ ID34,
             SEQ ID84
         (B) LOCATION: 1..21
```

(xi) SEQUENCE DESCRIPTION: SEQ ID NO: 184:

TGTAACAGGG GACATGGGAA G                                              21

(2) INFORMATION FOR SEQ ID NO: 185:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID35,
            SEQ ID85
        (B) LOCATION: 1..20

(xi) SEQUENCE DESCRIPTION: SEQ ID NO: 185:

CAATTTTGTA TGGATGACAG                                                20

(2) INFORMATION FOR SEQ ID NO: 186:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID36,
            SEQ ID86
        (B) LOCATION: 1..21

(xi) SEQUENCE DESCRIPTION: SEQ ID NO: 186:

TGGTGGTGGA AAAAAGAAG G                                               21

(2) INFORMATION FOR SEQ ID NO: 187:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID37,
            SEQ ID87
        (B) LOCATION: 1..21

(xi) SEQUENCE DESCRIPTION: SEQ ID NO: 187:

CTATAACTCT TATCAGTGAA C                                              21

(2) INFORMATION FOR SEQ ID NO: 188:

(i) SEQUENCE CHARACTERISTICS:
        (A) LENGTH: 20 base pairs

```
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID38,
            SEQ ID88
        (B) LOCATION: 1..20

(xi) SEQUENCE DESCRIPTION: SEQ ID NO: 188:

AGGTCACTCA AGTATTATGG                                                  20

(2) INFORMATION FOR SEQ ID NO: 189:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID39,
            SEQ ID89
        (B) LOCATION: 1..21

(xi) SEQUENCE DESCRIPTION: SEQ ID NO: 189:

CCCCAGCTCC CAAATAATGA C                                                21

(2) INFORMATION FOR SEQ ID NO: 190:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID40,
            SEQ ID90
        (B) LOCATION: 1..20

(xi) SEQUENCE DESCRIPTION: SEQ ID NO: 190:

TCCACAACAG ACACTTAAAC                                                  20

(2) INFORMATION FOR SEQ ID NO: 191:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
```

(A) NAME/KEY: downstream amplification primer for SEQ ID41,
            SEQ ID91
        (B) LOCATION: 1..18

(xi) SEQUENCE DESCRIPTION: SEQ ID NO: 191:

TCTCTTTCCC CATCTCTC                                                        18

(2) INFORMATION FOR SEQ ID NO: 192:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID42,
            SEQ ID92
        (B) LOCATION: 1..19

(xi) SEQUENCE DESCRIPTION: SEQ ID NO: 192:

TCCCCTTCTA TTGTCTACC                                                       19

(2) INFORMATION FOR SEQ ID NO: 193:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID43,
            SEQ ID93
        (B) LOCATION: 1..18

(xi) SEQUENCE DESCRIPTION: SEQ ID NO: 193:

GGTTTGTGTT CAGTACGG                                                        18

(2) INFORMATION FOR SEQ ID NO: 194:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID44,
            SEQ ID94
        (B) LOCATION: 1..21

(xi) SEQUENCE DESCRIPTION: SEQ ID NO: 194:

TGTATATGCC TGGTGGAAAT G                                                    21

(2) INFORMATION FOR SEQ ID NO: 195:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID45,
            SEQ ID95
        (B) LOCATION: 1..21

(xi) SEQUENCE DESCRIPTION: SEQ ID NO: 195:

GTGAAAGAAA CTTGATAGAG G                                              21

(2) INFORMATION FOR SEQ ID NO: 196:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID46,
            SEQ ID96
        (B) LOCATION: 1..18

(xi) SEQUENCE DESCRIPTION: SEQ ID NO: 196:

CCTCCAACAG TAAGAATC                                                  18

(2) INFORMATION FOR SEQ ID NO: 197:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID47,
            SEQ ID97
        (B) LOCATION: 1..20

(xi) SEQUENCE DESCRIPTION: SEQ ID NO: 197:

CAGAACCATT AACTATTCAC                                                20

(2) INFORMATION FOR SEQ ID NO: 198:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:

(A) ORGANISM: Homo sapiens (ix) FEATURE:
        (A) NAME/KEY: downstream amplification primer for SEQ ID48,
            SEQ ID98
        (B) LOCATION: 1..20

(xi) SEQUENCE DESCRIPTION: SEQ ID NO: 198:

GCCATTTGGA ATTTTGATAG                                                        20

(2) INFORMATION FOR SEQ ID NO: 199:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID49,
            SEQ ID99
        (B) LOCATION: 1..19

(xi) SEQUENCE DESCRIPTION: SEQ ID NO: 199:

TGCAGCATCC CTGGAAGTC                                                         19

(2) INFORMATION FOR SEQ ID NO: 200:

(i) SEQUENCE CHARACTERISTICS:
        (A) LENGTH: 21 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID50,
            SEQ ID100
        (B) LOCATION: 1..21

(xi) SEQUENCE DESCRIPTION: SEQ ID NO: 200:

GAGACATCAT ATCTGTGTTT G                                                      21

(2) INFORMATION FOR SEQ ID NO: 201:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2103-270.mis1
        (B) LOCATION: 1..19

(xi) SEQUENCE DESCRIPTION: SEQ ID NO: 201:

GATTCATATG AGACAGCTA                                                         19

(2) INFORMATION FOR SEQ ID NO: 202:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2228-301.mis1
        (B) LOCATION: 1..23

(xi) SEQUENCE DESCRIPTION: SEQ ID NO: 202:

CCCTGCTTAT CCCTGTAAGG TGG                                             23

(2) INFORMATION FOR SEQ ID NO: 203:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2229-240.mis1
        (B) LOCATION: 1..23

(xi) SEQUENCE DESCRIPTION: SEQ ID NO: 203:

TCGTCATCGT GGCCTGGGCT ACA                                             23

(2) INFORMATION FOR SEQ ID NO: 204:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2240-281.mis1
        (B) LOCATION: 1..19

(xi) SEQUENCE DESCRIPTION: SEQ ID NO: 204:

TCTTAATAAC TTTTTATTT                                                  19

(2) INFORMATION FOR SEQ ID NO: 205:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
            (A) NAME/KEY:  microsequencing oligo 99-2242-206.mis1
            (B) LOCATION: 1..19

(xi) SEQUENCE DESCRIPTION: SEQ ID NO: 205:

TTTCTTTTAG TCAAATTAT                                                      19

(2) INFORMATION FOR SEQ ID NO: 206:

(i) SEQUENCE CHARACTERISTICS:
            (A) LENGTH: 23 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: potential microsequencing oligo 99-2244-83.mis1
            (B) LOCATION: 1..23

(xi) SEQUENCE DESCRIPTION: SEQ ID NO: 206:

TAATTGTAGA TACTAAGACC ATT                                                 23

(2) INFORMATION FOR SEQ ID NO: 207:

(i) SEQUENCE CHARACTERISTICS:
            (A) LENGTH: 23 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: potential microsequencing oligo 99-2246-340.mis1
            (B) LOCATION: 1..23

(xi) SEQUENCE DESCRIPTION: SEQ ID NO: 207:

ATTTATATGT TAAATGCAGA GAA                                                 23

(2) INFORMATION FOR SEQ ID NO: 208:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY:  microsequencing oligo 99-2248-76.mis1
            (B) LOCATION: 1..19

(xi) SEQUENCE DESCRIPTION: SEQ ID NO: 208:

GAGAGGGAAG GTAATCTTC                                                      19

(2) INFORMATION FOR SEQ ID NO: 209:

(i) SEQUENCE CHARACTERISTICS:

```
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2250-236.mis1
        (B) LOCATION: 1..23

(xi) SEQUENCE DESCRIPTION: SEQ ID NO: 209:

TTTTATCCAA AACAGAATTA ACA                                              23

(2) INFORMATION FOR SEQ ID NO: 210:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2251-151.mis1
        (B) LOCATION: 1..23

(xi) SEQUENCE DESCRIPTION: SEQ ID NO: 210:

TGAAAAGAAG TTCAGACGAT TGC                                              23

(2) INFORMATION FOR SEQ ID NO: 211:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2269-179.mis1
        (B) LOCATION: 1..23

(xi) SEQUENCE DESCRIPTION: SEQ ID NO: 211:

AAAATAAAGA AATTCCTAGA GAC                                              23

(2) INFORMATION FOR SEQ ID NO: 212:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2271-403.mis1
        (B) LOCATION: 1..23
```

(xi) SEQUENCE DESCRIPTION: SEQ ID NO: 212:

AGGCATTTAT TTCATATTTA TTA                                                  23

(2) INFORMATION FOR SEQ ID NO: 213:

(i) SEQUENCE CHARACTERISTICS:
         (A) LENGTH: 23 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2272-409.mis1
         (B) LOCATION: 1..23

(xi) SEQUENCE DESCRIPTION: SEQ ID NO: 213:

AAAAGCACTG CAATTATTTT GGA                                                  23

(2) INFORMATION FOR SEQ ID NO: 214:

(i) SEQUENCE CHARACTERISTICS:
         (A) LENGTH: 19 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2273-528.mis1
         (B) LOCATION: 1..19

(xi) SEQUENCE DESCRIPTION: SEQ ID NO: 214:

GAAGATAAGA AAATCAAGG                                                       19

(2) INFORMATION FOR SEQ ID NO: 215:

(i) SEQUENCE CHARACTERISTICS:
         (A) LENGTH: 19 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2275-466.mis1
         (B) LOCATION: 1..19

(xi) SEQUENCE DESCRIPTION: SEQ ID NO: 215:

TGATAGCATT AAATACTCC                                                       19

(2) INFORMATION FOR SEQ ID NO: 216:

(i) SEQUENCE CHARACTERISTICS:
         (A) LENGTH: 23 base pairs
         (B) TYPE: NUCLEIC ACID
         (C) STRANDEDNESS: SINGLE
         (D) TOPOLOGY: LINEAR

```
    (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2278-276.mis1
         (B) LOCATION: 1..23

(xi) SEQUENCE DESCRIPTION: SEQ ID NO: 216:

GAAAAAAATG GGAACATCTT CAC                                              23

(2) INFORMATION FOR SEQ ID NO: 217:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2312-358.mis1
         (B) LOCATION: 1..23

(xi) SEQUENCE DESCRIPTION: SEQ ID NO: 217:

TTTTAGAGAG AGATGGAAAA AAA                                              23

(2) INFORMATION FOR SEQ ID NO: 218:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2315-213.mis1
         (B) LOCATION: 1..23

(xi) SEQUENCE DESCRIPTION: SEQ ID NO: 218:

AGATGGATTC TACCCACAGG CAA                                              23

(2) INFORMATION FOR SEQ ID NO: 219:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2320-292.mis1
         (B) LOCATION: 1..19

(xi) SEQUENCE DESCRIPTION: SEQ ID NO: 219:

TCATTCACTA AACTTCAAC                                                   19
```

(2) INFORMATION FOR SEQ ID NO: 220:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: microsequencing oligo 99-2321-82.mis1
        (B) LOCATION: 1..19

(xi) SEQUENCE DESCRIPTION: SEQ ID NO: 220:

GCTTACTGAG TGTCCACTC                                              19

(2) INFORMATION FOR SEQ ID NO: 221:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: microsequencing oligo 99-2324-338.mis1
        (B) LOCATION: 1..19

(xi) SEQUENCE DESCRIPTION: SEQ ID NO: 221:

AGAAGACAAA ATCGCAGGA                                              19

(2) INFORMATION FOR SEQ ID NO: 222:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2333-423.mis1
        (B) LOCATION: 1..23

(xi) SEQUENCE DESCRIPTION: SEQ ID NO: 222:

GAGACGCTAT CTATGCAAGG AGG                                         23

(2) INFORMATION FOR SEQ ID NO: 223:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:

(A) ORGANISM: Homo sapiens (ix) FEATURE:
        (A) NAME/KEY:  microsequencing oligo 99-2341-485.mis1
        (B) LOCATION: 1..23

(xi) SEQUENCE DESCRIPTION: SEQ ID NO: 223:

TTTTATCTGT CTGTTACCTA CAC                                               23

(2) INFORMATION FOR SEQ ID NO: 224:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2342-217.mis1
        (B) LOCATION: 1..23

(xi) SEQUENCE DESCRIPTION: SEQ ID NO: 224:

TTTTGCCTTG GACTTTCATG ACA                                               23

(2) INFORMATION FOR SEQ ID NO: 225:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2362-270.mis1
        (B) LOCATION: 1..23

(xi) SEQUENCE DESCRIPTION: SEQ ID NO: 225:

TCTCTCTTGG GTGGTTCCTC AAC                                               23

(2) INFORMATION FOR SEQ ID NO: 226:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2364-329.mis1
        (B) LOCATION: 1..19

(xi) SEQUENCE DESCRIPTION: SEQ ID NO: 226:

AAAATGATGA ACCATATAC                                                    19

(2) INFORMATION FOR SEQ ID NO: 227:

```
    (i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2367-61.mis1
        (B) LOCATION: 1..23

(xi) SEQUENCE DESCRIPTION: SEQ ID NO: 227:

TAAACATTTC ATTATTTCAG AAA                                                 23

(2) INFORMATION FOR SEQ ID NO: 228:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2371-93.mis1
        (B) LOCATION: 1..23

(xi) SEQUENCE DESCRIPTION: SEQ ID NO: 228:

TTTTAAACTT TCCTAATACT TAC                                                 23

(2) INFORMATION FOR SEQ ID NO: 229:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2378-200.mis1
        (B) LOCATION: 1..23

(xi) SEQUENCE DESCRIPTION: SEQ ID NO: 229:

GAGAACTTCC TGTTGAACCT GTT                                                 23

(2) INFORMATION FOR SEQ ID NO: 230:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2381-394.mis1
```

(B) LOCATION: 1..23

(xi) SEQUENCE DESCRIPTION: SEQ ID NO: 230:

AGTGGTCTTC AGGTTATTGG TAG                                               23

(2) INFORMATION FOR SEQ ID NO: 231:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2413-368.mis1
        (B) LOCATION: 1..23

(xi) SEQUENCE DESCRIPTION: SEQ ID NO: 231:

ATTTTAAGAG GAAAACTTAA TGG                                               23

(2) INFORMATION FOR SEQ ID NO: 232:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2419-285.mis1
        (B) LOCATION: 1..19

(xi) SEQUENCE DESCRIPTION: SEQ ID NO: 232:

GATCAAGCAG TGCCCACTC                                                    19

(2) INFORMATION FOR SEQ ID NO: 233:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2559-253.mis1
        (B) LOCATION: 1..23

(xi) SEQUENCE DESCRIPTION: SEQ ID NO: 233:

CAGGTGTTTT CATGCCCTCT TAG                                               23

(2) INFORMATION FOR SEQ ID NO: 234:

(i) SEQUENCE CHARACTERISTICS:
        (A) LENGTH: 23 base pairs
        (B) TYPE: NUCLEIC ACID
        (C) STRANDEDNESS: SINGLE

```
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: potential microsequencing oligo 99-2566-112.mis1
            (B) LOCATION: 1..23

(xi) SEQUENCE DESCRIPTION: SEQ ID NO: 234:

GCCTTCACAA CCGCAGAGGC AAG                                               23

(2) INFORMATION FOR SEQ ID NO: 235:

(i) SEQUENCE CHARACTERISTICS:
            (A) LENGTH: 23 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: potential microsequencing oligo 99-2567-329.mis1
            (B) LOCATION: 1..23

(xi) SEQUENCE DESCRIPTION: SEQ ID NO: 235:

CACTGTCAGA TATGAAATGA TGC                                               23

(2) INFORMATION FOR SEQ ID NO: 236:

(i) SEQUENCE CHARACTERISTICS:
            (A) LENGTH: 19 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY:  microsequencing oligo 99-2570-218.mis1
            (B) LOCATION: 1..19

(xi) SEQUENCE DESCRIPTION: SEQ ID NO: 236:

AGTTCCAAAT TATGAGAAG                                                    19

(2) INFORMATION FOR SEQ ID NO: 237:

(i) SEQUENCE CHARACTERISTICS:
            (A) LENGTH: 23 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: potential microsequencing oligo 99-2571-242.mis1
            (B) LOCATION: 1..23

(xi) SEQUENCE DESCRIPTION: SEQ ID NO: 237:
```

ATAATGAATG AGTATTTGAT ATT                                            23

(2) INFORMATION FOR SEQ ID NO: 238:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2610-121.mis1
        (B) LOCATION: 1..23

(xi) SEQUENCE DESCRIPTION: SEQ ID NO: 238:

TTTTCCCTTC CCTAGGTATG GCT                                            23

(2) INFORMATION FOR SEQ ID NO: 239:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2615-83.mis1
        (B) LOCATION: 1..23

(xi) SEQUENCE DESCRIPTION: SEQ ID NO: 239:

TTTTAATCAC AAGTTGGCAA AAG                                            23

(2) INFORMATION FOR SEQ ID NO: 240:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2620-227.mis1
        (B) LOCATION: 1..23

(xi) SEQUENCE DESCRIPTION: SEQ ID NO: 240:

TTGACTGGGC TCCTGATGTG TCC                                            23

(2) INFORMATION FOR SEQ ID NO: 241:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA

```
    (vi) ORIGINAL SOURCE:
         (A) ORGANISM: Homo sapiens (ix) FEATURE:
         (A) NAME/KEY: potential microsequencing oligo 99-2624-407.mis1
         (B) LOCATION: 1..23

(xi) SEQUENCE DESCRIPTION: SEQ ID NO: 241:

ATCTGGCCAT AGGCAGAACA TTG                                              23

(2) INFORMATION FOR SEQ ID NO: 242:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2625-70.mis1
         (B) LOCATION: 1..23

(xi) SEQUENCE DESCRIPTION: SEQ ID NO: 242:

AGTGACTCAA CCAGAAAGAG AGC                                              23

(2) INFORMATION FOR SEQ ID NO: 243:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2630-67.mis1
         (B) LOCATION: 1..23

(xi) SEQUENCE DESCRIPTION: SEQ ID NO: 243:

TAAATTCTGC CTAGAAGATT AAG                                              23

(2) INFORMATION FOR SEQ ID NO: 244:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2633-129.mis1
         (B) LOCATION: 1..23

(xi) SEQUENCE DESCRIPTION: SEQ ID NO: 244:

TTTTTATTTC TTCCCCTAGG CAA                                              23

(2) INFORMATION FOR SEQ ID NO: 245:
```

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2634-341.mis1
        (B) LOCATION: 1..23

(xi) SEQUENCE DESCRIPTION: SEQ ID NO: 245:

GGAATCAATA TTTATTTATT ATC                                              23

(2) INFORMATION FOR SEQ ID NO: 246:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2637-28.mis1
        (B) LOCATION: 1..23

(xi) SEQUENCE DESCRIPTION: SEQ ID NO: 246:

CCATCACTTC CTCCTAGTGA AAA                                              23

(2) INFORMATION FOR SEQ ID NO: 247:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2642-255.mis1
        (B) LOCATION: 1..23

(xi) SEQUENCE DESCRIPTION: SEQ ID NO: 247:

TGAGGGTGTT TCCAGAAGAG ACT                                              23

(2) INFORMATION FOR SEQ ID NO: 248:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:

```
        (A) NAME/KEY: potential microsequencing oligo 99-2645-118.mis1
        (B) LOCATION: 1..23

(xi) SEQUENCE DESCRIPTION: SEQ ID NO: 248:

CACAAATTAA TTGCATTGTT ATA                                              23

(2) INFORMATION FOR SEQ ID NO: 249:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2647-368.mis1
        (B) LOCATION: 1..23

(xi) SEQUENCE DESCRIPTION: SEQ ID NO: 249:

TTAAGGCCTT CAACTGATTA GAC                                              23

(2) INFORMATION FOR SEQ ID NO: 250:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2649-107.mis1
        (B) LOCATION: 1..19

(xi) SEQUENCE DESCRIPTION: SEQ ID NO: 250:

ACTCTGGAGC CTTTTATGA                                                   19

(2) INFORMATION FOR SEQ ID NO: 251:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2103-270.mis2
        (B) LOCATION: 1..23

(xi) SEQUENCE DESCRIPTION: SEQ ID NO: 251:

AGTGTAGAAA AATTGAAGGT CTG                                              23

(2) INFORMATION FOR SEQ ID NO: 252:

(i) SEQUENCE CHARACTERISTICS:
        (A) LENGTH: 19 base pairs
        (B) TYPE: NUCLEIC ACID
```

```
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2228-301.mis2
        (B) LOCATION: 1..19

(xi) SEQUENCE DESCRIPTION: SEQ ID NO: 252:

GGCCTTGCCC ATATGGGTC                                                   19

(2) INFORMATION FOR SEQ ID NO: 253:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2229-240.mis2
        (B) LOCATION: 1..19

(xi) SEQUENCE DESCRIPTION: SEQ ID NO: 253:

AAGGACTGGA ACAGGTAGT                                                   19

(2) INFORMATION FOR SEQ ID NO: 254:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2240-281.mis2
        (B) LOCATION: 1..23

(xi) SEQUENCE DESCRIPTION: SEQ ID NO: 254:

AGAAAAAAAA GATTCGAATT ACT                                              23

(2) INFORMATION FOR SEQ ID NO: 255:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2242-206.mis2
        (B) LOCATION: 1..23

(xi) SEQUENCE DESCRIPTION: SEQ ID NO: 255:
```

CTTAAGAAAA AAGTAAAATA TAA                    23

(2) INFORMATION FOR SEQ ID NO: 256:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2244-83.mis2
        (B) LOCATION: 1..19

(xi) SEQUENCE DESCRIPTION: SEQ ID NO: 256:

TACCTACATG GTTTAAGCA                         19

(2) INFORMATION FOR SEQ ID NO: 257:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2246-340.mis2
        (B) LOCATION: 1..19

(xi) SEQUENCE DESCRIPTION: SEQ ID NO: 257:

TGCAAAACTT ATTTTTCTT                         19

(2) INFORMATION FOR SEQ ID NO: 258:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2248-76.mis2
        (B) LOCATION: 1..23

(xi) SEQUENCE DESCRIPTION: SEQ ID NO: 258:

CCAGGGGATG GGCAGACTTC AGG                    23

(2) INFORMATION FOR SEQ ID NO: 259:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA

```
    (vi) ORIGINAL SOURCE:
         (A) ORGANISM: Homo sapiens (ix) FEATURE:
         (A) NAME/KEY: potential microsequencing oligo 99-2250-236.mis2
         (B) LOCATION: 1..23

(xi) SEQUENCE DESCRIPTION: SEQ ID NO: 259:

AATAAAAATA AAAAACCCAA AGT                                                23

(2) INFORMATION FOR SEQ ID NO: 260:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2251-151.mis2
         (B) LOCATION: 1..23

(xi) SEQUENCE DESCRIPTION: SEQ ID NO: 260:

TTTTACAGCC AAACTAGTCT ATC                                                23

(2) INFORMATION FOR SEQ ID NO: 261:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2269-179.mis2
         (B) LOCATION: 1..19

(xi) SEQUENCE DESCRIPTION: SEQ ID NO: 261:

TTGATCTTGA TAGGCTGTA                                                     19

(2) INFORMATION FOR SEQ ID NO: 262:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2271-403.mis2
         (B) LOCATION: 1..19

(xi) SEQUENCE DESCRIPTION: SEQ ID NO: 262:

GAAGATAAGA AAATCAAGG                                                     19
```

(2) INFORMATION FOR SEQ ID NO: 263:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2272-409.mis2
        (B) LOCATION: 1..23

(xi) SEQUENCE DESCRIPTION: SEQ ID NO: 263:

TTTTACTTGC AATATTTCAC AGT                                              23

(2) INFORMATION FOR SEQ ID NO: 264:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2273-528.mis2
        (B) LOCATION: 1..23

(xi) SEQUENCE DESCRIPTION: SEQ ID NO: 264:

AGGCATTTAT TTCATATTTA TTA                                              23

(2) INFORMATION FOR SEQ ID NO: 265:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2275-466.mis2
        (B) LOCATION: 1..23

(xi) SEQUENCE DESCRIPTION: SEQ ID NO: 265:

TAGTATCCCT ATTCACAGTT TTT                                              23

(2) INFORMATION FOR SEQ ID NO: 266:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens

```
    (ix) FEATURE:
         (A) NAME/KEY:  microsequencing oligo 99-2278-276.mis2
         (B) LOCATION: 1..19

(xi) SEQUENCE DESCRIPTION: SEQ ID NO: 266:

TTGTTGGAGA TGCACAGGC                                                      19

(2) INFORMATION FOR SEQ ID NO: 267:

(i) SEQUENCE CHARACTERISTICS:
         (A) LENGTH: 23 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2312-358.mis2
         (B) LOCATION: 1..23

(xi) SEQUENCE DESCRIPTION: SEQ ID NO: 267:

GGCCATTTAC CCAGAAGGCC TAC                                                 23

(2) INFORMATION FOR SEQ ID NO: 268:

(i) SEQUENCE CHARACTERISTICS:
         (A) LENGTH: 23 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2315-213.mis2
         (B) LOCATION: 1..23

(xi) SEQUENCE DESCRIPTION: SEQ ID NO: 268:

TTTTTTTTAA AATAAGGTTT TCT                                                 23

(2) INFORMATION FOR SEQ ID NO: 269:

(i) SEQUENCE CHARACTERISTICS:
         (A) LENGTH: 23 base pairs
         (B) TYPE: NUCLEIC ACID
         (C) STRANDEDNESS: SINGLE
         (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2320-292.mis2
         (B) LOCATION: 1..23

(xi) SEQUENCE DESCRIPTION: SEQ ID NO: 269:

AAATTCATTA AATTTATAAA AAC                                                 23

(2) INFORMATION FOR SEQ ID NO: 270:

(i) SEQUENCE CHARACTERISTICS:
         (A) LENGTH: 23 base pairs
```

(B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2321-82.mis2
        (B) LOCATION: 1..23

(xi) SEQUENCE DESCRIPTION: SEQ ID NO: 270:

AGGAAATATT TGAGTAGGTA TCC                                               23

(2) INFORMATION FOR SEQ ID NO: 271:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2324-338.mis2
        (B) LOCATION: 1..23

(xi) SEQUENCE DESCRIPTION: SEQ ID NO: 271:

TTTTTACTGT TGAGGGATTT CTT                                               23

(2) INFORMATION FOR SEQ ID NO: 272:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2333-423.mis2
        (B) LOCATION: 1..23

(xi) SEQUENCE DESCRIPTION: SEQ ID NO: 272:

TTTTGCTGTC CAAATGTTGA ACA                                               23

(2) INFORMATION FOR SEQ ID NO: 273:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2341-485.mis2
        (B) LOCATION: 1..23

```
    (xi) SEQUENCE DESCRIPTION: SEQ ID NO: 273:

AGAGCCTGTG CGATTCTTTG TAA                                              23

(2) INFORMATION FOR SEQ ID NO: 274:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2342-217.mis2
        (B) LOCATION: 1..23

(xi) SEQUENCE DESCRIPTION: SEQ ID NO: 274:

CACAATCTGG GCTGTTTCTA GAA                                              23

(2) INFORMATION FOR SEQ ID NO: 275:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2362-270.mis2
        (B) LOCATION: 1..23

(xi) SEQUENCE DESCRIPTION: SEQ ID NO: 275:

TTTTACTTGG TCAAGGTCAC ACA                                              23

(2) INFORMATION FOR SEQ ID NO: 276:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2364-329.mis2
        (B) LOCATION: 1..23

(xi) SEQUENCE DESCRIPTION: SEQ ID NO: 276:

CAATTATATG TTACCTTGCC TCA                                              23

(2) INFORMATION FOR SEQ ID NO: 277:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR
```

```
    (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2367-61.mis2
         (B) LOCATION: 1..23

(xi) SEQUENCE DESCRIPTION: SEQ ID NO: 277:

TTTTTTGGTG AAAATGCATA TTA                                               23

(2) INFORMATION FOR SEQ ID NO: 278:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2371-93.mis2
         (B) LOCATION: 1..23

(xi) SEQUENCE DESCRIPTION: SEQ ID NO: 278:

ATTATGTAAA AAGTAGGCAG TGA                                               23

(2) INFORMATION FOR SEQ ID NO: 279:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2378-200.mis2
         (B) LOCATION: 1..19

(xi) SEQUENCE DESCRIPTION: SEQ ID NO: 279:

GGACGACAGG ACAGTTCTA                                                    19

(2) INFORMATION FOR SEQ ID NO: 280:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2381-394.mis2
         (B) LOCATION: 1..19

(xi) SEQUENCE DESCRIPTION: SEQ ID NO: 280:

TTTAGCTCCC CTACTTTTC                                                    19
```

(2) INFORMATION FOR SEQ ID NO: 281:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2413-368.mis2
        (B) LOCATION: 1..19

(xi) SEQUENCE DESCRIPTION: SEQ ID NO: 281:

AAATATTATG TACAATTCT                                                   19

(2) INFORMATION FOR SEQ ID NO: 282:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2419-285.mis2
        (B) LOCATION: 1..23

(xi) SEQUENCE DESCRIPTION: SEQ ID NO: 282:

AGTCACAGCT CCCTGGAGGG TGG                                              23

(2) INFORMATION FOR SEQ ID NO: 283:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2559-253.mis2
        (B) LOCATION: 1..19

(xi) SEQUENCE DESCRIPTION: SEQ ID NO: 283:

GATGGATGAT GTGACACAC                                                   19

(2) INFORMATION FOR SEQ ID NO: 284:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens

```
    (ix) FEATURE:
         (A) NAME/KEY:  microsequencing oligo 99-2566-112.mis2
         (B) LOCATION: 1..19

(xi) SEQUENCE DESCRIPTION: SEQ ID NO: 284:

AGGGTGGCCA AGCTCCTTC                                                    19

(2) INFORMATION FOR SEQ ID NO: 285:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2567-329.mis2
         (B) LOCATION: 1..19

(xi) SEQUENCE DESCRIPTION: SEQ ID NO: 285:

TATAGCCCAA AGAAAGCCA                                                    19

(2) INFORMATION FOR SEQ ID NO: 286:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY: potential microsequencing oligo 99-2570-218.mis2
         (B) LOCATION: 1..23

(xi) SEQUENCE DESCRIPTION: SEQ ID NO: 286:

AACTTAGCCA CTTCAGAGGC CTC                                               23

(2) INFORMATION FOR SEQ ID NO: 287:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
         (A) ORGANISM: Homo sapiens (ix) FEATURE:
         (A) NAME/KEY:  microsequencing oligo 99-2571-242.mis2
         (B) LOCATION: 1..19

(xi) SEQUENCE DESCRIPTION: SEQ ID NO: 287:

GCTGACACAT TTAATTATA                                                    19

(2) INFORMATION FOR SEQ ID NO: 288:

(i) SEQUENCE CHARACTERISTICS:
```

(A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2610-121.mis2
        (B) LOCATION: 1..23

(xi) SEQUENCE DESCRIPTION: SEQ ID NO: 288:

GAGAATTTTC TAAGTGCAGC ATA                                              23

(2) INFORMATION FOR SEQ ID NO: 289:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2615-83.mis2
        (B) LOCATION: 1..23

(xi) SEQUENCE DESCRIPTION: SEQ ID NO: 289:

TTCCCAGAAG ATGAGAATTT GCT                                              23

(2) INFORMATION FOR SEQ ID NO: 290:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2620-227.mis2
        (B) LOCATION: 1..23

(xi) SEQUENCE DESCRIPTION: SEQ ID NO: 290:

TTTTAACAGC CAGCAAGATA CCC                                              23

(2) INFORMATION FOR SEQ ID NO: 291:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2624-407.mis2
        (B) LOCATION: 1..23

(xi) SEQUENCE DESCRIPTION: SEQ ID NO: 291:

TTTTCTCTTT CCCCATCTCT CCC                                                23

(2) INFORMATION FOR SEQ ID NO: 292:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2625-70.mis2
        (B) LOCATION: 1..23

(xi) SEQUENCE DESCRIPTION: SEQ ID NO: 292:

TTTTCTCTCT TCKTCCTCTC TCC                                                23

(2) INFORMATION FOR SEQ ID NO: 293:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2630-67.mis2
        (B) LOCATION: 1..23

(xi) SEQUENCE DESCRIPTION: SEQ ID NO: 293:

TTTTACTCCC TGTTCTGGAC CAA                                                23

(2) INFORMATION FOR SEQ ID NO: 294:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2633-129.mis2
        (B) LOCATION: 1..23

(xi) SEQUENCE DESCRIPTION: SEQ ID NO: 294:

TCAAGGGTTC TCTCATTGTC TAC                                                23

(2) INFORMATION FOR SEQ ID NO: 295:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR

```
        (ii) MOLECULE TYPE: DNA (vi) ORIGINAL SOURCE:
             (A) ORGANISM: Homo sapiens (ix) FEATURE:
             (A) NAME/KEY:  microsequencing oligo 99-2634-341.mis2
             (B) LOCATION: 1..23

(xi) SEQUENCE DESCRIPTION: SEQ ID NO: 295:

TTTTTAAATA ATGTCTCACC TGT                                               23

(2) INFORMATION FOR SEQ ID NO: 296:

(i) SEQUENCE CHARACTERISTICS:
             (A) LENGTH: 23 base pairs
             (B) TYPE: NUCLEIC ACID
             (C) STRANDEDNESS: SINGLE
             (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY:  microsequencing oligo 99-2637-28.mis2
             (B) LOCATION: 1..23

(xi) SEQUENCE DESCRIPTION: SEQ ID NO: 296:

TTTTAAAACC CACCCTCCTT TGA                                               23

(2) INFORMATION FOR SEQ ID NO: 297:

(i) SEQUENCE CHARACTERISTICS:
             (A) LENGTH: 19 base pairs
             (B) TYPE: NUCLEIC ACID
             (C) STRANDEDNESS: SINGLE
             (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY:  microsequencing oligo 99-2642-255.mis2
             (B) LOCATION: 1..19

(xi) SEQUENCE DESCRIPTION: SEQ ID NO: 297:

TCACTTCAGA TTCAAATGC                                                    19

(2) INFORMATION FOR SEQ ID NO: 298:

(i) SEQUENCE CHARACTERISTICS:
             (A) LENGTH: 23 base pairs
             (B) TYPE: NUCLEIC ACID
             (C) STRANDEDNESS: SINGLE
             (D) TOPOLOGY: LINEAR (ii) MOLECULE TYPE: DNA (vi) ORIGINAL SOURCE:
             (A) ORGANISM: Homo sapiens (ix) FEATURE:
             (A) NAME/KEY:  microsequencing oligo 99-2645-118.mis2
             (B) LOCATION: 1..23

(xi) SEQUENCE DESCRIPTION: SEQ ID NO: 298:

TTTTCAGATT CTTCATTGCT AGC                                               23
```

(2) INFORMATION FOR SEQ ID NO: 299:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2647-368.mis2
        (B) LOCATION: 1..19

(xi) SEQUENCE DESCRIPTION: SEQ ID NO: 299:

AGATAATGTG AGTGGGCCT                                                19

(2) INFORMATION FOR SEQ ID NO: 300:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-2649-107.mis2
        (B) LOCATION: 1..23

(xi) SEQUENCE DESCRIPTION: SEQ ID NO: 300:

AGTTTCAGTG CATTGCTGTC CTG                                           23

(2) INFORMATION FOR SEQ ID NO: 301:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-344
        (B) LOCATION: 1..47

(ix) FEATURE:
        (A) NAME/KEY: polymorphic base
        (B) LOCATION: 24
        (D) OTHER INFORMATION: base a (ix) FEATURE:
        (A) NAME/KEY: Potential microsequencing oligo 99-344-mis1
        (B) LOCATION: 1..23

(ix) FEATURE:
        (A) NAME/KEY: microsequencing oligo 99-344-mis2
        (B) LOCATION: complement 25..43

(xi) SEQUENCE DESCRIPTION: SEQ ID NO: 301:

TGCTGCCAAG GATCCATGTC AGCATGCTCC TCTCTGAGCC CTGGTCT                 47

(2) INFORMATION FOR SEQ ID NO: 302:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-366
        (B) LOCATION: 1..47

(ix) FEATURE:
        (A) NAME/KEY: polymorphic base
        (B) LOCATION: 24
        (D) OTHER INFORMATION: base t (ix) FEATURE:
        (A) NAME/KEY: microsequencing oligo 99-366-mis1
        (B) LOCATION: 5..23

(ix) FEATURE:
        (A) NAME/KEY: Potential microsequencing oligo 99-366-mis2
        (B) LOCATION: complement 25..47

(xi) SEQUENCE DESCRIPTION: SEQ ID NO: 302:

AGGGCCTGGC TTCAGGGACA GCTTAGGAAA TGTTTGTTGA GTTAGTG          47

(2) INFORMATION FOR SEQ ID NO: 303:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-359
        (B) LOCATION: 1..47

(ix) FEATURE:
        (A) NAME/KEY: polymorphic base
        (B) LOCATION: 24
        (D) OTHER INFORMATION: base g (ix) FEATURE:
        (A) NAME/KEY: Potential microsequencing oligo 99-359-mis1
        (B) LOCATION: 1..23

(ix) FEATURE:
        (A) NAME/KEY: microsequencing oligo 99-359-mis2
        (B) LOCATION: complement 25..43

(xi) SEQUENCE DESCRIPTION: SEQ ID NO: 303:

CTACAGAGTC ATCGCCTCCA TCCGGTCTCA ACAAATCCTG GCAGCTC          47

(2) INFORMATION FOR SEQ ID NO: 304:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-355
            (B) LOCATION: 1..47

(ix) FEATURE:
            (A) NAME/KEY: polymorphic base
            (B) LOCATION: 24
            (D) OTHER INFORMATION: base g (ix) FEATURE:
            (A) NAME/KEY: Potential microsequencing oligo 99-355-mis1
            (B) LOCATION: 1..23

(ix) FEATURE:
            (A) NAME/KEY: microsequencing oligo 99-355-mis2
            (B) LOCATION: complement 25..43

(xi) SEQUENCE DESCRIPTION: SEQ ID NO: 304:

GGAGTTTCGG GGAGTTTCGG GAGGGTTCCT GGGAAGAAGC TCCTCCC                            47

(2) INFORMATION FOR SEQ ID NO: 305:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-365
            (B) LOCATION: 1..47

(ix) FEATURE:
            (A) NAME/KEY: polymorphic base
            (B) LOCATION: 24
            (D) OTHER INFORMATION: base c (ix) FEATURE:
            (A) NAME/KEY: microsequencing oligo 99-365-mis1
            (B) LOCATION: 5..23

(ix) FEATURE:
            (A) NAME/KEY: Potential microsequencing oligo 99-365-mis2
            (B) LOCATION: complement 25..47

(xi) SEQUENCE DESCRIPTION: SEQ ID NO: 305:

CCTACCAAGC AAGCAGCCCC AGCCTAGGGT CAGACAGGGT GAGCCTC                            47

(2) INFORMATION FOR SEQ ID NO: 306:

(i) SEQUENCE CHARACTERISTICS:
            (A) LENGTH: 47 base pairs
            (B) TYPE: NUCLEIC ACID
            (C) STRANDEDNESS: SINGLE
            (D) TOPOLOGY: LINEAR (ii) MOLECULE TYPE: DNA (vi) ORIGINAL SOURCE:
            (A) ORGANISM: Homo sapiens (ix) FEATURE:
            (A) NAME/KEY: polymorphic fragment 99-2452
            (B) LOCATION: 1..47

(D) OTHER INFORMATION: Extracted from sequence gb:M10065
            (3909..3955)

(ix) FEATURE:
        (A) NAME/KEY: polymorphic base
        (B) LOCATION: 24
        (D) OTHER INFORMATION: base c (ix) FEATURE:
        (A) NAME/KEY: microsequencing oligo 99-2452-mis1
        (B) LOCATION: 5..23

(ix) FEATURE:
        (A) NAME/KEY: Potential microsequencing oligo 99-2452-mis2
        (B) LOCATION: complement 25..47

(xi) SEQUENCE DESCRIPTION: SEQ ID NO: 306:

TGGGCGCGGA CATGGAGGAC GTGCGCGGCC GCCTGGTGCA GTACCGC                    47

(2) INFORMATION FOR SEQ ID NO: 307:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-344
        (B) LOCATION: 1..47
        (D) OTHER INFORMATION: variant version of SEQ ID301

(ix) FEATURE:
        (A) NAME/KEY: polymorphic base
        (B) LOCATION: 24
        (D) OTHER INFORMATION: base g; a in SEQ ID301

(ix) FEATURE:
        (A) NAME/KEY: Potential microsequencing oligo 99-344-mis1
        (B) LOCATION: 1..23

(ix) FEATURE:
        (A) NAME/KEY: microsequencing oligo 99-344-mis2
        (B) LOCATION: complement 25..43

(xi) SEQUENCE DESCRIPTION: SEQ ID NO: 307:

TGCTGCCAAG GATCCATGTC AGCGTGCTCC TCTCTGAGCC CTGGTCT                    47

(2) INFORMATION FOR SEQ ID NO: 308:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-366
        (B) LOCATION: 1..47
        (D) OTHER INFORMATION: variant version of SEQ ID302

(ix) FEATURE:
        (A) NAME/KEY: polymorphic base
        (B) LOCATION: 24
        (D) OTHER INFORMATION: base c; t in SEQ ID302

(ix) FEATURE:
        (A) NAME/KEY: microsequencing oligo 99-366-mis1
        (B) LOCATION: 5..23

(ix) FEATURE:
        (A) NAME/KEY: Potential microsequencing oligo 99-366-mis2
        (B) LOCATION: complement 25..47

(xi) SEQUENCE DESCRIPTION: SEQ ID NO: 308:

AGGGCCTGGC TTCAGGGACA GCTCAGGAAA TGTTTGTTGA GTTAGTG                    47

(2) INFORMATION FOR SEQ ID NO: 309:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-359
        (B) LOCATION: 1..47
        (D) OTHER INFORMATION: variant version of SEQ ID303

(ix) FEATURE:
        (A) NAME/KEY: polymorphic base
        (B) LOCATION: 24
        (D) OTHER INFORMATION: base a; g in SEQ ID303

(ix) FEATURE:
        (A) NAME/KEY: Potential microsequencing oligo 99-359-mis1
        (B) LOCATION: 1..23

(ix) FEATURE:
        (A) NAME/KEY: microsequencing oligo 99-359-mis2
        (B) LOCATION: complement 25..43

(xi) SEQUENCE DESCRIPTION: SEQ ID NO: 309:

CTACAGAGTC ATCGCCTCCA TCCAGTCTCA ACAAATCCTG GCAGCTC                    47

(2) INFORMATION FOR SEQ ID NO: 310:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-355
        (B) LOCATION: 1..47
        (D) OTHER INFORMATION: variant version of SEQ ID304

(ix) FEATURE:
        (A) NAME/KEY: polymorphic base
        (B) LOCATION: 24
        (D) OTHER INFORMATION: base a; g in SEQ ID304

(ix) FEATURE:
        (A) NAME/KEY: Potential microsequencing oligo 99-355-mis1
        (B) LOCATION: 1..23

(ix) FEATURE:
        (A) NAME/KEY: microsequencing oligo 99-355-mis2

(B) LOCATION: complement 25..43

(xi) SEQUENCE DESCRIPTION: SEQ ID NO: 310:

GGAGTTTCGG GGAGTTTCGG GAGAGTTCCT GGGAAGAAGC TCCTCCC                47

(2) INFORMATION FOR SEQ ID NO: 311:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-365
        (B) LOCATION: 1..47
        (D) OTHER INFORMATION: variant version of SEQ ID305

(ix) FEATURE:
        (A) NAME/KEY: polymorphic base
        (B) LOCATION: 24
        (D) OTHER INFORMATION: base t; c in SEQ ID305

(ix) FEATURE:
        (A) NAME/KEY: microsequencing oligo 99-365-mis1
        (B) LOCATION: 5..23

(ix) FEATURE:
        (A) NAME/KEY: Potential microsequencing oligo 99-365-mis2
        (B) LOCATION: complement 25..47

(xi) SEQUENCE DESCRIPTION: SEQ ID NO: 311:

CCTACCAAGC AAGCAGCCCC AGCTTAGGGT CAGACAGGGT GAGCCTC                47

(2) INFORMATION FOR SEQ ID NO: 312:

(i) SEQUENCE CHARACTERISTICS:
        (A) LENGTH: 47 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: polymorphic fragment 99-2452
        (B) LOCATION: 1..47
        (D) OTHER INFORMATION: variant version of SEQ ID306

(ix) FEATURE:
        (A) NAME/KEY: polymorphic base
        (B) LOCATION: 24
        (D) OTHER INFORMATION: base t; c in SEQ ID306

(ix) FEATURE:
        (A) NAME/KEY: microsequencing oligo 99-2452-mis1
        (B) LOCATION: 5..23

(ix) FEATURE:
        (A) NAME/KEY: Potential microsequencing oligo 99-2452-mis2
        (B) LOCATION: complement 25..47

(xi) SEQUENCE DESCRIPTION: SEQ ID NO: 312:

TGGGCGCGGA CATGGAGGAC GTGTGCGGCC GCCTGGTGCA GTACCGC                47

(2) INFORMATION FOR SEQ ID NO: 313:

(i) SEQUENCE CHARACTERISTICS:
        (A) LENGTH: 20 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID301 and
            SEQ ID307
        (B) LOCATION: 1..20

(xi) SEQUENCE DESCRIPTION: SEQ ID NO: 313:

GCTCTCATAT TCATTGGGTG                                                      20

(2) INFORMATION FOR SEQ ID NO: 314:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID302 and
            SEQ ID308
        (B) LOCATION: 1..18

(xi) SEQUENCE DESCRIPTION: SEQ ID NO: 314:

TCTCTCCCGT GTTAAATG                                                        18

(2) INFORMATION FOR SEQ ID NO: 315:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID303 and
            SEQ ID309
        (B) LOCATION: 1..18

(xi) SEQUENCE DESCRIPTION: SEQ ID NO: 315:

AATCTTCTTG CTCCTGTC                                                        18

(2) INFORMATION FOR SEQ ID NO: 316:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA -continued (vi) ORIGINAL SOURCE:
        (A) ORGANISM: Homo sapiens (ix) FEATURE:
        (A) NAME/KEY: upstream amplification primer for SEQ ID304 and
            SEQ ID310
        (B) LOCATION: 1..18

(xi) SEQUENCE DESCRIPTION: SEQ ID NO: 316:

AGGTTAGGGG TGTATTTC                                                    18

(2) INFORMATION FOR SEQ ID NO: 317:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID305 and
            SEQ ID311
        (B) LOCATION: 1..18

(xi) SEQUENCE DESCRIPTION: SEQ ID NO: 317:

AGACTGTGAC CTTAGACC                                                    18

(2) INFORMATION FOR SEQ ID NO: 318:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: upstream amplification primer for SEQ ID306 and
            SEQ ID312
        (B) LOCATION: 1..18
        (D) OTHER INFORMATION: Extracted from sequence gb:M10065
           (3791..3808)

(xi) SEQUENCE DESCRIPTION: SEQ ID NO: 31    8:

GACGAGACCA TGAAGGAG                                                    18

(2) INFORMATION FOR SEQ ID NO: 319:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID301
            and SEQ ID307
        (B) LOCATION: 1..19

-continued (xi) SEQUENCE DESCRIPTION: SEQ ID NO: 319:

TGGCTGCGGT TAGATGCTC                                              19

(2) INFORMATION FOR SEQ ID NO: 320:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID302
            and SEQ ID308
        (B) LOCATION: 1..18

(xi) SEQUENCE DESCRIPTION: SEQ ID NO: 320:

AGGGGTAACT CTTGATTG                                               18

(2) INFORMATION FOR SEQ ID NO: 321:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID303
            and SEQ ID309
        (B) LOCATION: 1..18

(xi) SEQUENCE DESCRIPTION: SEQ ID NO: 321:

ACCAAGGCAT AGCTTCTC                                               18

(2) INFORMATION FOR SEQ ID NO: 322:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID304
            and SEQ ID310
        (B) LOCATION: 1..18

(xi) SEQUENCE DESCRIPTION: SEQ ID NO: 322:

ATACAGCCAG GGAGATAG                                               18

(2) INFORMATION FOR SEQ ID NO: 323:

(i) SEQUENCE CHARACTERISTICS:
        (A) LENGTH: 18 base pairs
        (B) TYPE: NUCLEIC ACID

```
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID305
            and SEQ ID311
        (B) LOCATION: 1..18

(xi) SEQUENCE DESCRIPTION: SEQ ID NO: 323:

AATTGCTACC CCCAATTC                                                18

(2) INFORMATION FOR SEQ ID NO: 324:

(i) SEQUENCE CHARACTERISTICS:
        (A) LENGTH: 18 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: downstream amplification primer for SEQ ID306
            and SEQ ID312
        (B) LOCATION: 1..18
        (D) OTHER INFORMATION: Extracted from sequence gb:M10065
            (complement 4378..4395)

(xi) SEQUENCE DESCRIPTION: SEQ ID NO: 324:

TCGAACCAGC TCTTGAGG                                                18

(2) INFORMATION FOR SEQ ID NO: 325:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  potential microsequencing oligo 99-344.mis1
        (B) LOCATION: 1..23

(xi) SEQUENCE DESCRIPTION: SEQ ID NO: 325:

TGCTGCCAAG GATCCATGTC AGC                                          23

(2) INFORMATION FOR SEQ ID NO: 326:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
```

-continued (A) NAME/KEY: microsequencing oligo 99-366.mis1
        (B) LOCATION: 1..19

(xi) SEQUENCE DESCRIPTION: SEQ ID NO: 326:

CCTGGCTTCA GGGACAGCT                                                19

(2) INFORMATION FOR SEQ ID NO: 327:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-359.mis1
        (B) LOCATION: 1..23

(xi) SEQUENCE DESCRIPTION: SEQ ID NO: 327:

CTACAGAGTC ATCGCCTCCA TCC                                           23

(2) INFORMATION FOR SEQ ID NO: 328:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: potential microsequencing oligo 99-355.mis1
        (B) LOCATION: 1..23

(xi) SEQUENCE DESCRIPTION: SEQ ID NO: 328:

GGAGTTTCGG GGAGTTTCGG GAG                                           23

(2) INFORMATION FOR SEQ ID NO: 329:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY: microsequencing oligo 99-365.mis1
        (B) LOCATION: 1..19

(xi) SEQUENCE DESCRIPTION: SEQ ID NO: 329:

CCAAGCAAGC AGCCCCAGC                                                19

(2) INFORMATION FOR SEQ ID NO: 330:

(i) SEQUENCE CHARACTERISTICS:
        (A) LENGTH: 19 base pairs
        (B) TYPE: NUCLEIC ACID

```
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-2452.mis1
        (B) LOCATION: 1..19

(xi) SEQUENCE DESCRIPTION: SEQ ID NO: 330:

CGCGGACATG GAGGACGTG                                                       19

(2) INFORMATION FOR SEQ ID NO: 331:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-344.mis2
        (B) LOCATION: 1..19

(xi) SEQUENCE DESCRIPTION: SEQ ID NO: 331:

CAGGGCTCAG AGAGGAGCA                                                       19

(2) INFORMATION FOR SEQ ID NO: 332:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  potential microsequencing oligo 99-366.mis2
        (B) LOCATION: 1..23

(xi) SEQUENCE DESCRIPTION: SEQ ID NO: 332:

CACTAACTCA ACAAACATTT CCT                                                  23

(2) INFORMATION FOR SEQ ID NO: 333:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-359.mis2
        (B) LOCATION: 1..19

(xi) SEQUENCE DESCRIPTION: SEQ ID NO: 333:
```

```
TGCCAGGATT TGTTGAGAC                                                      19

(2) INFORMATION FOR SEQ ID NO: 334:

(i) SEQUENCE CHARACTERISTICS:
        (A) LENGTH: 19 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:  microsequencing oligo 99-355.mis2
        (B) LOCATION: 1..19

(xi) SEQUENCE DESCRIPTION: SEQ ID NO: 334:

GGAGCTTCTT CCCAGGAAC                                                      19

(2) INFORMATION FOR SEQ ID NO: 335:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:   potential microsequencing oligo 99-365.mis2
        (B) LOCATION: 1..23

(xi) SEQUENCE DESCRIPTION: SEQ ID NO: 335:

GAGGCTCACC CTGTCTGACC CTA                                                 23

(2) INFORMATION FOR SEQ ID NO: 336:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: DNA (vi) ORIGINAL SOURCE:
        (A) ORGANISM: Homo sapiens (ix) FEATURE:
        (A) NAME/KEY:   potential microsequencing oligo 99-2452.mis2
        (B) LOCATION: 1..23

(xi) SEQUENCE DESCRIPTION: SEQ ID NO: 336:

GCGGTACTGC ACCAGGCGGC CGC                                                 23
```

METHODS OF IDENTIFYING INDIVIDUALS FOR INCLUSION IN DRUG STUDIES

BACKGROUND OF THE INVENTION

Recent advances in genetic engineering and bioinformatics have enabled the manipulation and characterization of large portions of the human genome. While efforts to obtain the full sequence of the human genome are rapidly progressing, there are many practical uses for genetic information which can be implemented with partial knowledge of the sequence of the human genome.

As the full sequence of the human genome is assembled, the partial sequence information available can be used to identify genes responsible for detectable human traits, such as genes associated with human diseases, and to develop diagnostic tests capable of identifying individuals who express a detectable trait as the result of a specific genotype or individuals whose genotype places them at risk of developing a detectable trait at a subsequent time. Each of these applications for partial genomic sequence information is based upon the assembly of genetic and physical maps which order the known genomic sequences along the human chromosomes.

The present invention relates to human genomic sequences which can be used to construct a high resolution map of the human genome, methods for constructing such a map, methods of identifying genes associated with detectable human traits, and diagnostics for identifying individuals who carry a gene which causes them to express a detectable trait or which places them at risk of expressing a detectable trait in the future.

SUMMARY OF THE INVENTION

A first embodiment of the present invention is a method of obtaining a set of biallelic markers comprising the steps of obtaining a nucleic acid library comprising a plurality of genomic DNA fragments comprising the full genome or a portion thereof, determining the order of said plurality of genomic DNA fragments in the genome, determining the sequence of selected regions of said plurality of genomic DNA fragments, and identifying nucleotides in said plurality of genomic DNA fragments which vary between individuals, thereby defining a set of biallelic markers.

In one aspect of this first embodiment, the identifying step comprises identifying about 20,000 biallelic markers. In another aspect of this first embodiment, the identifying step comprises identifying about 40,000 biallelic markers. In a further aspect of this embodiment, the identifying step comprises identifying about 60,000 biallelic markers. In still another aspect of this first embodiment, the identifying stop comprises identifying about 80,000 biallelic markers. In still another aspect of this first embodiment, the identifying step comprises identifying about 100,000 biallelic markers. In still another aspect of this first embodiment the identifying step comprises identifying about 120,000 biallelic markers.

In still another aspect of this first embodiment, the biallelic markers are separated from one another by an average distance of 10 kb–200 kb. In still another aspect of this first embodiment, the biallelic markers are separated from one another by an average distance of 15 kb–150 kb. In still another aspect of this first embodiment the biallelic markers are separated from one another by an average distance of 20 kb–100 kb. In still another aspect of this first embodiment, the biallelic markers are separated from one another by an average distance of 100 kb–150 kb. In still another aspect of this first embodiment, the biallelic markers are separated from one another by an average distance of 50–100 kb. In still another aspect of this first embodiment, the biallelic markers are separated from one another by an average distance of 25 kb–50 kb.

In still another aspect of this first embodiment, the step of determining the sequence of selected regions of said plurality of genomic DNA fragments comprises inserting fragments of said plurality of genomic DNA fragments into a vector to generate a plurality of subclones and determining the sequence of a region of the inserts in said plurality of subclones or a subset thereof. For example, in this aspect of the first embodiment, the step of determining the sequence of a region of said inserts or a subset thereof may comprise determining the sequence of one or both end regions of said inserts or a subset thereof. In this aspect of the first embodiment, the step of determining the sequence of one or both end regions of said plurality of subclones comprises determining the sequence of about 500 bases at each end of said subclones or a subset thereof.

In still another aspect of this first embodiment, a set of about 10,000 to about 20,000 genomic DNA inserts with an average size between 100 kb and 300 kb are ordered. In still another aspect of this first embodiment, a set of about 10,000 to about 30,000 genomic DNA inserts with an average size between 100 kb and 150 kb are ordered. In still another aspect of this first embodiment, a set of about 15,000 to about 25,000 genomic DNA inserts with an average size between 100 kb and 200 kb are ordered.

In still another aspect of this first embodiment, the identifying step comprises identifying between 1 and 6 biallelic markers per genomic DNA fragment. In still another aspect of this first embodiment, the identifying step comprises identifying an average of 3 biallelic markers per genomic DNA insert.

In still another aspect of this first embodiment, the genomic DNA fragments are in a Bacterial Artificial Chromosome. In still another aspect of this first embodiment the genomic DNA fragments are in a Yeast Artificial Chromosome.

In still another aspect of this first embodiment, the method further comprises determining the position of said biallelic markers along the genome or a portion thereof. In this aspect of the first embodiment, the step of determining the position of said biallelic markers along the genome or portion thereof may comprise determining the position of said biallelic markers along a chromosome. In this aspect of the first embodiment, the step of determining the position of said biallelic markers along the genome or portion thereof comprises determining the position of said biallelic markers along a subchromosomal region.

In still another aspect of this first embodiment, the method further comprises identifying biallelic markers which are in linkage disequilibrium with one another. In this aspect of the first embodiment, the method may further comprise optimizing the intermarker spacing between said biallelic markers such that each identified marker is in linkage disequilibrium with at least one other identified marker.

In still another aspect of this first embodiment, the portion of the genome comprises at least 200 kb of contiguous genomic DNA. In still another aspect of this first embodiment, the portion of the genome comprises at least 300 kb of contiguous genomic DNA. In still another aspect of this first embodiment, the portion of the genome comprises at least 500 kb of contiguous genomic DNA. In still another aspect of this first embodiment, the portion of the genome comprises at least 2 Mb of contiguous genomic DNA. In still another aspect of this first embodiment, the portion of the genome comprises at least 5 Mb of contiguous genomic DNA. In still another aspect of this first embodiment, the portion of the genome comprises at least 10 Mb of contiguous genomic DNA. In still another aspect of this first embodiment, the portion of the genome comprises at least 20 Mb of contiguous genomic DNA.

In still another aspect of this first embodiment, the method further comprises the step of identifying one or more groups of biallelic markers which are in proximity to one another in the genome. In this aspect of the first embodiment, the biallelic markers in each of these groups may be located within a genomic region spanning less than 1 kb. Alternatively, in this aspect of the first embodiment, the biallelic markers in each of these groups may be located within a genomic region spanning from 1 to 5 kb. Alternatively, in this aspect of the first embodiment, the biallelic markers in each of these groups may be located within a genomic region spanning from 5 to 10 kb. Alternatively, in this aspect of the first embodiment, the biallelic markers in each of these groups may be located within a genomic region spanning from 10 to 25 kb. Alternatively, in this aspect of the first embodiment, the biallelic markers in each of these groups may be located within a genomic region spanning from 25 to 50 kb. Alternatively, in this aspect of the first embodiment, the biallelic markers in each of these groups may be located within a genomic region spanning from 50 to 150 kb. Alternatively, in this aspect of the first embodiment, the biallelic markers in each if these groups may be located within a genomic region spanning from 150 to 250 kb. Alternatively, in this aspect of the first embodiment, the biallelic markers in each of these groups may be located within a genomic region spanning from 250 to 500 kb. Alternatively, in this aspect of the first embodiment, the biallelic markers in each of these groups may be located within a genomic region spanning from 500 kb to 1 Mb. Alternatively, in this aspect of the first embodiment, the biallelic markers in each of these groups may he located within a genomic region spanning more than 1 Mb.

A second embodiment of the present invention is a method of obtaining a set of biallelic markers comprising the steps of obtaining a nucleic acid library comprising genomic DNA fragments comprising the full genome or a portion thereof, determining the sequence of selected regions of said genomic DNA fragments, identifying nucleotides in said genomic DNA fragments which vary between individuals, thereby defining a set of biallelic markers, and determining the order of said biallelic markers along the genome or portion thereof.

A third embodiment of the present invention is a set of biallelic markers obtained by the method of the first embodiment. In one aspect of this third embodiment, the markers in said set have a known genomic position. In another aspect of this third embodiment, the markers in said set have a known genomic relationship to one another.

A fourth embodiment of the present invention is a set of biallelic markers having a known relationship to one another and a known genomic position, said set of biallelic markers being obtained by the method of the first embodiment. In one aspect of this fourth embodiment, the biallelic markers have heterozygosity rates of at least about 0.18. In another aspect of this fourth embodiment, the biallelic markers have heterozygosity rate of at least about 0.32. In still another aspect of this fourth embodiment, the biallelic markers have a heterozygosity rate of at least about 0.42.

A fifth embodiment of the present invention is a map comprising an ordered array of at least 20,000 biallelic markers obtained by the method of the first embodiment. In one aspect of this fifth embodiment, the map comprises an ordered array of at least 60,000 biallelic markers obtained by the method of the first embodiment. In another aspect of this fifth embodiment, the map comprises an ordered array of at least 120,000 biallelic markers obtained by the method of the first embodiment.

In another aspect of this fifth embodiment, biallelic markers are distributed at an average marker density of one marker every 150 kb. In a further aspect of this fifth embodiment, the biallelic markers are distributed at an average marker density of one marker every 50 kb. In a further aspect of this fifth embodiment, the biallelic markers are distributed at an average marker density of one marker every 25 kb.

A sixth embodiment of the present invention is a method of identifying one or more biallelic markers associated with a detectable trait comprising the steps of determining the frequencies of each allele of one or more biallelic markers obtained by the method of the first embodiment in individuals who express said detectable trait and individuals who do not express said detectable trait, and identifying one or more alleles of said one or more biallelic markers which are statistically associated with the expression of said detectable trait. In one aspect of this sixth embodiment, the detectable trait is selected from the group consisting of disease, drug response, drug efficacy, and drug toxicity. In another aspect of this sixth embodiment, the phenotype of said individuals who express said detectable trait and the phenotype of said individuals who do not express said detectable trait are readily distinguishable from one another. In still another aspect of this sixth embodiment the individuals who express said detectable trait and the individuals who do not express said detectable trait are selected from a bimodal phenotype distribution. In still another aspect of this sixth embodiment, the individuals who express said detectable trait are at one phenotypic extreme of the population and said individuals who do not express said detectable trait are at the other phenotypic extreme of the population.

A seventh embodiment of the present invention is a method of identifying a haplotype associated with a trait comprising the steps of obtaining nucleic acid samples from trait positive and trait negative individuals, determining the frequencies of the alleles of each member of a group of biallelic markers obtained by the method of the first embodiment which are known to be located proximity to one another in the genome in said nucleic acid samples, and identifying a plurality of alleles of biallelic markers having a statistically significant association with said trait. In one aspect of this seventh embodiment, the detectable trait is selected from the group consisting of disease, drug response, drug efficacy, and drug toxicity.

In another aspect of this seventh embodiment, the biallelic markers in each of these groups are located within a genomic region spanning less than 1 kb. In still another aspect of this seventh embodiment, the biallelic markers in each of these groups are located within a genomic region spanning from 1 to 5 kb. In still another aspect of this seventh embodiment, the biallelic markers in each of these groups are located within a genomic region spanning from 5 to 10 kb. In still another aspect of this seventh embodiment, the biallelic markers in each of these groups are located within a genomic region spanning from 10 to 25 kg. In still another aspect of this seventh embodiment, the biallelic markers in each of these groups are located within a genomic region spanning from 25 to 50 kb. In still another aspect of this seventh embodiment, the biallelic markers in each of these groups are located within a genomic region spanning from 50 to 150 kb. In still another aspect of this seventh embodiment, the biallelic markers in each of these groups are located within a genomic region spanning from 150 to 250 kb. In still another aspect of this seventh embodiment, the biallelic markers in each of these groups are located within a genomic region spanning from 250 to 500 kb. In still another aspect of this seventh embodiment, the biallelic markers in each of these groups are located within a genomic region spanning from 500 kb to 1 Mb. In still another aspect of this seventh embodiment, the biallelic markers in each of these groups are located within a genomic region spanning more than 1 Mb.

An eighth embodiment of the present invention is a method of identifying one or more biallelic markers associated with a detectable trait comprising the steps of selecting a gene in which mutations result in a detectable trait or a gene suspected of being associated with a detectable trait and identifying one or more biallelic markers obtained by the method of claim 1 within the genomic region harboring said gene which are associated with said detectable trait. In one aspect of this eighth embodiment, the detectable trait is selected from the group consisting of disease, drug response, drug efficacy, and drug toxicity. In another aspect of this eighth embodiment, the identifying step comprises determining the frequencies of said one or more biallelic markers in individuals who express said detectable trait and individuals who do not express said detectable trait and identifying one or more biallelic markers which are statistically associated with the expression of said detectable trait.

A ninth embodiment of the present invention is an array of nucleic acids fixed to a support, said nucleic acids comprising at least 8 consecutive nucleotides, including the polymorphic nucleotide, of one or more biallelic markers obtained by the method of the first embodiment. In one aspect of this ninth embodiment, the nucleic acids comprise at least 15 consecutive nucleotides, including the polymorphic nucleotide, of at least five biallelic markers obtained by the method of the first embodiment. In another aspect of this ninth embodiment, the nucleic acids comprise at least 8 consecutive nucleotides, including the polymorphic nucleotide, of at least ten biallelic markers obtained by the method of the first embodiment.

A tenth embodiment of the present invention is an array of nucleic acids fixed to a support, said nucleic acids comprising at least 8 consecutive nucleotides, including the polymorphic nucleotide, of one or more groups of biallelic markers known to be located in proximity to one another in the genome.

An eleventh embodiment of the present invention is an array of nucleic acids fixed to a support, said nucleic acids comprising amplification primers for generating an amplification product comprising at least 8 consecutive nucleotides, including the polymorphic nucleotide, of one or more biallelic markers obtained by the method of the first embodiment.

A twelfth embodiment of the present invention is an array of nucleic acids fixed to a support, said nucleic acids of comprising amplification primers for generating an amplification product comprising at least 15 consecutive nucleotides, including the polymorphic nucleotide, of one or more groups of biallelic markers known to be located in proximity to one another in the genome.

A thirteenth embodiment of the present invention is an array of nucleic acids fixed to a support, said nucleic acids comprising one or more microsequencing primers for determining the identity of the polymorphic base of one or more nucleic acids comprising at least 15 consecutive nucleotides, including the polymorphic nucleotide, of one or more biallelic markers obtained by the method of the first embodiment.

A fourteenth embodiment of the present invention is an array of nucleic acids fixed to a support, said nucleic nucleic acids comprising one or more microsequencing primers for determining the identity of the polymorphic bases of one or more groups of biallelic markers known to be located in proximity to one another in the genome.

A fifteenth embodiment of the present invention is an array of nucleic acids fixed to a support, wherein said nucleic acids are complementary to one or more microsequencing primers for determining the identities of the polymorphic bases of one or more biallelic markers obtained by the method of the first embodiment. In one aspect of this fifteenth embodiment, the nucleic acids are complementary to at least five microsequencing primers for determining the identities of the polymorphic bases of at least five biallelic markers obtained by the method of five first embodiment. In another aspect of this fifteenth embodiment, the nucleic acids are complementary to at least ten microsequencing primers for determining the identities of the polymorphic bases of at least ten biallelic markers obtained by the method of the first embodiment.

A sixteenth embodiment of the present invention is an array of nucleic acids fixed to a support, said nucleic acids comprising one or more nucleic acids complementary to one or more microsequencing primers for determining the identity of the polymorphic bases of one or more groups of biallelic markers known to be located in proximity to one another in the genome.

Another aspect of the present invention is an array of any one of the tenth, twelfth, fourteenth or sixteenth embodiments, wherein the members of each of said one or more groups of biallelic markers are located in physical proximity to one another on said support.

Another aspect of the present invention is an array of any one of claims of the tenth, twelfth, fourteenth or sixteenth embodiments, wherein said biallelic markers in each of these groups are located within a genomic region spanning less than 1 kb.

Another aspect of the present invention is an array of any one of the tenth, twelfth, fourteenth or sixteenth embodiments, wherein said biallelic markers in each of these groups are located within a genomic region spanning from 1 to 5 kb.

Another aspect of the present invention is an array of any one of the tenth, twelfth, fourteenth or sixteenth embodiments, wherein the biallelic markers in each of these groups are located within a genomic region spanning from 5 to 10 kb.

Another aspect of the present invention is an array of any one of of the tenth, twelfth, fourteenth or sixteenth embodiments, wherein the biallelic markers in each of these groups are located within a genomic region spanning from 10 to 25 kb.

Another aspect of the present invention is an array of any one of of the tenth, twelfth, fourteenth or sixteenth embodiments, wherein the biallelic markers in each of these groups are located within a genomic region spanning from 25 to 50 kb.

Another aspect of the present invention is an array of any one of of the tenth, twelfth, fourteenth or sixteenth embodiments, wherein the biallelic markers in each of these groups are located within a genomic region spanning from 50 to 150 kb.

Another aspect of the present invention is an array of any one of of the tenth, twelfth, fourteenth or sixteenth embodiments, wherein the biallelic markers in each of these groups are located within a genomic region spanning from 150 to 250 kb.

Another aspect of the present invention is an array of any one of of the tenth, twelfth, fourteenth or sixteenth embodiments, wherein the biallelic markers in each of these groups are located within a genomic region spanning from 250 to 500 kb.

Another aspect of the present invention is an array of any one of of the tenth, twelfth, fourteenth or sixteenth embodiments, wherein the biallelic markers in each of these groups are located within a genomic region spanning from 500 kb to 1 Mb.

Another aspect of the present invention is an array of any one of of the tenth, twelfth, fourteenth or sixteenth embodiments, wherein the biallelic markers in each of these groups are located within a genomic region spanning more than 1 Mb.

Another aspect of the present invention is an array of any one of of the tenth, twelfth, fourteenth or sixteenth embodiments, wherein each group of biallelic markers comprises at least 3 biallelic markers.

Another aspect of the present invention is an array of any one of of the tenth, twelfth, fourteenth or sixteenth embodiments, wherein each group of biallelic markers comprises at least 6 biallelic markers.

Another aspect of the present invention is an array of any one of of the tenth, twelfth, fourteenth or sixteenth embodiments, wherein each group of biallelic markers comprises at least 20 biallelic markers.

A seventeenth embodiment of the present invention is a method for determining whether an individual is at risk of developing a detectable trail or suffers from a detectable trait associated with said trait comprising the steps of obtaining a nucleic acid sample from said individual, screening said nucleic acid sample with one or more biallelic markers obtained by the method of the first embodiment, and determining whether said nucleic acid sample contains one or more of biallelic markers statistically associated with said detectable trait. I one aspect of this seventeenth embodiment, the detectable trait is selected from the group consisting of disease, drug response, drug efficacy and drug toxicity. In another aspect of this seventeenth embodiment the biallelic markers were obtained by the method of the sixth embodiment. In another aspect of this seventeenth embodiment, the biallelic markers were obtained by the method of the eighth embodiment.

An eighteenth embodiment of the present invention is a method of using a drug comprising obtaining a nucleic acid sample from an individual, determining the identity of the polymorphic base of one or more biallelic markers obtained by the method of the first embodiment which is associated with a positive response to treatment with said drug or one or more biallelic markers obtained by the method of the first embodiment which is associated with a negative response to treatment with said drug, and administering said drug to said individual if said nucleic acid sample contains one or more biallelic markers associated with a positive response to treatment with said drug or if said nucleic acid sample lacks one or more biallelic markers associated with a negative response to said drug. In one aspect of this eighteenth embodiment, the determining step comprises determining the identity of the polymorphic base of one or more biallelic markers obtained by the method of the aspect of the sixth embodiment wherein the trait is drug response which is associated with a positive response to treatment with said drug or one or more biallelic markers obtained by the aspect of the sixth embodiment wherein the trait is drug response which is associated with a negative response to treatment with said drug. In another aspect of this eighteenth embodiment, the determining step comprises determining the identity of the polymorphic base of one or more biallelic markers obtained by the aspect of the eighth embodiment wherein the trait is drug response which is associated with a positive response to treatment with said drug or one or more biallelic markers obtained by the method of the aspect of the eighth embodiment wherein the trait is drug response which is associated with a negative response to treatment with said drug.

A nineteenth embodiment of the present invention is a method of selecting an individual for inclusion in a clinical trial of a drug comprising obtaining a nucleic acid sample from an individual, determining the identity of the polymorphic base of one or more biallelic markers obtained by the method of the first embodiment which is associated with a positive response to treatment with said drug or one or more biallelic markers associated with a negative response to treatment with said drug in said nucleic acid sample, and including said individual in said clinical trial if said nucleic acid sample contains one or more biallelic markers obtained by the method of the first embodiment which is associated with a positive response to treatment with said drug or if said nucleic acid sample lacks one or more biallelic markers associated with a negative response to said drug. In one aspect of this nineteenth embodiment, the determining step comprises determining the identity of the polymorphic base of one or more biallelic markers obtained by the aspect of the sixth embodiment wherein the trait is drug response which is associated with a positive response to treatment with said drug or one or more biallelic markers obtained by the aspect of the sixth embodiment wherein the trait is drug respons which is associated with a negative response to treatment with said drug. In another aspect of this nineteenth embodiment, the determining step comprises determining the identity of the polymorphic base of one or more biallelic markers obtained by the aspect of the eighth embodiment wherein the trait is drug response which is associated with a positive response to treatment with said drug or one or more biallelic markers obtained by the aspect of the eighth embodiment wherein the trait is drug response which is associated with a negative response to treatment with said drug.

A twentieth embodiment of the present invention is a method of identifying a gene associated with a detectable trait comprising the steps of determining the frequency of each allele of one or more biallelic markers obtained by the method of the first embodiment in individuals having said detectable trait and individuals lacking said detectable trait, identifying one or more alleles of one or more biallelic markers having a statistically significant association with said detectable trait, and identifying a gene in linkage disequilibrium with said one or more alleles. In one aspect of this twentieth embodiment, the method further comprises identifying a mutation in the gene which is associated with said detectable trait. In another aspect of this twentieth embodiment, the detectable trait is selected from the group consisting of disease, drug response, drug efficacy, and drug toxicity.

A twenty-first embodiment of the present invention is a method of identifying a gene associated with a detectable trait comprising selecting a gene suspected of being associated with a detectable trait and identifying one or more biallelic markers obtained by the method of the first embodiment within the genomic region harboring said gene which are associated with said detectable trait. In one aspect of this twenty-first embodiment, the detectable trait is selected from the group consisting of disease, drug response, drug efficacy, and drug toxicity. In another aspect of this twenty-first embodiment, the identifying step comprises determining the frequencies of said one or more biallelic markers in individuals who express said detectable trait and individuals who do not express said detectable trait and identifying one or more biallelic markers which are statistically associated with the expression of said detectable trait.

A twenty-second embodiment of the present invention is a method of identifying a haplotype associated with a trait comprising the steps of obtaining nucleic acid samples from trait positive and trait negative individuals, conducting an amplification reaction of said nucleic acid samples using amplification primers capable of generating amplification products containing the polymorphic bases of a plurality of biallelic markers, contacting one or more arrays according to the tenth embodiment with said amplification products, determining the identities of the polymorphic bases of said amplification products, and identifying a haplotype having a statistically significant association with said trait.

A twenty-third embodiment of the present invention is a method of identifying a haplotype associated with a trait comprising the steps of obtaining nucleic acid samples from trait positive and trait negative individuals, conducting amplification reactions on said nucleic acid samples using amplification primers capable of generating amplification products containing the polymorphic bases of a plurality of biallelic markers, contacting one or more arrays according to the fourteenth embodiment with said amplification products, conducting microsequencing reactions on said amplification products using microsequencing primers on said arrays, thereby generating elongated microsequencing primers comprising the polymorphic bases of said amplification products, determining the identities of said polymorphic bases, and identifying a haplotype having a statistically significant association with said trait.

A twenty-fourth embodiment of the present invention is a method of identifying a haplotype associated with a trait comprising the steps of obtaining nucleic acid samples from trait positive and trait negative individuals, conducting amplification reactions on said nucleic acid samples using amplification primers which are capable of generating amplification products containing the polymorphic bases of a plurality of biallelic markers, conducting microsequencing reactions on said nucleic acid samples, thereby generating microsequencing products containing the polymorphic bases of one or more biallelic markers at their 3' ends, said polymorphic bases being detectably labeled, contacting one or more arrays according to the sixteenth embodiment with said microsequencing products such that said microsequencing products specifically hybridize to said nucleic acids complementary to said microsequencing primers, determining the identities of the polymorphic bases of said microsequencing products, and identifying a haplotype having a statistically significant association with said trait.

A twenty-fifth embodiment of the present invention is a method of identifying a haplotype associated with a trait comprising the steps of obtaining nucleic acid samples from trait positive and trait negative individuals, contacting one or more arrays according to the twelfth embodiment with said nucleic acid sample, conducting an amplification reaction on said nucleic acid samples using amplification primers on said array which are capable of generating amplification products containing the polymorphic bases of a plurality of biallelic markers, determining the identities of the polymorphic bases of said amplification products, and identifying a haplotype having a statistically significant association with said trait.

A twenty-sixth embodiment of the present invention is a method of determining whether an individual is at risk of developing Alzheimer's disease or whether the individual suffers from Alzheimer's disease as a result of possessing the Apo E ε4 Site A allele comprising obtaining a nucleic acid sample from said individual, and determining the identity of the polymorphic base in one or more of the sequences selected from the group consisting of SEQ ID Nos. 301–305 and SEQ ID Nos. 307–311 or the sequences complementary thereto in said nucleic acid sample. In one aspect of this twenty-sixth embodiment, the method further comprises determining whether said nucleic acid sample contains the sequence of SEQ ID No. 306 or the sequence complementary thereto. In another aspect of this twenty-sixth embodiment, the step of determining the identity of the polymorphic bases in one or more of the sequences selected from the group consisting of SEQ ID Nos. 301–305 and SEQ ID Nos. 307–311 or the sequences complementary thereto comprises determining whether said nucleic acid sample contains the sequence of SEQ ID NO. 311 (the T allele of marker 99-365/344) or the sequence complementary thereto. In another version of the preceding aspect, the further comprises determining whether said nucleic acid sample contains the sequence of SEQ ID No. 306 or the sequence complementary thereto.

A twenty-seventh embodiment of the present invention is an isolated nucleic acid comprising a sequence selected from the group consisting of SEQ ID No. 301, SEQ ID No. 307, the sequences complementary thereto, and fragments comprising at least 8 consecutive nucleotides, including the polymorphic nucleotide, thereof.

A twenty-eighth embodiment of the present invention is an isolated nucleic acid comprising a sequence selected from the group consisting of SEQ ID No. 302 SEQ ID No. 308, the sequences complementary thereto, and fragments comprising at least 8 consecutive nucleotides thereof.

A twenty-ninth embodiment of the present invention is an isolated nucleic acid comprising a sequence selected from the group consisting of SEQ ID No. 303, SEQ ID No. 309, the sequences complementary thereto, and fragments comprising at least 3 consecutive nucleotides, including the polymorphic nucleotide, thereof.

A thirtieth embodiment of the present invention is an isolated nucleic acid comprising a sequence selected from the group consisting of SEQ ID No. 304, SEQ ID No. 310 , the sequences complementary thereto, and fragments comprising at least 8 consecutive nucleotides, including the polymorphic nucleotide, thereof.

A thirty first embodiment of the present invention is an isolated nucleic acid comprising a sequence selected from the group consisting of SEQ ID No. 305, SEQ ID No. 311, the sequences complementary thereto, and fragments comprising at least 8 consecutive nucleotides, including the polymorphic nucleotide, thereof.

A thirty second embodiment of the present invention is an isolated nucleic acid comprising a sequence selected from the group consisting of SEQ ID Nos. 313–317, SEQ ID Nos. 319–323, and fragments comprising at least 8 consecutive nucleotides thereof.

A thirty third embodiment of the present invention is isolated nucleic acid comprising a sequence selected from the group consisting of SEQ ID Nos. 325–329, SEQ ID Nos. 331–335, the sequence complementary thereto, and fragments comprising at least 8 consecutive nucleotides thereof.

A thirty fourth embodiment of the present invention is set of nucleic acids comprising at least 8 consecutive nucleotides, including the polymorphic nucleotide, of one or more biallelic markers obtained by the method of the first embodiment.

A thirty fifth embodiment of the present invention is a set of nucleic acids comprising amplification primers for generating an amplification product comprising at least 8 consecutive nucleotides, including the polymorphic nucleotide, of one at more biallelic markers obtained by the method of the first embodiment.

A thirty sixth embodiment of the present invention is a set of nucleic acids comprising one or more microsequencing primers for determining the identity of the polymorphic base of one or more nucleic acids comprising at least 8 consecutive nucleotides, including the polymorphic nucleotide, of one or more biallelic markers obtained by the method of the first embodiment.

BRIEF DESCRIPTION OF THE DRAWINGS

FIG. 3 shows, for a series of hypothetical sample sizes, the p-value significance obtained in association studies performed using individual markers from the high-density biallelic map, according to various hypotheses regarding the difference of allelic frequencies between the T+ and T− samples.

FIG. 7 is a haplotype analysis using biallelic markers in the Apo E region.

FIG. 12 is a haplotype analysis using the biallelic markers in the genomic region of the gene associated with prostate cancer.

FIG. 13 is a simulated haplotype using the six markers included in haplotype 5 of FIG. 12

DETAILED DESCRIPTION OF THE PREFERRED EMBODIMENT

Figure 1:
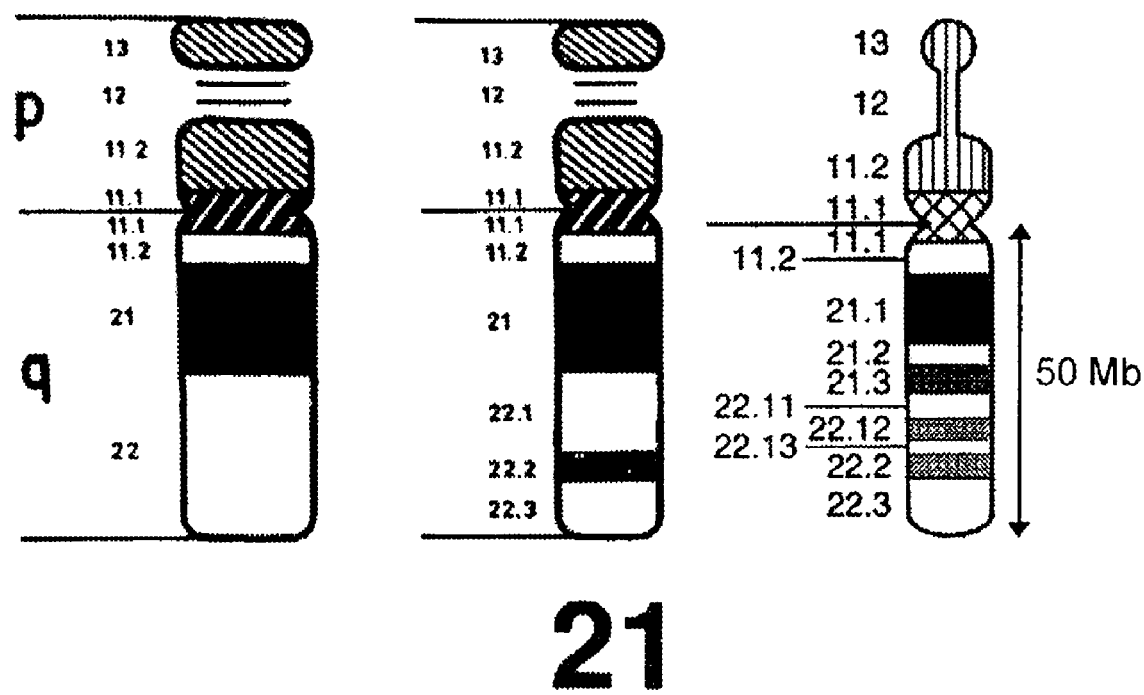
FIG. 1 is a cytogenetic map of chromosome 21.

The human haploid genome contains an estimated 80,000 to 100,000 or more genes scattered on a $3\times10^9$ base-long double stranded DNA shared among the 24 chromosomes. Each human being is diploid, i.e. possesses two haploid genomes, one from paternal origin, the other from maternal origin. The sequence of the human genome varies among individuals in a population. About $10^7$ sites scattered along the $3\times10^9$ base pairs at DNA are polymorphic, existing in at least two variant forms called alleles. Most of these polymorphic sites are generated by single base substitution mutations and are biallelic. Less than $10^5$ polymorphic sites are due to more complex changes and are very often multi-allelic, i.e. exist in more than two allelic forms. At a given polymorphic site, any individual (diploid), can be either homozygous (twice the same allele) or heterozygous (two different alleles). A given polymorphism or rare mutation can be either neutral (no effect on trail), or functional, i.e. responsible for a particular genetic trail.

Genetic Maps

The first step towards the identification of genes associated with a detectable trait, such as a disease or any other detectable trait, consists in the localization of genomic regions containing trait-causing genes using genetic mapping methods. The preferred traits contemplated within the present invention relate to fields of therapeutic interest; in particular embodiments, they will be disease traits and/or drug response traits, reflecting drug efficacy or toxicity, Traits can either be "binary", e.g. diabetic vs non diabetic, or "quantitative", e.g. elevated blood pressure. Individuals affected by a quantitative trait can be classified according to an appropriate scale of trait values, e.g. blood pressure ranges. Each trait value range can then be analyzed as a binary trait. Patients showing a trait value within one such range will be studied in comparison with patients showing a trait value outside of this range. In such a case, genetic analysis methods will be applied to subpopulations of individuals showing trait values within defined ranges.

Genetic mapping involves the analysis of the segregation of polymorphic loci in trait positive and trait negative populations. Polymorphic loci constitute a small fraction of the human genome (less than 1%), compared to the vast majority of human genomic DNA which is identical in sequence among the chromosomes of different individuals. Among all existing human polymorphic loci, genetic markers can be defined as genome-derived polynucleotides which are sufficiently polymorphic to allow a reasonable probability that a randomly selected person will be heterozygous, and thus informative for genetic analysis by methods such as linkage analysis or association studies.

A genetic map consists of a collection of polymorphic markers which have been positioned on the human chromosomes. Genetic maps may be combined with physical maps, collections of ordered overlapping fragments of genomic DNA whose arrangement along the human chromosomes is known. The optimal genetic map should possess the following characteristics:

the density of the genetic markers scattered along the genome should be sufficient to allow the identification and localization of any trait-related polymorphism.

each marker should have an adequate level of heterozygosity, so as to be informative in a large percentage of different meioses, all markers should be easily typed an a routine basis, at a reasonable expense, and in a reasonable amount of time, the entire set of markers per chromosome should be ordered in a highly reliable fashion.

However, while the above maps are optimal, it will be appreciated that the maps of the present invention may be used in the the individual marker and haplotype association analyses described below without the necessity of determining the order of biallelic markers derived from a single BAC with respect to one another.

Genetic Maps Based on RFLPs or VNTRs

The analysis of DNA polymorphisms has relied on the following types of polymorphisms. The first generation of genetic markers were restriction fragment length polymorphisms (RFLPs), single nucleotide polymorphisms which occur at restriction sites, thereby modifying the cleavage pattern of the corresponding restriction enzyme. Though the original methods used to type RFLPs were material-, effort- and time-consuming, today these markers can easily be typed by PCR-based technologies. Since they are biallelic markers (they present only two alleles, the restriction site being either present or absent), their maximum heterozygosity is 0.5. The theoretical number of RFLPs distributed along the entire human genome is more than $10^5$, which leads to a potential average inter-marker distance of 30 kilobases. However, in reality the number of evenly distributed RFLPs which occur at a sufficient frequency in the population to make them useful for tracking of genetic polymorphisms is very limited.

The second generation of genetic markers was VNTRs (Variable Number of Tandem Repeats), which can he categorized as either minisatellites or microsatellites. Minisatellites are tandemly repeated DNA sequences present in units of 5–50 repeats which are distributed along regions of the human chromosomes ranging from 0.1 in 20 kilobases in length. Since they present many possible alleles, their polymorphic informative content is very high. Minisatellites are scored by performing Southern blots to identify the number of tandem repeats present in a nucleic acid sample from the individual being tested. However, there are only $10^4$ potential VNTRs that can be typed by Southern blotting.

Microsatellites (also called simple tandem repeat polymorphisms, or simple sequence length polymorphisms) constitute the most developed category of genetic markers. They include small arrays of tandem repeats of simple sequences (di-tri-tetra- nucleotide repeats) which exhibit a high degree of length polymorphism and thus a high level of informativeness. Slightly more than 5,000 microsatellites easily typed by PCR-derived technologies, have been ordered along the human genome (Dib et al., Nature 380:152 (1996), the disclosure of which is incorporated herein by reference).

A number of these available microsatellites were used to construct integrated physical and genetic maps containing less than 5,000 markers. For example, CEPH (Chumakov et al., Nature 377: 175–298 (1995) and Cohen et al., Nature 366: 698–701 (1993), the disclosures of which are incorporated herein by reference), and Whitehead Institute and Généthon (Hudson et al., 1995), constructed genetic and physical maps covering 75% to 95% of the based on 2500 to 5000 microsatellite markers.

However, the number of easily typed informative markers in these maps was too small for the average distance between informative markers to fulfill the above-listed requirements for genetic maps.

Biallelic Markers

Biallelic markers are genome-derived polynucleotides which exhibit biallelic polymorphism. As used herein, the term biallelic marker means a biallelic single nucleotide polymorphism. As used herein, the term polymorphism may include a single base substitution, insertion, or deletion. By definition, the lowest allele frequency of a biallelic polymorphism is 1% (sequence variants which show allele frequencies below 1% are called rare mutations. There are potentially more than $10^7$ biallelic markers which can easily be typed by routine automated techniques, such as sequence- or hybridization-based techniques, out of which $10^6$ are sufficiently informative for mapping purposes. However, a biallelic marker will show a sufficient degree of informativeness for use in genetic mapping only if the frequency of its loss frequent allele is not less than about 10% (i.e. a heterozygosity rate of at least 0.18) (the heterozygosity rate for a biallelic marker is $2 P_a (1-P_a)$, where $P_a$ is the frequency of allele a). Preferably, the frequency of the less frequent allele of the biallelic markers in the present maps is at least 20% (i.e. a heterozygosity rate of at least 0.32). More preferably, the frequency of the less frequent allele of the biallelic markers in the present maps is at least 30% (i.e. its heterozygosity rate is higher than about 0.42).

Initial attempts to construct genetic maps based on non-RFLP biallelic markers have focused on identifying biallelic markers lying within sequence tagged sites (STS), pieces of genomic DNA having a known sequence and averaging about 250 bases in length. More than 30,000 STSs have been identified and ordered along the genome (Hudson et al., Science 270:1945–1954 (1995); Schuler et al., Science 274: 540–546 (1996), the disclosures of which are incorporated herein by reference). For example, the Whitehead Institute and Généthon's integrated map contains 15,086 STSs.

These sequence tagged sites can be screened to identify polymorphisms, preferably Single Nucleotide Polymorphisms (SNPs), more preferably non RFLP biallelic markers therein. Generally polymorphisms are identified by determining the sequence of the STSs in 5 to 10 individuals.

Wang et al. (Cold Spring harbor laboratory: *Abstracts of papers pressented on genome Mapping and sequencing* p. 17 (May 14–18, 1997), the disclosure of which is incorporated herein by reference) recently announced the identification and mapping of 750 Single Nucleotide Polymorphisms issued from the sequencing of 12,000 STSs from the Whitehead/MIT map, in eight unrelated individuals. The map was assembled using a high throughput system based on the utilization of DNA chip technology available from Affymetrix (Chee et al., Science 274:610–614 (1996), the disclosure of which is incorporated herein by reference).

However, according to experimental data and statistical calculations, less than one out of 10 of all STSs mapped today will contain an informative Single Nucleotide Polymorphism. This is primarily due to the shirt length of existing STSs (usually less than 250 bp). If one assumes $10^8$ informative SNPs spread along the human genome, there would on average be one marker of interest every $3 \times 10^9/10^6$, i.e. every 3,000 bp. The probability that one such marker is present on a 250 bp stretch is thus less than $1/10$.

While it could produce a high density map, the STS approach based on currently existing markers does not put any systematic effort into making sure that the markers obtained are optimally distributed throughout the entire genome. Instead, polymorphisms are limited to those locations for which STSs are available.

The even distribution of markers along the chromosomes is critical to the future success of genetic analyses. In particular, a high density map having appropriately spaced markers is essential for conducting association studies on sporadic cases, aiming at identifying genes responsible for detectable traits such as those which are described below.

As will be further explained below, genetic studies have mostly relied in the past on a statistical approach called linkage analysis, which took advantage of microsatellite markers to study their inheritance pattern within families from which a sufficient number of individuals presented the studied trait. Because of intrinsic limitations of linkage analysis, which will be further detailed below, and because these studies necessitate the recruitment of adequate family pedigrees, they are not well suited to the genetic analysis of all traits, particularly those for which only sporadic cases are available (e.g. drug response traits), or those which have a low penetrance within the studied population.

Association studies offer an alternative to linkage analysis. Combined with the use of a high density map of appropriately spaced, sufficiently informative markers, association studies, including linkage disequilibrium-based genome wide association studies, will enable the identification of most genes involved in complex traits.

The present invention relates to a method for generating a high density linkage disequilibrium-based genetic map of the human genome which will allow the identification of sufficiently informative markers spaced at intervals which permit their use in identifying genes responsible for detectable traits using genome-wide association studies and linkage disequilibrium mapping.

Construction of a Physical Map

The first step in constructing a high density genetic map of biallelic markers is the construction of a physical map. Physical maps consist of ordered, overlapping cloned fragments of genomic DNA covering a portion of the genome, preferably covering one or all chromosomes. Obtaining a physical map of the genome entails constructing and ordering a genomic DNA library.

Physical mapping in complex genomes such as the human genome (3,000 Megabases) requires the construction of DNA libraries containing large inserts (on the order of 0.1 to 1 Megabase). It is crucial that such libraries be easy to construct, screen and manipulate, and that the DNA inserts be stable and relatively free of chimerism.

Yeast artificial chromosomes (YACs; Burke et al., *Science* 236:806–812 (1987), the disclosure of which is incorporated herein by reference) have provided an invaluable tool in the analysis of complex genomes since their cloning capacity is extremely high (in the Mb range). YAC libraries containing large DNA inserts (up to 2 Mb) have been used to generate STS-content maps of individual chromosomes or of the entire human genome (Chumakov at al. (1995), supra; Hudson et al. (1995), supra; Cohen et al., *Nature* 366: 698–701 (1993; Chumakov et al., *Nature* 359:380–387 (1992); Gemmill et al. *Nature* 377:299–319 (1995); Doggett et al., *Nature* 377:335–365 (1995): the disclosures of which are incorporated herein by reference).

The present genetic maps may be constructed using currently available YAC genomic libraries such as the CEPH human YAC library as a starting material (Chumakuv et al. (1995), supra). Alternatively, one may construct a YAC genomic library as described in Chumakov et al., 1995, the disclosure of which is incorporated herein by reference, or as described below.

Once a YAC genomic library has been obtained, the genomic DNA fragments therein are ordered. Ordering may be performed directly on the genomic DNA in the YAC library. However, direct ordering of YAC inserts is not preferred because YAC libraries often exhibit a high rate of chimerism (40 to 50% of YAC clones contain fragments from more than one genomic region), often suffer from clonal instability within their genomic DNA inserts, and require tedious procedures to manipulate and isolate the insert DNA. Instead, it is preferable to conduct the mapping and sequencing procedures required for ordering the genomic DNA in a system which enables the stable cloning of large inserts while being easy to manipulate using standard molecular biology techniques.

Accordingly, it is preferable to clone the genomic DNA into bacterial single copy plasmids, for example BACs (Bacterial Artificial Chromosomes), rather than into YACs. Bacterial artificial chromosomes are well suited for use in ordering genomic DNA fragments. BACs provide a low rate of chimerism and fragment rearrangement, together with relative ease of insert isolation. Thus BAC libraries are well suited to integrate genetic, STS and cytogenetic information while providing direct access to stable, readily-sequenceable genomic DNA. An example of bacterial artificial chromosome is the BAC cloning system of Shizuya et al., which is capable of stably propagating and maintaining relatively large genomic DNA fragments (up to 300 kb long) as single-copy plasmids in *E. coli* (Shizuya et al., *Proc. Natl. Acad. Sci. USA* 89:8794–8797 (1992), the disclosure of which is incorporated herein by reference).

Example 1 describes the construction of a BAC library containing human genomic DNA. It will be appreciated that the source of the genomic DNA, the enzymes used to digest the DNA, the vectors into which the genomic DNA is inserted, and the size of the DNA inserts which are cloned into said vectors need not be identical to those described in Example 1 below. Rather, the genomic DNA may be obtained from any appropriate source, may be digested with any appropriate enzyme, and may be cloned into any suitable vector. Insert size may vary within any range compatible with the cloning system chosen and with the intended purpose of the library being constructed. Typically, using BAC vectors to construct DNA libraries covering the entire human genome, insert size may vary between 50 kb and 300 kb, preferably 100 kb and 200 kb.

EXAMPLE 1

Construction of a BAC Library

Three different human genomic DNA libraries were produced by cloning partially digested DNA from a human lymphoblastoid cell line (derived from individual N° 8445, CEPH families) into the pBeloBAC11 vector (Kim et al., *Genomics* 34:213–218 (1996), the disclosure of which is incorporated herein by reference). One library was produced using a BamHI partial digestion of the genomic DNA from the lymphoblastoid cell line and contains 110,000 clones having an average insert size of 150 kb (corresponding to 5 human haploid genome equivalents). Another library was prepared from a HindIII partial digest and corresponds to 3 human genome equivalents with an average insert size of 150 kb. A third library was prepared from a NdeI partial digest and corresponds to 4 human genome equivalents with an average insert size of 150 kb.

Alternatively, the genomic DNA may be inserted into BAC vectors which possess both a high copy number origin of replication, which facilitates the isolation of the vector DNA, and a low copy number origin of replication. Cloning of a genomic DNA insert into the high copy number origin of replication inactivates the origin such that clones containing a genomic insert replicate at low copy number. The low copy number of clones having a genomic insert therein permits the inserts to be stably maintained. In addition, selection procedures may be designed which enable low copy number plasmids (i.e. vectors having genomic inserts therein) to be selected. Such vectors and selection procedures are described in the U.S. Patent Application entitled "High Throughout DNA Sequencing Vector" (GENSET.015A. Ser. No. 09/058,746) now U.S. Pat. No. 6,022,716, the disclosure of which is incorporated herein by reference.

It will be appreciated that the present methods may be practiced using BAC vectors other than those of Shizuya et al. (1992, supra), or derived from those, or vectors other than BAC vectors which possess the above-described characteristics.

To construct a physical map of the genome from genomic DNA libraries, the library clones have to be ordered along the human chromosomes. In a preferred embodiment, a minimal subset of the ordered clones will then be chosen that completely covers the entire genome. For example the genomic DNA in the inserts of the above described BAC vectors are ordered using STS markers whose positions relative to one another and locations along the genome are known using procedures such as those described herein. The STS markers used to order the BAC inserts may be the STS markers contained in the integrated maps described above. Alternatively, the STSs may be STSs which are not contained in any of the physical maps described above. In another embodiment, the STSs may be a combination of STSs included in the physical maps described above and STSs which are not included in the integrated maps described above.

The BAC vectors are screened with STSs until there is at least one positive BAC clone per STS. Preferably, a minimally overlapping set of 10,000 to 30,000 BACs having genomic inserts spanning the entire human genome are identified. More preferably, a minimally overlapping set of 10,000 to 30,000 BACs having genomic inserts of about 100–300 kb in length spanning the entire human genome are identified. In a preferred embodiment, a minimally overlapping set of 10,000 to 30,000 BACs having genomic inserts of about 100–150 kb in length spanning the entire human genome is identified. In a highly preferred embodiment, a minimally overlapping set of 15,000 to 25,000 BACs having genomic inserts of about 100–200 kb in length spanning the entire human genome is identified. Alternatively, a smaller number of BACs spanning a set of chromosomes, a single chromosome, a particular subchromosomal region, or any other desired portion of the genome may be ordered. The BACs may be screened for the presence of STSs as described in Example 2 below.

EXAMPLE 2

Ordering of a BAC Library: Screening Clones with STSs

The BAC library is screened with a set of PCR-typeable STSs to identify clones containing the STSs. To facilitate PCR screening of several thousand clones, for example 200,000 clones, pools of clones are prepared.

Three-dimensional pools of the BAC libraries are prepared as described in Chumakov et al. and are screened for the ability to generate an amplification fragment in amplification reactions conducted using primers derived from the ordered STSs. (Chumakov et al. (1995), supra). A BAC library typically contains 200,000 BAC clones. Since the average size of each insert is 100–300 kb, the overall size of such a library is equivalent to the size of at least about 7 human genomes. This library is stored as an array of individual clones in 518 384-well plates. It can be divided into 74 primary pools (7 plates each). Each primary pool can than be divided into 48 subpools prepared by using a three-dimensional pooling system based on the plate, row and column address of each clone (more particularly, 7 subpools consisting of all clones residing in a given microtiter plate: 16 subpools consisting of all clones in a given row; 24 subpools consisting of all clones in a given column).

Amplification reactions are conducted on the pooled BAC clones using primers specific for the STSs. For example, the three dimensional pools may be screened with 45,000 STSs whose positions relative to one another and locations along the genome are known. Preferably, the three dimensional pools are screened with about 30,000 STSs whose positions relative to one another and locations along the genome are known. In a highly preferred embodiment, the three dimensional pools are screened with about 20,000 STSs whose positions relative to one another and locations along the genome are known.

Amplification products resulting from the amplification reactions are detected by conventional agarose gel electrophoresis combined with automatic image capturing and processing. PCH screening for a STS involves three steps: (1) identifying the positive primary pools; (2) for each positive primary pool, identifying the positive plate, row and column 'subpools' to obtain the address of the positive clone; (3) directly confirming the PCR assay on the identified clone. PCR assays are performed with primers specifically defining the STS.

Screening is conducted as follows. First BAC DNA containing the genomic inserts is prepared as follows. Bacteria containing the BACs are grown overnight at 37° C. in 120 μl of LB containing chloramphenical (12 μg/ml). is extracted by the following protocol:

Centrifuge 10 min at 4° C. and 2000 rpm

Eliminate supernatant and resuspend pellet in 120 μl TE 10-2 (Tris HCl 10 mM, EDTA 2 mM)

Centrifuge 10 min at 4° C. and 2000 rpm

Eliminate supernatant and incubate pellet with 20 μl lyzozyme 1 mg/ml during 15 min at room temperature Add 20 μl proteinase K 100 μg/ml and incubate 15 min at 60° C.

Add 8 µl DNAse 2U/µl and incubate 1 hr at room temperature

Add 100 µl TE 10-2 and keep at −80° C.

PCR assays are performed using the following protocol:

| | |
|---|---|
| Final volume | 15 µl |
| BAC DNA | 1.7 ng/µl |
| MgCl$_2$ | 2 mM |
| dNTP (each) | 200 µM |
| primer (each) | 2.9 ng/µl |
| Ampli Taq Gold DNA polymerase | 0.05 unit/µl |
| PCR buffer (10x − 0.1 M TrisHCl pH 8.3 0.5 M KCl) | 1x |

The amplification is performed on a Genius II thermocycler. After heating at 95° C. for 10 min, 40 cycles are performed. Each cycle comprises: 30 sec at 95° C., 54° C. for 1 min, and 30 sec at 72° C. For final elongation, 10 min at 72° C. end the amplification. PCR products are analyzed on 1% agarose gel with 0.1 mg/ml ethidium bromide.

Alternatively, a YAC (Yeast Artificial Chromosome) library can be used. The very large insert size, of the order of 1 megabase, is the main advantage of the YAC libraries. The library can typically include about 33,000 YAC clones as described in Chumakov et al. (1995, supra). The YAC screening protocol may be the same as the one used for BAC screening.

The known order of the STSs is then used to align the BAC inserts in an ordered array (contig) spanning the whole human genome. If necessary new STSs to be tested can be generated by sequencing the ends of selected BAC, inserts. Subchromosomal localization of the BACs can be established and/or verified by fluorescence in situ hybridization (FISH), performed on metaphasic chromosomes as described by Cherif et al. 1990 and in Example 8 below. BAC insert size may be determined by Pulsed Field Gel Electrophoresis after digestion with the restriction enzyme NotI.

Finally, a minimally overlapping set of BAC clones, with known insert size and subchromosomal location, covering the entire genome, a set of chromosomes, a single chromosome, a particular subchromosomal region, or any other desired portion of the genome is selected from the DNA library. For example, the BAC clones may cover at least 100 kb of contiguous genomic DNA, at least 250 kb of contiguous genomic DNA, at least 500 kb of contiguous genomic DNA, at least 2 Mb of contiguous genomic DNA, at least 5 Mb of contiguous genomic DNA, at least 10 Mb of contiguous genomic DNA, or at least 20 Mb of contiguous genomic DNA.

Identification of Biallelic Markers

In order to generate polymorphisms having the adequate informative content to be used as biallelic markers for genetic mapping, the sequences of random genomic fragments from an appropriate number of unrelated individuals are compared. Genomic sequences to be screened for biallelic markers may be generated by partially sequencing BAC inserts, preferably by sequencing the ends of BAC subclones. Sequencing the ends of an adequate number of BAC subclones derived from a minimally overlapping array of BACs such as those described above will allow the generation of biallelic markers spanning the entire genome, a set of chromosomes, a single chromosome, a particular subchromosomal region, or any other desired portion of the genome with an optimized inter-marker spacing.

Thus, portions of the BACs in the selected ordered array are then subcloned and sequenced using, for example, the procedures described below.

EXAMPLE 3

Subcloning of BACs

The cells obtained from three liters overnight culture of each BAC clone are treated by alkaline lysis using conventional techniques to obtain the BAC DNA containing the genomic DNA inserts. After centrifugation of the BAC DNA in a cesium chloride gradient, ca. 50 µg of BAC DNA are purified. 5–10 µg of BAC DNA are sonicated using three distinct conditions, to obtain fragments within a desired size range. The obtained DNA fragments are end-repaired in a 50 µl volume with two units of Vent polymerase for 20 min at 70° C., in the presence of the four deoxytriphosphates (100 µM). The resulting blunt-ended fragments are separated by electrophoresis on preparative low-melting point 1% agarose gels (60 Volts for 3 hours). The fragments lying within a desired size range, such as 600 to 6,000 bp, are excised from the gel and treated with agarase. After chloroform extraction and dialysis on Microcon 100 columns, DNA in solution is adjusted to a 100 ng/µl concentration. A ligation to a linearised, dephosphorylated, blunt-ended plasmid cloning vector is performed overnight by adding 100 ng of BAC fragmented DNA to 20 ng of pBluescript II Sk (+) vector DNA linearized by enzymatic digestion, and treating with alkaline phosphatase. The ligation reaction is performed in a 10 µl final volume in the presence of 40 units/µl T4 DNA ligase (Epicentre). The ligated products are electroporated into the appropriate cells (ElectroMAX *E.coli* DH10B cells). IPTG and X-gal are added to the cell mixture, which is then spread on the surface of an ampicillin-containing agar plate. After overnight incubation at 37° C., recombinant (white) colonies are randomly picked and arrayed in 96 well microplates for storage and sequencing.

Alternatively, BAC subcloning may be performed using vectors which possess both a high copy number origin of replication, which facilitates the isolation of the vector DNA, and a low copy number origin of replication. Cloning of a genomic DNA fragment into the high copy number origin of replication inactivates the origin such that clones containing a genomic insert replicate at low copy number. The low copy number of clones having a genomic insert therein permits the inserts to be stably maintained. In addition, selection procedures may be designed which enable low copy number plasmids (i.e. vectors having genomic inserts therein) to be selected. In a preferred embodiment, BAC subcloning will be performed in vectors having the above described features and moreover enabling high throughput sequencing of long fragments of genomic DNA. Such high throughput high quality sequencing may be obtained after generating successive deletions within the subcloned fragments to be sequenced, using transposition-based or enzymatic systems. Such vectors are described in the U.S. Patent Application entitled "High Throughput DNA Sequencing Vector" (GENSET.015A, Ser. No. 09/058,746), the disclosure of which is incorporated herein by reference.

It will be appreciated that other subcloning methods familiar to those skilled in the art may also be employed.

The resulting subclones are then partially sequenced using, for example, the procedures described below.

EXAMPLE 4

Partial Sequencing of BAC Subclones

The genomic DNA inserts in the subclones, such as the BAC subclones prepared above, are amplified by conducting PCR reactions on the overnight bacterial cultures, using primers complementary to vector sequences flanking the insertions.

The sequences of the insert extremities (on average 500 bases at each end, obtained under routine sequencing conditions) are determined by fluorescent automated sequencing on AB1 377 sequencers, using AB1 Prism DNA Sequencing Analysis software. Following gel image analysis and DNA sequence extraction, sequence data are automatically processed with adequate software to assess sequence quality. A proprietary base-caller, automatically flags suspect peaks, taking into account the shape of the peaks, the inter-peak resolution, and the noise level. The proprietary base caller also performs an automatic trimming. Any stretch of 25 or fewer bases having more than 4 suspect peaks is usually considered unreliable and is discarded.

The sequenced regions of the subclones, such as the BAC subclones prepared above, are then analyzed in order to identify biallelic markers lying therein. The frequency at which biallelic markers will be detected in the screening process varies with the average level of heterozygosity desired. For example, if biallelic markers having an average heterozygosity rate of greater than 0.42 are desired, they will occur every 2.5 to 3 kb on average. Therefore, on average, six 500 bp-genomic fragments have to be screened in order to derive 1 biallelic marker having an adequate informative content.

As a preferred alternative to sequencing the ends of an adequate number of BAC subclones, the above mentioned high throughput deletion-based sequencing vectors, which allow the generation of a high quality sequence information covering fragments of ca. 6 kb, may be used. Having sequence fragments longer than 25 or 3 kb enhances the chances of identifying biallelic markers therein. Methods of constructing and sequencing a nested set of deletions are disclosed in the U.S. Patent Application entitled "High Throughput DNA Sequencing Vector" (GENSET.015A, Ser. No. 09/058,746), the disclosure of which is incorporated herein by reference.

To identify biallelic markers using partial sequence information derived from subclone ends, such as the ends of the BAC subclones prepared above, pairs of primers, each one specifically defining a 500 bp amplification fragment, are designed using the above mentioned partial sequences. The primers used for the genomic amplification of fragments derived from the subclones, such as the BAC subclones prepared above, may be designed using the OSP software (Hillier L. and Green P., *Methods Appl.*, 1:124–8 (1991), the disclosure of which is incorporated herein by reference). The GC content of the amplification primers preferably ranges between 10 and 75%, more preferably between 35 and 60%, and most preferably between 40 and 55%. The length of amplification primers can range from 10 to 100 nucleotides, preferably from 10 to 50, 10 to 30 or more preferably 10 to 20 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures.

All primers may contain, upstream of the specific target bases, a common oligonucleotide tail that serves as a sequencing primer. Those skilled in the art are familiar with primer extensions which can be used for these purposes.

To identify biallelic markers, the sequences corresponding to the partial sequences determined above are determined and compared in a plurality of individuals. The population used to identify biallelic markers having an adequate informative content preferably consists of ca. 100 unrelated individuals from a heterogeneous population.

First, DNA is extracted from the peripheral venous blood of each donor using methods such as those described in Example 5.

EXAMPLE 5

Extraction of DNA 30 ml of blood are taken from the individuals in the presence of EDTA. Cells (pellet) are collected after centrifugation for 10 minutes at 2000 rpm. Red cells are lysed by a lysis solution (50 ml final volume 10 mM Tris pH7.6:5 mM $MgCl_2$; 10 mM NaCl). The solution is centrifuged (10 minutes, 2000 rpm) as many times as necessary to eliminate the residual red cells present in the supernatant, after resuspension of the pellet in the lysis solution.

The pellet of white cells is lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) is added. After vigorous agitation, the solution is centrifuged for 20 minutes at 10000 rpm. For the precipitation of DNA, 2 to 3 volumes of 100% ethanol are added to the previous supernatant, and the solution is centrifuged for 30 minutes at 2000 rpm. The DNA solution is rinsed three times with 70% ethanol to eliminate salts, and centrifuged for 20 minutes at 2000 rpm. The pellet is dried at 37° C., and resuspended in 1 ml TE 10-1 or 1 ml water. The DNA concentration is evaluated by measuring the OD at 260 nm (1 unit OD–50 µg/ml DNA).

To evaluate the presence of proteins in the DNA solution, the OD 260/OD 280 ratio is determined. Only DNA preparations having a OD 260/OD 280 ratio between 1.8 and 2 are used in the subsequent steps described below.

Once genomic DNA from every individual in the given population has been extracted, it is preferred that a fraction of each DNA sample is separated, after which a pool of DNA is constituted by assembling equivalent DNA amounts of the separated fractions into a single one.

Second, the DNA obtained from peripheral blood as described above is amplified using the above mentioned amplification primers.

Example 6 provides procedures that may be used in the amplification reactions, and the detection of polymorphisms within the obtained amplicons.

EXAMPLE 6

Amplification of DNA from Peripheral Blood and Identification of Biallelic Markers The amplification of each sequence is performed on pooled DNA samples obtained as in Example 5 above, using PCR (Polymerase Chain Reaction) as follows:

| | |
|---|---|
| final volume | 25 µl |
| genomic DNA | 2 ng/µl |
| MgCl$_2$ | 2 mM |
| dNTP (each) | 200 µM |
| primer (each) | 2.9 ng/µl |
| Ampli Taq Gold DNA polymerase (Perkin) | 0.05 unit/µl |
| PCR buffer (10X – 0.1 M Tris HCl pH 8.3. 0.5 M KCl) | 1X. |

The synthesis of primers is performed following the phosphoramidite method, on a GENSET UFPS 24.1 synthesizer.

To reduce the expense of preparing amplification primers for use in the above procedures, short primers may be used. While primers and probes having between 15 and 20 (or more) nucleotides are usually highly specific to a given nucleic acid sequence, it may be inconvenient and expensive to synthesize a relatively long oligonucleotide for each analysis. In order to at least partially circumvent this problem, it is often possible to use smaller but still relatively specific oligonucleotides that are shorter in length to create a manageable library. For example, a library of oligonucleotides comprising about 8 to 10 nucleotides is conceivable and has already been used for sequencing of a 40,000 bp cosmid DNA (Studior, *Proc. Natl. Acad. Sci.* USA 86(18): 6917–6921 (1989), the disclosure of which is incorporated herein by reference).

Another potential way to obtain specific primers and probes with a small library of oligonucleotides is to generate longer, more specific primers and probes from combinations of shorter, less specific oligonucleotides. Libraries of shorter oligonucleotides, each one being from about five to eight nucleotides in length, have already been used (Kieleczawa at al., *Science* 258:1787–1791 (1992); Kotler et al., *Proc. Natl. Acad. Sci. USA* 90:4241–4245 (1993); Kaczorowski and Szybalski, *Anal Biochem.* 221:127–135 (1994), the disclosures of which are incorporated herein by reference). Suitable probes and primers of appropriate length can therefore be designed through the association of two or three shorter oligonucleotides to constitute modular primers. The association between primers can be either covalent resulting from the activity of DNA T4 ligase or non-covalent through base-stacking energy.

The amplification is performed on a Perkin Elmer 9600 Thermocycler or MJ Research PTC200 with heating lid. After heating at 95° C. for 10 minutes, 40 cycles are performed. Each cycle comprises: 30 sec at 95° C., 1 minute at 54° C., and 30 sec at 72° C. For final elongation, 10 minutes at 72° C. ends the amplification.

The quantities of the amplification products obtained are determined on 96-well microtiter plates, using a fluorimeter and Picogreen as intercalating agent (Molecular Probes).

The sequences of the amplification products are determined using automated dideoxy terminator sequencing reactions with a dye-primer cycle sequencing protocol. The products of the sequencing reactions are run on sequencing gels and the sequences are determined using gel image analysis.

The sequence data are evaluated using software designed to detect the presence of biallelic sites among the pooled amplified fragments. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. The software evaluates the intensity ratio between the two peaks and the intensity ratio between a given peak and surrounding peaks of the same color.

However, the presence of two peaks can be an artifact due to background noise. To exclude such an artifact, the two DNA strands are sequenced and a comparison between the peaks is carried out. In order to be registered as a polymorphic sequence, the polymorphism has to be detected on bolt strands.

The above procedure permits those amplification products which contain biallelic markers to be identified.

The detection limit for the frequency of biallelic polymorphisms detected by sequencing pools of 100 individuals is about 10% for the minor allele, as verified by sequencing pools of known allelic frequencies. However, more than 90% of the biallelic polymorphisms detected by the pooling method have a frequency for the minor allele higher than 25%. Therefore, the biallelic markers selected by this method have a frequency of at least 10% for the minor allele and 90% or less for the major allele, preferably at least 20% for the minor allele and 80% or less for the major allele, more preferably at least 30% for the minor allele and 70% or less for the major allele, thus a heterozygosity rate higher than 0.18, preferably higher than 0.32, more preferably higher than 0.42.

In an initial study to determine the frequency of biallelic markers in the human genome that can be obtained using the above methods the following results were obtained. 300 different amplicons derived from 100 individuals, and covering a total of 150 kb obtained from different genomic regions, were sequenced. A total of 54 biallelic polymorphisms were identified, indicating that there is one biallelic polymorphism with a heterozygosity rate higher than 0.18 (frequency of the minor allele higher than 10%), preferably higher than 0.38 (frequency of the minor allele higher than 25%), every 2.5 to 3 kb. Given that the human genome is about $3.10^6$ kb long, this indicates that, out of the $10^7$ biallelic markers present on the human genome, approximately $10^6$ have adequate heterozygosity rates for genetic mapping purposes.

Using the procedures of Examples 1–6, sets containing increasing numbers of biallelic markers may be constructed. For example, the procedures of Examples 1–6 are used to identify 1 to about 50 biallelic markers. In some embodiments, the procedures of Examples 1–6 are used to identify about 50 to about 200 biallelic markers. In other embodiments, the procedures of Examples 1–6 are used to identify about 200 to about 500 biallelic markers. In some embodiments, the procedures of Examples 1–6 are used to identify about 1,000 biallelic markers. In other embodiments, the procedures of Examples 1–6 are used to identify about 3,000 biallelic markers. In further embodiments, the procedures of Examples 1–6 are used to identity about 5,000 biallelic markers. In another embodiment, the procedures of Examples 1–6 are used to identify about 10,000 biallelic markers. In still another embodiment, the procedures of Examples 1–6 are used to identify about 20,000 biallelic markers. In still another embodiment, the procedures of Examples 1–6 are used to identify about 40,000 biallelic markers. In still another embodiment, the procedures of Examples 1–6 are used to identify about 60,000 biallelic markers. In still another embodiment, the procedures of Examples 1–6 are used to identify about 80,000 biallelic markers. In still another embodiment, the procedures of Examples 1–6 are used to identify more than 100,000 biallelic markers. In a further embodiment, the procedures of Examples 1–6 are used to identify more than 120,000 biallelic markers.

As discussed above, the ordered nucleic acids, such as the inserts in BAC clones, which contain the biallelic markers of the present invention may span a portion of the genome. For example, the ordered nucleic acids may span at least 100 kb of contiguous genomic DNA, at least 250 kb of contiguous genomic DNA, at least 500 kb of contiguous genomic DNA, at least 2 Mb of contiguous genomic DNA, at least 5Mb of contiguous genomic DNA, at least 10 Mb of contiguous genomic DNA, or at least 20 Mb of contiguous genomic DNA.

In addition, groups of biallelic markers located in proximity to one another along the genome may be identified within these portions of the genome for use in haplotyping analyses as described below. The biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb. It will be appreciated that the ordered DNA fragments containing these groups of biallelic markers need not completely cover the genomic regions of these lengths but may instead be incomplete contigs having one or more gaps therein. As discussed in further detail below, biallelic markers may be used in single maker and haplotype association analyses regardless of the completeness of the corresponding physical contig harboring them.

Using the procedures above, 653 biallelic markers, each having two alleles, were identified using sequences obtained from BACs which had been localized on the genome. In some cases, markers were identified using pooled BACs and thereafter reassigned to individual BACs using STS screening procedures such as those described in Examples 2 and 7. The sequences of 50 of these 653 biallelic markers are provided in the accompanying Sequence Listing as SEQ ID Nos. 1–50 and 51–100 (with SEQ. ID Nos. 1–50 being one allele of these 50 biallelic markers and SEQ ID Nos. 51–100 being the other allele of these 50 biallelic markers). Although the sequences of SEQ ID Nos. 1–50 and 51–100 will be used as exemplary markers throughout the present application, it will be appreciated that the biallelic markers used in the maps of the present invention are not limited to these particular markers, nor are they limited to having the exact flanking sequences surrounding the polymorphic bases which are enumerated in SEQ ID Nos. 1–50 and 51–100 Rather, it will be appreciated that the flanking sequences surrounding the polymorphic bases of SEQ ID Nos. 1–50 and 51–100 may be lengthened or shortened to any extent compatible with their intended use and the present invention specifically contemplates such sequences. The sequences of these 653 biallelic markers, including the sequences of SEQ ID Nos. 1–50 and 51–100 may be used to construct the maps of the present invention as well as in the gene identification and diagnostic techniques described herein. It will be appreciated that the biallelic markers referred to herein may be of any length compatible with their intended use provided that the markers include the polymorphic base, and the present invention specifically contemplates such sequences.

Ordering of Biallelic Markers

Biallelic markers can be ordered to determine their positions along chromosomes, preferably subchromosomal regions, most preferably along the above described minimally overlapping ordered BAC arrays, as follows.

The positions of the biallelic markers along chromosomes may be determined using a variety of methodologies. In one approach, radiation hybrid mapping is used. Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends an the radiation dose. These fragments are rescued by fusion with cultured rodent cells, yielding subclones containing different portions of the human genome. This technique is described by Benham et al. (*Genomics* 4:509–517, 1989) and Cox et al. (*Science* 250:245–250, 1990) the entire contents of which are hereby incorporated by reference. The random and independent nature of the subclones permits efficient mapping of any human genome marker. Human DNA isolated from a panel of 80–100 cell lines provides a mapping reagent for ordering biallelic markers. In this approach, the frequency of breakage between markers is used to measure distance, allowing construction of fine resolution maps as has been done for ESTs (Schuler et al., *Science* 274:540–546, 1996, hereby incorporated by reference).

RH mapping has been used to generate a high-resolution whole genome radiation hybrid map of human chromosome 17q22–q25.3 across the genes for growth hormone (GH) and thymidine kinase (TK) (Foster et al., *Genomics* 33:185–192, 1996), the region surrounding the Gorlin syndrome gene (Obermayr et al., *Eur. J. Hum. Genet.* 4:242–245, 1996), 60 loci covering the entire short arm of chromosome 12 (Raeymaekers et al., *Genomics* 29:170–178, 1995), the region of human chromosome 22 containing the neurofibromatosis type 2 locus (Frazer et al., *Genomics* 14:574–584, 1992) and 13 loci on the long arm of chromosome 5 (Warrington et al., *Genomics* 11:701–708, 1991).

Alternatively, PCR based techniques and human-rodent somatic cell hybrids may be used to determine the positions of the biallelic markers on the chromosomes. In such approaches, oligonucleotide primer pairs which are capable of generating amplification products containing the polymorphic bases of the biallelic markers are designed. Preferably, the oligonucleotide primers are 18–23 bp in length and are designed for PCR amplification. The creation of PCR primers from known sequences is well known to those with skill in the art. For a review of PCR technology see Erlich, H. A., *PCR Technology; Principles and Applications for DNA Amplification*, 1992, W.H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 μCu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the length expected for an amplification product containing the polymorphic base of the biallelic marker, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given biallelic marker. DNA is isolated from the somatic hybrids and used as starting templates for PCR reactions using the primer pairs from the biallelic marker. Only those somatic cell hybrids with chromosomes containing the human sequence corresponding to the biallelic marker will yield an amplified fragment. The biallelic markers are assigned to a chromosome by analysis of the segregation pattern of PCR products from the somatic hybrid DNA templates. The single human chromosome present in all cell hybrids that give rise to an amplified fragment is the chromosome containing that biallelic marker. For a review of techniques and analysis of results from somatic cell gene mapping experiments. (See Ledbetter et al., *Genomics* 6:475–481 (1990).)

Example 7 describes a preferred method for positioning of biallelic markers on clones, such as BAC clones, obtained from genomic DNA libraries.

EXAMPLE 7

Screening BAC Libraries with Biallelic Markers

Amplification primers enabling the specific amplification of DNA fragments carrying the biallelic markers (including the 653 biallelic markers obtained above (which include the sequences of SEQ ID Nos 1–50 and 51–100) may be used to screen clones in any genomic DNA library, preferably the BAC libraries described above for the presence of the biallelic markers.

Pairs of primers were designed which allowed the amplification of fragments carrying the 653 biallelic markers obtained above. The amplification primers may be used to screen clones in a genomic DNA library for the presence of the 653 biallelic markers. For example, pairs of amplification primers of SEQ ID Nos. 101–150 and 151–200 may be used to amplify fragments which include the polymorphic bases of the biallelic markers of SEQ ID Nos. 1–50 and 51–100.

It will be appreciated that amplification primers for the biallelic markers may be any sequences which allow the specific amplification of any DNA fragment carrying the markers and may be designed using techniques familiar to those skilled in the art. The amplification primers may be oligonucleotides of 8, 10, 15, 20 or more bases in length which enable the amplification of any fragment carrying the polymorphic site in the markers. The polymorphic base may be in the center of the amplification product or, alternatively, it may be located off-center. For example, in some embodiments, the amplification product produced using these primers may be at least 100 bases in length (i.e. 50 nucleotides on each side of the polymorphic base in amplification products in which the polymorphic base is centrally located). In other embodiments, the amplification product produced using these primers may be at least 500 bases in length (i.e. 250 nucleotides on each side of the polymorphic base in amplification products in which the polymorphic base is centrally located). In still further embodiments, the amplification product produced using these primers may be at least 1000 bases in length (i.e. 500 nucleotides on each side of the polymorphic base in amplification products in which the polymorphic base is centrally located). Amplification primers such as those described above are included within the scope of the present invention.

The localization of biallelic markers on BAC clones is performed essentially as described in Example 2.

The BAC clones to be screened are distributed in three dimensional pools as described in Example 2.

Amplification reactions are conducted on the pooled BAC clones using primers specific for the biallelic markers to identify BAC clones which contain the biallelic markers, using procedures essentially similar to those described in Example 2.

Amplification products resulting from the amplification reactions are detected by conventional agarose gel electrophoresis combined with automatic image capturing and processing. PCH screening for a biallelic marker involves three steps; (1) identifying the positive primary pools: (2) for each positive primary pools, identifying the positive plate, raw and column 'subpools' to obtain the address of the positive clone; (3) directly confirming the PCR assay on the identified clone. PCR assays are performed with primers defining the biallelic marker.

Screening is conducted as follows. First BAC DNA is isolated as follows. Bacteria containing the genomic inserts are grown overnight at 37° C. in 120 µl of LB containing chloramphenical (12 µg/ml). DNA is extracted by the following protocol:

Centrifuge 10 min at 4° C. and 2000 rpm
Eliminate supernatant and resuspend pellet in 120 µl TE 10-2 (Tris HCl 10 mM, EDTA 2 mM)
Centrifuge 10 min at 4° C. and 2000 rpm
Eliminate supernatant and incubate pellet with 20 µl lyzozyme 1 mg/ml during 15 min at room temperature
Add 20 µl proteinase K 100 µg/ml and incubate 15 min at 60° C.
Add 8 µl DNAse 2U/µl and incubate 1 hr at room temperature
Add 100 µl TE 10-2 and keep at −80° C.

PCR assays are performed using the following protocol:

| | |
|---|---|
| Final volume | 15 µl |
| BAC DNA | 1.7 ng/µl |
| MgCl$_2$ | 2 mM |
| dNTP (each) | 200 µM |
| primer (each) | 2.9 ng/µl |
| Ampli Taq Gold DNA polymerase | 0.05 unit/µl |
| PCR buffer (10x − 0.1 M Tris HCl pH 8.3 0.5M KCl | 1x |

The amplification is performed on a Genius II thermocycler. After heating at 95° C. for 10 min, 40 cycles are performed. Each cycle comprises: 30 sec at 95° C., 54° C., for 1 min, and 30 sec at 72° C. For final elongation, 10 min at 72° C. end the amplification. PCR products are analyzed on 1% agarose gel with 0.1 mg/ml ethidium bromide.

Using such procedures, a number of BAC clones carrying selected biallelic markers can be isolated. The position of those BAC clones on the human genome can be defined by performing STS screening as described in Example 2. Preferably, to decrease the number of STSs to be tested, each BAC can be localized on chromosomal or subchromosomal regions by procedures such as those described in Examples 8 and 9 below. This localization will allow the selection of a subset of STSs corresponding to the identified chromosomal or subchromosomal region. Testing each BAC with such a subset of STSs and taking account of the position and order of the STSs along the genome will allow a refined positioning of the corresponding biallelic marker along the genome.

In other embodiments, if the DNA library used to isolate BAC inserts or any type of genomic DNA fragments harboring the selected biallelic markers already constitute a physical map of the genome or any portion thereof, using the known order of the DNA fragments will allow the order of the biallelic markers to be established.

As discussed above, it will be appreciated that markers carried by the same fragment of genomic DNA, such as the insert in a BAC clone, need not necessarily be ordered with respect to one another within the genomic fragment to conduct single point or haplotype association analysis. However, in other embodiments of the present maps, the order of biallelic markers carried by the same fragment of genomic DNA may be determined.

The positions of the biallelic markers used to construct the maps of the present invention, including the 653 biallelic markers obtained above, may be assigned to subchromosomal locations using Fluorescence In Situ Hybridization (FISH) (Cherif et al. *Proc. Natl. Acad. Sci USA.*, 87:6639–6643 (1990), the disclosure of which is incorporated herein by reference). FISH analysis is described in Example 8 below.

EXAMPLE 8

Assignment of Biallelic Markers to Subchromosomal Regions

Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 µM) is added for 17 h, followed by addition of 5-bromodeoxyuridine (5-BudR, 0.1 mM) for 6 h. Calcemid (1 µg/ml) is added for the last 15 min before harvesting the cells. Cells are collected, washed in RPMI, incubated with a hypotonic solution of KCl (75 mM) at 37° C. for 15 min and fixed in three changes of methanol:acetic acid (3:1). The cell suspension is dropped onto a glass slide and air-dried.

BAC clones carrying the biallelic markers used to construct the maps of the present invention (including the 653 biallelic markers obtained aboveto) can be isolated as described above. These BACs or portions thereof, including fragments carrying said biallelic markers, obtained for example from amplification reactions using pairs of amplification primers as described above, can be used as probes to be hybridized with metaphasic chromosomes. It will be appreciated that the hybridization probes to be used in the contemplated method may be generated using alternative methods well known to those skilled in the art. Hybridization probes may have any length suitable for this intended purpose.

Probes are then labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 min Slides kept at −20° C. are treated for 1 h at 37° C. with RNase A (100 µg/ml), rinsed three times in 2×SSC and dehydrated in an ethanol series. Chromosome preparations are denatured in 70% formamide, 2×SSC for 2 min at 70° C. then dehydrated at 4° C. The sides are treated with proteinase K (10 µg/100 ml in 20 mM Tris-HCl, 2 mM $CaCl_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al.,(1990) supra.) The slides are observed under a LEICA fluorescence microscope (DM-RXA). Chromosomes are counterstained with propidium iodide and the fluorescent signal of the probe appears as two symmetrical yellow-green spots on both chromatids of the fluorescent R-band chromosome (red). Thus, a particular biallelic marker may be localized to a particular cytogenetic R-band on a given chromosome.

The above procedure was used to confirm the subchromosomal location of 95% of the BAC clones harboring the 653 markers obtained above. In particular, the 50 markers of SEQ ID Nos. 1–50 and 51–100 were assigned to subchromosomal regions of chromosome 21. Simple identification numbers were attributed to each BAC from which the markers are derived. FIG. 1 is a cytogenetic map of chromosome 21 indicating the subchromosomal regions therein. Table 1 lists the internal identification number of the localized biallelic markers, the internal identification number of the BACs from which the markers were derived, the size of the BAC insert, the average intermarker distance in the BAC insert, and the subchromosomal locations of the biallelic markers. The sequences of the localized markers are provided as SEQ ID Nos. 1–50 and 51–100 in the accompanying sequence listing. Amplification primers for generating amplification products containing the polymorphic bases of these markers are also provided as SEQ ID Nos. 101–150 and 151–200 in the accompanying sequence listing. Microsequencing primers for use in determining the identities of the polymorphic bases of these biallelic markers are provided in the accompanying Sequence Listing as SEQ ID Nos. 201–250 and 251–300.

The rate at which biallelic markers may be assigned to subchromosomal regions may be enhanced through automation. For example, probe preparation may be performed in a microtiter plate format, using adequate robots. The rate at which biallelic markers may be assigned to subchromosomal regions may be enhanced using techniques which permit the in situ hybridization of multiple probes on a single microscope slide, such as those disclosed in Larin et al., Nucleic Acids Research 22:3689–3692(1994), the disclosure of which is incorporated herein by reference. In the largest test format described, different probes were hybridized simultaneously by applying them directly from a 96-well microtiter dish which was inverted on a glass plate. Software for image data acquisition and analysis that is adapted to each optical system, test format, and fluorescent probe used, can be derived from the system described in Lichter et al. Science 247:64–89 (1990), the disclosure of which is incorporated herein by reference. Such software measures the relative distance between the center of the fluorescent spot corresponding to the hybridized probe and the telomeric end of the short arm of the corresponding chromosome, as compared to the total length of the chromosome. The rate at which biallelic markers are assigned to subchromosomal locations may be further enhanced by simultaneously applying probes labeled with different flouorescent tags to each well of the 96 well dish. A further benefit of conducting the analysis on one slide is that it facilitates automation, since a microscope having a moving stage and the capability of detecting fluorescent signals in different metaphase chromosomes could provide the coordinates of each probe on the metaphase chromosomes distributed on the 96 well dish.

Example 9 below describes an alternative method to position biallelic markers which allows their assignment to human chromosomes.

EXAMPLE 9

Assignment of Biallelic Markers to Human Chromosomes

The biallelic markers used to construct the maps of the present invention, including the 653 biallelic markers obtained above which include the sequences of SEQ ID Nos. 1–50 and 51–100) may be assigned to a human chromosome using monosomal analysis as described below.

The chromosomal localization of a biallelic marker can be performed through the use of somatic cell hybrid panels. For example 24 panels, each panel containing a different human chromosome, may be used (Russell et al., Somat Cell Mol. Genet 22:425–431 (1996): Drwinga et al., Genomics 16:311–314 (1993), the disclosures of which are incorporated herein by reference).

The biallelic markers are localized as follows. The DNA of each somatic cell hybrid is extracted and purified. Genomic DNA samples from a somatic cell hybrid panel are prepared as follows. Cells are lysed overnight at 42° C. with 3.7 ml of lysis solution composed of:

3 ml TE 10-2 (Tris HCl 10 mM, EDTA 2 mM)/NaCl 0.4 M

200 µl SDS 10%

500 µl K-proteinase (2 mg K-proteinase in TE 10-2/NaCl 0.4 M)

For the extraction of proteins, 1 ml saturated NaCl (6M) (1/3.5 v/v) is added. After vigorous agitation, the solution is centrifuged for 20 min at 10,000 rpm. For the precipitation of DNA, 2 to 3 volumes of 100% ethanol are added to the previous supernatant, and the solution is centrifuged for 30 min at 2,000 rpm. The DNA solution is rinsed three times with 70% ethanol to eliminate salts, and centrifuged for 20 min at 2,000 rpm. The pellet is dried at 37° C. and resuspended in 1 ml TE 10-1 or 1 ml water. The DNA concentration is evaluated by measuring the OD at 260 nm (1 unit OD–50 µg/ml DNA). To determine the presence of proteins in the DNA solution, the $OD_{260}/OD_{280}$ ratio is determined. Only DNA preparations having a $OD_{260}/OD_{280}$ ratio between 1.8 and 2 are used in the PCR assay.

Then, a PCR assay is performed on genomic DNA with primers defining the biallelic marker. The PCR assay is performed as described above for BAC screening. The PCR products are analyzed on a 1% agarose gel containing 0.2 mg/ml ethidium bromide.

The ordering analyses described above may be conducted to generate an integrated genome wide genetic map comprising about 20,000 biallelic markers (1 biallelic marker per BAC if 20,000 BAC inserts are screened). In some embodiments, the map includes one or more of the 653 markers obtained above (which include the sequences of SEQ ID Nos. 1–50 and 51–100 or the sequences complementary thereto).

In another embodiment, the above procedures are conducted to generate a map comprising about 40,000 markers (an average of 2 biallelic markers per BAC if 20,000 BAC inserts are screened). In some embodiments, the map includes one or more of the 653 markers obtained above (which include the sequences of SEQ ID Nos. 1–50 and 51–100 or the sequences complementary thereto).

In a further embodiment preferred embodiment, the above procedures are conducted to generate a map comprising about 80,000 markers ( an average of 3 biallelic markers per BAC if 20,000 BAC inserts are screened). In some embodiments, the map includes one or more of the 653 markers obtained above (which include the sequences of SEQ ID Nos. 1–50 and 51–100 or the sequences complementary thereto).

In a further embodiment preferred embodiment, the above procedures are conducted to generate a map comprising about 80,000 markers (an average of 4 biallelic markers per BAC if 20,000 BAC inserts are screened). In some embodiments, the map includes one or more of the 653 markers obtained above (which include the sequences of SEQ ID Nos. 1–50 and 51–100 or the sequences complementary thereto).

In yet another embodiment, the above procedures are conducted to generate a map comprising about 100,000 markers (an average of 5 biallelic markers per BAC if 20,000 BAC inserts are screened). In some embodiments, the map includes one or more of the 653 markers obtained above (which include the sequences of SEQ ID Nos. 1–50 and 51–100 or the sequences complementary thereto).

In a further embodiment, the above procedures are conducted to generate a map comprising about 120,000 markers (an average of 6 biallelic markers per BAC if 20,000 BAC inserts are screened). In some embodiments, the map includes one or more of the 653 markers obtained above (which include the sequences of SEQ ID Nos. 1–50 and 51–100 or the sequences complementary thereto.

Alternatively, maps having the above-specified average numbers of biallelic markers per BAC which comprise smaller portions of the genome, such as a set of chromosomes, a single chromosome, a particular subchromosomal region, or any other desired portion of the genome, may also be constructed using the procedures provided herein.

In some embodiments, the biallelic markers in the map are separated from one another by an average distance of 10–200 kb. In further embodiments, the biallelic markers in the map are separated from one another by an average distance of 15–150 kb. In yet another embodiment, the biallelic markers in the map are separated from one another by an average distance of 20–100 kb. In other embodiments, the biallelic markers in the map are separated from one another by an average distance of 100–150 kb. In further embodiments, the biallelic markers in the map are separated from one another by an average distance of 50–100 kb. In yet another embodiment, the biallelic markers in the map are separated from one another by an average distance of 25–50 kb. Maps having the above-specified intermarker distances which comprise smaller portions of the genome, such as a set of chromosomes, a single chromosome, a particular subchromosomal region, or any other desired portion of the genome, may also be constructed using the procedures provided herein.

FIG. 2, showing the results of computer simulations of the distribution of inter-marker spacing on a randomly distributed set of biallelic markers, indicates the percentage of biallelic markers which will be spaced a given distance apart for a given number of markers/BAC in the genomic map (assuming 20,000 BACs constituting a minimally overlapping array covering the entire genome are evaluated). One hundred iterations were performed for each simulation (20,000 marker map, 40,000 marker map, 60,000 marker map, 120,000 marker map).

Figure 2A:
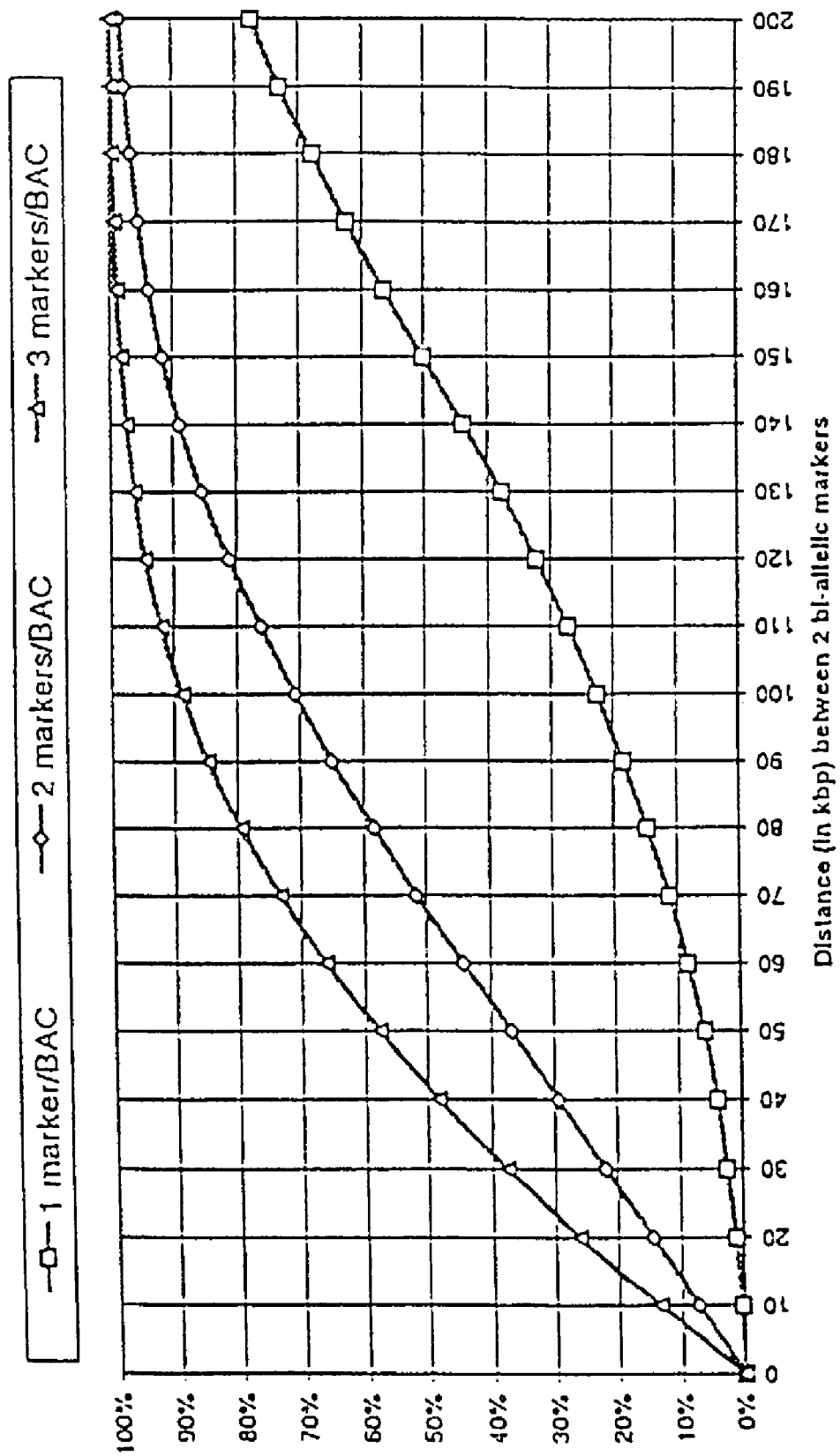
FIG. 2a shows the results of a computer simulation of the distribution of inter-marker spacing on a randomly distributed set of biallelic markers indicating the percentage of biallelic markers which will be spaced a given distance apart for 1, 2, or 3 markers/BAC in a genomic map (assuming a set of 20,000 minimally overlapping BACs covering the genome are evaluated).

As illustrated in FIG. 2a, 98% of inter-marker distances will be lower than 150 kb provided 60,000 evenly distributed markers are generated (3 per BAC); 90% of inter-marker distances will be lower than 150 kb provided 40,000 evenly distributed markers are generated (2 per BAC); and 50% of inter-marker distances will be lower than 150 kb provided 20,000 evenly distributed markers are generated (1 per BAC).

Figure 2B:
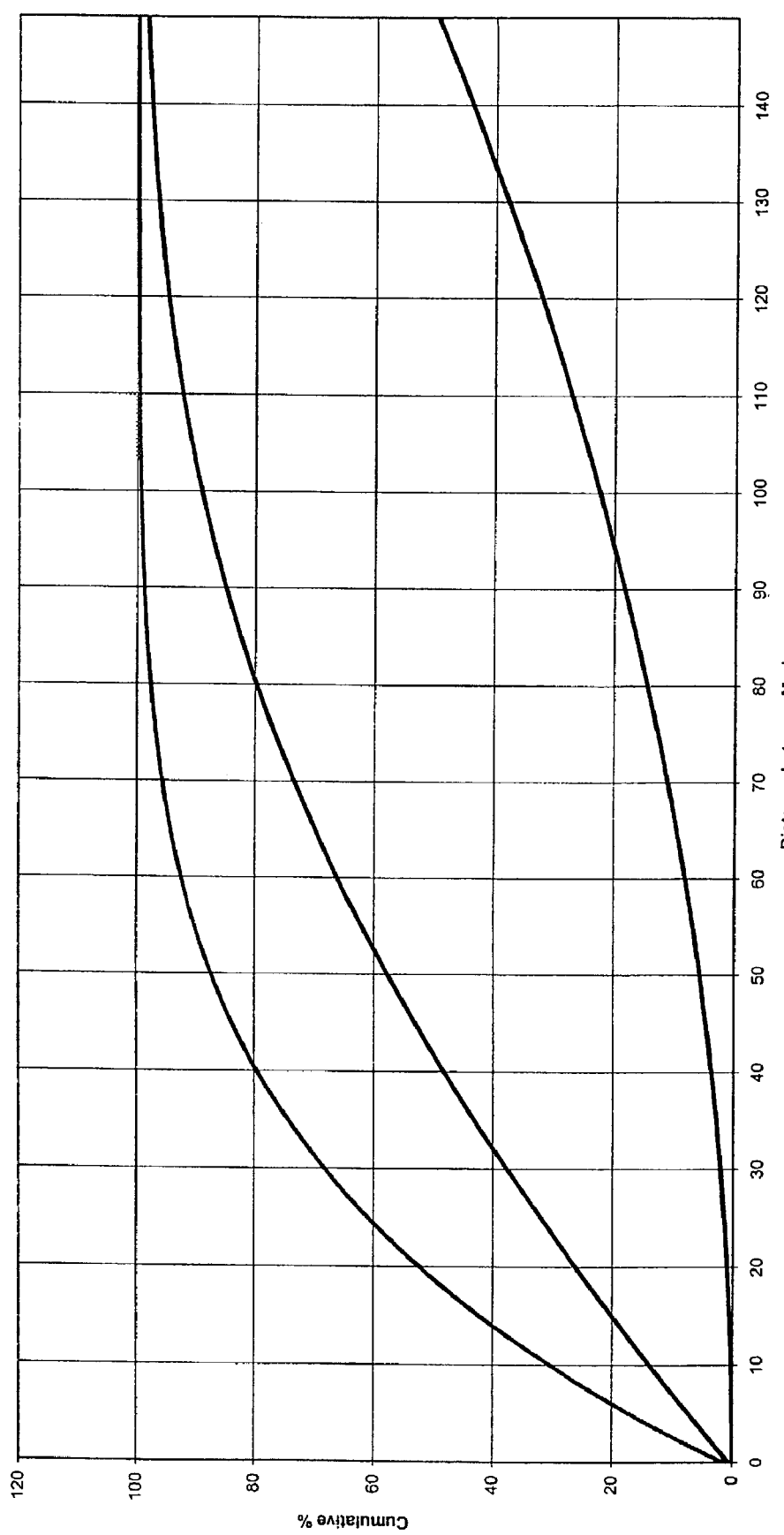
FIG. 2b shows the results of a computer simulation of the distribution of inter-marker spacing an a randomly distributed set of biallelic markers indicating the percentage of biallelic markers which will be spaced a given distance apart for 1, 3, or 6 markers/BAC in a genomic map (assuming a set of 20,000 minimally overlapping BACs covering the genome are evaluated).

As illustrated in FIG. 2b, 98% of inter-marker distances will be lower than 80 kb provided 120,000 evenly distributed markers are generated (6 per BAC); 80% of inter-marker distances will be lower than 80 kb provided 60,000 evenly distributed markers are generated (3 per BAC); and 15% of inter-marker distances will be lower than 80 kb provided 20,000 evenly distributed markers are generated (1 per BAC).

As already mentioned, high density biallelic marker maps allow association studies to be performed to identify genes involved in complex traits.

Association studies examine the frequency of marker alleles in unrelated trait positive (T+) individuals compared with trait negative (T−) controls, and are generally employed in the detection of polygenic inheritance.

Association studies as a method of mapping genetic traits rely on the phenomenon of linkage disequilibrium, which is described below.

Linkage Disequilibrium

If two genetic loci lie on the same chromosome, then sets of alleles on the same chromosomal segment (called haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium (LD).

If a specific allele in a given gene is directly involved in causing a particular trait T, its frequency will be statistically increased in a T+ population when compared to the frequency in a T− population. As a consequence of the existence of LD, the frequency of all other alleles present in the haplotype carrying the trait-causing allele (TCA) will also be increased in T+ individuals compared to T− individuals. Therefore, association between the trait and any allele in linkage disequilibrium with the trait-causing allele will suffice to suggest the presence of a trait-related gene in that particular allele's region. Linkage disequilibrium allows the relative frequencies in T+ and T− populations of a limited number of genetic polymorphisms (specifically biallelic markers) to be analyzed as an alternative to screening all possible functional polymorphisms in order to find trait-causing alleles.

The present invention then also concerns biallelic markers in linkage disequilibrium with the specific biallelic markers described above and which are expected to present similar characteristics in terms of their respective association with a given trait. In a preferred embodiment, the present invention concerns the biallelic markers that are in linkage disequilibrium with the 653 biallelic markers obtained above (which include the sequences of SEQ ID Nos. 1–50 and 51–100 or the sequences complementary thereto).

LD among a set of biallelic markers having an adequate heterozygosity rate can be determined by genotyping between 50 and 1000 unrelated individuals, preferably between 75 and 200, more preferably around 100. Genotyping biallelic marker consists of determining the specific allele carried by an individual at the given polymorphic base of the biallelic marker. Genotyping can be performed using similar methods as those described above for the generation of the biallelic markers, or using other genotyping methods such as these further described below.

LD between any pair of biallelic markers comprising at least one of the biallelic markers of the present invention $(M_i, M_j)$ can be calculated for every allele combination $(M_{i1}, M_{j1}; M_{i1}, M_{j2}; M_{i2}, M_{j1}$ and $M_{i2}, M_{j2})$, according to the Piazza formula:

$\Delta M_{lk}, M_{j1} = \sqrt{\theta 4} \cdot \sqrt{(\theta 4+\theta 3)(\theta 4+\theta 2)}$, where:

θ4———frequency of genotypes not having allele k at $M_i$ and nut having allele l at $M_j$ θ3—+—frequency of genotypes not having allele k at $M_i$ and having allele l at $M_j$ θ2—+—frequency of genotypes having allele k at $M_i$ and not having allele l at $M_j$ Linkage disequilibrium (LD) between pairs of biallelic markers (Mi, Mj) can also be calculated for every allele combination (Mi1, Mj1; Mi1, Mj2; Mi2, Mj1; Mi2, Mj2) according to the maximum likelihood estimate (MLE) for delta (the composite linkage disequilibrium coefficient), as described by Weir (B. S. Weir, Genetic Data Analysis, (1996), Sinauer Ass. Eds, the disclosure of which is incorporated herein by reference). This formula allows linkage disequilibrium between alleles to be estimated when only genotype, and not haplotype, data are available. This LD composite test makes no assumption for random mating in the sampled population, and thus seems to be more appropriate than other LD tests for genotypic data.

The skilled person win readily appreciate that other LD calculation methods can be used without undue experimentation.

Example 10 illustrates the measurement of LD between a publicly known biallelic marker, the "ApoE Site A", located within the Alzheimer's related ApoE gene, and other biallelic markers randomly derived from the genomic region containing the ApoE gene.

EXAMPLE 10

Measurement of Linkage Disequilibrium

As originally reported by Strittmatter et al. and by Saunders et al. in 1993, the Apo E ε4 allele is strongly associated with both late-onset familial and sporadic Alzheimer's disease (AD). (Saunders, A. M. Lancet 342:710–711 (1993) and Strittmater, W. J. et al., Proc. Natl. Acad. Sci. U.S.A. 90:1977–1981 (1993), the disclosures of which are incorporated herein by reference). The 3 major isoforms of human Apolipoprotein E (apoE2, -E3, and -E4), as identified by isoelectric focusing, are coded for by 3 alleles (ε2, 3, and 4). The ε2, ε3, and ε4 isoforms differ in amino acids sequence at 2 sites, residue 112 (called site A) and residue 158 (called site B). The ancestral isoform of the protein is Apo E3, which at sites A/B contains cysteine/arginine, while ApoE2 and -E4 contain cysteine/cysteine and arginine/arginine, respectively (Weisgreber, K. H. et al., J. Biol. Chem. 256:9077–9083 (1981); Rall, S. C. et al., Proc. Natl. Acad. Sci. U.S.A. 79:4696–4700 (1982), the disclosures of which are incorporated herein by reference).

Apo E ε4 is currently considered as a major susceptibility risk factor for AD development in individuals of different ethnic groups (specially in Caucasians and Japanese compared to Hispanics or African Americans), across all ages between 40 and 90 years, and in both men and women, as reported recently in a study performed on 5930 AD patients and 8607 controls (Farrer et al., *JAMA* 278:1349–1356 (1997), the disclosure of which is incorporated herein by reference). More specifically, the frequency of a C base coding for arginine 112 at site A is significantly increased in AD patients.

Although the mechanistic link between Apo E ε4 and neuronal degeneration characteristic of AD remains to be established, current hypotheses suggest that the Apo E genotype may influence neuronal vulnerability by increasing the deposition and/or aggregation of the amyloid beta peptide in the brain or by indirectly reducing energy availability to neurons by promoting atherosclerosis.

Using the methods of the present invention, biallelic markers that are in the vicinity of the Apo E site A were generated and the association of one of their alleles with Alzheimer's disease was analyzed. An Apo E public marker (stSG94) was used to screen a human genome BAC library as previously described. A BAC, which gave a unique FISH hybridization signal on chromosomal region 19q13.2.3, the chromosomal region harboring the Apo E gene, was selected for finding biallelic markers in linkage disequilibrium with the Apo E gene as follows.

This BAC contained an insert of 205 kb that was subcloned as previously described. Fifty BAC subclones were randomly selected and sequenced. Twenty five subclone sequences were selected and used to design twenty five pairs of PCR primers allowing 500 bp-amplicons to be generated. These PCR primers were then used to amplify the corresponding genomic sequences in a pool of DNA from 100 unrelated individuals (blood donors of French origin) as already described.

Amplification products from pooled DNA were sequenced and analyzed for the presence of biallelic polymorphisms, as already described. Five amplicons were shown to contain a polymorphic base in the pool of 100 unrelated individuals, and therefore these polymorphisms were selected as random biallelic markers in the vicinity of the Apo E gene. The sequences of both alleles of these biallelic markers (99-344/439; 99-355/219; 99-359/308; 99-365/344; 99-366/274) correspond to SEQ ID Nos: 301–305 and 307–311 (See the accompanying Sequence Listing Table10). Corresponding pairs of amplification primers for generating amplicons containing these biallelic markers can be chosen from those listed as SEQ ID Nos: 313–317 and 319–323.

An additional pair of primers (SEQ ID Nos: 318 and 324) was designed that allows amplification of the genomic fragment carrying the biallelic polymorphism corresponding to the ApoE marker (99-2452/54: C/T; The C allele is designated SEQ ID NO: 306 in the accompanying sequence listing, while the T allele is designated SEQ ID NO: 312 in the accompanying Sequence Listing; (See also Table 10), publicly known as Apo E site A (Weisgraber et al. (1981), supra; Rall et al. (1982), supra) to be amplified.

The five random biallelic markers plus the Apo E site A marker were physically ordered by PCR screening of the corresponding amplicons using all available BACs originally selected from the genomic DNA libraries, as previously described, using the public Apo E marker stSG94. The amplicon's order derived from this BAC screening is as follows:

(99-344/99-366)-(99-365/99-2452)-99-359-99-355.

where brackets indicate that the exact order of the respective amplicons couldn't be established.

Linkage disequilibrium among the six biallelic markers (five random markers plus the Apo E site A) was determined by genotyping the same 100 unrelated individuals from whom the random biallelic markers were identified.

DNA samples and amplification products from genomic PCR were obtained in similar conditions as those described above for the generation of biallelic markers, and subjected to automated microsequencing reactions using fluorescent ddNTPs (specific fluorescence for each ddNTP) and the appropriate microsequencing primers having a 3' end immediately upstream of the polymorphic base in the biallelic markers. The sequence of these microsequencing primers is indicated within the corresponding sequence listings of SEQ ID Nos: 325–330. Once specifically extended at the 3' end by a DNA polymerase using the complementary fluorescent dideoxynucleotide analog (thermal cycling), the microsequencing primer was precipitated to remove the unincorporated fluorescent ddNTPs. The reaction products were analyzed by electrophoresis on ABI 377 sequencing machines. Results were automatically analyzed by an appropriate software further described in Example 13.

Linkage disequilibrium (LD) between all pairs of biallelic markers (Mi, Mj) was calculated for every allele combination (Mi1, Mj1; Mi1, Mj2; Mi2, Mj1; Mi2, Mj2) according to the maximum likelihood estimate (MLE) for delta (the composite linkage disequilibrium coefficient). The results of the LD analysis between the Apo E Site A marker and the five new biallelic markers (99-344/439 ; 99-355/219; 99-359/308; 99-365/344; 99-366/274) are summarized in Table 2 below:

TABLE 2

| Markers | d × 100 | SEQ ID Nos of the biallotic Markers | SEQ ID Nos of the amplification Primers |
|---|---|---|---|
| ApoE SitoA | | 306 | 318 |
| 99-2452/54 | | 312 | 324 |
| 99-344/439 | 1 | 301 | 313 |
| | | 307 | 319 |
| 99-366/274 | 1 | 305 | 317 |
| | | 311 | 323 |
| 99-365/344 | 8 | 304 | 318 |
| | | 310 | 322 |
| 99-359/308 | 2 | 303 | 315 |
| | | 309 | 321 |
| 99-355/219 | 1 | 302 | 314 |
| | | 308 | 320 |

The above LD results indicate that among the five biallelic markers randomly selected in a region of about 200 kb containing the Apo E gene, marker 99-365/344T is in relatively strong linkage disequilibrium with the Apo E site A allele (99-2452/54C).

Therefore, since the Apo E site A allele is associated with Alzheimer's disease, one can predict that the T allele of marker 99-365/344 will probably be found associated with AD. In order to test this hypothesis, the biallelic markers of SEQ ID Nos: 301–306 and 307–312 were used in association studies as described below.

225 Alzheimer's disease patients were recruited according to clinical inclusion criteria bused on the MMSE test. The 248 control cases included in this study were both ethnically- and age-matched to the affected cases. Both affected and control individuals corresponded to unrelated cases. The identities of the polymorphic bases of each of the biallelic markers was determined in each of these individuals using the methods described above. Techniques for conducting association studies are further described below.

The results of this study are summarized in Table 3 below:

TABLE 3

| | ASSOCIATION DATA | |
| --- | --- | --- |
| MARKER | Difference in allele frequency between individuals with Alzheimer's and control individuals | Corresponding p-value |
| 99-344/439 | 3.3% | 9.54E-02 |
| 99-366/274 | 1.6% | 2.09E-01 |
| 99-365/344 | 17.7% | 6.9E-10 |
| 99-2452/54 (ApoE Site A) | 23.8% | 3.95E-21 |
| 99-359/308 | 0.4% | 9.2E-01 |
| 99-355/219 | 2.5% | 2.54E-01 |

The frequency of the Apo E site A allele in both AD cases and controls was found in agreement with that previously reported (ca. 10% in controls and ca. 34% in AD cases, leading to a 24% difference in allele frequency), thus validating the Apo E ε4 association in the populations used for this study.

Moreover, as predicted from the LD analysis (Table 2), a significant association of the T allele of marker 99-365/344 with AD cases (18% increase in the T allele frequency in AD cases compared to controls, p value for this difference=6.9 E-10) was observed.

The above results indicate that any marker in LD with one given marker associated with a trait will be associated with the trait. It will be appreciated that, though in this case the ApoE Site A marker is the trait-causing allele (TCA) itself, the same conclusion could be drawn with any other non TCA marker associated with the studied trait.

These results further indicate that conducting association studies with a set of biallelic markers randomly generated within a candidate region at a sufficient density (here about one biallelic marker every 40 kb on average), allows the identification of at least one marker associated with the trait.

In addition, these results correlate with the physical order of the six biallelic markers contemplated within the present example (see above): marker 99-365/344, which had been found to be the closest in terms of physical distance to the ApoE Site A marker, also shows the strongest LD with the Apo E site A marker.

In order to further refine the relationship between physical distance and linkage disequilibrium between biallelic markers, a ca. 450 kb fragment from a genomic region on chromosome 8 was fully sequenced.

LD within ca. 230 pairs of biallelic markers derived therefrom was measured in a random French population and analyzed as a function of the known physical inter-marker spacing. This analysis confirmed that, on average, LD between 2 biallelic markers correlates with the physical distance that separates them. It further indicated that LD between 2 biallelic markers tends to decrease when their spacing increases. More particularly, LD between 2 biallelic markers tends to decrease when their inter-marker distance is greater than 50 kb, and is further decreased when the inter-marker distance is greater than 75 kb. It was further observed that when 2 biallelic markers were further than 150 kb apart, mast often no significant LD between them could be evidenced. It will be appreciated that the size and history of the sample population used to measure LD between markers may influence the distance beyond which LD tends not to be detectable.

Assuming that LD can be measured between markers spanning regions up to an average of 150 kb long, biallelic marker maps will allow genome-wide LD mapping, provided they have an average inter-marker distance lower than 150 kb.

Genome-wide LD mapping aims at identifying, for any TCA being searched, at least one biallelic marker in LD with said TCA. Preferably, in order to enhance the power of LD maps, in some embodiments, the biallelic markers therein have average inter-marker distances of 150 kb or less, 75 kb or less, or 50 kb or less, 30 kb or less, or 25 kb or less to accommodate the fact that, in some regions of the genome, the detection of LD requires lower inter-marker distances The present invention provides methods to generate biallelic marker maps with average inter-marker distances of 150 kb or less. In some embodiments, the mean distance between biallelic markers constituting the high density map will be less than 75 kb, preferably less than 50 kb. Further preferred maps according to the present invention contain markers that are less than 37.5 kb apart. In highly preferred embodiments, the average inter-marker spacing for the biallelic markers constituting very high density maps is less than 30 kb, most preferably less than 25 kb.

Genetic maps containing biallelic markers (including the 653 biallelic markers obtained above, which include the sequences of SEQ ID Nos. 1–50 and 51–100 or the sequences complementary thereto) may be used to identify and isolate genes associated with detectable traits. The use of the genetic maps of the present invention is described in more detail below.

Use of the High Density Biallelic Marker Map to Identify Genes Associated with a Detectable Trait One embodiment of the present invention comprises methods for identifying and isolating genes associated with a detectable trait using the biallelic marker maps of the present invention.

In the past, the identification of genes linked with detectable traits has relied on a statistical approach called linkage analysis. Linkage analysis is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offspring of all families. Those that co-segregate with the trait are tracked. After pooling data from all families, statistical methods are used to determine the likelihood that the marker and the trait are segregating independently in all families. As a result of the statistical analysis, one or several regions having a high probability of harboring a gene linked to the trait are selected as candidates for further analysis. The result of linkage analysis is considered as significant (i.e. there is a high probability that the region contains a gene involved in a detectable trait) when the chance of independent segregation of the marker and the trait is lower than 1 in 1000 (expressed as a LOD score>3). Generally, the length of the candidate region identified using linkage analysis is between 2 and 20 Mb.

Once a candidate region is identified as described above, analysis of recombinant individuals using additional markers allows further delineation of the candidate linked region.

Linkage analysis studies have generally relied on the use of a maximum of 5,000 microsatellite markers, thus limiting the maximum theoretical attainable resolution of linkage analysis to ca. 600 kb on average.

Linkage analysis has been successfully applied to map simple genetic traits that show clear Mendelian inheritance patterns and which have a high penetrance (penetrance is the ratio between the number of trait positive carriers of allele a and the total number of a carriers in the population). About 100 pathological trait-causing genes were discovered using linkage analysis over the last 10 years. In most of these cases, the majority of affected individuals had affected relatives and the detectable trait was rare in the general population (frequencies less than 0.1%). In about 10 cases, such as Alzheimer's Disease, breast cancer, and Type II diabetes, the detectable trait was more common but the allele associated with the detectable trait was rare in the affected population. Thus, the alleles associated with these traits were not responsible for the trait in all sporadic cases.

Linkage analysis suffers from a variety of drawbacks. First, linkage analysis is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis.

In addition, linkage analysis approaches have proven difficult when applied to complex genetic traits, such as those due to the combined action of multiple genes and/or environmental factors. In such cases, too large an effort and cost are needed to recruit the adequate number of affected families required for applying linkage analysis to these situations, as recently discussed by Risch, N. and Merikangas, K. (*Science* 273:1516–1517 (1996), the disclosure of which is incorporated herein by reference).

Finally, linkage analysis cannot be applied to the study of traits for which no large informative families are available. Typically, this will be the case in any attempt to identify trait-causing alleles involved in sporadic cases, such as alleles associated with positive or negative responses to drug treatment.

The present genetic maps and biallelic markers (including the 653 biallelic markers obtained above, which include the sequences of SEQ ID Nos. 1–50 and 51–100 or the sequences complementary thereto) may be used to identify and isolate genes associated with detectable traits using association studies, an approach which does not require the use of affected families and which permits tie identification of genes associated with sporadic traits.

Association studies are described in more detail below.

Association Studies

As already mentioned, any gene responsible or partly responsible for a given trait will be in LD with some flanking markers. To map such a gene, specific alleles of these flanking markers which are associated with the gene or genes responsible for the trait are identified. Although the following discussion of techniques for finding the gene or genes associated with a particular trait using linkage disequilibrium mapping, refers to locating a single gene which is responsible for the trait, it will be appreciated that the same techniques may also be used to identify genes which are partially responsible for the trait.

Association studies may be conducted within the general population (as opposed to the linkage analysis techniques discussed above which are limited to studies performed on related individuals in one or several affected families).

Association between a biallelic marker A and a trait T may primarily occur as a result of three possible relationships between the biallelic marker and the trait.

First, allele a of biallelic marker A may be directly responsible for trait T (e.g., Apo E ε4 site A and Alzheimer's disease). However, since the majority of the biallelic markers used in genetic mapping studies are selected randomly, they mainly map outside of genes. Thus, the likelihood of allele of being a functional mutation directly related to trait T is very low.

Second, an association between a biallelic marker A and a trait T may also occur when the biallelic marker is very closely linked to the trait locus. In other words, an association occurs when allele a is in linkage disequilibrium with the trait-causing allele. When the biallelic marker is in close proximity to a gene responsible for the trait, more extensive genetic mapping will ultimately allow a gene to be discovered near the marker locus which carries mutations in people with trait T (i.e. the gene responsible for the trait or one of the genes responsible for the trait). As will be further exemplified below, using a group of biallelic markers which are in close proximity to the gene responsible for the trait the location of the causal gene can be deduced from the profile of the association curve between the biallelic markers and the trait. The causal gene will usually be found in the vicinity of the marker showing the highest association with the trait.

Finally, an association between a biallelic marker and a trait may occur when people with the trait and people without the trait correspond to genetically different subsets of the population who, coincidentally, also differ in the frequency of allele a (population stratification). This phenomenon may be avoided by using ethnically matched large heterogeneous samples.

Association studies are particularly suited to the efficient identification of genes that present common polymorphisms, and are involved in multifactorial traits whose frequency is relatively higher than that of diseases with monofactorial inheritance.

Association studies mainly consist of four steps: recruitment of trait-positive (T+) and trait-negative (T−) populations with well-defined phenotypes, identification of a candidate region suspected of harboring a trait causing gene, identification of said gene among candidate genes in the region, and finally validation of mutation(s) responsible for the trait in said trait causing gene.

In a first step, trait + and trait − phenotypes have to be well-defined. In order to perform efficient and significant association studies such as those described herein, the trait under study should preferably follow a bimodal distribution in the population under study, presenting two clear non-overlapping phenotypes, trait + and trait −.

Nevertheless, in the absence of such a bimodal distribution (as may in fact be the case for complex genetic traits), any genetic trait may still be analyzed using the association method proposed herein by carefully selecting the individuals to be included in the trait + and trait − phenotypic groups. The selection procedure involves selecting individuals at opposite ends of the non-bimodal phenotype spectrum of the trait under study, so as to include in these trait + and trait − populations individuals who clearly represent non-overlapping, preferably extreme phenotypes.

The definition of the inclusion criteria for the trait + and trait − populations is an important aspect of the present invention. The selection of those drastically different but relatively uniform phenotypes enables efficient comparisons in association studies and the possible detection of marked differences at the genetic level, provided that the sample sizes of the populations under study are significant enough.

Generally, trait + and trait − populations to be included in association studies such as those proposed in the present invention consist of phenotypically homogeneous populations of individuals each representing 100% of the corresponding phenotype if the trait distribution is bimodal. If the trait distribution is non-bimodal, trait + and trait − populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and selected among individuals exhibiting non-overlapping phenotypes. In some embodiments, the $T^+$ and T groups consist of individuals exhibiting the extreme phenotypes within the studied population. The clearer the difference between the two trait phenotypes, the greater the probability of detecting an association with biallelic markers.

In preferred embodiments, a first group of between 50 and 300 trait + individuals, preferably about 100 individuals, are recruited according to their phenotypes. In each case, a similar number of trait negative individuals are included in such studies who are preferably both ethnically- and age-matched to the trait positive cases. Both trait + and trait − individuals should correspond to unrelated cases.

FIG. 3 shows, for a series of hypothetical sample sizes, the p-value significance obtained in association studies performed using individual markers from the high-density biallelic map, according to various hypotheses regarding the difference of allelic frequencies between the T + and T − samples. It indicates that, in all cases, samples ranging from 150 to 500 individuals are numerous enough to achieve statistical significance. It will be appreciated that bigger or smaller groups can be used to perform association studies according to the methods of the present invention.

In a second step, a marker/trait association study is performed that compares the genotype frequency of each biallelic marker in the above described T + and T − populations by means of a chi square statistical test (one degree of freedom). In addition to this single marker association analysis, a haplotype association analysis is performed to define the frequency and the type of the ancestral carrier haplotype. Haplotype analysis, by combining the informativeness of a set of biallelic markers increases the power of the association analysis, allowing false positive and/or negative data that may result from the single marker studies to be eliminated.

Genotyping can be performed using the microsequencing procedure described in Example 13, or any other genotyping procedure suitable for this intended purpose.

If a positive association with a trait is identified using an array of biallelic markers having a high enough density, the causal gene will be physically located in the vicinity of the associated markers, since the markers showing positive association with the trait are in linkage disequilibrium with the trait locus. Regions harboring a gene responsible for a particular trait which are identified through association studies using high density sets of biallelic markers will, on average, be 20–40 times shorter in length than those identified by linkage analysis.

Once a positive association is confirmed as described above, a third step consists of completely sequencing the BAC inserts harboring the markers identified in the association analyzes. These BACs are obtained through screening human genomic libraries with the markers probes and/or primers, as described above. Once a candidate region has been sequenced and analyzed, the functional sequences within the candidate region (e.g. exons, splice sites, promoters, and other potential regulatory regions) are scanned for mutations which are responsible for the trait by comparing the sequences of the functional regions in a selected number of T+ and T− individuals using appropriate software. Tools for sequence analysis are further described in Example 14.

Finally, candidate mutations are then validated by screening a larger population of T+ and T− individuals using genotyping techniques described below. Polymorphisms are confirmed as candidate mutations when the validation population shows association results compatible with those found between the mutation and the trait in the test population.

In practice, in order to define a region bearing a candidate gene, the trait+ and trait− populations are genotyped using an appropriate number of biallelic markers. The markers may include one or more of the 653 markers obtained above (much include the sequences of SEQ ID Nos: 1–50 and 51–100 or the sequences complementary thereto.

The markers used to define a region bearing a candidate gene may be distributed at an average density of 1 marker per 10–200 kb. Preferably, the markers used to define a region bearing a candidate gene are distributed at an average density of 1 marker every 15–150 kb. In further preferred embodiments, the markers used to define a region bearing a candidate gene are distributed at an average density of 1 marker every 20-100 kb. In yet another preferred embodiment, the markers used to define a region bearing a candidate gene are distributed at an average density of 1 marker every 100 to 150 kb. In a further highly preferred embodiment, the markers used to define a region bearing a candidate gene are distributed at an average density of 1 marker every 50 to 100 kb. In yet another embodiment, the biallelic markers used to define a region bearing a candidate gene are distributed at an average density of 1 marker every 25–50 kilobases. As mentioned above, in order to enhance the power of linkage disequilibrium based maps, in a preferred embodiment, the marker density of the map will be adapted to take the linkage disequilibrium distribution in the genomic region of interest into account.

In some embodiments, the initial identification of a candidate genomic region harboring a gene associated with a detectable phenotype may be conducted using a preliminary map containing a few thousand biallelic markers. Thereafter, the genomic region harboring the gene responsible for the detectable trait may be better delineated using a map containing a larger number of biallelic markers. Furthermore, the genomic region harboring the gene responsible for the detectable trait may be further delineated using a high density map of biallelic markers. Finally, the gene associated with the detectable trait may be identified and isolated using a very high density biallelic marker map.

Example 11 describes a hypothetical procedure for identifying a candidate region harboring a gene associated with a detectable trait. It will be appreciated that although Example 11 compares the results of analyzes using markers derived from maps having 3,000, 20,000, and 60,000 markers, the number of markers contained in the map is not restricted to these exemplary figures. Rather, Example 11 exemplifies the increasing refinement of the candidate region with increasing marker density. As increasing numbers of markers are used in the analysis, points in the association analysis become broad peaks. The gene associated with the detectable trait under investigation will lie within or near the region under the peak.

EXAMPLE 11

Identification of a Candidate Region Harboring a Gene Associated with a Detectable Trait The initial identification of a candidate genomic region harboring a gene associated with a detectable trait may be conducted using a genome-wide map comprising about 20,000 biallelic markers. The candidate genomic region may be further defined using a map having a higher marker density, such as a map comprising about 40,000 markers, about 60,000 markers, about 80,000 markers, about 100,000 markers, or about 120,000 markers.

The use of high density maps such as those described above allows the identification of genes which are truly associated with detectable traits, since the coincidental associations will be randomly distributed along the genome while the true associations will map within one or more discrete genomic regions. Accordingly, biallelic markers located in the vicinity of a gene associated with a detectable trait will give rise to broad peaks in graphs plotting the frequencies of the biallelic markers in T+ individuals versus T− individuals. In contrast, biallelic markers which are not in the vicinity of the gene associated with the detectable trait will produce unique points in such a plot. By determining the association of several markers within the region containing the gene associated with the detectable trait, the gene associated with the detectable trait can be identified using an association curve which reflects the difference between the allele frequencies within the T+ and T− populations for each studied marker. The gene associated with the detectable trait will be found in the vicinity of the marker showing the highest association with the trait.

Figure 4:
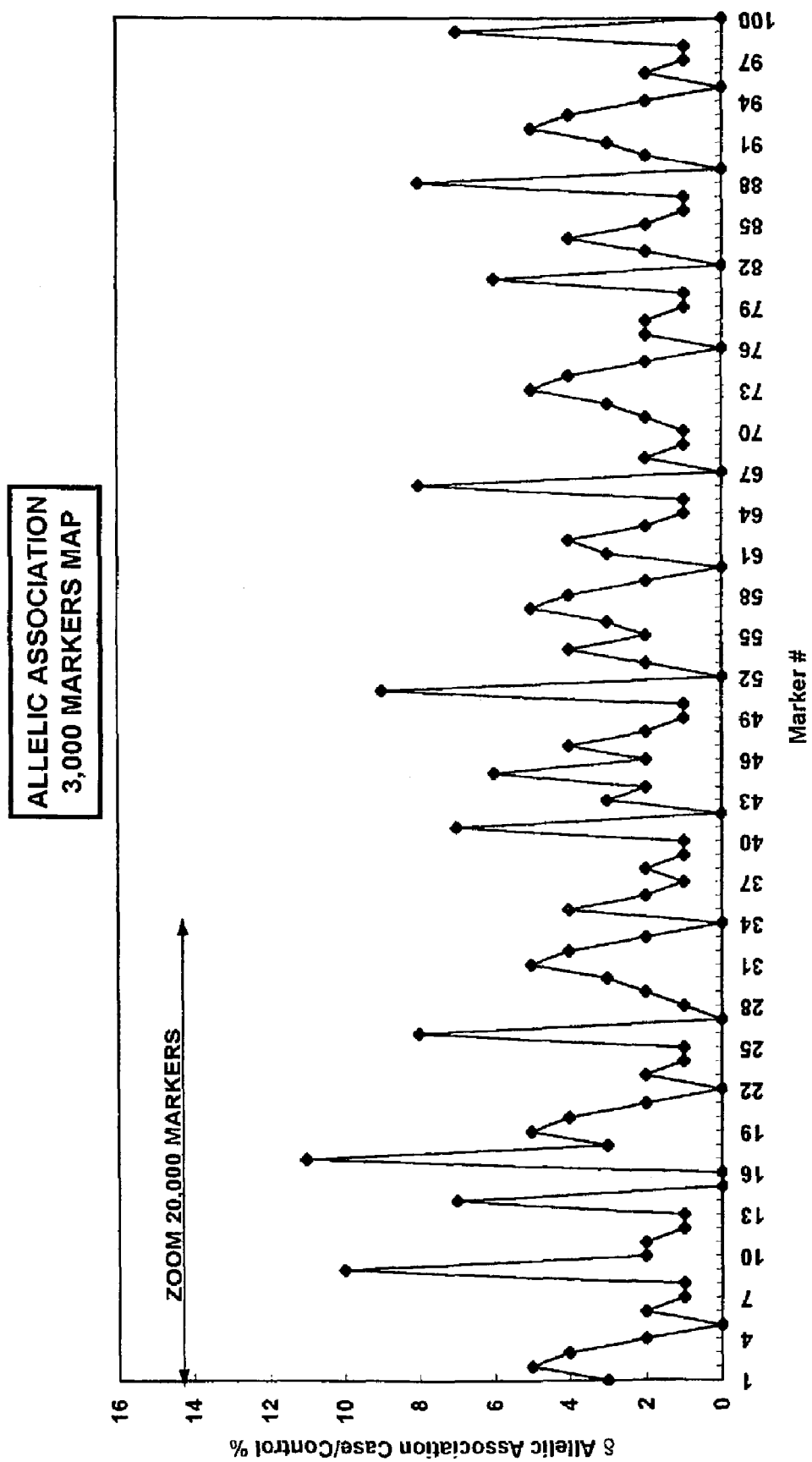
FIG. 4 is a hypothetical association analysis conducted with a map comprising about 3,000 biallelic markers.
Figure 5:
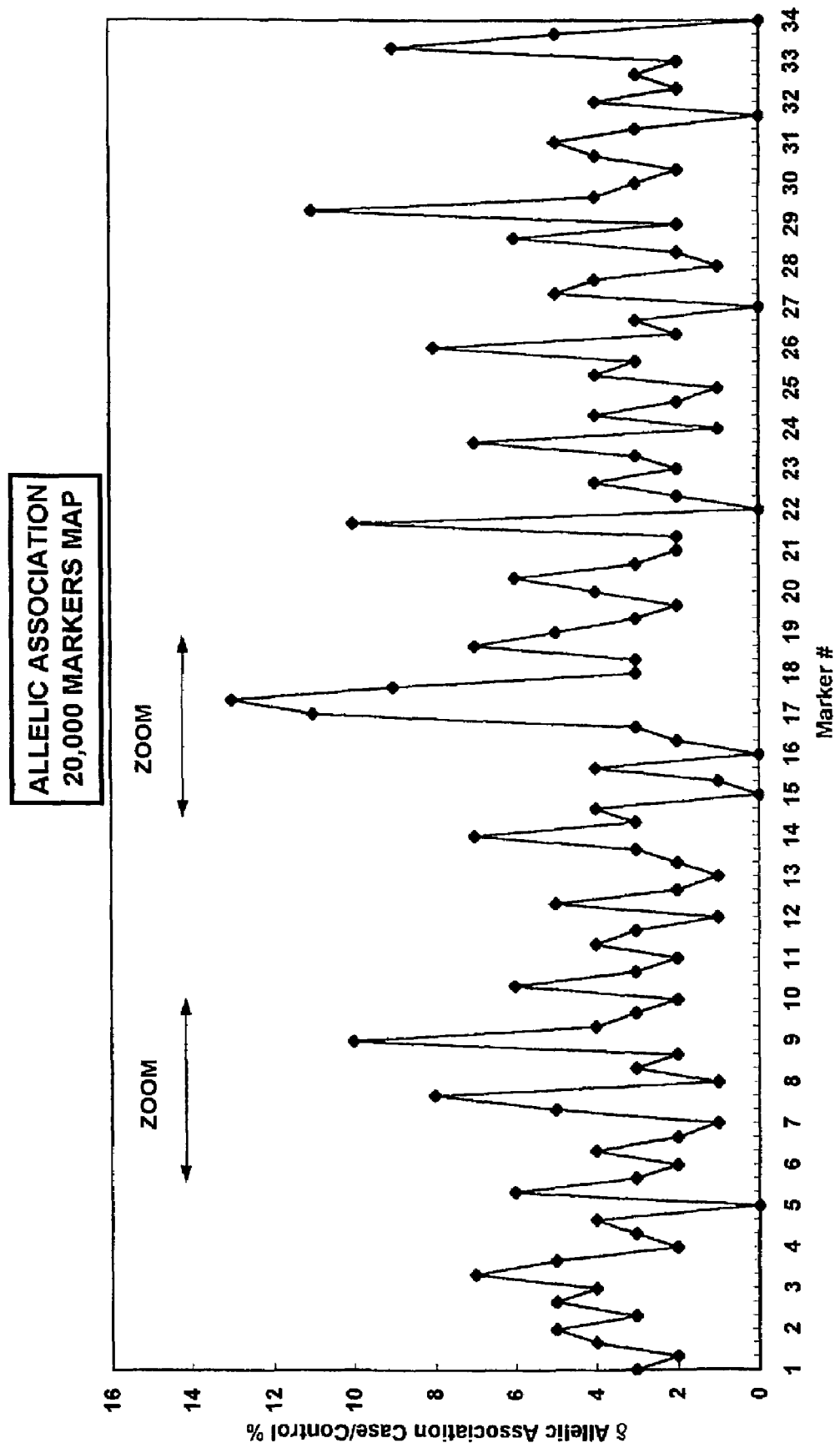
FIG. 5 is a hypothetical association analysis conducted with a map comprising about 20,000 biallelic markers.
Figure 6:
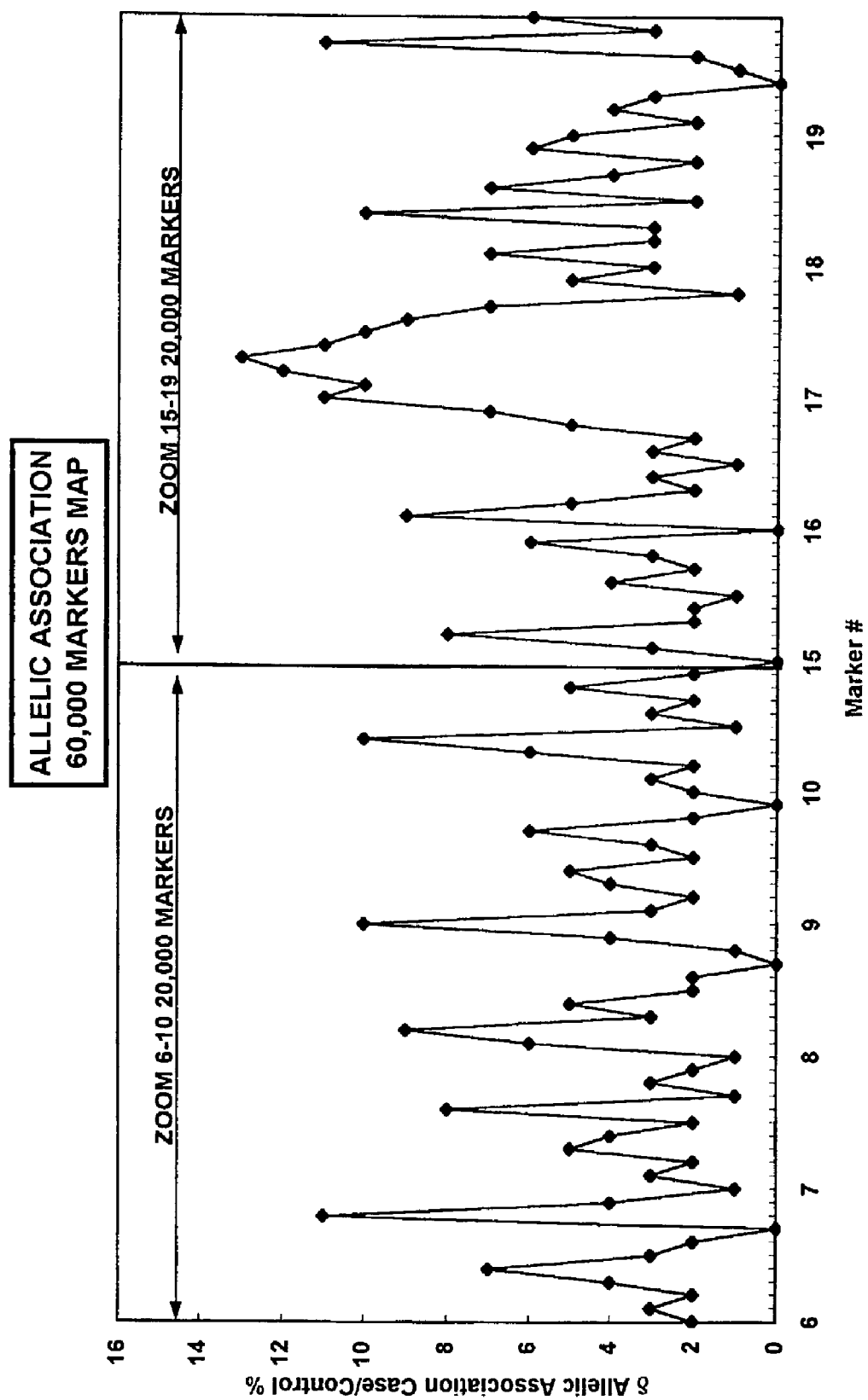
FIG. 6 is a hypothetical association analysis conducted with a map comprising about 60,000 biallelic markers.

FIGS. 4, 5, and 6 illustrate the above principles. As illustrated in FIG. 4, an association analysis conducted with a map comprising about 3,000 biallelic markers yields a group of points. However, when an association analysis is performed using a denser map which includes additional biallelic markers, the points become broad peaks indicative of the location of a gene associated with a detectable trait. For example, the biallelic markers used in the initial association analysis may be obtained from a map comprising about 20,000 biallelic markers, as illustrated in FIG. 5. In some embodiments, one or more of the 653 biallelic markers obtained above (which include the sequences of SEQ ID Nos. 1–50 and 51–100 or the sequences complementary thereto) are used in the association analysis.

In the hypothetical example of FIG. 4, the association analysis with 3,000 markers suggests peaks near markers 9 and 17.

Next, a second analysis is performed using additional markers in the vicinity of markers 9 and 17, as illustrated in the hypothetical example of FIG. 5, using a map of about 20,000 markers. This step again indicates an association in the close vicinity of marker 17, since more markers in this region show an association with the trail. However, none of the additional markers around marker 9 shows a significant association with the trait, which makes marker 9 a potential false positive. In some embodiments, one or more of the 653 biallelic markers obtained above (which include the sequences of SEQ ID Nos. 1–50 and 51–100 or the sequences complementary thereto) are used in the second analysis. In order to further test the validity of these two suspected associations, a third analysis may be obtained with a map comprising about 60,000 biallelic markers. In some embodiments, one or more at the 653 biallelic markers obtained above are used in the third association analysis. In the hypothetical example of FIG. 6, more markers lying around marker 17 exhibit a high degree of association with the detectable trait. Conversely, no association is confirmed in the vicinity of marker 9. The genomic region surrounding marker 17 can thus be considered a candidate region for the hypothetical trait of this simulation.

The statistical power of LD mapping using a high density marker map is also reinforced by complementing the single point association analysis described above with a multi-marker association analysis, called haplotype analysis.

When a chromosome carrying a disease allele is first introduced into a population as a result of either mutation or migration, the mutant allele necessarily resides on a chromosome having a unique set of linked markers: the ancestral haplotype. As already mentioned, a haplotype association analysis allows the frequency and the type of the ancestral carrier haplotype to be defined.

A haplotype analysis is performed by estimating the frequencies of all possible haplotypes for a given set of biallelic markers in the T+ and T− populations, and comparing these frequencies by means of a chi square statistical test (one degree of freedom). Haplotype estimations are usually performed by applying the Expectation-Maximization (EM) algorithm (Excoffier L and Slatkin M. *Mol. Biol. Evol.* 12:921–927 (1995), the disclosure of which is incorporated herein by reference), using the EM-HAPLO program (Hawley M E, Pakstis A J & Kidd K K, *Am. J. Phys. Anthropol.* 18:104 (1994), the disclosure of which is incorporated herein by reference). The EM algorithm is used to estimate haplotype frequencies in the case when only genotype data from unrelated individuals are available. The EM algorithm is a generalized iterative maximum likelihood approach to estimation that is useful when data are ambiguous and/or incomplete.

To improve the statistical power of the individual marker association analyses conducted as described above using maps of increasing marker densities, haplotype studies can be performed using groups of markers located in proximity to one another within regions of the genome. For example, using the methods described above in which the association of an individual marker with a detectable phenotype was analyzed using maps of 3,000 markers, 20,000 markers, and 60,000 markers, a series of haplotype studies can be performed using groups of contiguous markers from such maps or from maps having higher marker densities.

In a preferred embodiment, a series of successive haplotype studies including groups of markers spanning regions of more than 1 Mb may be performed. In some embodiments, the biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb, to 1 Mb, or more than 1 Mb. Preferably, the genomic regions containing the groups of biallelic markers used in the successive haplotype analyses are overlapping. It will be appreciated that the groups of biallelic markers need not completely cover the genomic regions of the above-specified lengths but may instead be obtained from incomplete contigs having one or more gaps therein. As discussed in further detail below, biallelic markers may be used in single point and haplotype association analyses regardless of the completeness of the corresponding physical contig harboring them.

Without wishing to be limited to any particular numerical value, it is believed that those haplotypes displaying a coefficient of relative risk above 1, preferably about 5 or more, preferably of about 7 or more are indicative of a "significant risk" for the individuals carrying the identified haplotype to develop the given trait. However, it is difficult to evaluate accurately quantified boundaries for the so-called "significant risk". Indeed, and as it has been demonstrated previously, several traits observed in a given population are multifactorial in that they are not only the result of a single genetic predisposition but also of other factors such as environmental factors. Thus, the evaluation of a significant risk must take these parameters into consideration in order to, in a certain manner, weigh the potential importance of external parameters in the development of a given trait. Thus, the relative risk which constitutes a "significant risk" to develop a given trait is evaluated differently depending on the trait under consideration and the populations tested.

Genome wide mapping using association studies with dense enough arrays of markers permit a case-by-case best estimate of p-value significance thresholds. Given a test population comprising two ethnically matched trait positive and trait negative groups of about 50 to about 500 individuals or more, conducting the above described association studies will allow a p-value "cut-off" to be established by, for example, analyzing significant numbers of allele frequency differences or, in some cases where appropriate, running computer simulations or control studies as described in Examples 11, 20, and 31.

For a p-value above the threshold, a corresponding association between the trait and a studied marker will be deemed not significant, while for a p-value below such a threshold, said association will be deemed significant. If the p-value is significant, the genomic region around the marker will be further scrutinized for a trait-causing gene.

It is preferred that p-value significance thresholds be assessed for each case/control population comparison. Both the genetic distance between sampled population "stratification"—and the dispersion due to random selection of samples may indeed influence the p-value significance thresholds.

It will be appreciated that the above approaches may be conducted on any scale (i.e. over the whole genome, a set of chromosomes, a single chromosome, a particular subchromosomal region, or any other desired portion of the genome). As mentioned above, once significance thresholds have been assessed, population sample sizes may be adapted as exemplified in FIG. 3.

Example 12 below illustrates the increase in statistical power brought to an association study by a haplotype analysis.

EXAMPLE 12

Haplotype Analysis: Identification of Biallelic Markers Delineating a Genomic Region Associated with Alzheimer's Disease (AD)

As shown in Table 3 within Example 10, at an average map density of one marker per 40 kb only one marker (99-365/344) out of five random biallelic markers from a ca. 200 kb genomic region around the Apo E gene showed a clear association to AD (delta allelic frequency in cases and controls=18%; p value=6.9 E-10). The allelic frequencies of the other four random markers were not significantly different between AD cases and controls (p-values≧E-01). However, since linkage disequilibrium can usually be detected between markers located further apart than an average 40 kb as previously discussed, one should expect that, performing an association study with a local excerpt of a biallelic marker map covering ca. 200 kb with an average inter-marker distance of ca. 40 kb should allow the identification of more than one biallelic marker associated with AD.

A haplotype analysis was thus performed using the biallelic markers 99-344/439: 99-355/219; 99-359/308; 99-365/344; and 99-366/274 (of SEQ ID Nos: 301–305 and 307–311).

In a first step, marker 99-365/344 that was already found associated with AD was not included in the haplotype study. Only biallelic markers 99-344/439; 99-355/219; 99-359/308; and 99-366/274, which did not show any significant association with AD when taken individually, were used. This first haplotype analysis measured frequencies of all possible two-, three-, or four-marker haplotypes in the AD case and control populations. As shown in FIG. 7, there was one haplotype among all the potential different haplotypes based on the four individually non-significant markers ("haplotype 8", TAGG comprising SEQ ID No. 305 which is the T allele of marker 99-366/274, SEQ ID No. 301 which is the A allele of marker 99-344/439, SEQ ID No. 303 which is the G allele of 99-359/308 and SEQ ID No. 302 which is the G allele of marker 99-355/219), that was present at statistically significant different frequencies in the AD case and control populations (Δ=12%; p value=2.05 E-06). Moreover, a significant difference was already observed for a three-marker haplotype included in the above mentioned "haplotype 8" ("haplotype 7", TGG, Δ=10%: p value=4.76 E-05). Haplotype 7 comprises SEQ ID No. 305 which is the T allele of marker 99-366/274, SEQ ID No. 303 which is the G allele of marker 99-359/308 and SEQ ID No. 302 which is the G allele of marker 99-355/219). The haplotype association analysis thus clearly increased the statistical power of the individual marker association studies by more than four orders of magnitude when compared to single-marker analysis (from p values≧E-01 for the individual markers—see Table 3—to p value≦2 E-06 for the four-marker "haplotype 8").

Figure 8:
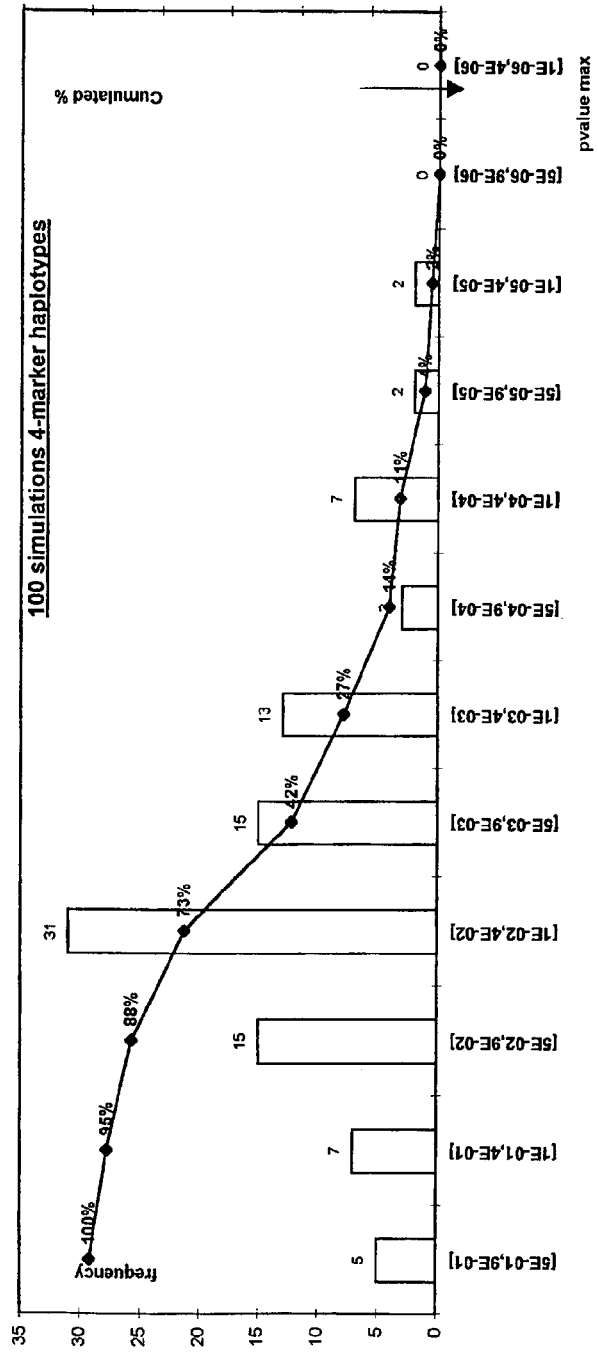
FIG. 8 is a simulated haplotype analysis using the biallelic markers in the Apo E region included in the haplotype analysis of FIG. 7.

The significance of the values obtained for this haplotype association analysis was evaluated by the following computer simulation. The genotype data from the AD cases and the unaffected controls were pooled and randomly allocated to two groups which contained the same number of individuals as the case/control groups used to produce the data summarized in FIG. 7. A four-marker haplotype analysis (99-344/439; 99-355/219; 99-359/308; and 99-366/274) was run on these artificial groups. This experiment was reiterated 100 times and the results are shown in FIG. 8. No haplotype among those generated was found for which the p-value of the frequency difference between both populations was more significant than 1 E-05. In addition, only 4% of the generated haplotypes showed p-values lower than 1 E-04. Since both these p-value thresholds are less significant than the 2 E-06 p-value showed by "haplotype 8", this haplotype can be considered significantly associated with AD.

In a second step, marker 99-365/344 was included in the haplotype analyzes. The frequency differences between the affected and non affected populations was calculated for all two-, three-, four- or five-marker haplotypes involving markers: 99-344/439; 99-355/219; 99-359/308; 99-366/274: and 99-365/344. The most significant p-values obtained in each category of haplotype (involving two, three, four or five markers) were examined depending on which markers were involved or not within the haplotype. This showed that all haplotypes which included marker 99-365/344 showed a significant association with AD (p-values in the range of E-04 to E-11).

An additional way of evaluating the significance of the values obtained in the haplotype association analysis was to perform a similar AD case-control study on biallelic markers generated from BACs containing inserts corresponding to genomic regions derived from chromosomes 13 or 21 and not known to be involved in Alzheimer's disease. Performing similar haplotype and individual association analyzes as those described above and in Example 10 did not generate any significant association results (all p-values for haplotype analyzes were less significant than E-03; all p-values for single marker association studies were less significant than E-02).

The results described in Examples 10 and 12, generated from individual and haplotype studies using a biallelic marker set of an average density equal to ca. 40 kb in the region of an Alzheimer's disease trait causing gene, indicate that all biallelic markers of sufficient informative content located within a ca 200 kb genomic region around a TCA can potentially be successfully used to localize a trait causing gene with the methods provided by the present invention. This conclusion is further supported by the results obtained through measuring the linkage disequilibrium between markers 99-365/344 or 99-359/308 and ApoE 4 Site A marker within Alzheimer's patients: as one could predict since LD is supporting basis for association studies, LD between these pairs of markers was enhanced in the diseased population vs. the control population. In a similar way as the haplotype analysis enhanced the significance of the corresponding association studies.

Once a given polymorphic site has been found and characterized as a biallelic marker according to the methods of the present invention, several methods can be used in order to determine the specific allele carried by an individual at the given polymorphic base.

In some embodiments, genotyping will be applied to one or more of the markers of SEQ ID Nos: 301–305 and 307–311 or the sequences complementary thereto. In additional embodiments, genotyping will be applied to the markers of SEQ ID Nos. 306 and 312 as well as one or more of the markers of SEQ ID Nos. 301–305 and 307–311. In some embodiments, genotyping will be applied to one or more of the 653 biallelic markers obtained above (which include the sequences of SEQ ID Nos. 1–50 and 51–100 or the sequences complementary thereto). The present invention further contemplates the genotyping of any biallelic marker within the provided maps, including those that are in linkage disequilibrium with the 653 biallelic markers obtained above (which include the sequences of SEQ ID Nos. 1–50 and 51–100 or the sequences complementary thereto) or the markers of SEQ ID Nos. 301–312 or the sequences complementary thereto.

Most genotyping methods require the previous amplification of a DNA region carrying the polymorphic site of interest.

The identification of biallelic markers described previously, allows the design or appropriate oligonucleotides, which can be used as primers to amplify a DNA fragment containing the polymorphic site of interest and for the detection of such polymorphisms.

In particularly preferred embodiments, pairs of primers of SEQ ID Nos: 313–318 and 319–324 may be used to generate amplicons harboring the markers of SEQ ID Nos: 301–306/307–312 or the sequences complementary thereto. In further embodiments, pairs of amplification primers may be used to generate amplicons harboring the 653 markers obtained above (which include the sequences of SEQ ID Nos. 1–50 and 51–100 or the sequences complementary thereto. In highly preferred embodiments, pairs of the amplification primers of SEQ ID Nos. 101–150 and 151–200 may be used to generate amplicons harboring the markers of SEQ ID Nos: 1–50 and 51–100 or the sequences complementary thereto.

It will be appreciated that amplification primers may be designed having any length suitable for their intended purpose, in particular any length allowing their hybridization with a region of the DNA fragment to be amplified.

It will be further appreciated that the hybridization site of said amplification primers may be located at any distance from the polymorphic base to be genotyped, provided said amplification primers allow the proper amplification of a DNA fragment carrying said polymorphic site. The amplification primers may be oligonucleotides of 10, 15, 20 or more bases in length which enable the amplification of the polymorphic site in the markers. In some embodiments, the amplification product produced using these primers may be at least 100 bases in length (i.e. on average 50 nucleotides on each side of the polymorphic base). In other embodiments, the amplification product produced using these primers may be at least 500 bases in length (i.e. on average 250 nucleotides on each side of the polymorphic base). In still further embodiments, the amplification product produced using these primers may be at least 1000 bases in length (i.e. on average 500 nucleotides on each side of the polymorphic base).

The amplification of polymorphic fragments can be carried as described in Example 6 on DNA samples extracted as described in Example 5.

As already mentioned, allele frequencies of biallelic markers tested in association studies (individual or haplotype) may be determined using microsequencing procedures.

A first step in microsequencing procedures consists in designing microsequencing primers adapted to each biallelic marker to be genotyped. Microsequencing primers hybridize upstream of the polymorphic base to be genotyped, either with the coding or with the non-coding strand. Microsequencing primers may be oligonucleotides of 8, 10, 15, 20 or more bases in length. Preferably, the 3' end of the microsequencing primer is immediately upstream of the polymorphic base of the biallelic marker being genotyped, such that upon extension of the primer, the polymorphic base is the first base incorporated. Such microsequencing primers are included within the scope of the present invention.

In preferred embodiments, the microsequencing primers are those indicated as features within the sequence listings corresponding to markers of SEQ ID Nos: 325–330/331–336. In some embodiments, the 653 biallelic markers obtained above (which include the sequences of SEQ ID Nos. 1–50 and 51–100 or the sequences complementary thereto) are genotyped using appropriate microsequencing oligonucleotides such as those of SEQ ID Nos. 201–250 or 251–300.

It will be appreciated that the biallelic markers of the present invention may be genotyped using microsequencing primers having any desirable length, and hybridizing to any of the strands of the marker to be tested, provided their design is suitable for their intended purpose. In some embodiments, the amplification primers or microsequencing primers may be labeled. For example, in some embodiments, the amplification primers or microsequencing primers may be biotinylated.

Typical microsequencing procedures that can be used in the context of the present invention are described in Example 13 below.

EXAMPLE 13

Genotyping of Biallelic Markers Using Microsequencing Procedures

Several microsequencing protocols conducted in liquid phase are well known to those skilled in the art. A first possible detection analysis allowing the allele characterization of the microsequencing reaction products relies on detecting fluorescent ddNTP- extended microsequencing primers after gel electrophoresis. A first alternative to this approach consists in performing a liquid phase microsequencing reaction, the analysis of which may be carried out in solid phase.

For example, the microsequencing reaction may be performed using 5'-biotinylated oligonucleotide primers and fluorescein-dideoxynucleotides. The biotinylated oligonucleotide is annealed to the target nucleic acid sequence immediately adjacent to the polymorphic nucleotide position of interest. It is then specifically extended at its 3'-end following a PCR cycle, wherein the labeled dideoxynucleotide analog complementary to the polymorphic base is incorporated. The biotinylated primer is then captured on a microtiter plate coated with streptavidin. The analysis is thus entirely carried out in a microtiter plate format. The incorporated ddNTP is detected by a fluorescein antibody—alkaline phosphatase conjugate.

In practice this microsequencing analysis is performed as follows 20 µl of the microsequencing reaction is added to 80 µl of capture buffer (SSC 2X, 2.5% PEG 8000, 0.25 M Tris pU 7.5, 1.8% BSA, 0.05% TWEEN 20 (Polysorbate20)) and incubated for 20 minutes on a microtiter plate coated with streptavidin (Boehringer). The plate is rinsed once with washing buffer (0.1 M Tris pII 7.5, 0.1 M NaCl, 0.1% TWEEN 20 (Polysorbate_20)). 100 µl of anti-fluorescein antibody conjugated with phosphatase alkaline, diluted 1/5000 in washing buffer containing 1.8% BSA is added to the microtiter plate. The antibody is incubated on the microtiter plate for 20 minutes. After washing the microtiter plate four times, 100 µof 4-methylumbelliferyl phosphate (Sigma) diluted to 0.4 mg/ml in 0.1 M diethanolamine pH 9.6, 10 mM $MgCl_2$ are added The detection of the microsequencing reaction is carded out on a fluorimeter (Dynatech) after 20 minutes of incubation.

As another alternative, solid phase microsequencing reactions have been developed, for which either the oligonucleotide microsequencing primers or the PCR-amplified products derived from the DNA fragment of interest are immobilized. For example, immobilization can be carried out via an interaction between biotinylated DNA and streptavidin-coated microtitration wells or avidin-coated polystyrene particles.

As a further alternative, the PCR reaction generating the amplicons to be genotyped can be performed directly in solid phase conditions, following procedures such as those described in WO 96/13609, the disclosure of which is incorporated herein by reference.

In such solid phase microsequencing reactions, incorporated ddNTPs can either be radiolabeled (see Syvanen. *Clin. Chim. Acta.* 226:225–236 (1994), the disclosure of which is incorporated herein by reference) or linked to fluorescein (see Livak and Hainer, *Hum. Metat.* 3:379–385 (1994), the disclosure of which is incorporated herein by reference). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible reporter-detection couples for use in the above microsequencing procedures include: ddNTP linked to dinitrophenyl (DNP) and anti-DNP alkaline phosphatase conjugate (see Harju et al., *Clin Chem*.39(11Pt 1):2282–2287 (1993), incorporated herein by reference) biotinylated ddNTP and horseradish peroxidase-conjugated streptavidin with o-phenylenediamine as a substrate (see WO 92/15712, incorporated herein by reference).

A diagnosis kit based on fluorescein-linked ddNTP with antifluorescein antibody conjugated with alkaline phosphatase has been commercialized under the name PRONTO by GamidaGen Ltd.

As yet another alternative microsequencing procedure, Nyren et al. (*Anal. Biochem.* 208:171–175 (1993), the disclosure of which is incorporated herein by reference) have described a solid-phase DNA sequencing procedure that relies on the detection of DNA polymerase activity by an enzymatic luminometric inorganic pyrophosphate detection assay (ELIDA). In this procedure, the PCR-amplified products are biotinylated and immobilized on beads. The microsequencing primer is annealed and four aliquots of this mixture are separately incubated with DNA polymerase and one of the four different ddNTPs. After the reaction, the resulting fragments are washed and used as substrates in a primer extension reaction with all four dNTPs present. The progress of the DNA-directed polymerization reactions is monitored with the ELIDA. Incorporation of a ddNTP in the first reaction prevents the formation of pyrophosphate during the subsequent dNTP reaction. In contrast, no ddNTP incorporation in the first reaction gives extensive pyrophosphate release during the dNTP reaction and this leads to generation of light throughout the ELIDA reactions. From the ELIDA results, the identity of the first base after the primer is easily deduced.

It will be appreciated that several parameters of the above-described microsequencing procedures may be successfully modified by those skilled in the art without undue experimentation. In particular, high throughput improvements to these procedures may be elaborated, following principles such as those described further below.

It will be further appreciated that any other genotyping procedure may be applied to the genotyping of biallelic markers.

Once the candidate region has been delineated using the high density biallelic marker map, a sequence analysis process will allow the detection of all genes located within said region, together with a potential functional characterization of said genes. The identified functional features may allow preferred trait-causing candidates to be chosen from among the identified genes. More biallelic markers may then be generated within said candidate genes, and used to perform refined association studies that will support the identification of the trait causing gene. Sequence analysis processes are described in Example 14 below.

EXAMPLE 14

Sequence Analysis

DNA sequences, such as BAC inserts, containing the region carrying the candidate gene associated with the detectable trait are sequenced and their sequence is analyzed using automated software which eliminates repeat sequences while retaining potential gene sequences. The potential gene sequences are compared to numerous databases to identify potential exons using a set of scoring algorithms such as trained Hidden Markov Models, statistical analysis models (including promoter prediction tools) and the GRAIL neural network. Preferred databases for use in this analysis, the construction and use of which are further detailed in Example 22 below, include the following:

NetGene Database:

This proprietary database contains sequences of 5' cDNA tags, obtained from a number of tissues and cells. Currently more than 50,000 different 5' clones representing more than 50,000 different genes are included in NetGene. The sequences in the NetGene database correspond specifically to the 5' regions of transcripts (first exons) and therefore allow mapping of the beginning of genes within raw genomic sequences.

NRPU (Non-Redundant Protein-Unique) Database:

NRPU is a non-redundant merge of the publicly available NBRF/PIR. Genpept, and SwissProt databases. Homologies found with NRPU allow the identification of regions potentially coding for already known proteins or related to known proteins (translated exons).

NREST (Non-Redundant EST Database):

NREST is a merge of the EST subsection of the publicly available GenBank database. Homologies found with NREST allow the location of potentially transcribed regions (translated or non-translated exons).

NRN (Non-Redundant Nucleic Acid Database):

NRN is a merge of GenBank, EMBL and their daily updates.

Any sequence giving a positive hit with NRPU, NREST or an "excellent" score using GRAIL or/and other scoring algorithms is considered a potential functional region, and is then considered a candidate for genomic analysis.

While this first screening allows the detection of the "strongest" exons, a semi-automatic scan is further applied to the remaining sequences in the context of the sequence assembly. That is, the sequences neighboring a 5' site or an exon are submitted to another round of bioinformatics analysis with modified parameters. In this way, new exon candidates are generated for genomic analysis.

Using the above procedures, genes associated with detectable traits may be identified.

Examples 15–23 illustrate the application of the above methods using biallelic markers to identify a gene associated with a complex disease, prostate cancer, within a ca. 450 kb candidate region. Additional details of the identification of the gene associated with prostate cancer are provided in the U.S. Patent Application entitled "Prostate Cancer Gene" (GENSET.018A, Ser. No. 08/996,306 now U.S. Pat. No. 5,945,522), the disclosure of which is incorporated herein by reference.

Use of Biallelic Markers to Identify a Gene Associated with Prostate Cancer

Substantial amounts of LOH data supported the hypothesis that genes associated with distinct cancer types are located within a particular region of the human genome. More specifically, this region was likely to harbor a gene associated with prostate cancer. Association studies were performed as described below in order to identify this prostate cancer gene. A YAC contig containing the genomic region suspected of harboring a gene associated with prostate cancer was constructed as described in Example 15 below.

EXAMPLE 15

YAC Contig Construction in the Candidate Genomic Region

First, a YAC contig which contains the candidate genomic region was constructed as follows. The CEPH-Genethon YAC map for the entire human genome (Chumakov et al. (1995), supra) was used for detailed contig building in the genomic region containing genetic markers known to map in the candidate genomic region. Screening data available for several publicly available genetic markers were used to select a set of CEPH YACs localized within the candidate region. This set of YACs was tested by PCR with the above mentioned genetic markers as well as with other publicly available markers supposedly located within the candidate region. As a result of these studies, a YAC STS contig map was generated around genetic markers known to map in this genomic region. Two CEPH YACs were found to constitute a minimal tiling path in this region, with an estimated size of ca. 2 Megabases.

During this mapping effort, several publicly known STS markers were precisely located within the contig.

Example 16 below describes the identification of sets of biallelic markers within the candidate genomic region.

EXAMPLE 16

BAC Contig Construction and Biallelic Markers Isolation Within the Candidate Chromosomal Region Next, a BAC contig covering the candidate genomic region was constructed as follows. BAC libraries were obtained as described in Woo et al., *Nucleic Acids Res.* 22:4922–4931 (1994), the disclosure of which is incorporated herein by reference. Briefly, the two whole human genome BamHI and HindIII libraries already described in Example 1 were constructed using the pBeloBAC11 vector (Kim et al. (1996), supra).

The BAC libraries were then screened with all of the above mentioned STSs, following the procedure described in Example 2 above.

The ordered BACs selected by STS screening and verified by FISH, were assembled into contigs and new markers were generated by partial sequencing of insert ends from some of them. These markers were used to fill the gaps in the contig of BAC clones covering the candidate chromosomal region having an estimated size of 2 megabases.

FIG. 8 illustrates a minimal array of overlapping clones which was chosen for further studies, and the positions of the publicly known STS markers along said contig.

Selected BAC clones from the contig were subcloned and sequenced, essentially following the procedures described in Examples 3 and 4.

Biallelic markers lying along the contig were identified following the processes described in Examples 5 and 6.

Figure 9:
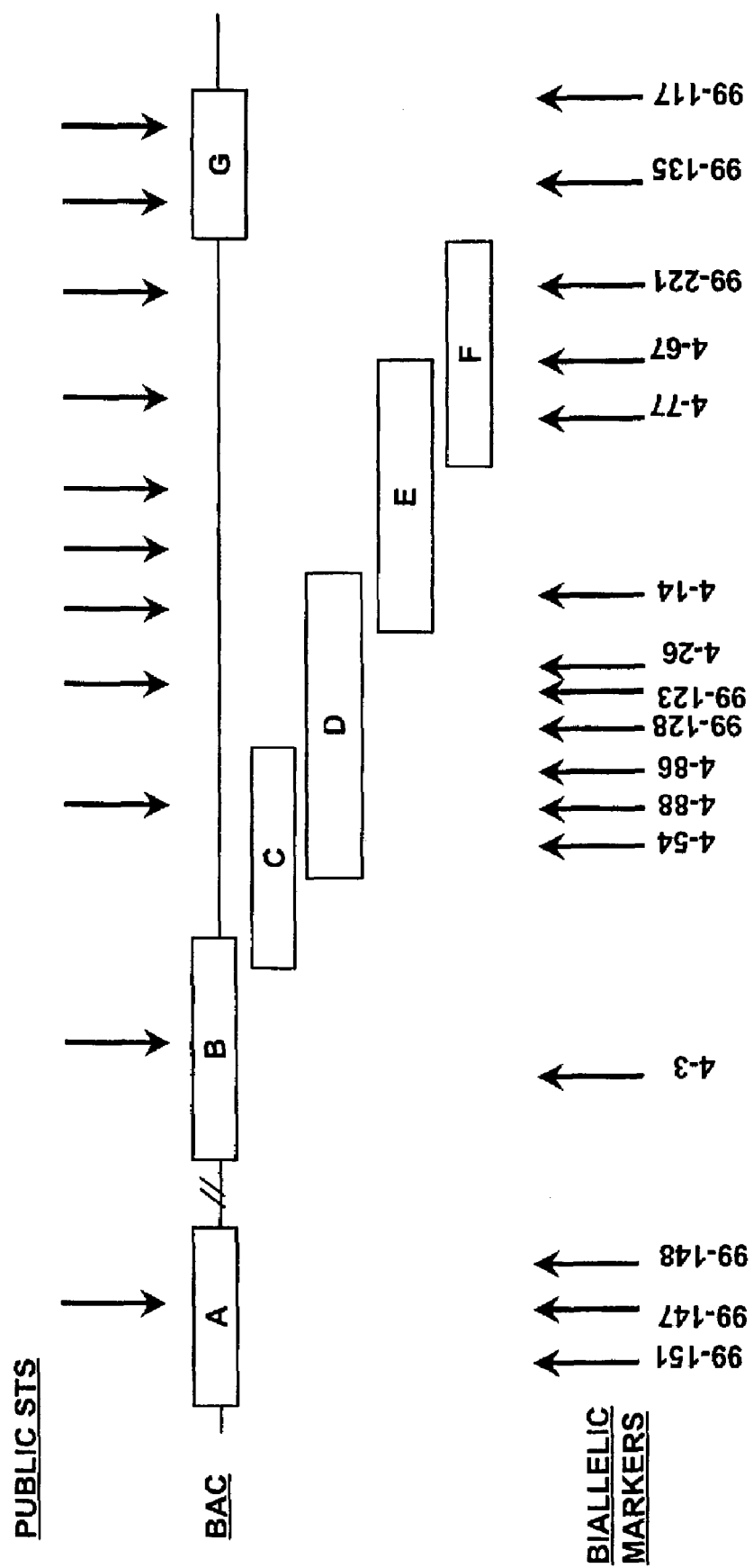
FIG. 9 shows a minimal array of overlapping clones which was chosen for further studies of biallelic markers associated with prostate cancer, the positions of STS markers known to map in the candidate genomic region along the contig, and the locations of biallelic markers along the BAC contig harboring a genomic region harboring a candidate gene associated with prostate cancer which were identified using the methods of the present invention.

FIG. 9 shows the locations of the biallelic markers along the BAC contig. This first set of markers corresponds to a medium density map of the candidate locus, with an inter-marker distance averaging 50 kb–150 kb.

A second set of biallelic markers was then generated as described above in order to provide a very high-density map of the region identified using the first set of markers which can be used to conduct association studies, as explained below. This very high density map has markers spaced on average every 2–50 kb.

The biallelic markers were then used in association studies. DNA samples were obtained from individuals suffering from prostate cancer and unaffected individuals as described in Example 17.

EXAMPLE 17

Collection of DNA Samples from Affected and Non-affected Individuals

Prostate cancer patients were recruited according to clinical inclusion criteria based on pathological or radical prostatectomy records. Control cases included in this study were both ethnically- and age-matched to the affected cases; they were checked for both the absence of all clinical and biological criteria defining the presence or the risk of prostate cancer, and for the absence of related familial prostate cancer cases. Both affected and control individuals were all unrelated.

The two following groups of independent individuals were used in the association studies. The first group, comprising individuals suffering from prostate cancer, contained 185 individuals. Of these 185 cases of prostate cancer, 47 cases were sporadic and 138 cases were familial. The control group contained 104 non-diseased individuals.

Haplotype analysis was conducted using additional diseased (total samples: 281) and control samples (total samples: 130), from individuals recruited according to similar criteria.

DNA was extracted from peripheral venous blood of all individuals as described in Example 5.

The frequencies of the biallelic markers in each population were determined as described in Example 18.

EXAMPLE 18

Genotyping Affected and Control Individuals

Genotyping was performed using the following microsequencing procedure. Amplification was performed on each DNA sample using primers designed as previously explained. The pairs of primers were used to generate amplicons harboring the biallelic markers 99-123, 4-26, 4-14, 4-77, 99-217, 4-67, 99-213, 99-221, 99-135, 99-1482, 4-73, and 4-65 using the protocols described in Example 8 above.

Microsequencing primers were designed for each of the biallelic markers, as previously described. After purification of the amplification products, the microsequencing reaction mixture was prepared by adding, in a 20 μl final volume; 10 pmol microsequencing oligonucleotide, 1 U Thermosequenase (Amersham E79000G), 1.25 μl Thermosequenase buffer (260 mM Tris HCl pH 9.5, 65 mM MgCl$_2$, and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C. 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized as homozygous or heterozygous based on the height ratio.

Association analyzes were then performed using the biallelic markers as described below.

EXAMPLE 19

Association Analysis

Figure 10:
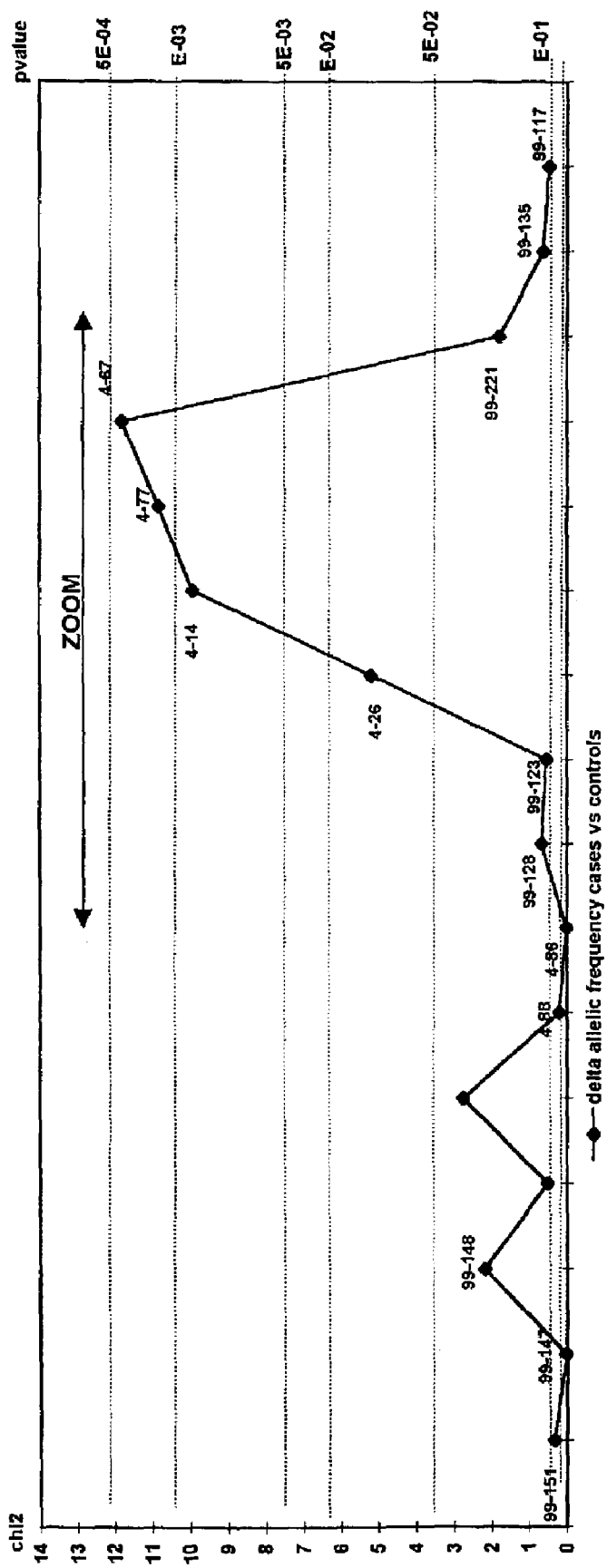
FIG. 10 is a rough localization of a candidate gene for prostate cancer which was obtained by determining the frequencies of the biallelic markers of FIG. 9 in affected and unaffected populations.

Association studies were run in two successive steps. In a first step, a rough localization of the candidate gene was achieved by determining the frequencies of the biallelic markers of FIG. 9 in the affected and unaffected populations. The results of this rough localization are shown in FIG. 10. This analysis indicated that a gene responsible for prostate cancer was located near the biallelic marker designated 4-67. In a second phase of the analysis, the position of the gene responsible for prostate cancer was further refined using the very high density set of markers including the 99-123, 4-26, 4-14, 4-77, 99-217, 4-87, 99-213, 99-221, 99-135, 99-1482, 4-73, and 4-65 markers.

Figure 11:
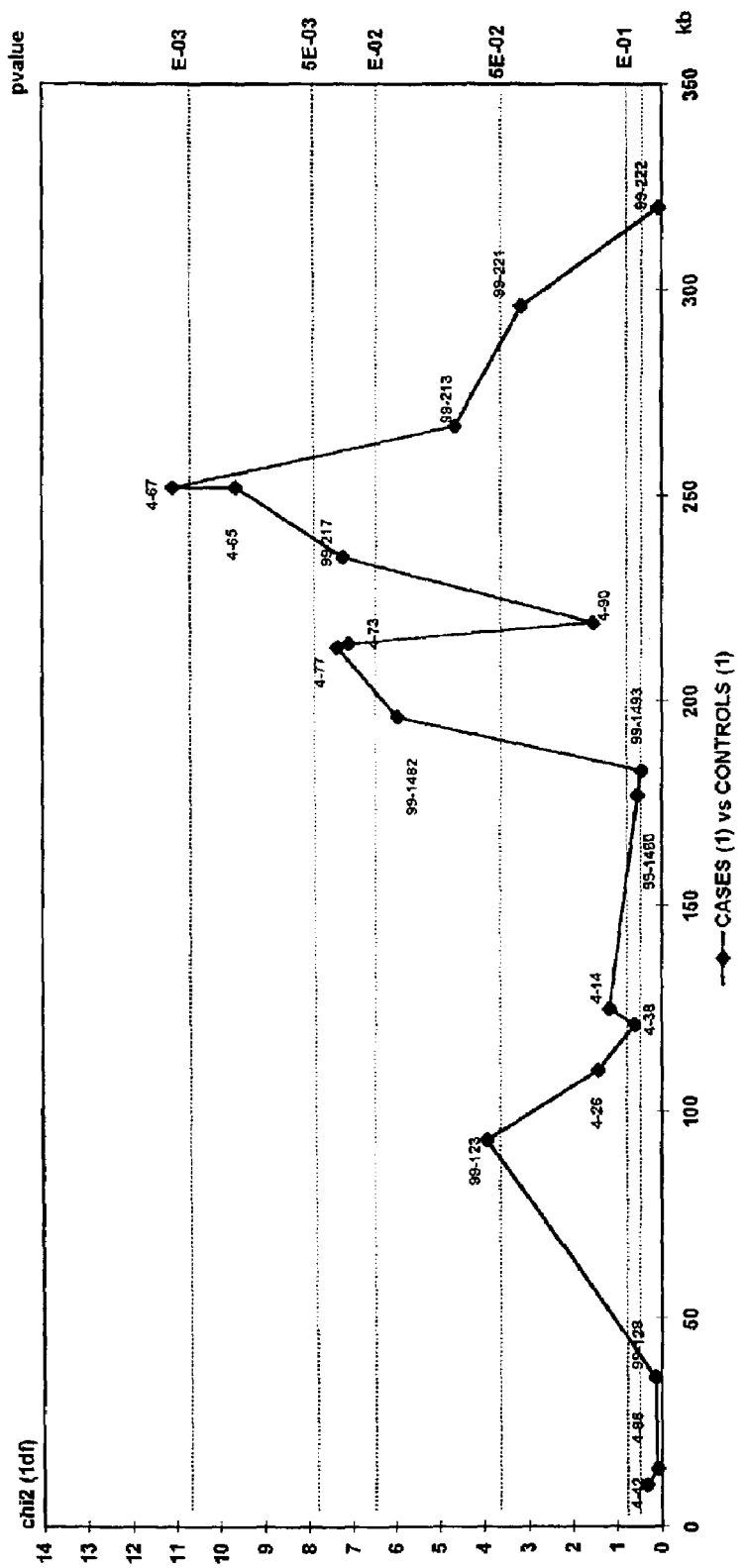
FIG. 11 is a further refinement of the localization of the candidate gene for prostate cancer using additional biallelic markers which were not included in the rough localization illustrated in FIG. 10.

As shown in FIG. 11, the second phase of the analysis confirmed that the gene responsible for prostate cancer was near the biallelic marker designated 4-67, most probably within a ca. 150 kb region comprising the marker.

A haplotype analysis was also performed as described in Example 20.

EXAMPLE 20

Haplotype Analysis

The allelic frequencies of each of the alleles of biallelic markers 99-123, 4-26, 4-14, 4-77, 99-217, 4-67, 99-213, 99-221, and 99-135 were determined in the affected and unaffected populations. Table 4 lists the internal identification numbers of the markers used in the haplotype analysis, the alleles of each marker, the most frequent allele in both unaffected individuals and individuals suffering from prostate cancer, the least frequent allele in both unaffected individuals and individuals suffering from prostate cancer, and the frequencies of the least frequent alleles in each population.

TABLE 4

| | | Frequency of least frequent allele** | |
|---|---|---|---|
| Markers | Polymorphic base* | Cases | Controls |
| 99-123 | C/T | 0.35 | 0.3 |
| 4-26 | A/G | 0.39 | 0.45 |
| 4-14 | C/T | 0.35 | 0.41 |
| 4-77 | C/G | 0.33 | 0.24 |
| 99-217 | C/T | 0.31 | 0.23 |
| 4-67 | C/T | 0.26 | 0.16 |
| 99-213 | T/C | 0.45 | 0.38 |

TABLE 4-continued

| | | Frequency of least frequent allele** | |
|---|---|---|---|
| Markers | Polymorphic base* | Cases | Controls |
| 99-221 | C/A | 0.43 | 0.43 |
| 99-135 | A/G | 0.25 | 0.3 | most frequent allele/least frequent allele
standard deviations
0.023 to 0.031 for controls
0.018 to 0.021 for cases Among all the theoretical potential different haplotypes based on 2 to 9 markers, 11 haplotypes showing a strong association with prostate cancer were selected. The results of these haplotype analyzes are shown in FIG. 12.

FIGS. 11, and 12 aggregate association analysis results with sequencing results—generated following the procedures further described in Example 21—which permitted the physical order and/or the distance between markers to be estimated.

The significance of the values obtained in FIG. 12 are underscored by the following results of computer simulations. For the computer simulations, the data from the affected individuals and the unaffected controls were pooled and randomly allocated to two groups which contained the same number of individuals as the affected and unaffected groups used to compile the data summarized in FIG. 12. A haplotype analysis was run on these artificial groups for the six markers included in haplotype 5 of FIG. 12. This experiment was reiterated 100 times and the results are shown in FIG. 13. Among 100 iterations, only 5% of the obtained haplotypes are present with a p-value less significant than E-04 as compared to the p-value of $9^E$-07 for haplotype 5 of FIG. 12. Furthermore, for haplotype 5 of FIG. 12, only 6% of the obtained haplotypes have a significance level below $5^E$-03, while none of them show a significance level below $5^E$-03.

Thus, using the data of FIG. 13 and evaluating the associations for single marker alleles or for haplotypes will permit estimation of the risk a corresponding carrier has to develop prostate cancer. It will be appreciated that significance thresholds of relative risks will be more finely assessed according to the population tested.

Diagnostic techniques for determining an individual's risk of developing prostate cancer may be implemented as described below for the markers in the maps of the present invention, including the 99-123, 4-26, 4-14, 4-77, 99-217, 4-87, 99-213, 99-221, and 99-135markers.

The above haplotype analysis indicated that 171 kb of genomic DNA between biallelic markers 4-14 and 99-221 totally or partially contains a gene responsible for prostate cancer. Therefore, the protein coding sequences lying within this region were characterized to locate the gene associated with prostate cancer. This analysis, described in further detail below, revealed a single protein coding sequence in the 171 kb genomic region, which was designated as the PG1 gene.

EXAMPLE 21

Identification of the Genomic Sequence in the Candidate Region

Template DNA for sequencing the PG1 gene was obtained as follows. BACs E and F from FIG. 9 were subcloned as previously described. Plasmid inserts were first amplified by PCR on PE 9600 thermocyclers (Perkin-Elmer), using appropriate primers, AmpliTaqGold (Perkin-Elmer), dNTPs Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data obtained as described above were transferred to a proprietary database, where quality control and validation steps were performed. A proprietary base-caller flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded.

The sequence fragments from BAC subclones isolated as described above were assembled using Gap4 software from R. Staden (Bonfield et al. 1995). This software allows the reconstruction of a single sequence from sequence fragments. The sequence deduced from the alignment of different fragments is called the consensus sequence. Directed sequencing techniques (primer walking) were used to complete sequences and link contigs.

Potential functional sequences were then identified as described in Example 22.

EXAMPLE 22

Identification of Functional Sequences

Potential exons in BAC-derived human genomic sequences were located by homology searches on protein, nucleic acid and EST (Expressed Sequence Tags) public databases. Main public databases were locally reconstructed as mentioned in Example 14. The protein database, NRPU (Non-redundant Protein Unique) is formed by a non-redundant fusion of the Genpept (Benson et al., *Nucleic Acids Res.* 24:1–5 (1996), the disclosure of which is incorporated herein by reference), Swissprot (Bairoch, A. and Apweiler, R., *Nucleic Acids Res.* 24:21–25 (1996), the disclosure of which is incorporated herein by reference) and PIR/NBRF (George et al., *Nucleic Acids Res.* 24:17–20 (1996), the disclosure of which is incorporated herein by reference) databases. Redundant data were eliminated by using the NROB software (Benson et al. (1996), supra) and internal repeats were masked with the XNU software (Benson et al., supra). Homologies found using the NRPU database allowed the identification of sequences corresponding to potential coding exons related to known proteins.

The EST local database is composed by the gbest section (1–9) of GenBank (Benson et al. (1996), supra), and thus contains all publicly available transcript fragments.

Homologies found with this database allowed the localization of potentially transcribed regions.

The local nucleic acid database contained all sections of GenBank and EMBL (Rodriguez-Tome et al., *Nucleic Acids Res.* 24:6–12 (1996), the disclosure of which is incorporated herein by reference) except the EST sections. Redundant data were eliminated as previously described.

Similarity searches in protein or nucleic acid databases were performed using the BLAST software (Altschul et al., *J. Mol. Biol.* 215:403–410 (1990), the disclosure of which is incorporated herein by reference). Alignments were refined using the Fasta software, and multiple alignments used Clustal W. Homology thresholds were adjusted for each analysis based on the length and the complexity of the tested region, as well as on the size of the reference database.

Potential exon sequences identified as above were used as probes to screen cDNA libraries. Extremities of positive clones were sequenced and the sequence stretches were positioned on the genomic sequence determined above. Primers were then designed using the results from these alignments in order to enable the cloning of cDNAs derived from the gene associated with prostate cancer that was identified using the above procedures.

The obtained cDNA molecules were then sequenced and results of Northern blot analysis of prostate mRNAs supported the existence of a major cDNA having a 5–6 kb length. The structure of the gene associated with prostate cancer was evaluated as described in Example 23.

EXAMPLE 23

Analysis of Gene Structure

The intron/exon structure of the gene was finally completely deduced by aligning the mRNA sequence from the cDNA obtained as described above and the genomic DNA sequence obtained as described above. This alignment permitted the determination of the positions of the introns and exons, the positions of the start and end nucleotides defining each of the at least 8 exons, the locations and phases of the 5' and 3' splice sites, the position of the codon, and the position of the polyadenylation site to be determined in the genomic sequence. This analysis also yielded the positions of the coding region in the mRNA, and the locations of the polyadenylation signal and polyA stretch in the mRNA.

The gene identified as described above comprises at least 8 exons and spans more than 52 kb. A G/C rich putative promoter region was identified upstream of the coding sequence. A CCAAT in the putative promoter was also identified. The promoter region was identified as described in Prestridge, D. S. Predicting Pol II Promoter Sequences Using Transcription Factor Binding Sites, *J. Mol. Biol.* 249:923–932 (1995), the disclosure of which is incorporated herein by reference.

Additional analysis using conventional techniques, such as a 5'RACE reaction using the Marathon-Ready human prostate cDNA kit from Clontech (Catalog. No. PT1156-1), may be performed to confirm that the 5' of the cDNA obtained above is the authentic 5' end in the mRNA.

Alternatively, the 5' sequence of the transcript can be determined by conducting a PCR amplification with a series of primers extending from the 5' end of the identified coding region.

The above methods were also used to identify biallelic markers in a gene which was an attractive candidate for a gene associated with asthma. Examples 24–31 show how the use of methods of the present invention allowed this gone to be identified as a gene responsible, at least partially, for asthma in the studied populations. Additional details of the identification of the gene associated with asthma are provided in U.S. Provisional Application Ser. Nos. 60/081,893 (Genset.026PR) and U.S. Provisional Patent Application Ser. No. 60/091 314 (GENSET .026PR2 the disclosures of which are incorporated herein by reference.

EXAMPLE 24

Dejection of Biallelic Markers in the Candidate Gene: DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM MgCl2; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
3 ml TE 10-2 (Tris-HCl 10 mM, EDTA 2 mM)/NaCl 0.4 M
200 µl SDS 10%
500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm. For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD—50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

EXAMPLE 25

Detection of the Biallelic Markers: Amplification of Genomic DNA by PCR

The amplification of specific genomic sequences of the DNA samples of Example 24 was carried out on the pool of DNA obtained previously. In addition, 50 individual samples were similarly amplified.

PCR assays were performed using the following protocol:

| | |
|---|---|
| Final volume | 25 µl |
| DNA | 2 ng/µl |

-continued

| PCR assays were performed using the following protocol: | |
|---|---|
| MgCl2 | 2 mM |
| dNTP (each) | 200 μM |
| primer (each) | 2.9 ng/μl |
| Ampli Taq Gold DNA polymerase | 0.05 unit/μl |
| PCR buffer (10x – 0.1 M TrisHCl pH 8.3 0.5 M KCl) | 1x |

Pairs of first primers were designed to amplify the promoter region, exons, and 3' end of the candidate asthma-associated gene using the sequence information of the candidate gene and the OSP software (Hillier & Green, 1991). These first primers were about 20 nucleotides in length and contained a common oligonucleotide tail upstream of the specific bases targeted for amplification which was useful for sequencing. The synthesis of these primers was performed following the phosphoramidite method, on a GENSET UFPS 24.1 synthesizer.

DNA amplification was performed on a Genius II thermocycler. After heating at 94° C. for 10 min, 40 cycles were performed. Each cycle comprised: 30 sec at 94° C., 55° C. for 1 min, and 30 sec at 72° C. For final elongation, 7 min at 72° C. ended the amplification. The quantities of the amplification products obtained were determined on 96-well microtiter plates, using a fluorometer and Picogreen as intercalant agent (Molecular Probes).

EXAMPLE 26

Detection of the Biallelic Markers: Sequencing of Amplified Genomic DNA and Identification of Polymorphisms The sequencing of the amplified DNA obtained in Example 25 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were analyzed as formerly described.

The sequence data were further evaluated using the above mentioned polymorphism analysis software designed to detect the presence of biallelic markers among the pooled amplified fragments. The polymorphism search was based on the presence of superimposed peaks in the electrophoresis pattern resulting from different bases occurring at the same position as described previously.

Six fragments of amplification were analyzed. In these segments, 8 biallelic markers were detected. The localization of the biallelic markers, the polymorphic bases of each allele, and the frequencies of the most frequent alleles was as shown in Table 5.

TABLE 5

| Amplicon | Marker Name | Origin of DNA | Localization in gene | Polymorphism | Frequency |
|---|---|---|---|---|---|
| 1 | 204/326 | Ind. | Promoter | A/G | 96.2 (G) |
| 2 | 32/357 | Pool | Intron 1 | A/C | 67.7 (C) |
| 3 | 33/175 | Ind. | Exon 2 | C/T | 97.3 (C) |
| 3 | 33/234 | Pool | Intron 2 | A/C | 56.7 (C) |
| 3 | 33/327 | Ind. | Intron 2 | C/T | 75.3 (T) |
| 5 | 35/358 | Pool | Intron 4 | C/G | 67.9 (G) |

TABLE 5-continued

| Amplicon | Marker Name | Origin of DNA | Localization in gene | Polymorphism | Frequency |
|---|---|---|---|---|---|
| 5 | 35/390 | Ind. | Intron 4 | C/T | 82 (C) |
| 6 | 36/164 | Ind. | Exon 5 | A/G | 99.5 (G) |

Allelic frequencies were determined in a population of random blood donors from French Caucasian origin. Their wide range is due to the fact that, besides screening a pool of 100 individuals to generate biallelic markers as described above, polymorphism searches were also conducted in an individual testing format for 50 samples. This strategy was chosen here to provide a potential shortcut towards the identification of putative causal mutations in the association studies using them. As the 36/164 biallelic marker was found in only one individual, this marker was not considered in the association studies.

The fourth fragment of amplification carrying exon 3 (not shown in the Table) was not polymorphic in the tested samples (1 pool+50 individuals).

EXAMPLE 27

Validation of the Polymorphisms Through Microsequencing

The biallelic markers identified in Example 26 were further confirmed and their respective frequencies were determined through microsequencing. Microsequencing was carried out for each individual DNA sample described in Example 24.

Amplification from genomic DNA of individuals was performed by PCR as described above for the detection of the biallelic markers with the same set of PCR primers described above.

The preferred primers used in microsequencing had about 19 nucleotides in length and hybridized just upstream of the considered polymorphic base. Five primers hybridized with the non-coding strand of the gene. For the biallelic markers 204/326, 35/358 and 36/164, primers hybridized with the coding strand of the gene.

The microsequencing reaction was performed as described in Example 18.

EXAMPLE 28

Association Study Between Asthma and the Biallelic Markers of the Candidate Gene: Collection of DNA Samples from Affected and Non-affected Individuals The asthmatic population used to perform association studies in order to establish whether the candidate gene was an asthma-causing gene consisted of 298 individuals. More than 90% of these 298 asthmatic individuals had a Caucasian ethnic background.

The control population consisted of 373 unaffected individuals, among which 279 French (at least 70% were of Caucasian origin) and 94 American (at least 90% were of Caucasian origin).

DNA samples were obtained from asthmatic and non-asthmatic individuals as described above.

EXAMPLE 29

Association Study Between Asthma and the Biallelic Markers of the Candidate Gene:Genotyping of Affected and Control Individuals The general strategy to perform the association studies was to individually scan the DNA samples from all individuals in each of the populations described above in order to establish the allele frequencies of the above described biallelic markers in each of these populations.

Allelic frequencies of the above-described biallelic markers in each population were determined by performing microsequencing reactions on amplified fragments obtained by genomic PCR performed on the DNA samples from each individual. Genomic PCR and microsequencing were performed as detailed above in Examples 25 and 27 using the described amplification and microsequencing primers.

EXAMPLE 30

Association Study Between Asthma and the Biallelic Markers of the Candidate Gene population (373 individuals) was homogeneous enough to be used as a control population for the present association study.

EXAMPLE 31

Association Studies: Haplotype Frequency Analysis

As already shown, one way of increasing the statistical power of individual markers, is by performing haplotype association analysis. A haplotype analysis for association of markers in the candidate gone and asthma was performed by estimating the frequencies of all possible haplotypes for biallelic markers 32/357, 33/234, 33/327, 35/358 and 35/390 in the asthmatic and control populations described in Example 30 (Table 6), and comparing those frequencies by means of a chi square statistical test (one degree of freedom). Haplotype estimations were performed by applying the Expectation-Maximization (EM) algorithm (Excoffier L & Slatkin M 1995. Mol.Biol.Evol. 12:921–927), using the EM-HAPLO program (Hawley M E, Pakstis AJ & Kidd KK, 1994, Am. J. Phys. Anthropol. 18:104).

The results of such haplotype analysis are shown in Table 7.

TABLE 7

| Markers | Haplotype frequencies | | | | | Asthm. | Controls | Odds ratio | P value |
| --- | --- | --- | --- | --- | --- | --- | --- | --- | --- |
| | 32/357 | 33/234 | 33/327 | 35/358 | 35/390 | | | | |
| Frequency diff. | 8.8 | 4.7 | 3.9 | 5.4 | 10.1 | | | | |
| P value | $7.34 \times 10^{-4}$ | $8.88 \times 10^{-2}$ | $1.0 \times 10^{-1}$ | $3.59 \times 10^{2}$ | $2.33 \times 10^{-5}$ | | | | |
| Haplotype 1 | A | | | | T | 0.2 | 0.11 | 2.02 | $8.47 \times 10^{5}$ |
| Haplotype 2 | | A | T | G | | 0.27 | 0.18 | 1.68 | $2.81 \times 10^{-4}$ |
| Haplotype 3 | A | A | T | G | T | 0.18 | 0.09 | 2.22 | $3.95 \times 10^{5}$ |

Table 6 shows the results of the association study between five biallelic markers in the candidate gene and asthma.

TABLE 6

| | Allelic frequencies (%) | | | |
| --- | --- | --- | --- | --- |
| Markers | Asthmatics 298 individuals | Controls 373 individuals | Frequency diff. | P value |
| 32/357 | A 38.6 | A 29.8 | 8.8 | $7.34 \times 10^{-4}$ |
| 33/234 | A 49 | A 44.3 | 4.7 | $8.86 \times 10^{-2}$ |
| 33/327 | T 78.5 | T 74.6 | 3.9 | $1.0 \times 10^{-1}$ |
| 35/358 | G 72.3 | G 66.9 | 5.4 | $3.59 \times 10^{-2}$ |
| 35/390 | T 30.4 | T 20.3 | 10.1 | $2.33 \times 10^{-5}$ |

As shown in Table 6, markers 32/357 and 35/390 presented a strong association with asthma, this association being highly significant (pvalue=7.34×10–4 for marker 32/357 and 2.33×10–5 for marker 35-390).

Three markers showed moderate association when tested independently, namely 33/234, 33/327, 35/358.

It is worth mentioning that allelic frequencies for each of the biallelic markers of Table 6 were separately measured within the French control population (279 individuals) and the American control population (94 individuals). The differences in allele frequencies between the two populations were between 1% and 7%, with p-values above $10^{-1}$. These data confirmed that the combined French/American control A two-marker haplotype covering markers 32/357 and 35/390 (haplotype 1, AT alleles respectively) presented a p value of 8.47×10-6, an adds ratio of 2.02 and haplotype frequencies of 0.2 for asthmatic and 0.11 for control populations respectively.

A three marker haplotype covering markers 33/234, 33/327 and 35/358 haplotype 2, ATG alleles respectively) presented a p value of 2.81×10–4, an odds ratio of 1.68 and haplotype frequencies of 0.27 for asthmatic and 0.18 control populations respectively.

A five-marker haplotype covering markers 32/357, 33/234, 33/327, 35/358 and 35/390 (haplotype 3, AATGT alleles respectively) presented a p value of 3.95×10–5, an odds ratio of 2.22 and haplotype frequencies of 0.18 for asthmatic and 0.09 for control populations respectively.

Haplotype association analysis thus increased the statistical power of the individual marker association studies when compared to single-marker analysis (from p values between $10^{-1}$ and $2 \times 10^{-5}$ for the individual markers values between $3 \times 10^{-4}$ and $8 \times 10^{-6}$ for the three-marker haplotype, haplotype 2).

The significance of the values obtained for the haplotype association analysis was evaluated by the following computer simulation test. The genotype data from the asthmatic and control individuals were pooled and randomly allocated to two groups which contained the same number of individuals as the trait positive and trait negative groups used to produce the data summarized in Table 7. A haplotype analysis was then run on these artificial groups for the three haplotypes presented in Table 7. This experiment was reiterated 1000 times and the results are shown in Table 8.

TABLE 8

| | Pormutation Test | | | |
|---|---|---|---|---|
| Haplotype | Chi-Square | Average Chi-Square | Maximal Chi-Square | P value |
| Haplotype 1 (A---T) | 19.70 | 1.2 | 11.6 | $1.0 \times 10^{-3}$ |
| Haplotype 2 (·ATG·) | 13.49 | 1.2 | 10.5 | $1.0 \times 10^{-3}$ |
| Haplotype 3 (AATGT) | 16.66 | 1.2 | 9.3 | $1.0 \times 10^{-3}$ |

The results in Table 8 show that among 1000 iterations only 1% of the obtained haplotypes has a pvalue comparable to the one obtained in Table 7.

These results clearly validate the statistical significance of the haplotypes obtained (haplotypes 1, 2 and 3, Table 7).

While Examples 15–31 illustrate the use of the maps and markers of the present invention for identifying a nes gene associated with a complex disease within a 2 Mb genomic region for establishing that a candidate gene is, at least partially, responsible for a disease, the maps and markers of the present invention may also be used to identify one or more biallelic markers or one or more genes associated with other detectable phenotypes, including drug response, drug toxicity, or drug efficacy. The biallelic markers used in such drug response analyses or shown, using the methods of the present invention to be associated with such traits, may lie within or near genes responsible for or partly responsible for a particular disease, for example a disease against which the drug is meant to act, or may lie within genomic regions which are not responsible for or partly responsible for a disease. For example, the genomic region harboring markers associated with a particular drug response may carry a drug metabolism gene, or a gene encoding a protein with a role in the drug response mechanism. Thus, biallelic markers within or near genes known to be involved in drug response, toxicity, or efficacy or genes suspected of being involved in drug response, toxicity, or efficacy may be used to identify individuals likely to respond positively or negatively to drug treatment. In the context of the present invention, a "positive response" to a medicament can be defined as comprising a reduction of the symptoms related to the disease or condition to be treated. In the context of the present invention, a "negative response" to a medicament can be defined as comprising either a lack of positive response to the medicament which does not lead to a symptom reduction or to a side-effect observed following administration of the medicament.

Drug efficacy, response and tolerance/toxicity can be considered as multifactorial traits involving a genetic component in the same way as complex diseases such as Alzheimer's disease, prostate cancer, hypertension or diabetes. As such, the identification of genes involved in drug efficacy and toxicity could be achieved following a positional cloning approach, e.g. performing linkage analysis within families in order to obtain the subchromosomal location of the gene(s). However, this type of analysis is actually impractical in the case of drug responsiveness, due to the lack of availability of familial cases. In fact, the likelihood of having more than one individual in a particular family being exposed to the same drug at the same time is very low. Therefore, drug efficacy and toxicity can only be analyzed as sporadic traits.

In order to conduct association studies to analyze the individual response to a given drug in groups of patients affected with a disease, up to four groups are screened to determine their patterns of biallelic markers using the techniques described above. The four groups are:
Non-diseased or random controls,
Diseased patients/drug responders,
Diseased patients/drug non-responders,
Diseased patients/drug side effects.

In preferred embodiments, the above mentioned groups are recruited according to phenotyping criteria having the characteristics described above, so that the phenotypes defining the different groups are non-overlapping, preferably extreme phenotypes.

In highly preferred embodiments, such phenotyping criteria have the bimodal distribution described above.

The final number and composition of the groups for each drug association study is adapted to the distribution of the above described phenotypes within the studied population.

After selecting a suitable population, association and haplotype analyses may be performed as described herein to identify one or more biallelic markers associated with drug response, preferably drug toxicity or drug efficacy. The identification of such one or more biallelic markers allows one to conduct diagnostic tests to determine whether the administration of a drug to an individual will result in drug response, preferably drug toxicity, or drug efficacy.

The methods described above for identifying a gene associated with prostate cancer and biallelic markers indicative of a risk of suffering from asthma may be utilized to identify genes associated with other detectable phenotypes. In particular, the above methods may be used with any marker or combination of markers included in the maps of the present invention, including the 653 biallelic markers obtained above (which include the sequences of SEQ ID Nos. 1–50 and 51–100 or the sequences complementary thereto), the PG1 markers, the asthma-associated markers, and the Apo E markers of SEQ ID Nos. 301–305/307–311 or the sequences complementary thereto. As described above, the general strategy to perform the association studies using the maps and markers of the present invention is to scan two groups of individuals (trait positive individuals and trait negative controls) characterized by a well defined phenotype in order to measure the allele frequencies of the biallelic markers in each of these groups. Preferably, the frequencies of markers with inter-marker spacing of about 150 kb are determined in each groups. More preferably, the frequencies of markers with inter-marker spacing of about 75 kb are determined in each group. Even more preferably, markers with inter-marker spacing of about 50 kb, about 37.5 kb, about 30 kb, or about 25 kb will be tested in each population. For genome-wide studies, it will be preferred to measure the frequencies of about 20,000, or about 40,000 biallelic markers in each group. In a highly preferred embodiment, the frequencies of about 60,000, about 80,000, about 100,000, or about 120,000 biallelic markers are determined in each group. In some embodiments, haplotype analyses may be run using groups of markers located within regions spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb.

Allele frequency can be measured using microsequencing techniques described herein; preferred high throughput microsequencing procedures are further exemplified below; it will be further appreciated that any other large scale genotyping method suitable with the intended purpose contemplated herein may also be used.

In some embodiments of the present invention a computer-based system may support the on-line coordination between the identification of biallelic markers and the corresponding analysis of their frequency in the different groups.

It will be appreciated that it is not necessary to use a full high density biallelic marker map in order to start a genome-wide association study. It is sufficient to generate and use a first set of about 20,000 markers (one marker per BAC, average inter-marker spacing of about 150 kb). Maps having higher densities of biallelic markers (two or more markers per BAC, average inter-marker spacing of about 75 kb or less) may then be generated by starting first on those BACs for which a candidate association has been established at the first step.

In cases when one or more candidate regions have previously been delineated, such as cases where a particular gene or genomic region is suspected of being associated with a trait, local excerpts of biallelic marker maps having densities above one marker per 150 kb may be exploited using BACs harboring said genomic regions, or genes, or portions thereof. In these cases also, successive association studies may be performed using sets of biallelic markers showing increasing densities, preferably from about one every 150 kb to about one every 75 kb; more preferably, sets of markers with inter-marker spacing below about 50 kb, below about 37.5 kb, below about 30 kb, most preferably below about 25 kb, will be used.

Haplotype analyses may also be conducted using groups of biallelic markers within the candidate region. The biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 kb to 500 kb, from 500 kb to 1 Mb, or more than 1 Mb. It will be appreciated that the ordered DNA fragments containing these groups of biallelic markers need not completely cover the genomic regions of those lengths but may instead be incomplete contigs having one or more gaps therein. As discussed in further detail below, biallelic markers may he used in association studies and haplotype analyses regardless of the completeness of the corresponding physical contig harboring them, provided linkage disequilibrium between the markers can be assessed.

As described above, if a positive association with a trait, such as a disease, or a drug efficacy and/or toxicity, is identified using the biallelic markers and maps of the present invention, the maps will provide not only the confirmation of the association, but also a shortcut towards the identification of the gene involved in the trait under study. As described above, since the markers showing positive association to the trait are in linkage disequilibrium with the trait loci, the causal gene will be physically located in the vicinity of these markers. Regions identified through association studies using high density maps will on average have a 20–40 times shorter length than those identified by linkage analysis (2 to 20 Mb).

As described above, once a positive association is confirmed with the high density biallelic marker maps of the present invention, BACs from which the most highly associated markers were derived are completely sequenced and the mutations in the causal gene are searched by applying genomic analysis tools. As described above, once a region harboring a gene associated with a detectable trait has been sequenced and analyzed, the candidate functional regions (e.g. exons and splice sites, promoters and other regulatory regions) are scanned for mutations by comparing the sequences of a selected number of controls and cases, using adequate software.

In some embodiments, trait positive samples being compared to identify causal mutations are selected among those carrying the ancestral haplotype; in these embodiments, control samples are chosen from individuals not carrying said ancestral haplotype.

In further embodiments, trait positive samples being compared to identify causal mutations are selected among those showing haplotypes that are as close as possible to the ancestral haplotype; in these embodiments, control samples are chosen from individuals not carrying any of the haplotypes selected for the case population.

The mutation detection procedure is essentially similar to that used for biallelic site identification. A pair of oligonucleotide primers are designed in order to amplify the sequences to be tested. In preferred embodiments, priority is given to the testing of functional sequences; in such embodiments, sequences covering every exon/promoter predicted region, preferably including potential splice sites, are determined and compared between the T+ and T− populations. Amplification is carried out on DNA samples from T+ and T− individuals using the polymerase chain reaction under the above described conditions. To be sequenced, amplification products from genomic PCR may be subjected to automated dideoxy terminator sequencing reactions and electrophoresed on ABI 377 sequencers. Following gel image analysis and DNA sequence extraction, ABI sequence data are automatically analyzed to detect the presence of sequence variations among T+ and T− individuals. Sequences are preferably verified by comparing the sequences of both DNA strands of each individual.

It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results.

The maps and biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate p-values can be considered as a haplotype analysis, similar to those described in further details within the present invention.

Use of Biallelic Markers to Identify Individuals Likely to Exhibit a Detectable Trait Associated with a Particular Allele of a Known Gene In addition to their utility in searches for genes associated with detectable traits on a genome-wide, chromosome wide, or subchromosomal level, the maps and biallelic markers of the present invention may be used in more targeted approaches for identifying individuals likely to exhibit a particular detectable trait or individuals who exhibit a particular detectable trait as a consequence of possessing a particular allele of a gene associated with the detectable trait.

For example, the biallelic markers and maps of the present invention may be used to identify individuals who carry an allele of a known gene that is suspected of being associated with a particular detectable trait. In particular, the target genes may be genes having alleles which predispose an individual to suffer from a specific disease state. In other cases, the target genes may be genes having alleles that predispose an individual to exhibit a desired or undesired response to a drug or other pharmaceutical composition, a food, or any administered compound. The known gene may encode any of a variety of types of biomolecules. For example, the known genes targeted in such analyzes may be genes known to be involved in a particular step in a metabolic pathway in which disruptions may cause a detectable trait. Alternatively, the target genes may be genes encoding receptors or ligands which bind to receptors in which disruptions may cause a detectable trait, genes encoding transporters, genes encoding proteins with signaling activities, genes encoding proteins involved in the immune response, genes encoding proteins involved in hematopoesis, or genes encoding proteins involved in wound healing. It will be appreciated that the target genes are not limited to those specifically enumerated above, but may be any gone known to be or suspected of being associated with a detectable trait.

As previously mentioned, the maps and markers of the present invention may be used to identify genes associated with drug response. Accordingly, the present invention comprises a method of using a drug comprising obtaining a nucleic acid sample from an individual, determining the identity of the polymorphic base of one or more biallelic markers obtained by the methods described above which is or are associated with a positive response to treatment with the drug or one or more biallelic markers obtained by the methods described above which is or are associated with a negative response to treatment with the drug, and administering the drug to the individual if the nucleic acid sample contains one or more alleles of biallelic markers associated with a positive response to treatment with the drug or if said nucleic acid sample lacks one or more alleles of biallelic markers associated with a negative response to the drug. In some embodiments of the method, the administering step comprises administering the drug to (the individual if the nucleic acid sample contains one or more alleles of biallelic markers associated with a positive response to treatment with the drug and the nucleic acid sample lacks one or more alleles of biallelic markers associated with a negative response to the drug.

The biallelic markers of the present invention may also be used to select individuals for inclusion in the clinical trials of a drug. By selecting individuals who are likely to respond favorably to a drug for inclusion in the trial, the effectiveness of the drug can be assessed without lowering the measured effectiveness as a result of including non-responders or negative responders in the clinical trial. May be more importantly, using such selection may avoid including patients who may suffer from undesirable side effects if administered the drug under trial, thus increasing the safety of clinical trials. Accordingly, the present invention also includes a method of selecting an individual for inclusion in a clinical trial of a drug comprising obtaining a nucleic acid sample from an individual, determining the identity of the polymorphic base of one or more biallelic markers obtained by the methods described above which is or are associated with a positive response to treatment with the drug or one or more biallelic markers associated with a negative response to treatment with the drug in the nucleic acid sample, and including the individual in the clinical trial if the nucleic acid sample contains one or more alleles of biallelic markers obtained by the methods described above which is or are associated with a positive response to treatment with said drug or it the nucleic acid sample lacks one or more alleles of biallelic markers associated with a negative response to the drug. In one embodiment of the method, the inclusion step comprises including the individual in the clinical trial if the nucleic acid sample contains one or more alleles of biallelic markers associated with a positive response to treatment with the drug and the nucleic acid sample lacks one or more alleles of biallelic markers associated with a negative response to the drug.

In particular embodiments, one or several of the ApoE linked markers of SEQ ID Nos 301–305/307–311 or the sequences complementary thereto may be used in targeted approaches to identify individuals who are likely to develop Alzheimer's disease, or to identify individuals who do suffer from Alzheimer's disease. In other embodiments, one or more of the markers of SEQ ID Nos. 306 and 312 and one or more of the the ApoE linked markers of SEQ ID Nos 301–305/307–311 or the sequences complementary thereto are genotyped approaches to identify individuals who are likely to develop Alzheimer's disease, or to identify individuals who do suffer from Alzheimer's disease. In further embodiments, one or several of the PG1 linked markers may be tested in targeted approaches to identify individuals who are likely to develop prostate cancer, or to identify individuals who do suffer from prostate cancer. Finally individuals likely to be asthmatic, or asthmatic individuals, can be identified using one or more of the asthma-associated markers to conduct the procedures of the present invention.

Given the high number of cancer types in which the PG1 chromosomal region is involved, it will be appreciated that the PG1 markers may be employed to identify individuals at risk of developing cancers other than prostate cancer, or to identify individuals suffering from cancers other than prostate cancer. It will be further appreciated that the asthma associated markers may be tested to identify individuals likely to exhibit, or exhibiting, inflammatory traits other than the asthmatic state (e.g. arthritis, or psoriasis, among others). The present invention provides adequate methods to establish associations between markers, such as those mentioned above and candidate traits expressly contemplated herein, thus legitimating the corresponding targeted approaches to identify individuals likely to exhibit, or exhibiting said candidate traits.

In some embodiments, the 653 biallelic markers obtained above (which include the sequences of SEQ ID Nos. 1–50 and 51–100 or the sequences complementary thereto) may be used in targeted approaches to identify individuals at risk of developing a detectable trait for example a complex disease or desired/understood drug response, or to identify individuals exhibiting said trait. The present invention provides methods to establish putative associations between any of the biallelic markers described herein and any detectable traits, including those specifically described herein.

To use the maps and markers of the present invention in further targeted approaches, biallelic markers which are in linkage disequilibrium with any of the above disclosed markers may be identified. In cases where one or more biallelic markers of the present invention have been shown to be associated with a detectable trait, more biallelic markers in linkage disequilibrium with said associated biallelic markers may be generated and used to perform targeted approaches aiming at identifying individuals exhibiting, or likely to exhibit, said detectable trait, according to the methods provided herein.

Furthermore, in cases where a candidate gene is suspected of being associated with a particular detectable trait or suspected of causing the detectable trait, biallelic markers in linkage disequilibrium with said candidate gene may be identified and used in targeted approaches, such as the approaches utilized above for the asthma-associated gene and the Apo E gene.

Biallelic markers that are in linkage disequilibrium with markers associated with a detectable trait, or with genus associated with a detectable trait, or suspected of being so, are identified by performing single marker analyzes, haplotype association analyzes, or linkage disequilibrium measurements on samples from trait positive and trait negative individuals as described above using biallelic markers lying in the vicinity of the target marker or gene. In this manner, a single biallelic marker or a group of biallelic markers may be identified which indicate that an individual is likely to possess the detectable trait or does possess the detectable trait as a consequence of a particular allele of the target marker or gene.

Nucleic acid samples from individuals to be tested for predisposition to a detectable trait or possession of a detectable trait as a consequence of a particular allele of the target gene may be examined using the diagnostic methods described below.

Diagnostic Methods

To use the maps and biallelic markers of the present invention to diagnose whether an individual is predisposed to express a detectable trait or whether the individual expresses a detectable trait as a result of a particular mutation, one or more biallelic markers indicative of such a predisposition or causative mutation are identified by performing association studies and haplotype analysis on affected and non-affected individuals as described above.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The trait analyzed using the present diagnostics may be any detectable trait, including diseases, drug response, drug efficacy, or drug toxicity. A "positive" drug response may refer to a response indicating either some drug efficacy or no drug toxicity. Diagnostics which analyze drug response, drug efficacy, or drug toxicity may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the maps and markers of the present invention. One or more markers indicative of drug response, drug efficacy, or drug toxicity may be identified using the techniques described above. Thereafter, potential participants in clinical trials of the drug may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

In each of the diagnostic methods, a nucleic acid sample is obtained from the test subject and the biallelic marker pattern for one or more of the biallelic markers included in the maps of the present invention, including the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers, including those of SEQ ID Nos. 301–305/307–311 or the sequences complementary thereto. In other embodiments, the biallelic marker pattern of one or more of the markers of SEQ ID Nos. 306 and 312 is determined in addition to determining the biallelic marker pattern of one or more of the biallelic markers included in the maps of the present invention, including the 653 biallelic markers obtained above (which include the sequences of SEQ ID Nos. 1–50 and 51–100 or the sequences complementary thereto, the asthma-associated biallelic markers, the PG1 biallelic markers, and the Apo E biallelic markers, including those of SEQ ID Nos. 301–305/307–311 or the sequences complementary thereto. In some embodiments, the biallelic marker pattern is determined by conducting an amplification reaction to generate amplicons containing the polymorphic bases of the one or more biallelic markers to be genotyped. The identies of the polymorphic bases of the one or more biallelic markers to be analyzed may be determined using a variety of methods, including hybridization assays which specifically detect amplification products containing particular alleles of the one or more biallelic markers, and microsequencing reactions which identify the polymorphic bases of the one or more biallelic markers to be analyzed.

While the following discussion utilizes the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers as examples of the diagnostics of the present invention, it will be appreciated that the same diagnostics may be used in conjunction with any marker or any group of markers included in the maps of the present invention.

Examples of amplification primers enabling the amplification, from subjects genomic DNA samples, of DNA fragments that carry each of the markers of SEQ ID Nos: 1–50 and 51–100 or the sequences complementary thereto, are oligonucleotides of SEQ ID NOs: 101–150 and 151–200; pairs of corresponding primers for a given biallelic marker may be reconstituted by choosing the adequate upstream oligonucleotide from SEQ ID Nos. 101–150 together with the corresponding downstream oligonucleotide from SEQ ID Nos: 151–100.

SEQ ID Nos: 1–50 correspond to the sequence identification number for a first allele of the biallelic markers of SEQ ID Nos: 1–50 and 51–100 and SEQ ID Nos 51–100 correspond to the sequence identification number for a second allele of the biallelic markers of SEQ ID Nos: 1–50 and 51–100.

SEQ ID Nos: 313–318 correspond to sequence identification numbers of upstream amplification primers that may be used to generate amplification products containing the polymorphic bases of the biallelic markers of respective SEQ ID Nos: 301–306/307–312, SEQ ID Nos: 319–324 correspond to downstream amplification primers that may be used to generate amplification products containing the polymorphic bases of the biallelic markers of respective SEQ ID Nos:Δ301–306/307–312.

For all markers of SEQ ID Nos: 1–50/51–100 and 301–306/307–312 or the sequences complementary thereto, the enclosed listings indicate the position and identity of the polymorphic base in each biallelic marker. Potential microsequencing primers are also included in the sequence listing. The sequences of SEQ ID Nos. 201–250 may be used in microsequencing procedures such as those described herein to determine the sequence of the polymorphic bases of the biallelic markers of SEQ ID Nos. 1–50/51–100. The sequences of SE Ill Nos. 325–330 or 331–336 may be microsequencing procedures such as those described herein to determine the sequence of the polymorphic bases of the biallelic markers of SEQ ID Nos. 301–306/307–312. All listings indicate the internal identification number corresponding to the biallelic marker to which the listed sequence is related to.

One aspect of the present invention is a method for determining whether an individual is at risk of developing Alzheimer's Disease or whether an individual suffers from Alzheimer's Disease as a consequence of possessing the Apo E ε4 site A allele. The method involves obtaining a nucleic acid sample from the individual and determining whether the nucleic acid sample contains one or more markers indicative of a risk of developing Alzheimer's Disease or one or more markers indicative that the individual suffers from Alzheimer's Disease as a result of possessing the Apo E ε4 site A allele. In one embodiment, the method comprises determining the identity of the polymorphic base of one or more biallelic markers selected from the group consisting of SEQ ID Nos. 301–305/307–312 or the sequences complementary thereto in the nucleic acid sample. In a further embodiment, the method involves determining whether the nucleic acid sample contains the sequence of SEQ ID No. 306 (the C allele of marker 99-2452/54 containing the Apo E ε4 site A allele) or the sequence complementary thereto. In a further embodiment the method comprises determining whether the nucleic acid sample contains SEQ ID No. 311 (the T allele of marker 99-365/344) or the sequence complementary thereto. In another embodiment, the method comprises determining whether the nucleic acid sample contains SEQ ID No. 311 (the T allele of marker 99-365/344) and SEQ ID No. 306 (the C allele of marker 99-2452/54 containing E site A allele) or the sequence complementary thereto.

In still a further embodiment, the method comprises determining whether the nucleic acid sample contains SEQ ID No. 302, 301, 303, and 304 or the sequences complementary thereto. In still a further embodiment, the method comprises determining whether the nucleic acid sample contains SEQ ID Nos. 302, 303, and 304 or the sequences complementary thereto. In a further embodiment the method comprises determining whether the nucleic acid sample contains SEQ ID No. 311 (the T allele of marker 99-365/344) or the sequence complementary thereto.

In some embodiments, the step of determining the identity of the polymorphic base of one or more biallelic markers selected from the group consisting of SEQ ID Nos. 301–305 and SEQ ID Nos. 307–311 or the sequences complementary thereto in the nucleic acid sample comprises conducting an amplification reaction on said nucleic acid sample using one or more of the amplification primers selected from the group consisting of SEQ ID Nos. 313–317 and SEQ ID Nos. 319–323 and determining the identity of the polymorphic base in said one or more biallelic markers.

In some embodiments, the identity of the polymorphic base may be determined using one or more of the microsequencing primers listed as SEQ ID Nos. 325–329 or 331–335. In embodiments comprising the step of determining whether the nucleic acid sample contains the sequence of SEQ ID No. 306, the method may comprise conducting an amplification reaction on the nucleic acid sample using the pair of amplification primers consisting of SEQ ID Nos. 318 and 324. In some embodiments, the step of determining whether the nucleic acid sample contains the sequence of SEQ ID 306 comprises conducting a microsequencing reaction using one of the microsequencing primers listed as SEQ ID Nos. 330 or 336.

Another aspect of the present invention relates to a method of determining whether an individual is at risk of developing a trait or whether an individual expresses a trait as a consequence of possessing a particular trait-causing allele. Alternatively, another aspect of the present invention relates to a method of determining whether an individual is at risk of developing a plurality of traits or whether an individual expresses a plurality of traits as a result of possessing particular trait-causing alleles. Those methods involve obtaining a nucleic acid sample from the individual and determining whether the nucleic acid sample contains one or more markers indicative of a risk of developing the trait or one or more markers indicative that the individual expresses the trait as a result of possessing a particular trait-causing allele. In one embodiment, the methods comprise determining the identity of the polymorphic base of one or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1biallelic markers, and the new Apo E biallelic markers. In a further embodiment, the methods comprise determining the identities of the polymorphic bases of at least two, at least three, at least five, at least eight, at least 20, at least 100, at least 200, at least 300, at least 400, between 400 and 2,000, between 2000 and 4000, between 4,000 and 10,000, between 10,000 and 20,000 or more than 20,000 of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers.

In some embodiments, the step of determining the identity of the polymorphic base of one or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, comprises conducting an amplification reaction on said nucleic acid sample using appropriate amplification primers and determining the identity of the polymorphic base in said one or more biallelic markers. In some embodiments, the identity of the polymorphic base may be determined using appropriate microsequencing primers.

As described herein, the diagnostics may be based on a single biallelic marker or a group of biallelic markers. Without wishing to be limited to any particular value, it is preferred that the biallelic marker used in single marker diagnostics either as a positive basis for further diagnostic tests or as a preliminary starting point for early preventive therapy, exhibit a p value in preliminary screening association analyzes of about $1 \times 10^{-2}$ or less. More preferably the p value is about $1 \times 10^{-4}$ or less.

Similarly, without wishing to be limited to any particular value for diagnostics based on more than one biallelic marker, it is preferred that the haplotype exhibit a p value of $1 \times 10^{-3}$ or less, still more preferably $1 \times 10^{-6}$ or most preferably of about $1 \times 10^{-6}$ or less in a preliminary screening haplotype analysis. These values are believed to be applicable to any association studies involving single or multiple marker combinations. Significance thresholds may be refined according to the methods previously described.

Example 32 describes methods for determining the biallelic marker pattern in a nucleic acid sample.

EXAMPLE 32

A nucleic acid sample is obtained from an individual to be tested for susceptibility to a detectable trait or for a detectable trait caused by a particular mutation. The nucleic acid sample may be a RNA sample or a DNA sample.

A PCR amplification is conducted using primer pairs which generate amplification products containing the polymorphic nucleotides of one or more biallelic markers associated with such a predisposition or causative mutation. For example, the amplification products may contain the polymorphic bases of one or more of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers or biallelic markers in linkage disequilibrium with any of these biallelic markers. In some embodiments, the PCR amplication is conducted using primer pairs which generate amplification products containing the polymorphic nucleotides of several biallelic markers. For example, in one embodiment, amplification products containing the polymorphic bases of one or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PC1 biallelic markers, and the Apo E biallelic markers, biallelic markers which are in linkage disequilibrium therewith or with a causative mutation associated with a detectable phenotype may be generated. In another embodiment, amplification products containing the polymorphic bases of five or more biallelic markers in the maps of the present invention, including any of the the 653 biallelic markers obtained above (which include the sequences or SEQ ID Nos. 1–50 and 51 –100 or the sequences complementary thereto), the asthma-associated biallelic markers, the PG1 biallelic markers, and the Apo E biallelic markers, biallelic markers which are in linkage disequilibrium therewith or with a causative mutation associated with a detectable phenotype may be generated. In another embodiment, amplification products containing the polymorphic bases of 20 or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers, biallelic markers which are in linkage disequilibrium therewith or with the causative mutation may be generated. In another embodiment, amplification products containing the polymorphic bases of 100 or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers, biallelic markers which are in linkage disequilibrium therewith or with a causative mutation associated with a detectable phenotype may be generated. In another embodiment, amplification products containing the polymorphic bases of 200 or more biallelic markers in the maps of the present invention, including any of the the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers, biallelic markers which are in linkage disequilibrium therewith or with a causative mutation associated with a detectable phenotype may be generated. In another embodiment, amplification products containing the polymorphic bases of 300 or more biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the Apo E biallelic markers, biallelic markers which are in linkage disequilibrium therewith or with the causative mutation may be generated. In another embodiment, amplification products containing the polymorphic bases of 400 or more biallelic markers in the maps of the present invention, including any of the the 653 biallelic markers obtained above (which include the sequences of SEQ ID Nos. 1–50 and 51–100 of the sequences complementary thereto), the asthma-associated biallelic markers, the PG1 biallelic markers, and the Apo E biallelic markers, biallelic markers which are in linkage disequilibrium therewith or with a causative mutation associated with a detectable phenotype may be generated.

The primers used to generate the amplification products may be designed as described herein. Representative amplification primers for generating amplification products containing the polymorphic bases of the biallelic markers of SEQ ID Nos. 1–50 and 51–100 are provided as SEQ ID Nos. 101–150/151–200 in the accompanying Sequence Listing. The PCR primers may be oligonucleotides of 10, 15, 20 or more bases in length which enable the amplification of the polymorphic site in the markers. In some embodiments, the amplification product produced using those primers may be at least 100 bases in length (i.e. about 50 nucleotides on each side of the polymorphic base). In other embodiments, the amplification product produced using these primers may be at least 500 bases in length (i.e. about 250 nucleotides on each side of the polymorphic base). In still further embodiments, the amplification product produced using these primers may be at least 1000 bases in length (i.e. about 500 nucleotides on each side of the polymorphic base).

Table 9 lists the internal identification numbers of the 50 localized markers described herein and the Apo E markers described herein, the SEQ ID Nos. for each of the two alleles of these biallelic markers, the SEQ ID Nos. of representative upstream and downstream amplification primers which can be used to generate amplification products including the polymorphic bases of these biallelic markers, and the SEQ ID Nos of microsequencing primers which can be used to determine the identies of the polymorphic bases of these markers.

TABLE 10

| Marker (Genset code) | SEQ ID Nos First allele | SEQ ID Nos Second allele | SEQ ID Nos Amplification primers Up-stream | SEQ ID Nos Amplification primers Down-stream | SEQ ID Nos Microsequencing primers 1 | SEQ ID Nos Microsequencing primers 2 |
|---|---|---|---|---|---|---|
| 99-2103 | 1 | 51 | 101 | 151 | 201 | 251 |
| 99-2228 | 2 | 52 | 102 | 152 | 202 | 252 |
| 99-2229 | 3 | 53 | 103 | 153 | 203 | 253 |
| 99-2240 | 4 | 54 | 104 | 154 | 204 | 254 |
| 99-2242 | 5 | 55 | 105 | 155 | 205 | 255 |
| 99-2244 | 6 | 56 | 106 | 156 | 206 | 256 |
| 99-2246 | 7 | 57 | 107 | 157 | 207 | 257 |
| 99-2248 | 8 | 58 | 108 | 158 | 208 | 258 |
| 99-2250 | 9 | 59 | 109 | 159 | 209 | 259 |
| 99-2251 | 10 | 60 | 110 | 160 | 210 | 260 |
| 99-2269 | 11 | 61 | 111 | 161 | 211 | 261 |
| 99-2271 | 12 | 62 | 112 | 162 | 212 | 262 |
| 99-2272 | 13 | 63 | 113 | 163 | 213 | 263 |
| 99-2273 | 14 | 64 | 114 | 164 | 214 | 264 |
| 99-2275 | 15 | 65 | 115 | 165 | 215 | 265 |
| 99-2278 | 16 | 66 | 116 | 166 | 216 | 266 |
| 99-2312 | 17 | 67 | 117 | 167 | 217 | 267 |
| 90-2315 | 18 | 68 | 118 | 168 | 218 | 268 |
| 99-2320 | 19 | 69 | 119 | 169 | 219 | 269 |
| 99-2321 | 20 | 70 | 120 | 170 | 220 | 270 |
| 99-2324 | 21 | 71 | 121 | 171 | 221 | 271 |
| 99-2333 | 22 | 72 | 122 | 172 | 222 | 272 |
| 99-2341 | 23 | 73 | 123 | 173 | 223 | 273 |
| 99-2342 | 24 | 74 | 124 | 174 | 224 | 274 |
| 99-2362 | 25 | 75 | 125 | 175 | 225 | 275 |
| 99-2364 | 26 | 76 | 126 | 176 | 226 | 276 |
| 99-2367 | 27 | 77 | 127 | 177 | 227 | 277 |
| 99-2371 | 28 | 78 | 128 | 178 | 228 | 278 |
| 99-2378 | 29 | 79 | 129 | 179 | 229 | 279 |
| 99-2381 | 30 | 80 | 130 | 180 | 230 | 280 |
| 99-2413 | 31 | 81 | 131 | 181 | 231 | 281 |
| 99-2419 | 32 | 82 | 132 | 182 | 232 | 282 |
| 99-2559 | 33 | 83 | 133 | 183 | 233 | 283 |
| 99-2566 | 34 | 84 | 134 | 184 | 234 | 284 |
| 99-2567 | 35 | 85 | 135 | 185 | 235 | 285 |
| 99-2570 | 36 | 86 | 136 | 186 | 236 | 286 |
| 99-2571 | 37 | 87 | 137 | 187 | 237 | 287 |
| 99-2610 | 38 | 88 | 138 | 188 | 238 | 288 |
| 99-2615 | 39 | 89 | 139 | 189 | 239 | 289 |
| 99-2620 | 40 | 90 | 140 | 190 | 240 | 290 |
| 99-2624 | 41 | 91 | 141 | 191 | 241 | 291 |
| 99-2625 | 42 | 92 | 142 | 192 | 242 | 292 |
| 99-2630 | 43 | 93 | 143 | 193 | 243 | 293 |
| 99-2633 | 44 | 94 | 144 | 194 | 244 | 294 |
| 99-2634 | 45 | 95 | 145 | 195 | 245 | 295 |
| 99-2637 | 46 | 96 | 146 | 196 | 246 | 296 |
| 99-2642 | 47 | 97 | 147 | 197 | 247 | 297 |
| 99-2645 | 48 | 98 | 148 | 198 | 248 | 298 |
| 99-2647 | 49 | 99 | 149 | 199 | 249 | 299 |
| 99-2649 | 50 | 100 | 150 | 200 | 250 | 300 |

It will be appreciated that the primers listed in Table 9 are merely exemplary and that any other set of primers which produce amplification products containing the polymorphic nucleotides of one or more of the biallelic markers of SEQ ID Nos: 1–50 and 51–100 or biallelic markers in linkage disequilibrium therewith or with a causative mutation for a detectable trait, or a combination thereof may be used in the diagnostic methods. It will also be appreciated that these diagnostic methods may be performed with any biallelic marker or combination of biallelic markers included in the maps of the present invention.

Following the PCR amplification, the identities of the polymorphic bases of one or more of the biallelic markers in the nucleic acid sample are determined. The identities of the polymorphic bases may be determined using the microsequencing procedures described in Example 13. It will be appreciated that the microsequencing primers listed as SEQ ID NOs: 201–250 and 251–300 are merely exemplary and that any primer having a 3' end near the polymorphic nucleotide, and preferably immediately adjacent to the polymorphic nucleotide, may be used. Similarly, it will be appreciated that microsequencing analysis may be performed for any marker or combination of markers in the maps of the present invention.

Alternatively, the microsequencing analysis may be performed as described in Pastinen et al., *Genome Research* 7:606-614 (1997), the disclosure of which is incorporated herein by reference, and which is described in more detail below.

Alternatively, the PCR product may be completely sequenced to determine the identities of the polymorphic bases in the biallelic markers. In another method, the identities of the polymorphic bases in the biallelic markers are determined by hybridizing the amplification products to microarrays containing allele specific oligonucleotides specific for the polymorphic bases in the biallelic markers. The use of microarrays comprising allele specific oligonucleotides is described in more detail below.

It will be appreciated that the identities of the polymorphic bases in the biallelic markers may be determined using techniques other than those listed above, such as conventional dot blot analyzes.

Nucleic acids used in the above diagnostic procedures may comprise at least 10 consecutive nucleotides, including the polymorphic bases, of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. Alternatively, the nucleic acids used in the above diagnostic procedures may comprise at least 15 consecutive nucleotides, including the polymorphic bases, of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. In some embodiments, the nucleic acids used in the above diagnostic procedures may comprise at least 20 consecutive nucleotides, including the polymorphic bases, of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. In still other embodiments, the nucleic acids used in the above diagnostic procedures may comprise at least 30 consecutive nucleotides, including the polymorphic bases, of the biallelic markers in the maps of the present invention, including any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. In further embodiments, the nucleic acids used in the above diagnostic procedures may comprise more than 30 consecutive nucleotides, including the polymorphic bases, of the biallelic markers in the maps of the present invention, including any of the the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. In still further embodiments, the nucleic acids used in the above diagnostic procedures may comprise the entire sequence of the biallelic markers in the maps of the present invention, including any of the the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers, including those of SEQ ID Nos. 301–305/307–311 or the sequences complementary thereto. In some embodiments the nucleic acids used in the diagnostic procedures are longer than the sequences of SEQ ID Nos. 1–50, 51–100, 301–305 and 307–311 because they contain nucleotides adjacent to these sequences.

The diagnostics of the present invention may also employ nucleic acid arrays attached to DNA chips or any other suitable solid support, including beads. As used herein, the term array means a one dimensional, two dimensional, or multidimensional arrangement of a plurality of nucleic acids of sufficient length to permit specific detection of nucleic acids capable of hybridizing thereto.

DNA chips allow the integration of micro-biochemical processes (such as DNA hybridization), systems of signal detection (such as fluorescence) and data processing into a single system which can be used to obtain information on polymorphism. The solid surface of the chip is often made of silicon or glass but it can be a polymeric membrane. Efficient access to polymorphism information is obtained through a basic structure comprising high-density arrays of oligonucleotide probes attached to a solid support (the chip) at selected positions. The immobilization of arrays of DNA probes on solid supports has been rendered possible by the development of a technology generally identified as "Very Large Scale Immobilized Polymer Synthesis" (VLSIPS™) and in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070. WO 92/10092 and WO 95/11995, the disclosures of which are incorporated herein by reference, which describe methods for forming oligonucleotide arrays through techniques such as light-directed synthesis techniques.

In designing strategies aimed at providing arrays of nucleotides immobilized on solid supports, further presentation strategies were developed to order and display the probe arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference.

Each DNA chip can contain thousands to millions of individual synthetic DNA probes arranged in a grid-like pattern and miniaturized to the size of a dime.

The chip technology has been successfully used to detect mutations in numerous cases. For example, the screening of mutations has been undertaken in the BRCA1 gene, in S. cerevisiae mutant strains, and in the protease gene of HIV-1 virus (see Hacia et al., Nat. Genet. 14:441–447(1996); Shoemaker et al., Nat. Genet. 14:450–456 (1996); Kozal et al., Nat. Med. 2:753–759 (1996), the disclosures of which are incorporated herein by reference). At least three companies propose chips able to detect biallelic polymorphisms: Affymetrix (GeneChip), Hyseq (HyChip and HyGnostics), and Protogene Laboratories.

In some embodiments, the efficiency of hybridization of nucleic acids in the sample with the probes attached to the chip may be improved by using polyacrylamide gel pads isolated from one another by hydrophobic regions in which the DNA probes are covalently linked to an acrylamide matrix.

The polymorphic bases present in the biallelic marker or markers of the sample nucleic acids are determined as follows. Probes which contain at least a portion of one or more of the biallelic markers of the present invention are synthesized either in situ or by conventional synthesis and immobilized on an appropriate chip using methods known to the skilled technician.

The nucleic acid sample which includes the candidate region to be analyzed is isolated, amplified with primers capable of generating an amplification product containing the polymorphic bases of one or more biallelic markers, and labeled with a reporter group. The reporter group can be a fluorescent group such as phycoerythrin. The labeled nucleic acid is then incubated with the probes immobilized on the chip using a fluidics station. For example, Manz et al. (Avd. in Chromatogr. 33:1–66 (1993), the disclosure of which is incorporated herein by reference) describe the fabrication of fluidics devices and particularly microcapillary devices, in silicon and glass substrates.

After the reaction is completed, the chip is inserted into a scanner and patterns of hybridization are detected. The hybridization data is collected as a signal emitted from the reporter groups already incorporated into the nucleic acids generated in the amplification of the sample DNA, which is now bound to the probes attached to the chip. Probes that perfectly match a sequence of the nucleic acid sample generally produce stronger signals than those that have mismatches. Since the sequence end position of each probe immobilized on the chip is known, the identity of the nucleic acid hybridized to a given probe can be determined.

For single-nucleotide polymorphism analyzes, sets of four oligonucleotides are generally designed (one for each possible base) that span each position of a portion of the candidate region found in the nucleic acid sample, differing only in the identity of the central base. The relative intensity of hybridization to each series of probes at a particular location allows the identification of the base corresponding to the central base of the probe. For example, to detect single nucleotide polymorphisms such as those in the present biallelic markers, oligonucleotides having each of the two allelic bases at their central position are affixed to the chip. The amplification products resulting from amplification of the nucleic acids in the sample are hybridized to the chip under high stringency (at lower salt concentration and higher temperature over shorter time periods) to facilitate specific detection of the polymorphic sequences present in the nucleic acid sample.

The use of direct electric field control improves the determination of single base mutations (Nanogen). A positive field increases the transport rate of negatively charged nucleic acids and results in a 10-fold increase of the hybridization rates. Using this technique, single base pair mismatches are detected in less than 15 sec (see Sosnowski et al., Proc. Natl. Acad. Sci. USA 94:1119–1123 (1997), the disclosure of which is incorporated herein by reference).

Another technique which can be used to analyze polymorphisms includes multicomponent integrated systems which miniaturize and compartmentalize processes such as restriction enzyme digestion, PCR reactions, and capillary electrophoresis in a single functional device. An example of such technique is disclosed in U.S. Pat. No. 5,589,136, the disclosure of which is incorporated herein by reference, which concerns the integration of PCR amplification and capillary electrophoresis in chips. Integrated systems are best applied with microfluidic systems. These systems comprise a pattern of microchannels designed onto a glass, silicon, quartz, or plastic wafer included on a microchip. The movements of the samples are controlled by electric forces applied across different areas of the microchip to create functional microscopic valves and pumps with no moving parts. Regulating or varying the voltage controls the liquid flow at intersections between the micro-machined channels and changes the liquid flow rate for pumping across different sections of the microchip.

In the case of biallelic marker analyzes, the micro-chip integrates nucleic acid amplification, a microsequencing reaction (such as the one described above), capillary electrophoresis and a detection method such as laser-induced fluorescence detection.

In a first step, the DNA samples are amplified, preferably by PCR. Then, the amplification products are subjected to automated microsequencing reactions using ddNTPs (specific fluorescence for each ddNTP) and the appropriate oligonucleotide microsequencing primers which hybridize just upstream of the targeted polymorphic base. The microsequencing reactions may employ primers capable of being extended to the polymorphic bases of the biallelic markers. Preferably, the microsequencing primers comprise a sequence terminating at the base immediately preceding the polymorphic base of the biallelic markers. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. Preferably, the micro-chip can be used to process at least 96 samples in parallel. More preferably, the micro-chip can be used to process at least 384 samples in parallel. Preferably, the microchip is designed for use with detection procedures using four color laser induced fluorescence detection of the ddNTPs.

Any one or more alleles of the biallelic markers in the maps of the present invention, or fragments thereof containing the polymorphic bases, may be fixed to a solid support, such as a microchip or other immobilizing surface. The fragments of these nucleic acids may comprise at least 10,. at least 15, at least 20, at least 25, or more than 25 consecutive nucleotides of the biallelic markers described herein. Preferably, the fragments include the polymorphic bases of the biallelic markers.

A nucleic acid sample is applied to the immobilizing surface and analyzed to determine the identies of the polymorphic bases of one or more of the biallelic markers. In some embodiments, the solid support may also include one or more of the amplification primers described herein, or fragments comprising at least 10, at least 15, or at least 20 consecutive nucleotides thereof, for generating an amplification product containing the polymorphic bases of the biallelic markers to be analyzed in the sample.

Another embodiment of the present invention is a solid support which includes one or more of the microsequencing primers listed as in the accompying Sequence Listing, or fragments comprising at least 10, at least 15, or at least 20 consecutive nucleotides thereof and having a 3' terminus immediately upstream of the polymorphic base of the corresponding biallelic marker, for determining the identity of the polymorphic base of the one or more biallelic markers fixed to the solid support.

For example, one embodiment of the present invention is an array of nucleic acids fixed to a solid support, such as a microchip, bead, or other immobilizing surface, comprising one or more of the biallelic markers in the maps of the present invention or a fragment comprising at least 10, at least 15, at least 20, at least 25, or more than 25 consecutive nucleotides thereof including the polymorphic base. For example, the array may comprise one or more of any of the 653 biallelic markers obtained above (which include the sequences of SEQ ID Nos. 1–50 and 51–100), the asthma-associated biallelic markers, the PG1 biallelic markers, and the new Apo E biallelic markers (including SEQ ID Nos. 301–305/307–311) or the sequences complementary thereto, or a fragment comprising at least 10, at least 15, at least 20, at least 25, or more than 25 consecutive nucleotides thereof including the polymorphic base. In a further embodiment, the array comprises at least five of the biallelic markers in the maps of the present invention or a fragment comprising at least 10, at least 15, at least 20, at least 25, or more than 25 consecutive nucleotides thereof including the polymorphic base. For example, the arrays may comprise at least five of any of the 653 biallelic markers obtained above (which include the sequences of SEQ ID Nos. 1–50 and 51–100), the asthma-associated biallelic markers, the PG1 biallelic markers, and the new Apo E biallelic markers (including the sequences of SEQ ID Nos. 301–305/307–311) or the sequences complementary thereto, or a fragment comprising at least 10, at least 15, at least 20, at least 25, or more than 25 consecutive nucleotides thereof including the polymorphic base. In a further embodiment the array comprises at least 10 of the biallelic markers in the maps of the present invention or a fragment comprising at least 10, at least 15, at least 20, at least 25, or more than 25 consecutive nucleotides thereof consecutive nucleotides thereof including the polymorphic base. For example, the array may comprise at least 10 of any of the 653 biallelic markers obtained above (which include the sequences of SEQ ID Nos. 1–50 and 51–100), the asthma-associated biallelic markers, the PG1 biallelic markers, and the new Apo E biallelic markers (including the sequences of SEQ ID Nos. 301-305/307-311) or the sequences complementary thereto, or a fragment comprising at least 10, at least 15, at least 20, at least 25, or more than 25 consecutive nucleotides thereof including the polymorphic base. In a further embodiment the array comprises at least 20 of the biallelic markers in the maps of the present invention or a fragment comprising at least 15 consecutive nucleotides thereof including the polymorphic base. For example, the array may comprise at least 20 of any of the 653 biallelic markers obtained above (which include the sequences of SEQ ID Nos. 1–50 and 51–100), the asthma-associated biallelic markers, the PG1 biallelic markers, and the new Apo E biallelic markers (including the sequences of SEQ ID Nos. 301–305/307-311) or the sequences complementary thereto, or a fragment comprising at least 10, at least 15, at least 20, at least 25, or more than 25 consecutive nucleotides thereof including the polymorphic base. In a further embodiment the array comprises at least 100 of the biallelic markers in the maps of the present invention or a fragment comprising at least 10, at least 15, at least 20, at least 25, or more than 25 consecutive nucleotides thereof including the polymorphic base. For example, the array may comprise at least 100 of any of the 653 biallelic markers obtained above (which include the sequences of SEQ ID Nos. 1–50 and 51–100), the asthma-associated biallelic markers, the PG1 biallelic markers, and the new Apo E biallelic markers (including the sequences of SEQ ID Nos. 301–305/307–311) or the sequences complementary thereto, or a fragment comprising at least 10, at least 15, at least 20, at least 25, or more than 25 consecutive nucleotides thereof including the polymorphic base. In a further embodiment the array comprises at least 200 of the biallelic markers in the maps of the present invention or a fragment thereof comprising at least 10, at least 15, at least 20, at least 25, or more than 25 consecutive nucleotides thereof including the polymorphic base. For example, the array may comprise at least 200 of any of the 653 biallelic markers obtained above (which include the sequences of SEQ ID Nos. 1–50 and 51–100), the asthma-associated biallelic markers, the PG1 biallelic markers the new Apo E biallelic markers (including the sequences of SEQ ID Nos. 301–305/307–311 or the sequences complementary thereto, or a fragment comprising at least 10, at least 15, at least 20, at least 25, or more than 25 consecutive nucleotides thereof including the polymorphic base. In a further embodiment the array comprises at least 300 of the biallelic markers in the maps of the present invention or a fragment comprising at least 10, at least 15, at least 20, at least 25, or more than 25 consecutive nucleotides thereof including the polymorphic base. For example, the array may comprise at least 300 of any of the 653 biallelic markers obtained above (which include the sequences of SEQ ID Nos. 1–50 and 51–100), the asthma-associated biallelic markers, the PG1 biallelic markers, and the new Apo E biallelic marker (including the sequences of SEQ ID Nos. 301–305/307–311) or the sequences complementary thereto, or a fragment comprising at least 10, at least 15, at least 20, at least 25, or more than 25 consecutive nucleotides thereof including the polymorphic base. In a further embodiment the array comprises at least 400 of the biallelic markers in the maps of the present invention or a fragment comprising at least 10, at least 15, at least 20, at least 25, or more than 25 consecutive nucleotides thereof including the polymorphic base. For example, the array may comprise at least 400 of any of the 653 biallelic markers obtained above (which include the sequences of SEQ ID Nos. 1–50 and 51–100), the asthma-associated biallelic markers, the PG1 biallelic markers, and the new Apo E biallelic markers (including the sequences of SEQ ID Nos. 301–305/307–311) or the sequences complementary thereto, or a fragment comprising at least 10, at least 15, at least 20, at least 25, or more than 25 consecutive nucleotides thereof including the polymorphic base. In a further embodiment the array comprises more than 400 of the biallelic markers in the maps of the present invention or a fragment comprising at least 10, at least 15, at least 20, at least 25, or more than 25 consecutive nucleotides thereof including the polymorphic base. For example, the array may comprise at least 400 of any of the 653 biallelic markers obtained above (which include the sequences of SEQ ID Nos. 1–50 and 51–100), the asthma-associated biallelic markers, the PG1 biallelic markers and the new Apo E biallelic markers (including the sequences of SEQ ID Nos. 301–305/307–311) or the sequences complementary thereto, or a fragment comprising at least 10, at least 15, at least 20, at least 25, or more than 25 consecutive nucleotides thereof including the polymorphic base. Each of the embodiments listed above may also include one or more of the sequences of SEQ ID Nos. 306 and 312 in addition to those enumerated above.

Another embodiments of the present invention is an array comprising amplification primers for generating amplification products containing the polymorphic bases of one or more, at least five, at least 10, at least 20, at least 100. at least 200, at least 300, at least 400, or more than 400 of the biallelic markers in the maps of the present invention. For example, the array may comprise amplification primers for generating amplification products containing the polymorphic bases of one or more, at least five, at least 10, at least 20, at least 100, at least 200, at least 300, at least 400, or more than 400 of any of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers (including the sequences of SEQ ID Nos. 301–305/307–311 or the sequences complementary thereto). In such arrays, the amplification primers included in the array are capable of amplifying the biallelic marker sequences to be detected in the nucleic acid sample applied to the array (i.e. the amplification primers correspond to the biallelic markers affixed to the array). For example, if the array is designed to detect the biallelic marker of SEQ ID Nos. 1 and 51 it may also contain SEQ ID Nos. 101 and 151, the amplification primers capable of generating an amplicon which includes sequence ID Nos. 1 and 51. Thus, the arrays may include one or more of the amplification primers of SEQ ID Nos. 101–200, 313–317, and 319–323 corresponding to the one or more biallelic markers of SEQ ID Nos. 1–50 and 51–100, 301–305, and 307–311 which are included in the array. In other embodiments, the arrays may include amplification primers capable of generating an amplification product which includes the biallelic markers SEQ ID Nos. 306 and 312 in addition to amplification primers capable of generating an amplification product containing each of the markers enumerated above. Thus, in such embodiments, the arrays may further include the amplification primers of SEQ ID Nos. 318 and 324.

Another embodiment of the present invention is an array which includes microsequencing primers capable of determining the identity of the polymorphic bases one or more, at least five, at least 10, at least 20, at least 100, at least 200, at least 300, at least 400, or more than 400 of the biallelic markers in the maps of the present invention. For example, the array may comprise microsequencing primers capable of determining the identity of the polymorphic bases of one or more, at least five, at least 10, at least 20, at least 100, at least 200, at least 300, at least 400, or more than 400 of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers (including the sequences of SEQ ID Nos. 301–305/307–311 or the sequences complementary thereto). The sequences of representative microsequencing primers which may be included in the array are listed in the sequence listing as SEQ ID Nos. 201–300, 325–329, and 331–335. In other embodiments, the arrays may further include microsequencing primers for determining the identity of the polymorphic bases of one or more of the sequences of SEQ ID Nos. 306 and 312, such as the microsequencing primers of SEQ ID Nos. 330 and 336.

Arrays containing any combination of the above nucleic acids which permits the specific detection or identification of the polymorphic bases at the biallelic markers in the maps of the present invention, including any combination of the 653 biallelic markers obtained above (which include the sequences of SEQ ID Nos. 1–50 and 51–100 or the sequences complementary thereto), the asthma-associated biallelic markers, the PG1 biallelic markers, and the new Apo E biallelic markers (including the sequences of SEQ ID Nos. 301–305/307–311 or the sequences complementary thereto) are also within the scope of the present invention. Other embodiments of the arrays include nucleic acids which permit the specific detection or identification of the polymorphic bases of one or more of SEQ ID Nos. 306 and 312 in addition to the nucleic acids permitting the specific detection or identication of the polymorphic bases of the biallelic markers listed in the preceding sentence. For example, the array may comprise both the biallelic markers and amplification primers capable of generating amplification products containing the polymorphic bases of the biallelic markers. Alternatively, the array may comprise both amplification primers capable of generating amplification products containing the polymorphic bases of the biallelic markers and microsequencing primers capable of determining the identities at the polymorphic bases of these markers.

Although the above examples describe arrays comprising specific groups of biallelic markers and, in some embodiments, specific amplification primers and microsequencing primers, it will be appreciated that the present invention encompasses arrays including any biallelic marker, group of biallelic markers, amplification primer, group of amplification primers, microsequencing primer, or group of amplification primers described herein, as well as any combination of the preceding nucleic acids.

Alternatively, the microsequencing procedures described above may be used to determine whether an individual possesses a pattern of biallelic marker alleles associated with a detectable trait. In this approach, a PCR reaction is performed an the DNA or RNA of the individual to be tested to amplify the desired biallelic markers or portions thereof. The amplification product is hybridized to one or more oligonucleotides having their 3' end one base from the position of the polymorphic bases of the biallelic markers which are fixed to a surface. The oligonucleotides are extended one base using a detectably labeled dNTP and a polymerase. Incorporation of a pattern of detectably labeled bases indicative of a biallelic marker pattern associated with a detectable trait indicates that the individual suffers from a detectable trait as the result of a particular mutation or that the individual is at risk for developing the detectable trait at a subsequent time.

In addition to their use in diagnostic techniques such as those described above, any of the arrays described above may also be used to identify a haplotype (i.e. a set of alleles of biallelic markers) which is associated with a particular trait. As described above, in such analyses nucleic acid samples are obtained from trait positive and trait negative individuals and the alleles of biallelic markers present in each population are determined to identify a haplotype which is statistically associated with the trait. The arrays may be employed in haplotype analyses as follows. Nucleic acid samples obtained from trait positive and trait negative individuals are amplified with primers capable of generating amplification products which include the polymorphic bases of the biallelic markers. The amplification products are labeled with a reporter group and allowed to contact the biallelic marker probes which are attached to the support. As described above, the biallelic marker probes to which the labeled amplification products specifically hybridize are determined to indicate which alleles of the biallelic markers are present in the samples. The patterns of alleles of biallelic markers in the trait positive and trait negative individuals are then determined to identify a haplotype having a statistically significant association with the trait.

Alternatively, as described above, the nucleic acid samples from trait positive and trait negative individuals may be applied to an array comprising amplification primers capable of generating amplification products which include the polymorphic bases of the biallelic markers. The identities of the polymorphic bases in the amplification products are then determined using techniques such as the microsequencing procedures disclosed herein. Alternatively, amplification can be conducted in liquid phase and microsequencing may be conducted on the array.

Alternatively, both amplification and microsequencing reactions may be performed in liquid phase. In such embodiments, the labeled nucleotides incorporated in the microsequencing primers during the microsequencing reactions are detected by hybridizing the extended microsequencing primers to sequences complementary to the microsequencing primers. The sequences complementary to the microsequencing primers are immobilized on a support, such as those described above. The amplification and microsequencing reactions performed in liquid phase may be multiplexed, allowing the samples to be tested simultaneously for tens, hundreds, thousands or more biallelic markers.

Preferably, the array used in the haplotype analysis comprises one or more groups of biallelic markers known to be located in proximity to one another in the genome. For example, the biallelic markers in the groups may be derived from a single YAC insert, a single BAC insert or a BAC subclone. Alternatively, the biallelic markers in the groups may be derived from adjacent ordered clones. The biallelic markers in the groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1Mb, or more than 1Mb. In some embodiments, the biallelic markers in the groups comprise biallelic markers which have been localized to the same chromosome, subchromosomal region, or gene.

It will be appreciated that the ordered DNA containing the biallelic markers need not completely cover the genomic regions of these lengths but may instead be incomplete contigs having one or more gaps therein.

In some embodiments, the biallelic markers known to be located in proximity to one another in the genome may be located in physical proximity on the array. For example, the array may comprise one or more groups of at least 3 biallelic markers known to be located in proximity to one another in the genome. In some embodiments, the array may comprise one or more groups of at least 6 biallelic markers known to be located in proximity to one another in the genome. In other embodiments, the array may comprise one or more groups of at least 20 biallelic markers known to be located in proximity to one another in the genome.

The array may comprise one or more groups of biallelic markers known to be located on the same subchromosomal region. For example, the array could comprise two or more biallelic markers located at 21q11.2 (selected from the group consisting of SEQ ID Nos. 29, 79, 30 and 80), two or more markers located at 21q21 (selected from the group consisting SEQ ID Nos 1, 51, 2, 52, 3 and 53), two or more markers located at 21q21.2 (selected from the group consisting of SEQ ID Nos 17, 67, 18, 68, 19, 69, 20, 70, 21, and 71), two or more markers located at 21q21.3-q22.13 (selected from the group consisting of SEQ ID Nos 25, 75, 26, 76, 27, 77, 28, 78, 31, 81, 32, 82, 38, 88, 39, 89, 40, 90, 48, 98, 49, 99, 50, 100, 22, 72, 23, 73, 24, 74, 4, 54, 5, 55, 6, 56, 7, 57, 8, 58, 9, 59, 10, 60, 11, 61, 12, 62, 13, 63, 14, 64, 15, 65, 16, and 66), two or more markers located at 21q22.2 (selected from the group consisting of SEQ ID Nos 41, 91, 42, 92, 43, 93, 44, 94, 45, 95, 48, 96, 47, and 97), and two or more markers located at 21q22.3 (selected from the group consisting of SEQ ID Nos 33, 83, 34, 84, 35, 85, 36, 86, 37, and 87). Alternatively, the array could comprise amplification primers capable of generating an amplification product containing the polymorphic bases of two or more biallelic markers located at 21q11.2 (for example, amplification primers capable of generating an amplification product containing the polymorphic bases of two or more biallelic markers selected from the group consisting of SEQ ID Nos. 29, 79, 30 and 80), two or more markers located at 21q21 (for example amplification primers capable of generating an amplification product containing the polymorphic bases of two or more biallelic markers selected from the group consisting of SEQ ID Nos 1, 51, 2, 52, 3 and 53), two or more markers located at 21q21.2 (for example, amplification primers capable of generating an amplification product containing the polymorphic bases of two or more biallelic markers selected from the group consisting of SEQ ID Nos 17, 67, 18, 68, 19, 60, 20, 70, 21, and 71), two or more markers located at 21q21.3-q22.13 (for example, amplification primers capable of generating an amplification product containing the polymorphic bases of two or more biallelic markers selected from the group consisting of SEQ ID Nos 25, 75, 26, 76, 27, 77, 28, 78, 31, 81, 32, 82, 38, 88, 39, 89, 40, 90, 48, 98, 49, 99, 50, 100, 22, 72, 23, 73, 24, 74, 4, 54, 5, 55, 6, 56, 7, 57, 8, 58, 9, 59, 10, 60, 11, 61, 12, 62, 13, 63, 14, 64, 15, 65, 16, and 66), two or more markers located at 21q22.2 (for example, amplification primers capable of generating an amplification product containing the polymorphic bases of two or more biallelic markers selected from the group consisting of SEQ ID Nos 41, 91, 42, 92, 43, 93, 44, 94, 45, 95, 46, 96, 47, and 97), and two or more markers located at 21q22.3 (for example, amplification primers capable of generating an amplification product containing the polymorphic bases of two or more biallelic markers selected from the group consisting of SEQ ID Nos 33, 63, 34, 84, 35, 85, 36, 86, 37, and 87).

In some embodiments, the array may comprise one or more groups of biallelic markers derived from the same BAC insert. For example, the array could comprise two or more markers selected from the group consisting of SEQ ID Nos. 29, 79, 30, and 80 (derived from BAC 1), two or more markers selected from the group consisting of SEQ ID Nos. 1 and 51 (derived from BAC 2), two or more markers selected from the group consisting of SEQ ID Nos. 2, 52, 3, and 53 (derived from BAC 3), two or more markers selected from the group consisting of SEQ ID Nos. 17, 67, 16, 68, 19, 69, 20, 70, 21, and 71 (derived from BAC 4), two or more markers selected from the group consisting of SEQ ID Nos. 25, 75, 26, 76, 27, and 77 (derived from BAC 5), two or more markers selected from the group consisting of SEQ ID Nos. 28, 78, 31, 81, 32, and 82 (derived from BAC 6), two or more markers selected from the group consisting of SEQ ID Nos. 38, 88, 39, 89, 40, and 90 (derived from BAC 7), two or more markers selected from the group consisting of SEQ ID Nos. 46, 98, 49, 99, 50, and 100 (derived from BAC 8), two or more markers selected from the group consisting of SEQ ID Nos. 22, 72, 23, 73, 24, and 74 (derived from BAC 9), two or more markers selected from the group consisting of SEQ ID Nos 4, 54, 5, 55, 6, 56, 7, 57, 8, 58, 9, 59, 10, and 60 (derived from BAC 10), two or more markers selected from the group consisting of SEQ ID Nos. 11, 81, 12, 62, 13, 63, 14, 64, 15, 65, 16, and 66 (derived from BAC 11), two or more markers selected from the group consisting of SEQ ID Nos. 41, 91, 42, 92, 43, 93, 44, 94, 45, 95, 46, 96, 47, and 97 (derived from BAC 12), or two or more markers selected from the group consisting of SEQ ID Nos. 33, 83, 34, 84, 35, 85, 36, 86, 37, and 87 (derived from BAC 13).

Arrays comprising biallelic markers known to be located in proximity to one another in the genome permit haplotyping analyses to be conducted even when the chromosomal locations of the biallelic markers has not been determined. For example, using the procedures described above, the alleles of sets of biallelic markers which are present in nucleic acid samples from trait positive and trait negative individuals may be determined using a succession of arrays, with each array having one or more groups of nucleic acids known to be located in proximity to one another thereon. The succession of arrays may comprise biallelic markers spanning the entire genome having any of the average intermarker distances specified above. Alternatively, the succession of arrays need not span the entire genome but may instead be derived from two or more contigated YAC, BAC, or BAC subclone inserts. A statistical analysis is performed on the alleles of biallelic markers present in the trait positive and trait negative individuals to identify a haplotype having a statistically significant association with the trait. Once a statistically significant haplotype is identified, the genomic locations of the biallelic markers comprising the haplotype may be determined using the methods described herein. In addition, using the procedures described herein, the genomic region harboring the biallelic markers in the statistically significant haplotype may be evaluated to identify the genes associated with the trait.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

TABLE 1

| Biallelic marker (Genset code) | BAC | Insert size (kb) | average Intermarker distance (kb) | subchromosomal localization |
|---|---|---|---|---|
| 99-2378 | 1 | 150 | 75 | 21q11.2 |
| 99-2381 | 1 | 150 | 75 | 21q11.2 |
| 99-2103 | 2 | 110 | 110 | 21q21 |
| 99-2228 | 3 | 105 | 52.5 | 21q21 |
| 99-2229 | 3 | 105 | 52.5 | 21q21 |
| 99-2312 | 4 | 130 | 26 | 21q21.2 |
| 99-2315 | 4 | 130 | 26 | 21q21.2 |
| 99-2320 | 4 | 130 | 26 | 21q21.2 |
| 99-2321 | 4 | 130 | 26 | 21q21.2 |
| 99-2324 | 4 | 130 | 26 | 21q21.2 |

TABLE 1-continued

| Biallelic marker (Genset code) | BAC | Insert size (kb) | average Intermarker distance (kb) | subchromosomal localization |
|---|---|---|---|---|
| 99-2362 | 5 | 100 | 33.3 | 21q21.3–q22.13 |
| 99-2364 | 5 | 100 | 33.3 | 21q21.3–q22.13 |
| 99-2367 | 5 | 100 | 33.3 | 21q21.3–q22.13 |
| 99-2371 | 6 | 135 | 45 | 21q22.11–q22.13 |
| 99-2413 | 6 | 135 | 45 | 21q22.11–q22.13 |
| 99-2419 | 6 | 135 | 45 | 21q22.11–q22.13 |
| 99-2610 | 7 | 185 | 61.7 | 21q22.11–q22.13 |
| 99-2615 | 7 | 185 | 61.7 | 21q22.11–q22.13 |
| 99-2620 | 7 | 185 | 61.7 | 21q22.11–q22.13 |
| 99-2645 | 8 | 250 | 83.3 | 21q22.11–q22.13 |
| 99-2647 | 8 | 250 | 83.3 | 21q22.11–q22.13 |
| 99-2649 | 8 | 250 | 83.3 | 21q22.11–q22.13 |
| 99-2333 | 9 | 140 | 46.7 | 21q22.11–q22.13 |
| 99-2341 | 9 | 140 | 46.7 | 21q22.11–q22.13 |
| 99-2342 | 9 | 140 | 46.7 | 21q22.11–q22.13 |
| 99-2240 | 10 | 95 | 13.6 | 21q22.11–q22.13 |
| 99-2242 | 10 | 95 | 13.6 | 21q22.11–q22.13 |
| 99-2244 | 10 | 95 | 13.6 | 21q22.11–q22.13 |
| 99-2246 | 10 | 95 | 13.6 | 21q22.11–q22.13 |
| 99-2248 | 10 | 95 | 13.6 | 21q22.11–q22.13 |
| 99-2250 | 10 | 95 | 13.6 | 21q22.11–q22.13 |
| 99-2251 | 10 | 95 | 13.6 | 21q22.11–q22.13 |
| 99-2269 | 11 | 40 | 6.7 | 21q22.11–q22.13 |
| 99-2271 | 11 | 40 | 6.7 | 21q22.11–q22.13 |
| 99-2272 | 11 | 40 | 6.7 | 21q22.11–q22.13 |
| 99-2273 | 11 | 40 | 6.7 | 21q22.11–q22.13 |
| 99-2275 | 11 | 40 | 6.7 | 21q22.11–q22.13 |
| 99-2278 | 11 | 40 | 6.7 | 21q22.11–q22.13 |
| 99-2624 | 12 | 165 | 23.6 | 21q22.2 |
| 99-2625 | 12 | 165 | 23.6 | 21q22.2 |
| 99-2630 | 12 | 165 | 23.6 | 21q22.2 |
| 99-2633 | 12 | 165 | 23.6 | 21q22.2 |
| 99-2634 | 12 | 165 | 23.6 | 21q22.2 |
| 99-2637 | 12 | 165 | 23.6 | 21q22.2 |
| 99-2642 | 12 | 165 | 23.6 | 21q22.2 |
| 99-2559 | 13 | 205 | 41 | 21q22.3 |
| 99-2566 | 13 | 205 | 41 | 21q22.3 |
| 99-2567 | 13 | 205 | 41 | 21q22.3 |
| 99-2570 | 13 | 205 | 41 | 21q22.3 |
| 99-2571 | 13 | 205 | 41 | 21q22.3 |

We claim:
1. A method of selecting an individual for inclusion in clinical trial of a drug for the treatment of Alzheimer's disease, prostate cancer or asthma comprising:
   a) obtaining a nucleic acid sample from an individual;
   b) constructing a nucleic acid library comprising a plurality of genomic DNA fragments that comprise the full genome of the individual or a portion of the genome of the individual;
   c) determining the order of the plurality of genomic DNA fragments in the genome of the individual;
   d) determining the sequence of selected regions of said plurality of genomic DNA fragments;
   e) identifying nucleotides in said plurality of genomic DNA fragments that vary between individuals;
   f) determining the frequencies of each allele of one or more biallelic markers in individuals showing a detectable trait;
   g) identifying one or more alleles of said one or more biallelic markers that are statistically associated with said detectable trait, wherein said detectable trait is susceptibility to Alzheimer's disease and said biallelic markers are selected from: 99-365/344; the combination of biallelic markers 99-366/274, 99/344/439, 99-359/308 and 99-355/219 (IIAP8); or the combination of biallelic markers 99/359/308, 99-366/274, and 99-355/219 (IIAP7); wherein said detectable trait is susceptibility to prostate cancer and said biallelic markers are selected from the combination of 4-67 and 99-213 (haplotype 1.2); the combination of 99-217 and 4-67 (haplotype 1.1); 99-217, 4-67 and 99-213 (haplotype 2); the combination of biallelic markers 4-77, 99-217, and 4-67 (haplotype 2.2); the combination of biallelic markers 4-77, 99-217, 4-67 and 99-213 (haplotype 3.2); the combination of 99-217, 4-67, 99-213, and 99-221 (haplotype 3.1); 4-77, 99-217, 4-67, 99-213, and 99-221 (haplotype 4); the combination of 4-14, 4-77, 99-217, 4-67, 99-213, and 99-221 (haplotype 5); 4-26, 4-14, 4-77, 99-217, 4-67, 99-213, and 99-221 (haplotype 6); the combination of 4-26, 4-14, 4-77, 99-217, 4-67, 99-213, 99-221 and 99-135 (haplotype 7); or the combination of 4-26, 4-14, 4-77, 99-217, 4-67, 99-213, 99-221 and 99-135 (haplotype 8); or said detectable trait is susceptibility to asthma and said biallelic markers are selected from 32/357; 33/234; 33/327; 35/358; 35/390; the combination of biallelic markers 32/357 and 35/390 (haplotype 1); the combination of biallelic markers 33/234, 33/327, and 35/358 (haplotype 2); or the combination of biallelic markers 32/357, 33/234, 33/327, 35/358 and 35/390 (haplotype 3); and
   h) including tho individual said in clinical trial if said nucleic acid sample contains one or more of said biallelic markers or combinations or biallelic markers that are associated with the detectable trait.

2. The method according to claim 1, wherein said detectable trait is susceptibility to Alzheimer's disease and said biallelic marker is 99-365/344.

3. The method according to claim 1, wherein said detectable trait is susceptibility to Alzheimer's disease and said biallelic markers are the combination of biallelic markers 99-366/274, 99/344/439, 99-359/308 and 99-355/219 (IIAP8).

4. The method according to claim 1, wherein said detectable trait is susceptibility to prostate cancer and said biallelic markers are selected from the combination of 4-67 and 99-213 (haplotype 1.2).

5. The method according to claim 1, wherein said detectable trait is susceptibility to prostate cancer and said biallelic markers are selected from the combination of 99-217 and 4-67 (haplotype 1.1).

6. The method according to claim 1, wherein said detectable trait is susceptibility to prostate cancer and said biallelic markers are the combination of biallelic markers 99-217, 4-67 and 99-213 (haplotype 2).

7. The method according to claim 1, wherein said detectable trait is susceptibility to prostate cancer and said biallelic markers are the combination of biallelic markers 4-77, 99-217, and 4-67 (haplotype 2.2).

8. The method according to claim 1, wherein said detectable trait is susceptibility to prostate cancer and said biallelic markers are the combination of biallelic markers 4-77, 99-217, 4-67 and 99-213 (haplotype 3.2).

9. The method according to claim 1, wherein said detectable trait is susceptibility to prostate cancer and said biallelic markers are the combination of biallelic markers 99-217, 4-67, 99-213, and 99-221 (haplotype 3.1).

10. The method according to claim 1, wherein said detectable trait is susceptibility to prostate cancer and said biallelic markers are the combination of biallelic markers 4-77, 99-217, 4-67, 99-213, and 99-221 (haplotype 4).

11. The method according to claim 1, wherein said detectable trait is susceptibility to prostate cancer and said biallelic markers are the combination of biallelic markers 4-14, 4-77, 99-217, 4-67, 99-213, and 99-221 (haplotype 5).

12. The method according to claim 1, wherein said detectable trait is susceptibility to prostate cancer and said biallelic markers are the combination of biallelic markers 4-26, 4-14, 4-77, 99-217, 4-67, 99-213, and 99-221 (haplotype 6).

13. The method according to claim 1, wherein said detectable trait is susceptibility to prostate cancer and said biallelic markers are the combination of biallelic markers 4-26, 4-14, 4-77, 99-217, 4-67, 99-213, 99-221 and 99-135 (haplotype 7).

14. The method according to claim 1, wherein said detectable trait is susceptibility to prostate cancer and said biallelic markers are the combination of biallelic markers 4-26, 4-14, 4-77, 99-217, 4-67, 99-213, 99-221 and 99-135 (haplotype 8).

15. The method according to claim 1, wherein said detectable trait is susceptibility to asthma and said biallelic marker is 32/357.

16. The method according to claim 1, wherein said detectable trait is susceptibility to asthma and said biallelic marker is 33/234.

17. The method according to claim 1, wherein said detectable trait is susceptibility to asthma and said biallelic marker is 33/327.

18. The method according to claim 1, wherein said detectable trait is susceptibility to asthma and said biallelic marker is 35/358.

19. The method according to claim 1, wherein said detectable trait is susceptibility to asthma and said biallelic marker is 35/390.

20. The method according to claim 1, wherein said detectable trait is susceptibility to asthma and said biallelic markers are the combination of biallelic markers 32/357 and 3 5/390 (haplotype 1).

21. The method according to claim 1, wherein said detectable trait is susceptibility to asthma and said biallelic markers are the combination of biallelic markers 33/234, 33/327, and 35/358 (haplotype 2).

22. The method according to claim 1, wherein said detectable trait is susceptibility to asthma and said biallelic markers are the combination of biallelic markers 32/357, 33/234, 33/327, 35/358 and 35/390 (haplotype 3).

* * * * *

UNITED STATES PATENT AND TRADEMARK OFFICE
CERTIFICATE OF CORRECTION

| | |
|---|---|
| PATENT NO. | : 7,105,353 B2 |
| APPLICATION NO. | : 10/367438 |
| DATED | : September 12, 2006 |
| INVENTOR(S) | : Daniel Cohen, Marta Blumenfeld and Ilya Chumakov |

It is certified that error appears in the above-identified patent and that said Letters Patent is hereby corrected as shown below:

Column 1,
Line 52, "the identifying stop" should read --the identifying step--.

Column 6,
Line 20, "method of five first embodiment." should read --method of the first embodiment.--.

Column 7,
Line 35, "detectable trail" should read --detectable trait--.

Column 10,
Line 49, "at least 3 consecutive" should read --at least 8 consecutive--.

Column 11,
Line 36, "spacing an a randomly" should read --spacing on a randomly--.

Column 19,
Line 33, "selected BAC, inserts." should read --selected BAC inserts.--.

Column 21,
Line 39, "25 or 3 kb" should read --2.5 or 3 kb--.

Column 22,
Lines 20-21, "10mM Tris pH7.6:5mM $MgCl_2$;" should read --10mM Tris pH7.6; 5mM $MgCl_2$;--.

Column 24,
Lines 39-40, "the $10^7$biallelic" should read --the $10^7$ biallelic--.

Column 34,
Line 13, "and nut having" should read --and not having--.
Line 31, "person win readily" should read --person will readily--.

Column 35,
Lines 41-42, "Sequence Listing Table 10)." should read --Sequence Listing and Table 10).--.

UNITED STATES PATENT AND TRADEMARK OFFICE
CERTIFICATE OF CORRECTION

PATENT NO. : 7,105,353 B2
APPLICATION NO. : 10/367438
DATED : September 12, 2006
INVENTOR(S) : Daniel Cohen, Marta Blumenfeld and Ilya Chumakov It is certified that error appears in the above-identified patent and that said Letters Patent is hereby corrected as shown below:

Column 37,
Line 61, "mast often" should read --most often--.

Column 39,
Line 46, "permits tie identification" should read --permits the identification--.

Column 40,
Line 9, "allele of being a" should read --allele *a* being a--.

Column 43,
Line 56, "trail" should read --trait--.

Column 49,
Line 31, "pU 7.5" should read --pH7.5--.
Line 41, "100μof" should read --100 μl of--.

Column 54,
Line 31, "99-217, 4-87, 99-213" should read --99-217, 4-67, 99-213--.

Column 55,
Line 10, "allelelleast" should read --allele/least--.
Line 50, "99-135markers" should read --99-135 markers--.

Column 56,
Line 4, "Boehringer)" should read --(Boehringer)--.

Column 58,
Line 11, "Dejection of Biallelic" should read --Detection of Biallelic--.

Column 62,
Line 13, "candidate gone" should read --candidate gene--.

Column 63,
Line 7 (Table 8 heading), "Pormutation Test" should read --Permutation Test--.

Column 67,
Line 23, "any gone" should read --any gene--.

UNITED STATES PATENT AND TRADEMARK OFFICE
CERTIFICATE OF CORRECTION

PATENT NO. : 7,105,353 B2
APPLICATION NO. : 10/367438
DATED : September 12, 2006
INVENTOR(S) : Daniel Cohen, Marta Blumenfeld and Ilya Chumakov It is certified that error appears in the above-identified patent and that said Letters Patent is hereby corrected as shown below:

Column 68,
Line 5, "drug or it the" should read --drug or if the nucleic--.

Column 71,
Line 9, "Nos:Δ301-306/307-312" should read --Nos: 301-306/307-312--.
Line 19, "SE I11 Nos." should read --SEQ ID Nos.--.
Lines 19-20, "may be microsequencing" should read --may be used in microsequencing--.
Line 52, "containing E" should read --containing the Apo E)--.

Column 72,
Line 41, "PG1biallelic" should read --PG1 biallelic--.

Column 73,
Line 50, "the PC1" should read --the PG1--.

Column 74,
Line 55, "using those primers" should read --using these primers--.

Column 79,
Line 63, "at least 10,." should read --at least 10,--.

Column 85,
Line 17, "45, 95, 48, 96" should read --45, 95, 46, 96--.
Line 36, "19, 60, 20," should read --19, 69, 20,--.
Line 53, "33, 63" should read --33, 83--.
Line 64, "17, 67, 16, 68, 19" should read --17, 67, 18, 68, 19--.

Column 317,
Line 24, "(IIAP8)" should read --(HAP8)--.
Line 26, "(IIAP7)" should read --(HAP7)--.
Line 59, "(IIAP8)" should read --(HAP8)--.

UNITED STATES PATENT AND TRADEMARK OFFICE
CERTIFICATE OF CORRECTION

| | |
|---|---|
| PATENT NO. | : 7,105,353 B2 |
| APPLICATION NO. | : 10/367438 |
| DATED | : September 12, 2006 |
| INVENTOR(S) | : Daniel Cohen, Marta Blumenfeld and Ilya Chumakov |

It is certified that error appears in the above-identified patent and that said Letters Patent is hereby corrected as shown below:

<u>Column 318,</u>
Line 57, "3 5/390" should read --35/390--.

Signed and Sealed this

Twenty-fourth Day of June, 2008

JON W. DUDAS
*Director of the United States Patent and Trademark Office*